United States Patent [19]

Jacobsen

[11] Patent Number: 5,712,300
[45] Date of Patent: Jan. 27, 1998

[54] HYDROXAMIC ACID DERIVATIVES USEFUL FOR THE TREATMENT OF DISEASES RELATED TO CONNECTIVE TISSUE DEGRADATION

[75] Inventor: E. Jon Jacobsen, Plainwell, Mich.

[73] Assignee: Pharmacia & Upjohn Company, Kalamazoo, Mich.

[21] Appl. No.: 811,821

[22] Filed: Mar. 4, 1997

[51] Int. Cl.$^6$ .................. C07D 403/06; A61K 31/415; A61K 31/40
[52] U.S. Cl. .................. 514/389; 514/404; 514/414; 514/424; 544/141; 544/372; 546/208; 546/281; 548/319.5; 548/370.1; 548/468; 548/550
[58] Field of Search .................. 548/550, 468, 548/319.5, 370.1; 546/208, 281; 544/141, 372

[56] References Cited

FOREIGN PATENT DOCUMENTS

| 0 042 100 A | 6/1981 | European Pat. Off. ...... C07D 487/04 |
|---|---|---|
| 0574758A | 5/1993 | European Pat. Off. ...... C07D 209/48 |
| 2282598 | 12/1995 | United Kingdom ......... C07C 235/82 |
| 94/22820 | 3/1993 | WIPO ........................ C07D 207/26 |
| 93/21942 | 11/1993 | WIPO ........................ A61K 37/02 |
| 95/04033-A1 | 2/1995 | WIPO ........................ C07C 259/06 |
| 95/09841 | 4/1995 | WIPO ........................ C07C 323/60 |

OTHER PUBLICATIONS

Ghose et al, J. Am. Chem. Soc. 117, (16)4671, 1995.

*Primary Examiner*—Robert Gerstl
*Attorney, Agent, or Firm*—Lucy X. Yang

[57] ABSTRACT

The present invention provides novel hydroxamic acid derivatives represented by the compound of formula I

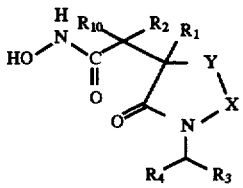

or pharmaceutical acceptable salts thereof, wherein the compounds of the present invention inhibit various enzymes from the matrix metalloproteinase family, including collagenase, stromelysin, and gelatinase, and hence are useful for the treatment of matrix metallo endoproteinase diseases such as osteoarthrits, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation.

21 Claims, No Drawings

HYDROXAMIC ACID DERIVATIVES USEFUL FOR THE TREATMENT OF DISEASES RELATED TO CONNECTIVE TISSUE DEGRADATION

CROSS-REFERENCE TO RELATED APPLICATIONS

This application claims the benefit of US provisional application Ser. No. 60/013,098, filed 8 Mar. 1996, under 35 USC §119(e)(i).

FIELD OF THE INVENTION

The present invention relates to novel hydroxamic acid derivatives or pharmaceutically acceptable salts thereof, their preparation, and pharmaceutical compositions containing them. Particularly, the present invention relates to hydroxamic acid derivatives substituted by a series of 2-pyrrolidinones, hydantions, and pyrazolidinones, which are useful in the treatment of diseases related to connective tissue degradation.

BACKGROUND OF THE INVENTION

Loss of connective tissue integrity occurs in many disease processes, including osteoarthritis, rheumatoid arthritis, septic arthritis, osteopenias such as osteoporosis, tumor metastasis (invasion and growth) periodontiitis, gingivitis, corneal ulceration, dermal ulceration, gastric ulceration, and other diseases related to connective tissue degradation. Although there is a high incidence of these diseases in the developed world, there is no treatment that prevents the tissue damage that occurs. Considerable lines of scientific evidence indicate that uncontrolled connective matrix metalloproteinase (MMPs) activity is responsible for the damage, and as a consequence the inhibition of these enzymes has become the target for therapeutic intervention (see Matrisian, L. M., Bases, Vol. 14, pp 445–463, (1992); Emonard, H. et al., Cellular and molecular Biology, Vol. 36, pp 131–153, (1990); Docherty, A. J. P. et al., Annals of the Rheumatic, Vol. 49, pp 469–479, (1990)).

The compounds of the present invention inhibit various enzymes from the matrix metalloproteinase family, including collagenase, stromelysin, and gelatinase, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation. These compounds may also inhibit the release of cytokines including tumor necrosis factor (TNFα) and hence may also be useful in the treatment of inflammation, fever, acute infections and shock.

INFORMATION DISCLOSURE

International Publication No. WO95/09841 discloses new hydroxamic acid derivatives of amino acid amide compounds useful as TNF release and matrix metalloprotease inhibitors, e.g., for treating inflammation, fever or arthritis.

International Publication No. WO95/04033-A1 discloses new succinimide derivatives useful as gelatinase and collagenase inhibitors.

International Publication No. WO93/21942 discloses matrix metallo protease inhibitors for promoting tumour regression by inhibiting cancer cell proliferation and angiogenesis, atherosclerosis, ovarian carcinoma, melanoma and sarcoma.

European Patent Publication 0,574,758A discloses new hydroxamic acid derivatives useful as collagenase inhibitors for the treatment of arthritis, tumours, atherosclerosis, etc.

UK Patent Application GB2,282,598A discloses hydroxysuccinyl hydroxyamines useful in the prophylaxis or treatment of diseases or conditions mediated by metalloproteinases and/or tumour necrosis factor.

SUMMARY OF THE INVENTION

The present invention provides novel hydroxamic acid derivatives represented by the formula I:

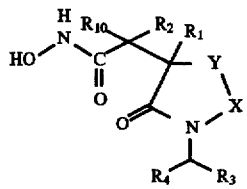

or pharmaceutical acceptable salts thereof wherein

X is
 a) —($CH_2$)—,
 b) —$NR_5$—, or
 c) —C(=O)—;

Y is
 a) —($CH_2$)—, or
 b) —$NR_5$—;

with the proviso that when X is —$NR_5$— then Y is —($CH_2$)—;

$R_1$ is
 a) H,
 b) $C_{1-20}$ alkyl,
 c) —($CH_2$)$_f$-Aryl,
 d) —($CH_2$)$_f$—O—$R_5$,
 e) —($CH_2$)$_f$-Het,
 f) —($CH_2$)$_i$—$CO_2R_5$,
 g) —($CH_2$)$_f$—C(=O)$NHR_5$,
 h) —($CH_2$)$_f$—$NR_6R_7$,
 i) —($CH_2$)$_f$—$SO_2$-Aryl,
 j) —($CH_2$)$_j$ cycloalkyl, or
 k) —($CH_2$)$_f$-Aryl-Aryl;

$R_2$ is
 a) H,
 b) $C_{1-20}$ alkyl,
 c) —($CH_2$)$_f$—$R_8$,
 d) —($CH_2$)$_f$—$OR_5$,
 e) —$CH_2CR_5$=$CR_5R_5$,
 f) —$NHR_5$,
 g) —($CH_2$)$_f$$NR_6R_7$,
 h) —$NHSO_2R_5$,
 i) —($CH_2$)$_f$—C(=O)$NR_6R_7$,
 j) —($CH_2$)$_f$—$NR_5$C(=O)$R_5$,
 k) —($CH_2$)$_f$—$NR_5SO_2R_5$, or
 l) —($CH_2$)$_f$—N(COR$_5$)$_2$;

$R_3$ is
 a) H,
 b) $C_{1-6}$ alkyl,
 c) —($CH_2$)$_f$-Aryl,
 d) —($CH_2$)$_f$—Het,
 e) —($CH_2$)$_f$—$C_{3-6}$ cycloalkyl, or
 f) —C(=O)$NHR_5$;

$R_4$ is
 a) H,
 b) —C(=O)$NHR_5$,
 c) —C(=O)$NR_6R_7$, d) —C(=O)NH(CH$_2$)$_k$NR$_6$R$_7$,
e) —C(=O)NH(CH$_2$)$_j$-Aryl,
f) —C(=O)NH(CH$_2$)$_k$—O—(CH$_2$)$_k$NR$_6$R$_7$,
g) —C(=O)NH(CH$_2$)$_k$—S—(CH$_2$)$_j$NR$_6$R$_7$,
h) —C(=O)NH(CH$_2$)$_k$—NHSO$_2$-Aryl,
i) C(=O)NH(CH$_2$)$_k$—NHSO$_2$—NR$_6$R$_7$, or j) 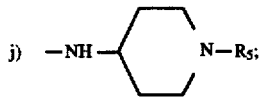

R$_5$ is
a) H,
b) C$_{1-6}$ alkyl,
c) —(CH$_2$)$_j$-Aryl,
d) —(CH$_2$)$_j$-Aryl-Aryl,
e) —(CH$_2$)$_j$-Aryl-(CH$_2$)$_j$-Aryl,
f) (CH$_2$)$_j$—Het, or
g) —(CH$_2$)$_j$-cycloalkyl R$_6$ and R$_7$ may be the same or differently
a) H,
b) C$_{1-6}$ alkyl,
c) —(CH$_2$)$_j$-Aryl,
d) Q, or
e) R$_6$ and R$_7$ taken together with the linking N-atom form azetidinyl, pyrrolidinyl, piperazinyl, piperidinyl, or morpholinyl, optionally substituted with one or more C$_{1-4}$ alkyl;

R$_8$ is
a) —S—R$_5$,
b) —SO—R$_5$,
c) —SO$_2$—R$_5$,
d) —S—(CH$_2$)$_j$—Het,
e) —NHCO$_2$R$_5$,
f) piperidinyl, g) 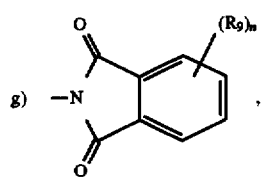

h) 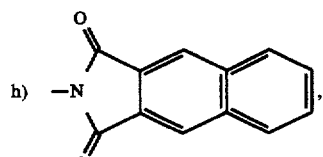

i) 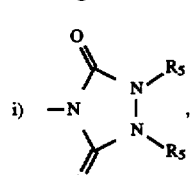

j) 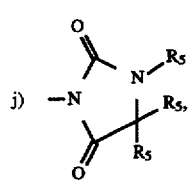

-continued k) 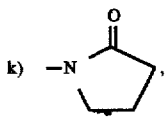

l) 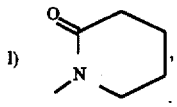

m) 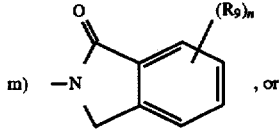, or n) 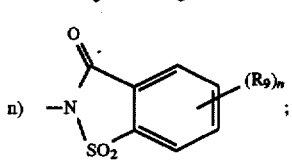;

R$_9$ is
a) halogen,
b) C$_{1-6}$ alkyl,
c) —OR$_5$,
d) —NR$_5$R$_5$,
e) —CONHR$_5$,
f) —SO$_2$NHR$_5$,
g) —NHSO$_2$R$_5$,
h) —NO$_2$,
i) —CO$_2$R$_5$, or
j) —CF$_3$;

R$_{10}$ is
a) H,
b) OH,
c) OR$_5$,
d) NHR$_5$, or
e) —(CH$_2$)$_j$—OR$_5$;

Aryl is phenyl, optionally substituted with one or more of the following:
a) halogen,
b) C$_{1-10}$ alkyl,
c) —OR$_5$,
d) —NR$_5$R$_5$,
e) —CONHR$_5$,
f) —SO$_2$NHR$_5$,
g) —NHSO$_2$R$_5$,
h) —NO$_2$,
i) —CO$_2$R$_5$, or
j) —CF$_3$;

Het is
a 5-, or 6-membered heteroaromatic moiety having one or more atoms selected from the group consisting of N, O, and S;

Q is
a saturated 5, or 6-membered heterocyclic moiety having 1–2 atoms selected from the group consisting of N, O, and S;

i is 1, 2, 3, 4, 5 or 6;
j is 0, 1, 2, 3, or 4;
k is 2, 3, or 4;
n is 0, 1, 2, 3, or 4;

C$_{1-6}$alkyl, C$_{1-10}$alkyl, or C$_{1-20}$alkyl in each of the above definitions, may be each and independently substituted with one to three halogen, hydroxy, or cyano; and with the proviso that when $R_1$ is methylbutyl $R_4$ is other than H.

The present invention provides novel hydroxamic acid derivatives useful as preventatives and therapeutics for diseases related to connective tissue degradation.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atom present from the integer "i" to the integer "j" inclusive. Thus, $C_{1-4}$ alkyl refers to alkyl of 1–4 carbon atoms, inclusive, or methyl, ethyl, propyl, butyl and isomeric forms thereof.

The terms "$C_{1-6}$ alkyl", "$C_{1-10}$ alkyl" or "$C_{1-20}$ alkyl", refers to methyl, ethyl, n-propyl, n-butyl, n-pentyl, n-hexyl, etc. and isomeric forms thereof, and preferably an alkyl group having 1 to 6 carbon atoms.

The $C_{1-6}$ alkyl group may optionally be substituted by one or more substituents selected from the group consisting of a halogen atom, a hydroxy group, or —CN group such as, for example, fluoromethyl, difluoromethyl, fluoroethyl, cyanomethyl and the like.

The term "$C_{3-6}$ cycloalkyl" refers to cyclopropyl, cyclobutyl, cyclopentyl, cyclohexyl and isomeric forms thereof, and preferably an cycloalkyl group having 4 to 6 carbon atom.

The term "halogen" refers to fluoro, chloro, bromo, or iodo, preferably fluoro and chloro.

The term "Q" refers to a saturated 5-, or 6-membered heterocyclic moiety having 1–2 atoms selected from the group consisting of nitrogen, oxygen, and sulfur forming such groups as, for example, dioxolane, imidazolidine, dithiolane, oxathiolane, oxazolidine, piperidinyl, piperazinyl, morpholino and thiomorpholino.

The term "Het" refers to a 5-, 6-membered heteroaromatic moiety having one or more atoms selected form the group consisting of nitrogen, oxygen, and sulfur forming such groups as, for example, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-furanyl, 3-furanyl, 1-pyrrolyl, 2-pyrrolyl, 3-pyrrolyl, 1-pyrazolyl. A preferred heteroaromatic ring within the definition is 2-thienyl and pyridyl.

Within the definition of the terms "Het", and "Q", the nitrogen atom forming the hetero rings may have a protective group such as an acetyl or hydroxyacetyl group.

The compounds of the present invention can be converted to their salts according to conventional methods.

The term "pharmaceutically acceptable salts" refers to salts useful for administering the compounds of this invention and these include hydrochloride, hydrobromide, hydroiodide, sulfate, phosphate, acetate, propionate, lactate, mesylate, maleate, malate, succinate, tartrate, citrate, 2-hydroxyethyl sulfonate, fumarate and the like. These salts may be in hydrated form. Some of the compounds of this invention may form metal salts such as sodium, potassium, calcium and magnesium salts and these are embraced by the term "pharmaceutically acceptable salts".

Certain of the hydroxamic acid derivatives of the present invention are preferred.

The preferred $R_1$ substituent is methylpropyl.

The preferred $R_2$ substituent is H, methyl, 2-(1,3-dihydro-1,3-dioxo-2H-isoindol-2-yl)ethyl, 2-(1,3-dihydro-1,3-dioxo-2H-naphthoisoindol-2-yl)ethyl, 2-(4,5,6,7,-tetrafluoro-1,3-dihydro-1,3-dioxo-2H-isoindol-2-yl)ethyl, 2-(5,6,dichloro-1,3-dihydro-1,3-dioxo-2H-isoindol-2-yl) ethyl, 2-(5-amino-1,3-dihydro-1,3-dioxo-2H-isoindol-2-yl) ethyl, 2-(4-nitro-1,3-dihydro-1,3-dioxo-2H-isoindol-2-yl) ethyl, 2-(5-nitro-1,3-dihydro-1,3-dioxo-2H-isoindol-2-yl) ethyl, 2-(4-fluoro-1,3-dihydro-1,3-dioxo-2H-isoindol-2-yl) ethyl, 2-(4,7-difluoro-1,3-dihydro-1,3-dioxo-2H-isoindol-2-yl)ethyl, 2-(5-fluoro-1,3-dihydro-1,3-dioxo-2H-isoindol-2-yl)ethyl, 2-(1,3-dihydro-1,3-dioxo-2H-isoindol-2-yl)propyl, 2-(1,3-dihydro-1,3-dioxo-2H-isoindol-2-yl)methyl, 2-(2-thienylthio)propyl, or 2-(2-thienylthio)methyl.

The preferred $R_3$ substituent is H, 2-methylpropyl, cyclohexylmethyl, benzyl, or phenyl.

The preferred $R_4$ substituent is H or acetamide.

The preferred absolute configurations of the compounds claimed in the present invention are as represented in the structures II–VII. The absolute configurations are determined under the Cahn-Ingold-Prelog nomenclature system. The compounds depicted in the Examples are racemic unless indicated otherwise by R or S to refer their optical activity. The pure enantiomers possess higher inhibitory activities. The racemic mixtures are useful in the same way and for the same purpose as the pure enantiomer; the difference is that more racemic material may be used to produce the same inhibitory effect. Optically pure material can be obtained by using chiral HPLC methods to provide the corresponding enantiomers as illustrated in Examples 2, 5, and 28. Optionally, optically pure materials can be obtained chemically to provide the desired enantiomer as illustrated in Examples 29–34.

Depending on substituents, the compounds of this invention may exist in geometric, optical and other isomeric forms and this invention embraces any of these isomers or enantiomers.

Particularly preferred compounds of this invention are as follows:

1a) N-Hydroxy-3-(2-methylpropyl)-2-oxo-1-(2-phenylethyl)-3-pyrrolidineacetamide, 1b) (3S)-N-Hydroxy-3-(2-methylpropyl)-2-oxo-1-(2-phenylethyl)-3-pyrrolidineacetamide, 1c) N-Hydroxy-α-methyl-3-(2-methylpropyl)-2-oxo-1-(2-phenylethyl)-3-pyrrolidineacetamide, 1d) α-[2-(1,3-Dihydro-1,3-dioxo-2H-isoindol-2-yl)ethyl]-N-hydroxy-3-(2-methylpropyl)-2-oxo-1-(2-phenylethyl)-3-pyrrolidineacetamide, 1e) (3S)-α-[2-(1,3-Dihydro-1,3-dioxo-2H-isoindol-2-yl) ethyl]-N-hydroxy-3-(2-methylpropyl)-2-oxo-1-(2-phenylethyl)-3-pyrrolidineacetamide, 1f) α-[2-(1,3-Dihydro-1,3-dioxo-2H-naphthoisoindol-2-yl) ethyl]-N-hydroxy-3-(2-methylpropyl)-2-oxo-1-(2-phenylethyl)-3-pyrrolidineacetamide, 1g) N-Hydroxy-3-(2-methylpropyl)-2-oxo-1-(2-phenylethyl)-α-[2-(4,5,6,7-tetrafluoro-1,3-dihydro-1,3-dioxo-2H-isoindol-2-yl)ethyl]-3-pyrrolidineacetamide, 1h) α-[2-(5,6-Dichloro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, 1i) α-[2-(5-Amino-1,3-dihydro-1,3-dioxo-2H-isoindol-2-yl) ethyl]-N-hydroxy-3-(2-methylpropyl)-2-oxo-1-(2-phenylethyl)-3-pyrrolidineacetamide, 1j) N-Hydroxy-3-(2-methylpropyl)-α-[2-(4-nitro-1,3-dihydro-1,3-dioxo-2H-isoindol-2-yl)ethyl]-2-oxo-1-(2-phenylethyl)-3-pyrrolidineacetamide, 1k) N-Hydroxy-3-(2-methylpropyl)-α-[2-(5-nitro-1,3-dihydro-1,3-dioxo-2H-isoindol-2-yl)ethyl]-2-oxo-1-(2-phenylethyl)-3-pyrrolidineacetamide, ll) α-[2-(4-Fluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, lm) α-[2-(4,7-Difluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, ln) α-[2-(5-Fluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, lo) α-[2-(1,3-Dihydro-1,3-dioxo-2H-isoindol-2-yl)propyl]-N-hydroxy-3-(2-methylpropyl)-2-oxo-1-(2-phenylethyl)-3-pyrrolidineacetamide, lp) α-[2-(1,3-Dihydro-1,3-dioxo-2H-isoindol-2-yl)methyl]-N-hydroxy-3-(2-methylpropyl)-2-oxo-1-(2-phenylethyl)-3-pyrrolidineacetamide, lq) N-Hydroxy-3-(2-methylpropyl)-2-oxo-1-(2-phenylethyl)-α-[2-(2-thienylthio)ethyl]-3-pyrrolidineacetamide, lr) N-Hydroxy-3-(2-methylpropyl)-2-oxo-1-(2-phenylethyl)-α-[2-(2-thienylthio)propyl]-3-pyrrolidineacetamide, ls) N-Hydroxy-3-(2-methylpropyl)-2-oxo-1-(2-phenylethyl)-α-[2-(2-thienylthio)methyl]-3-pyrrolidineacetamide, lt) $N^3$-Hydroxy-$N^1$-methyl-3-(2-methylpropyl)-2-oxo-1,3-pyrrolidinediacetamide, lu) $N^3$-Hydroxy-$N^1$-methyl-3-(2-methylpropyl)-2-oxo-$\alpha^1$-(phenylmethyl)-1,3-pyrrolidinediacetamide, lv) N-Hydroxy-3-(2-methylpropyl)-2-oxo-1-(phenylmethyl)-3-pyrrolidineacetamide, lw) α-[2-(1,3-Dihydro-1,3-dioxo-2H-isoindol-2-yl)ethyl]-N-hydroxy-3-(2-methylpropyl)-2-oxo-1-(phenylmethyl)-3-pyrrolidineacetamide, lx) N-Hydroxy-3-(2-methylpropyl)-2-oxo-1-(phenylmethyl)-α-[2-(4,5,6,7-tetrafluoro-1,3-dihydro-1,3-dioxo-2H-isoindol-2-yl)ethyl]-3-pyrrolidineacetamide, ly) 1-(3-Fluorophenyl)methyl)-α-[2-(1,3-dihydro-1,3-dioxo-2H-isoindol-2-yl)ethyl]-N-hydroxy-3-(2-methylpropyl)-2-oxo-3-pyrrolidineacetamide, lz) $\alpha^3$-[2-(1,3-Dihydro-1,3-dioxo-2H-isoindol-2-yl)ethyl]-$N^3$-hydroxy-$N^1$-methyl-3-(2-methylpropyl)-2-oxo-1,3-pyrrolidinediacetamide, 2a) $N^3$-Hydroxy-$N^1$-methyl-3-(2-methylpropyl)-2-oxo-$\alpha^3$-[2-(4,5,6,7-tetrafluoro-1,3-dihydro-1,3-dioxo-2H-isoindol-2-yl)ethyl]-1,3-pyrrolidinediacetamide, 2d) [S-(R*,R*)]-$N^3$-Hydroxy-$N^1$-methyl-3-(2-methylpropyl)-2-oxo-$\alpha^1$-(phenylmethyl)-1,3-pyrrolidinediacetamide, 2e) [S-(R*,R*)]-$N^3$-Hydroxy-3-(2-methylpropyl)-2-oxo-$N^1$-(2-phenethyl)-$\alpha^1$-(phenylmethyl)-1,3-pyrrolidinediacetamide, 2f) [S-(R*,R*)]-$N^3$-Hydroxy-$N^1$-methyl-$\alpha^1$,3-bis(2-methylpropyl)-2-oxo-1,3-pyrrolidinediacetamide, 2g) [S-(R*,R*)]-$\alpha^1$-(Cyclohexylmethyl)-$N^3$-hydroxy-$N^1$-methyl-3-(2-methylpropyl)-2-oxo-1,3-pyrrolidinediacetamide, 2h) [S-(R*,R*)]-$N^3$-Hydroxy-$N^1$-methyl-3-(3-methylbutyl)-2-oxo-$\alpha^1$-(phenylmethyl)-1,3-pyrrolidinediacetamide, 2i) N-Hydroxy-3-(2-methylpropyl)-2,5-dioxo-1-(2-phenylethyl)-3-pyrrolidineacetamide, 2j) N-Hydroxy-3-methyl-4-(2-methylpropyl)-2,5-dioxo-1-(2-phenylethyl)-4-imidazolidineacetamide, 2k) N-Hydroxy-4-(2-methylpropyl)-2,5-dioxo-1-(2-phenylethyl)-4-imidazolidineacetamide, 2l) N-Hydroxyl-4-(2-methylpropyl)-5-oxo-1-(2-phenylethyl)-4-pyrazolidineacetamide monohydrochloride, 2m) [S-(R*,R*)]-$N^3$-Hydroxy-3-(2-methylpropyl)-2-oxo-$N^1$-phenyl-$\alpha^1$-(phenylmethyl)-1,3-pyrrolidinediacetamide, 2n) [S-(R*,R*)]-$N^3$-Hydroxy-3-(2-methylpropyl)-2-oxo-$\alpha^1$-(phenylmethyl)-$N^1$-(2-pyridinylmethyl)-1,3-pyrrolidinediacetamide, 2o) [S-(R*,R*)]-$N^3$-Hydroxy-3-(2-methylpropyl)-2-oxo-$\alpha^1$-(phenylmethyl)-$N^1$-(4-pyridinyl)-1,3-pyrrolidinediacetamide, 2p) [S-(R*,R*)]-$N^1$-(4-Fluorophenyl)-$N^3$-hydroxy-3-(2-methylpropyl)-2-oxo-$\alpha^1$-(phenylmethyl)-1,3-pyrrolidinediacetamide, 2q) [S-(R*,R*)]-$N^3$-Hydroxy-3-(2-methylpropyl)-2-oxo-$\alpha^1$-(phenylmethyl)-$N^1$-[1-(phenylmethyl)-4-piperdinyl]-1,3-pyrrolidinediacetamide, 2r) [S-(R*,R*)]-$N^3$-Hydroxy-3-(2-methylpropyl)-2-oxo-$\alpha^1$-(phenylmethyl)-$N^1$-(4-piperdinyl)-1,3-pyrrolidinediacetamide, 2s) [S-(R*,R*)]-$N^3$-Hydroxy-3-(2-methylpropyl)-2-oxo-$\alpha^1$-(phenylmethyl)-$N^1$-(4-pyridinylmethyl)-1,3-pyrrolidinediacetamide, 2t) [S-(R*,R*)]-$N^1$-(4-Fluorophenylmethyl)-$N^3$-hydroxy-3-(2-methylpropyl)-2-oxo-$\alpha^1$-(phenylmethyl)-1,3-pyrrolidinediacetamide, 2u) [S-(R*,R*)]-$N^3$-Hydroxy-$N^1$-methyl-3-(2-methylpropyl)-2-oxo-$\alpha^1$-(2-phenylethyl)-1,3-pyrrolidinediacetamide, 2v) [S-(R*,R*)]-$N^3$-Hydroxy-3-(2-methylpropyl)-2-oxo-$\alpha^1$-(2-phenylethyl)-$N^1$-(phenylmethyl)-1,3-pyrrolidinediacetamide, 2w) [S-(R*,R*)]-$N^3$-Hydroxy-$\alpha^1$,3-bis(2-methylpropyl)-2-oxo-$N^1$-2-pyridinyl-1,3-pyrrolidinediacetamide, 2x) [S-(R*,R*)]-$\alpha^1$-Cyclohexyl-$N^3$-hydroxy-$N^1$-methyl-3-(2-methylpropyl)-2-oxo-1,3-pyrrolidinediacetamide, 2y) [S-(R*,R*)]-$\alpha^1$-Cyclohexyl-$N^3$-hydroxy-3-(2-methylpropyl)-2-oxo-$N^1$-2-pyridinyl-1,3-pyrrolidinediacetamide, 3a) [S-(R*,R*)]-3-(Cyclopentylmethyl)-$N^3$-hydroxy-$N^1$-methyl-2-oxo-$\alpha^1$-(phenylmethyl)-1,3-pyrrolidinediacetamide, 3b) [3S-[1(R*),3R*(R*)]]-$\alpha^3$-[2-(Benzoylamino)ethyl]-$N^3$-hydroxy-$N^1$-methyl-3-(2-methylpropyl)-2-oxo-$\alpha^1$-(phenylmethyl)-1,3-pyrrolidinediacetamide, 3c) [S-(R*,R*)]-$N^3$-Hydroxy-3-(2-methylpropyl)-$N^1$-[2-(4-morpholinyl)ethyl]-2-oxo-$\alpha^1$-(phenylmethyl)-1,3-pyrrolidinediacetamide, 3d) [S-(R*,R*)]-N-Hydroxy-3-(2-methylpropyl)-1-[2-(4-morpholinyl)-2-oxo-1-(phenylmethyl)ethyl]-2-oxo-3-pyrrolidineacetamide, 3e) [1(1S)-[1[R*(R*)],3α,5α]]-1-[2-(3,5-Dimethyl-1-piperazinyl)-2-oxo-1-(phenylmethyl)ethyl]-N-hydroxy-3-(2-methylpropyl)-2-oxo-3-pyrrolidineacetamide, 3f) [S-(R*,R*)]-$N^3$-Hydroxy-3-(2-methylpropyl)-2-oxo-$\alpha^1$-(phenylmethyl)-$N^1$-2-pyridinyl-1,3-pyrrolidinediacetamide, 3g) [3S-[1(R*),3R*(R*)]]-$\alpha^3$-[2-(1,3-Dihydro-1,3-dioxo-2H-isoindol-2-yl)ethyl]-$N^3$-hydroxy-$N^1$-methyl-3-(2-methylpropyl)-2-oxo-$\alpha^1$-(phenylmethyl)-1,3-pyrrolidinediacetamide, 3h) [S-(R*,R*)]-$\alpha^1$-Cyclohexyl-$N^1$-cyclopropylmethyl-$N^3$-hydroxy-3-(2-methylpropyl)-2-oxo-1,3-pyrrolidinediacetamide, 3i) [S-(R*,R*)]-$\alpha^1$-Cyclohexyl-$N^1$-(4-fluorophenyl)-$N^3$-hydroxy-3-(2-methylpropyl)-2-oxo-1,3-pyrrolidinediacetamide, 3j) [S-(R*,R*)]-$\alpha^1$-tert-Butyl-$N^3$-hydroxy-$N^1$-methyl-3-(2-methylpropyl)-2-oxo-1,3-pyrrolidinediacetamide, 3k) N-Hydroxy-3-(2-methylpropyl)-2'-oxo-1-(2-phenylethyl)-α-[2-(5-propyloxy-1,3-dihydro-1,3-dioxo-2H-isoindol-2-yl)ethyl]-3-pyrrolidineacetamide, 3l) [R-(R*,S*)]-5-Fluoro-1,3-dihydro-N-hydroxy-α-[3-(2-methylpropyl)-2-oxo-1-(2-phenylethyl)-3-pyrrolidinyl]-1,3-dioxo-2H-isoindole-2-butanamide, 3m) α-[2-(5,6-Difluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, 3n) N-Hydroxy-3-(2-methylpropyl)-2-oxo-1-(2-phenylethyl)-α-[2-(5-trifluoromethyl-1,3-dihydro-1,3-dioxo-2H-isoindol-2-yl)ethyl]-3-pyrrolidineacetamide, 3o) α-[2-(1,3,4,5,6,7-Hexahydro-1,3-dioxo-2H-isoindol-2-yl)ethyl]-N-hydroxy-3-(2-methylpropyl)-2-oxo-1-(2-phenylethyl)-3-pyrrolidineacetamide, 3p) α-[2-(1,3-Dihydro-1,3-dioxo-2H-isoindol-2-yl)ethyl]-N-hydroxy-3-(2-methylpropyl)-2-oxo-1-(3-phenylpropyl)-3-pyrrolidineacetamide, 3r) α-[2-(o-benzoic sulfimide)ethyl]-N-hydroxy-3-(2-methylpropyl)-2-oxo-1-(2-phenylethyl)-3-pyrrolidineacetamide, 3s) Ethyl Phenylmethyl[4-(hydroxyamino)-3-[3-(2-methylpropyl)-2-oxo-1-(2-phenylethyl)-3-pyrrolidinyl]-4-oxobutyl]imidodicarbonate, 3t) S-(R*,R*)]-1,3-Dihydro-N-hydroxy-α-[3-(2-methylpropyl)-2-oxo-1-(2-phenylethyl)-3-pyrrolidinyl]-1,3-dioxo-2H-isoindole-2-butanamide, 3u) 1,3-Dihydro-N-hydroxy-α-[3-(2-methylpropyl)-2-oxo-1-[2-(4-fluorophenyl)ethyl]-3-pyrrolidinyl]-1,3-dioxo-2H-isoindole-2-butanamide, 3v) α-[2-[(3,4-Difluorobenzoyl)amino]ethyl]-N-hydroxy-3-(2-methylpropyl)-2-oxo-1-(2-phenylethyl)-3-pyrrolidineacetamide, 3w) [R-(R*,S*)-α-[2-[(3-Fluorobenzoyl)amino]ethyl]-N-hydroxy-3-(2-methylpropyl)-2-oxo-1-(2-phenylethyl)-3-pyrrolidineacetamide, 3x) α-[2-[(4-Fluorobenzoyl)amino]ethyl]-N-hydroxy-3-(2-methylpropyl)-2-oxo-1-(2-phenylethyl)-3-pyrrolidineacetamide, 3y) N-Hydroxy-3-(2-methylpropyl)-α-[2-[(3-nitrobenzoyl)amino]ethyl]-2-oxo-1-(2-phenylethyl)-3-pyrrolidineacetamide, 3z) α-[2-[(3-Fluorobenzoyl)amino]ethyl]-N-hydroxy-3-(2-methylpropyl)-2-oxo-1-(2-phenylethyl)-3-pyrrolidineacetamide, 4a) α-[2-[(3-Fluorobenzoyl)amino]ethyl]-1-[2-(4-fluorophenyl)ethyl]-N-hydroxy-3-(2-methylpropyl)-2-oxo-3-pyrrolidineacetamide, 4b) α-[2-[(4-Biphenylcarbonyl)amino]ethyl]-N-hydroxy-3-(2-methylpropyl)-2-oxo-1-(2-phenylethyl)-3-pyrrolidineacetamide, 4c) N-Hydroxy-α-[2-[[(4-methylphenyl)sulfonyl]amino]ethyl]-3-(2-methylpropyl)-2-oxo-1-(2-phenylethyl)-3-pyrrolidineacetamide, 4d) α-[2-[[(4-Fluorophenyl)sulfonyl]amino]ethyl]-N-hydroxy-3-(2-methylpropyl)-2-oxo-1-(2-phenylethyl)-3-pyrrolidineacetamide, 4e) N-Hydroxy-α-[2-[[(4-methoxyphenyl)sulfonyl]amino]ethyl]-3-(2-methylpropyl)-2-oxo-1-(2-phenylethyl)-3-pyrrolidineacetamide, 4f) N-Hydroxy-3-(2-methylpropyl)-2-oxo-1-(2-phenylethyl)-α-[2-(phenylsulfonyl)amino]ethyl]-3-pyrrolidineacetamide, 4g) [R-(R*,S*)]-α-[2-[[(4-Fluorophenyl)sulfonyl]amino]ethyl]-N-hydroxy-3-(2-methylpropyl)-2-oxo-1-(2-phenylethyl)-3-pyrrolidineacetamide, 4h) 5,6-Difluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 4i) 1,3-Dihydro-N-hydroxy-α-[3-(2-methylpropyl)-2-oxo-1-(2-phenylethyl)-3-pyrrolidinyl]-1-oxo-2H-isoindole-2-butanamide, 4j) [R-(R*,S*)]-6-Fluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 4k) [R-(R*,S*)]-5-Fluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 4l) [R-(R*,S*)]-5,6-Difluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 4m) N-Hydroxy-α-[[[(4-methoxyphenyl)sulfonyl]amino]methyl]-3-(2-methylpropyl)-2-oxo-1-(2-phenylethyl)-3-pyrrolidineacetamide (αR-diastereomer), 4n) N-Hydroxy-α-[[[(4-methoxyphenyl)sulfonyl]amino]methyl]-3-(2-methylpropyl)-2-oxo-1-(2-phenylethyl)-3-pyrrolidineacetamide (αS-diastereomer), 4o) α-[[(4-Fluorophenyl)sulfonyl]amino]-N-hydroxy-3-(2-methylpropyl)-2-oxo-1-(2-phenylethyl)-3-pyrrolidineacetamide (R-diastereomer), 4p) α-[[(4-Fluorophenyl)sulfonyl]amino]-N-hydroxy-3-(2-methylpropyl)-2-oxo-1-(2-phenylethyl)-3-pyrrolidineacetamide (αS-diastereomer), 4q) α-[2-[(3,4-Difluorobenzoyl)amino]ethyl]-N-hydroxy-3-(3-hydroxypropyl)-2-oxo-1-(2-phenylethyl)-3-pyrrolidineacetamide, 4r) α-[2-[(3,4-Difluorobenzoyl)amino]ethyl]-N-hydroxy-3-(2-hydroxyethyl)-2-oxo-1-(2-phenylethyl)-3-pyrrolidineacetamide, 4s) [R-(R*,S*)]-α-[2-[(3-Fluorobenzoyl)amino]ethyl]-N-hydroxy-3-(3-hydroxypropyl)-2-oxo-1-(2-phenylethyl)-3-pyrrolidineacetamide, 4t) S-(R*,R*)]-N$^3$-hydroxy-N$^1$-methyl-α$^1$-(1-methylethyl)-3-(2-methylpropyl)-2-oxo-1,3-pyrrolidinediacetamide, 4u) [S-(R*,R*)]-N$^1$-cyclopropyl-N$^3$-hydroxy-α$^1$-(1-methylethyl)-3-(2-methylpropyl)-2-oxo-1,3-pyrrolidinediacetamide, 4v) [S-(R*,R*)]-N$^3$-hydroxy-α$^1$-(1-methylethyl)-3-(2-methylpropyl)-2-oxo-N$^1$-phenyl-1,3-pyrrolidinediacetamide, 4w) [S-(R*,R*)]-N$^1$-(4-fluorophenyl)-N$^3$-hydroxy-α$^1$-(1-methylethyl)-3-(2-methylpropyl)-2-oxo-1,3-pyrrolidinediacetamide, 4x) [S-(R*,R*)]-N$^3$-hydroxy-α$^1$-(1-methylethyl)-3-(2-methylpropyl)-2-oxo-N$^1$-(4-pyridinyl)-1,3-pyrrolidinediacetamide, 4y) [S-(R*,R*)]-α$^1$-tert-butyl-N$^1$-cyclopropyl-N$^3$-hydroxy-3-(2-methylpropyl)-2-oxo-1,3-pyrrolidinediacetamide, 4z) [S-(R*,R*)]-α$^1$-tert-butyl-N$^3$-hydroxy-3-(2-methylpropyl)-2-oxo-N$^1$-phenyl-1,3-pyrrolidinediacetamide, 5a) [S-(R*,R*)]-α$^1$-tert-butyl-N$^1$-(4-fluorophenyl)-N$^3$-hydroxy-3-(2-methylpropyl)-2-oxo-1,3-pyrrolidinediacetamide, 5b) [S-(R*,R*)]-α$^1$-tert-butyl-N$^3$-hydroxy-3-(2-methylpropyl)-2-oxo-N$^1$-(4-pyridinyl)-1,3-pyrrolidinediacetamide, 5c) [S-(R*,R*)]-α$^1$-cyclohexyl-N$^3$-hydroxy-3-(2-methylpropyl)-2-oxo-N$^1$-phenyl-1,3-pyrrolidinediacetamide, 5d) [S-(R*,R*)]-α$^1$-cyclohexyl-N$^3$-hydroxy-3-(2-methylpropyl)-2-oxo-N$^1$-(4-pyridinyl)-1,3-pyrrolidinediacetamide, 5e) [S-(R*,R*)]-3-(cyclopentylmethyl)-N$^3$-hydroxy-N$^1$-methyl-α$^1$-(1-methylethyl)-2-oxo-1,3-pyrrolidinediacetamide, 5f) [S-(R*,R*)]-3-(cyclopentylmethyl)-N$^1$-cyclopropyl-N$^3$-hydroxy-α$^1$-(1-methylethyl)-2-oxo-1,3-pyrrolidinediacetamide, 5g) [S-(R*,R*)]-3-(cyclopentylmethyl)-N$^3$-hydroxy-α$^1$-(1-methylethyl)-2-oxo-N$^1$-phenyl-1,3-pyrrolidinediacetamide, 5h) [S-(R*,R*)]-3-(cyclopentylmethyl)-N$^1$-(4-fluorophenyl)-N$^3$-hydroxy-α$^1$-(1-methylethyl)-2-oxo-1,3-pyrrolidinediacetamide, 5i) [S-(R*,R*)]-3-(cyclopentylmethyl)-N$^3$-hydroxy-α$^1$-(1-methylethyl)-2-oxo-N$^1$-(4-pyridinyl)-1,3-pyrrolidinediacetamide, 5j) [S-(R*,R*)]-α$^1$-tert-butyl-3-(cyclopentylmethyl)-N$^3$-hydroxy-N$^1$-methyl-2-oxo-1,3-pyrrolidinediacetamide, 5k) [S-(R*,R*)]-α$^1$-tert-butyl-3-(cyclopentylmethyl)-N$^1$-cyclopropyl-N$^3$-hydroxy-2-oxo-1,3-pyrrolidinediacetamide, 5l) [S-(R*,R*)]-α$^1$-tert-butyl-3-(cyclopentylmethyl)-N$^3$-hydroxy-2-oxo-N$^1$-phenyl-1,3-pyrrolidinediacetamide, 5m) [S-(R*,R*)]-α$^1$-tert-butyl-3-(cyclopentylmethyl)-N$^1$-(4-fluorophenyl)-N$^3$-hydroxy-2-oxo-1,3-pyrrolidinediacetamide, 5n) [S-(R*,R*)]-α$^1$-tert-butyl-3-(cyclopentylmethyl)-N$^3$-hydroxy-2-oxo-N$^1$-(4-pyridinyl)-1,3-pyrrolidinediacetamide, 5o) [S-(R*,R*)]-α$^1$-cyclohexyl-3-(cyclopentylmethyl)-N$^3$-hydroxy-N$^1$-methyl-2-oxo-1,3-pyrrolidinediacetamide, 5P) [S-(R*,R*)]-α$^1$-cyclohexyl-3-(cyclopentylmethyl)-N$^1$-cyclopropyl-N$^3$-hydroxy-2-oxo-1,3-pyrrolidinediacetamide, 5Q) [S-(R*,R*)]-α$^1$-cyclohexyl-3-(cyclopentylmethyl)-N$^3$-hydroxy-2-oxo-N$^1$-phenyl-1,3-pyrrolidinediacetamide, 5r) [S-(R*,R*)]-α$^1$-cyclohexyl-3-(cyclopentylmethyl)-N$^1$-(4-fluorophenyl)-N$^3$-hydroxy-2-oxo-1,3-pyrrolidinediacetamide, 5s) [S-(R*,R*)]-α$^1$-cyclohexyl-3-(cyclopentylmethyl)-N$^3$-hydroxy-2-oxo-N$^1$-(4-pyridinyl)-1,3-pyrrolidinediacetamide, 5t) [S-(R*,R*)]-N$^3$-hydroxy-N$^1$-methyl-α$^1$-(1-methylethyl)-2-oxo-3-(3-phenylpropyl)-1,3-pyrrolidinediacetamide, 5u) [S-(R*,R*)]-N$^1$-cyclopropyl-N$^3$-hydroxy-α$^1$-(1-methylethyl)-2-oxo-3-(3-phenylpropyl)-1,3-pyrrolidinediacetamide, 5v) [S-(R*,R*)]-N$^3$-hydroxy-α$^1$-(1-methylethyl)-2-oxo-N$^1$-phenyl-3-(3-phenylpropyl)-1,3-pyrrolidinediacetamide, 5w) [S-(R*,R*)]-N$^1$-(4-fluorophenyl)-N$^3$-hydroxy-α$^1$-(1-methylethyl)-2-oxo-3-(3-phenylpropyl)-1,3-pyrrolidinediacetamide, 5x) [S-(R*,R*)]-N$^3$-hydroxy-α$^1$-(1-methylethyl)-2-oxo-3-(3-phenylpropyl)-N$^1$-(4-pyridinyl)-1,3-pyrrolidinediacetamide, 5y) [S-(R*,R*)]-α$^1$-tert-butyl-N$^3$-hydroxy-N$^1$-methyl-2-oxo-3-(3-phenylpropyl)-1,3-pyrrolidinediacetamide, 5z) [S-(R*,R*)]-α$^1$-tert-butyl-N$^1$-cyclopropyl-N$^3$-hydroxy-2-oxo-3-(3-phenylpropyl)-1,3-pyrrolidinediacetamide, 6a) [S-(R*,R*)]-α$^1$-tert-butyl-N$^3$-hydroxy-2-oxo-N$^1$-phenyl-3-(3-phenylpropyl)-1,3-pyrrolidinediacetamide, 6b) [S-(R*,R*)]-α$^1$-tert-butyl-N$^1$-(4-fluorophenyl)-N$^3$-hydroxy-2-oxo-3-(3-phenylpropyl)-1,3-pyrrolidinediacetamide, 6c) [S-(R*,R*)]-α$^1$-tert-butyl-N$^3$-hydroxy-2-oxo-3-(3-phenylpropyl)-N$^1$-(4-pyridinyl)-1,3-pyrrolidinediacetamid, 6d) [S-(R*,R*)]-α$^1$-cyclohexyl-N$^3$-hydroxy-N$^1$-methyl-2-oxo-3-(3-phenylpropyl)-1,3-pyrrolidinediacetamide, 6e) [S-(R*,R*)]-α$^1$-cyclohexyl-N$^1$-cyclopropyl-N$^3$-hydroxy-2-oxo-3-(3-phenylpropyl)-1,3-pyrrolidinediacetamide, 6f) [S-(R*,R*)]-α$^1$-cyclohexyl-N$^3$-hydroxy-2-oxo-N$^1$-phenyl-3-(3-phenylpropyl)-1,3-pyrrolidinediacetamide, 6g) [S-(R*,R*)]-α$^1$-cyclohexyl-N$^1$-(4-fluorophenyl)-N$^3$-hydroxy-2-oxo-3-(3-phenylpropyl)-1,3-pyrrolidinediacetamide, 6h) [S-(R*,R*)]-α$^1$-cyclohexyl-N$^3$-hydroxy-2-oxo-3-(3-phenylpropyl)-N$^1$-(4pyridinyl)-1,3-pyrrolidinediacetamide, 6i) [S-(R*,R*)]-3-[3-(4-fluorophenyl)propyl]-N$^3$-hydroxy-N$^1$-methyl-α$^1$-(1-methylethyl)-2-oxo-1,3-pyrrolidinediacetamide, 6j) [S-(R*,R*)]-N$^1$-cyclopropyl-3-[3-(4-fluorophenyl)propyl]-N$^3$-hydroxy-α$^1$-(1-methylethyl)-2-oxo-1,3-pyrrolidinediacetamide, 6k) [S-(R*,R*)]-3-[3-(4-fluorophenyl)propyl]-N$^3$-hydroxy-α$^1$-(1-methylethyl)-2-oxo-N$^1$-phenyl-1,3-pyrrolidinediacetamide, 6l) [S-(R*,R*)]-N$^1$-(4-fluorophenyl)-3-[3-(4-fluorophenyl)propyl]-N$^3$-hydroxy-α$^1$-(1-methylethyl)-2-oxo-1,3-pyrrolidinediacetamide, 6m) [S-(R*,R*)]-3-[3-(4-fluorophenyl)propyl]-N$^3$-hydroxy-α$^1$-(1-methylethyl)-2-oxo-N$^1$-(4-pyridinyl)-1,3-pyrrolidinediacetamide, 6n) [S-(R*,R*)]-α$^1$-tert-butyl-3-[3-(4-fluorophenyl)propyl]-N$^3$-hydroxy-N$^1$-methyl-2-oxo-1,3-pyrrolidinediacetamide, 6o) [S-(R*,R*)]-α$^1$-tert-butyl-N$^1$-cyclopropyl-3-[3-(4-fluorophenyl)propyl]-N$^3$-hydroxy-2-oxo-1,3-pyrrolidinediacetamide, 6p) [S-(R*,R*)]-α$^1$-tert-butyl-3-[3-(4-fluorophenyl)propyl]-N$^3$-hydroxy-2-oxo-N$^1$-phenyl-1,3-pyrrolidinediacetamide, 6q) [S-(R*,R*)]-α$^1$-tert-butyl-N$^1$-(4-fluorophenyl)-3-[3-(4-fluorophenyl)-propyl]-N$^3$-hydroxy-2-oxo-1,3-pyrrolidinediacetamide, 6r) [S-(R*,R*)]-α$^1$-tert-butyl-3-[3-(4-fluorophenyl)propyl]-N$^3$-hydroxy-2-oxo-N$^1$-(4-pyridinyl)-1,3-pyrrolidinediacetamide, 6s) [S-(R*,R*)]-α$^1$-cyclohexyl-3-[3-(4-fluorophenyl)propyl]-N$^3$-hydroxy-N$^1$-methyl-2-oxo-1,3-pyrrolidinediacetamide, 6t) [S-(R*,R*)]-α$^1$-cyclohexyl-N$^1$-cyclopropyl-3-[3-(4-fluorophenyl)propyl]-N$^3$-hydroxy-2-oxo-1,3-pyrrolidinediacetamide, 6u) [S-(R*,R*)]-α$^1$-cyclohexyl-3-[3-(4-fluorophenyl)propyl]-N$^3$-hydroxy-2-oxo-N$^1$-phenyl-1,3-pyrrolidinediacetamide, 6v) [S-(R*,R*)]-α$^1$-cyclohexyl-N$^1$-(4-fluorophenyl)-3-[3-(4-fluorophenyl)propyl]-N$^3$-hydroxy-2-oxo-1,3-pyrrolidinediacetamide, 6w) [S-(R*,R*)]-α$^1$-cyclohexyl-3-[3-(4-fluorophenyl)propyl]-N$^3$-hydroxy-2-oxo-N$^1$-(4-pyridinyl)-1,3-pyrrolidinediacetamide, 6x) [S-(R*,R*)]-3-[3-(biphen-4-yl)propyl]-N$^3$-hydroxy-N$^1$-methyl-α$^1$-(1-methylethyl)-2-oxo-1,3-pyrrolidinediacetamide, 6y) [S-(R*,R*)]-3-[3-(biphen-4-yl)propyl]-N$^1$-cyclopropyl-N$^3$-hydroxy-α$^1$-(1-methylethyl)-2-oxo-1,3-pyrrolidinediacetamide, 6z) [S-(R*,R*)]-3-[3-(biphen-4-yl)propyl]-N$^3$-hydroxy-α$^1$-(methylethyl)-2-oxo-N$^1$-phenyl-1,3-pyrrolidinediacetamide, 7a) [S-(R*,R*)]-3-[3-(biphen-4-yl)propyl]-N$^1$-(4-fluorophenyl)-N$^3$-hydroxy-α$^1$-(1-methylethyl)-2-oxo-1,3-pyrrolidinediacetamide, 7b) [S-(R*,R*)]-3-[3-(biphen-4-yl)propyl]-N$^3$-hydroxy-α$^1$-(1methylethyl)-2-oxo-N$^1$-(4-pyridinyl)-1,3-pyrrolidinediacetamide, 7c) [S-(R*,R*)]-3-[3-(biphen-4-yl)propyl]-α¹-tert-butyl-N³-hydroxy-N¹-methyl-2-oxo-1,3-pyrrolidinediacetamide, 7d) [S-(R*,R*)]-3-[3-(biphen-4-yl)propyl]-α¹-tert-butyl-N¹-cyclopropyl-N³-hydroxy-2-oxo-1,3-pyrrolidinediacetamide, 7e) [S-(R*,R*)]-3-[3-(biphen-4-yl)propyl]-α¹-tert-butyl-N³-hydroxy-2-oxo-N¹-phenyl-1,3-pyrrolidinediacetamide, 7f) [S-(R*,R*)]-3-[3-(biphen-4-yl)propyl]-α¹-tert-butyl-N¹-(4-fluorophenyl)-N³-hydroxy-2-oxo-1,3-pyrrolidinediacetamide, 7g) [S-(R*,R*)]-3-[3-(biphen-4-yl)propyl]-α¹-tert-butyl-N³-hydroxy-2-oxo-N¹-(4-pyridinyl)-1,3-pyrrolidinediacetamide, 7h) [S-(R*,R*)]-3-[3-(biphen-4-yl)propyl]-α¹-cyclohexyl-N³-hydroxy-N¹-methyl-2-oxo-1,3-pyrrolidinediacetamide, 7i) [S-(R*,R*)]-3-[3-(biphen-4-yl)propyl]-α¹-cyclohexyl-N¹-cyclopropyl-N³-hydroxy-2-oxo-1,3-pyrrolidinediacetamide, 7j) [S-(R*,R*)]-3-[3-(biphen-4-yl)propyl]-α¹-cyclohexyl-N³-hydroxy-2-oxo-N¹-phenyl-1,3-pyrrolidinediacetamide, 7k) [S-(R*,R*)]-3-[3-(biphen-4-yl)propyl]-α¹-cyclohexyl-N¹-(4-fluorophenyl)-N³-hydroxy-2-oxo-1,3-pyrrolidinediacetamide, 7l) [S-(R*,R*)]-3-[3-(biphen-4-yl)propyl]-α¹-cyclohexyl-N³-hydroxy-2-oxo-N¹-(4-pyridinyl)-1,3-pyrrolidinediacetamide, 7m) [S-(R*,R*)]-3-[3-(4'-fluorobiphen-4-yl)propyl]-N³-hydroxy-N¹-methyl-α¹-(1-methylethyl)-2-oxo-1,3-pyrrolidinediacetamide, 7n) [S-(R*,R*)]-3-[3-(4'-fluorobiphen-4-yl)propyl]-N¹-cyclopropyl-N³-hydroxy-α¹-(1-methylethyl)-2-oxo-1,3-pyrrolidinediacetamide, 7o) [S-(R*,R*)]-3-[3-(4'-fluorobiphen-4-yl)propyl]-N³-hydroxy-α¹-(1-methylethyl)-2-oxo-N¹-phenyl-1,3-pyrrolidinediacetamide, 7p) [S-(R*,R*)]-3-[3-(4'-fluorobiphen-4-yl)propyl]-N¹-(4-fluorophenyl)-N³-hydroxy-α¹-(1-methylethyl)-2-oxo-1,3-pyrrolidinediacetamide, 7q) [S-(R*,R*)]-3-[3-(4'-fluorobiphen-4-yl)propyl]-N³-hydroxy-α¹-(1-methylethyl)-2-oxo-N¹-(4-pyridinyl)-1,3-pyrrolidinediacetamide, 7r) [S-(R*,R*)]-α¹-tert-butyl-3-[3-(4'-fluorobiphen-4-yl)propyl]-N³-hydroxy-N¹-methyl-2-oxo-1,3-pyrrolidinediacetamide, 7s) [S-(R*,R*)]-α¹-tert-butyl-N¹-cyclopropyl-3-[3-(4'-fluorobiphen-4-yl)propyl]-N³-hydroxy-2-oxo-1,3-pyrrolidinediacetamide, 7t) [S-(R*,R*)]-α¹-tert-butyl-3-[3-(4-fluorobiphen-4-yl)propyl]-N³-hydroxy-2-oxo-N¹-phenyl-1,3-pyrrolidinediacetamide, 7u) [S-(R*,R*)]-α¹-tert-butyl-3-[3-(4'-fluorobiphen-4-yl)propyl]-N¹-(4-fluorophenyl)-N³-hydroxy-2-oxo-1,3-pyrrolidinediacetamide, 7v) [S-(R*,R*)]-α¹-tert-butyl-3-[3-(4'-fluorobiphen-4-yl)propyl]-N³-hydroxy-2-oxo-N¹-(4-pyridinyl)-1,3-pyrrolidinediacetamide, 7w) [S-(R*,R*)]-α¹-cyclohexyl-3-[3-(4'-fluorobiphen-4-yl)propyl]-N³-hydroxy-N¹-methyl-2-oxo-1,3-pyrrolidinediacetamide, 7x) [S-(R*,R*)]-α¹-cyclohexyl-N¹-cyclopropyl-3-[3-(4'-fluorobiphen-4-yl)propyl]-N³-hydroxy-2-oxo-1,3-pyrrolidinediacetamide, 7y) [S-(R*,R*)]-α¹-cyclohexyl-3-[3-(4'-fluorobiphen-4-yl)propyl]-N³-hydroxy-2-oxo-N¹-phenyl-1,3-pyrrolidinediacetamide, 7z) [S-(R*,R*)]-α¹-cyclohexyl-3-[3-(4'-fluorobiphen-4-yl)propyl]-N¹-(4-fluorophenyl)-N³-hydroxy-2-oxo-1,3-pyrrolidinediacetamide, 8a) [S-(R*,R*)]-α¹-cyclohexyl-3-[3-(4'-fluorobiphen-4-yl)propyl]-N³-hydroxy-2-oxo-N¹-(4-pyridinyl)-1,3-pyrrolidinediacetamide, 8b) Preparation of [S-(R*,R*)]-3-heptyl-N³-hydroxy-N¹-methyl-α¹-(1-methylethyl)-2-oxo-1,3-pyrrolidinediacetamide, 8c) Preparation of [S-(R*,R*)]-N¹-cyclopropyl-3-heptyl-N³-hydroxy-α¹-(1-methylethyl)-2-oxo-1,3-pyrrolidinediacetmide, 8d) Preparation of [S-(R*,R*)]-3-heptyl-N³-hydroxy-α¹-(1-methylethyl)-2-oxo-N¹-phenyl-1,3-pyrrolidinediacetamide, 8e) Preparation of [S-(R*,R*)]-3-heptyl-N¹-(4-fluorophenyl)-N³-hydroxy-α¹-(1-methylethyl)-2-oxo-1,3-pyrrolidinediacetamide, 8f) Preparation of [S-(R*,R*)]-3-heptyl-N³-hydroxy-α¹-(1-methylethyl)-2-oxo-N¹-(4-pyridinyl)-1,3-pyrrolidinediacetamide, 8g) Preparation of [S-(R*,R*)]-α¹-tert-butyl-3-heptyl-N³-hydroxy-N¹-methyl-2-oxo-1,3-pyrrolidinediacetamide, 8h) Preparation of [S-(R*,R*)]-α¹-tert-butyl-N¹-cyclopropyl-3-heptyl-N³-hydroxy-2-oxo-1,3-pyrrolidinediacetamide, 8i) Preparation of [S-(R*,R*)]-α¹-tert-butyl-3-heptyl-N³-hydroxy-2-oxo-N¹-phenyl-1,3-pyrrolidinediacetamide, 8j) Preparation of [S-(R*,R*)]-α¹-tert-butyl-N¹-(4-fluorophenyl)-3-heptyl-N³-hydroxy-2-oxo-1,3-pyrrolidinediacetamide, 8k) Preparation of [S-(R*,R*)]-α¹-tert-butyl-3-heptyl-N³-hydroxy-2-oxo-N¹-(4-pyridinyl)-1,3-pyrrolidinediacetamide, 8l) Preparation of [S-(R*,R*)]-α¹-cyclohexyl-3-heptyl-N³-hydroxy-N¹-methyl-2-oxo-1,3-pyrrolidinediacetamide, 8m) Preparation of [S-(R*,R*)]-α¹-cyclohexyl-N¹-cyclopropyl-3-heptyl-N³-hydroxy-2-oxo-1,3-pyrrolidinediacetamide, 8n) Preparation of [S-(R*,R*)]-α¹-cyclohexyl-3-heptyl-N³-hydroxy-2-oxo-N¹-phenyl-1,3-pyrrolidinediacetamide, 8o) Preparation of [S-(R*,R*)]-α¹-cyclohexyl-3-heptyl-N¹-(4-fluorophenyl)-N³-hydroxy-2-oxo-1,3-pyrrolidinediacetamide, and 8p) Preparation of [S-(R*,R*)]-α¹-cyclohexyl-3-heptyl-N³-hydroxy-2-oxo-N¹-(4-pyridinyl)-1,3-pyrrolidinediacetamide.

The compounds represented by the general formula I can be prepared by the methods of reaction in Schemes A–D.

As shown in Scheme A-1, structure 2 is readily prepared from structure 1 (commercially available) according to the procedures described in J. Am. Chem. Soc. Vol. 75, 3679 (1953). Alkylation of structure 2 requires an alkyl group ($R_1$) attached to an appropriate leaving group. The alkylation occurs in the presence of a suitable base such as lithium diisopropylamide (LDA) at a suitable temperature in the range –78° C. to 5° C. to provide structure 3. The ester side chain of structure 4 is introduced by alkylation of 3 with an alkyl ($R'=C_{1-6}$ alkyl) bromoacetate in the presence of a suitable base such as LDA in a suitable solvent such as tetrahydrofuran (THF), at a suitable temperature in the range –78° C. to 0° C. Hydrolysis of structure 4 by the procedures well known to one of ordinary skill in the art affords structure 5, which is then converted to the hydroxamate 6 by reaction of structure 5 with hydroxylamine hydrochloride and 1-(3-dimethylaminopropyl)-3-ethylcarbodiimide hydrochloride (EDC) as an acid activating agent at a suitable temperature in the range −20° C. to 20° C. The reaction occurs in the presence of a catalyst such as 1-hydroxybenzotriazole hydrate (HOBT) and an appropriate acid scavenger such as N-methylmorpholine in a suitable solvent such as DMF, CH$_2$Cl$_2$ or a mixture thereof. Alternatively, alkylation of structure 4 with a halide compound I-R$_2$ (I is halogen, R$_2$ is defined as above) by procedures well known to one of ordinary skill in the art affords structure 7. For example, alkylation of 4 with allyl bromide introduces an allyl group on the α-position of side chain using a suitable base such as LDA in a suitable solvent such as THF at a suitable temperature in the range −78° C. to 25° C. The resultant allyl intermediate is then converted to the corresponding alcohol by ozonelysis and reduction NaBH$_4$ or by hydroboration with 9-BBN. In many cases the alcohols are converted to a phthalimide via the Mitsunobu protocol. Alternatively, the alcohol can be converted to a leaving group (such as Ms, Ts) which is subsequently displaced with the desired nucleophile such as SR, NR$_2$, OR, etc. The remaining synthetic steps which leads structure 7 to structure 9 is similar to that described above.

A slightly different approach is employed to prepare 16 as shown in Scheme A-2, which incorporates a terminal amide R$_4$ (R$_4$ is as defined above, except R$_4$ is not hydrogen). Alkylation of commercially available 10 affords lactam 11 according to the procedures described in Fisher, M. J. and Overman, L. E., J. Org. Chem., Vol. 55, pp 1447–1459 (1990). Lactam 11 is reacted with allyl bromide to provide 12. The yields for this reaction are generally quite high. Alkylation of 12 with ethyl bromoacetate provides ester 13. Structure 13 is then converted to the corresponding amide 14, which followed by oxidation with ruthenium tetroxide in a solvent mixture such as carbontetrachloride, water, and acetonitrile at room temperature affords pyrrolidineacetic acid 15. The step which leads from structure 15 to structure 16 is similar to that described above in Scheme A-1.

Scheme A-3 illustrates another method for preparing the compounds of formula I. As shown in Scheme A-3, reaction of structure 10 with di-tert-butyl dicarbonante in the presence of DMAP provided protected lactam 17. Alkylation of 17 with alkyl or alkenyl halides in the presence of HMPA provides lactam 18. The ester side chain of structure 19 is introduced by alkylation of 18 with alkyl bromoacetate as described in Scheme A-1. Structure 19 can then be deprotected using magnesium methoxide in a suitable solvent according the procedure described in Tetrahedron Lett. Vol. 35, p 847 (1994) to provide structure 20. Alteratively, alkylation of 19 with a halide compound I-R$_2$ by procedures well known to one of ordinary skill in the art affords structure 21. Deprotection of structure 21 affords structure 22. The R substituent can be introduced directly by N-alkylation of 20 or 22 with a desired halide compound using a suitable base such as sodium hydride in a suitable solvent such as THF or DMF to provide structures 4 or 7, respectively.

If desired, lactam 20 and 22 can be resolved using chiral HPLC or chemical methods to provide the corresponding enantiomers as illustrated in Examples 2 and 28. Each antipode can be converted to the appropriate chiral analogs 20a and 22a as shown in Scheme A-4. Lactam 20 and 22, either as the racemate or a single enantiomer, are used in the alkylation steps as described in Schemes A-3 and A-4. As shown in scheme A-4, the alkylation of lactam 20a or 22a with the triflate 23 affords 24 and 28, respectively. For simplicity, only a single antipode of 20a or 22a and triflate 23 are presented. This chemistry can be carried out for both the racemate or a single enantiomer. Triflate 23 can be prepared following the procedure described in J. Org. Chem. Vol. 58, pp 2725–2737 (1993). A preferred approach to provide 24 involves depretonation of 20a with a suitable base such as sodium hydride in a suitable solvent such as THF at a temperature in the range −20° C. to 15° C., followed by the addition of triflate 25. Warming to ambient temperature affords desired structure 24. If racemate 20 is utilized the diastereomers can be separated at this stage by silica gel chromatography or HPLC. Hydrolysis of the methyl ester 24 with aqueous NaOH provide 25, which following the formation of an amide by the procedure outlined in Scheme A-3, affords 26. The remaining synthetic steps which lead from structure 26 to structure 27 are similar to that described in Scheme A-1. In a similar fashion, the compounds represented by structure 31 are prepared.

Alternatively, an enantiospecific method can by employed to prepare a single antipode as shown in Scheme A-5. Alkylation of commercially available compound 32 requires an alkyl or allyl (R$_1$) attached to a leaving group in the presence of a suitable base such as lithium diisopropylamide (LDA) provides structure 33 as a mixture of diastereoisomers at the C-3 position of the ring. The mixture is alkylated with allyl bromide to provide 34 in optically pure form as shown in A-5. The trityl group is removed with TFA to provide 35, which is converted to lactol 36 following the protocol described in J. Chem. Soc. C.C. pp 1119–1122 (1989). The key cyclization step is effected quite simply by reaction of the lactol 36 with an amine 37 in the presence of sodium cyanoborohydride followed by heating the crude uncyclized intermediate at reflux in toluene to provide 38 as a single isomer. Amine 37 can be prepared through the conversion of a commercial available L-, or D-amino acid to the corresponding amine by procedures well known to one of ordinary skill in the art. Following the chemistry outlined in Schemes A-2, the olefin is oxidized with ruthenium tetroxide to provide 39, which is coupled with O-benzylhydroxylamine hydrochloride (CDI, THF) and then deprotected by hydrogenation with palladium on carbon to provide 41.

A series of other ring system are synthesized as shown in Schemes B–E. Scheme B illustrates a method for preparing 2,5-dioxo pyrrolidines. Exhaustive ruthenium tetroxide oxydation of 4 in the presence of sodium periodate in the suitable solvent such as water/acetonitrile/carbontetrachloride at an ambient temperature provides 42. In a similar fashion as described in Scheme A-1, hydroxamate 43 is prepared.

Two different synthetic routes are developed for the synthesis of the hydantoin analogs as shown in Schemes C-1 and C-2. In Scheme C-1, N-alkylation of 1-methylhydantoin 44 with 2-bromoethylbenzene occurs in the presence of a suitable base such as sodium hydride, in a suitable solvent such as DMF, at the temperature in the range −20° C. to 15° C. Following C-alkylation with a halide compound in the presence of a suitable base such as LDA at the temperature in the range −78° C. to 15° C. affords 46. Formation of the quaternary center through C-alkylation with an alkyl bromoacetate in the presence of a suitable base such as LDA at the temperature in the range −78° C. to 15° C. affords 47. Conversion of 47 to the hydroxamate 48 is conducted following the previously outlined procedures. An alternative approach is developed for the synthesis of the unsubstituted (1-H) hydantoin analog of 48. Amino acid 49 can be prepared according to the procedures described in Dellaria, J. F., J. ORG. Chem. Vol. 53, p 5607 (1988). Following the general procedure of Van der Veen, J. M. at el. J. C. S. Perkin II pp 653–658 (1979), amino acid 49 is reacted with an appropriate substituted isocyanate followed by cyclization under acidic conditions to provide hydantoin 50. The remaining synthetic steps which lead to structure 52 are similar to that described previously.

Scheme D illustrates an approach into a pyrazolidinone ring system. Protection of pyrrazolidinone 53 by the procedures described in Perri, S. T. at el., J. Org. Chem., Vol. 55, pp 6037–6047 (1990) provides 54. Following N-alkylation and C-alkylations as outlined previously, lead to structure 57. An atmosphere of hydrogen is placed over a mixture of 57 and Pearlman's catalyst in a suitable solvent such as MeOH at ambient temperature to afford the desired compound 58.

The pharmaceutical compositions of this invention may be prepared by combining the compounds of formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I according to this invention.

The quantity of active component, that is the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating a patient, suffering from or susceptible to a diseases involving connective tissue degradation, or inhibiting various enzymes from the matrix metallopreteinase family, including collagenase, stromelysin, and gelatinase, the compounds or pharmaceutical compositions thereof will be administered orally, parenterally and/or topically at a dosage to obtain and maintain a concentration, that is, an amount, or blood-level of active component in the patient undergoing treatment which will be effective to inhibit such enzymes. Generally, an effective amount of the active compound will be in the range of about 0.1 to about 100 mg/kg. It is to be understood that the dosages may vary depending upon the requirements of the patient, the severity of connective tissue degradation being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of the present invention inhibit various enzymes from the matrix metalloproteinase family, including collagenase, stromelysin, and gelatinase, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation. Such diseases and conditions are well known and readily diagnosed by physician of ordinary skill.

These compounds may also inhibit the release of cytokines including tumor necrosis factor (TNFa) and hence may also be useful in inflammation, fever, acute infections and shock. In general, the preferred form of administration is orally.

Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as, for example, water-for-injection and a suitably buffered isotonic solution having a pH of about 3.5–6. Suitable buffering agents include, for example, trisodium orthophosphate, sodium bicarbonate, sodium citrate, N-methylglucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned inhibitory effective amount of dosage. The compounds of formula I according to this invention are advantageously administered orally in solid and liquid dosage forms.

Inhibitory activity is evaluated in one or more of the MMP enzymes (stromelysin, gelatinase, and collagenase) in vitro using a particle concentration fluorescence techniques. An inhibitor binds to MMP enzymes prevents the degradation of a substrate of stromelysin, gelatinase, or collagenase. The substrate is attached with a fluorescein and a biotin. The intact substrate then binds to an avidin-coated particle via the biotin moiety. Once the particle is washed and dried, a fluorescent signal is generated since the fluorescent group is attached to the particle. Without an inhibitor present, the substrate is degraded by MMP enzymes and the fluorescein group is removed, therefore, no fluorescent signal can be detected. Testing compounds are dissolved in DMSO to the desired concentration, then the solutions are diluted to 1:5 with MMP buffer (50 mM Tris-HCl, pH 7.5; 150 mM NaCl; 0.02% $NAN_3$). Serial two-fold dilutions of each compound are prepared. A concentrated, activated enzyme solution is transferred into each plate of the testing compounds, and the mixture is incubated at room temperature for 15 minutes. Thawed MMP substrate is then added into all plates, and the plates are incubate in the dark for 1–3 hours at room temperature. At this point, the substrate mixture is reacted with 0.1% avidin-coated polystyrene particles. After 15 minutes, the inhibitory activities are evaluated by Ki assay. Inhibitory data for the compounds of this invention are shown in TABLE 1. Compounds with lower Ki value are expected to be more effective as MMP inhibitors. It is expected that a compound with a Ki less than 15 µM against any one of the MMP's will display therapeutic effects in connective tissue disorders.

TABLE 1

MMP Inhibition Constants (Ki, µM) for Hydroxamic Acid Derivatives

| Example No. | Stromelysin Ki (µM) | Gelatinase Ki (µM) | Collagenase Ki (µM) |
|---|---|---|---|
| Example 1 | 27.2 | 3.55 | 2.3 |
| Example 2 | 20.2 | 3.29 | 1.04 |
| Example 3 | 10.86 | 11.68 | 4.23 |
| Example 4 | 0.275 | 0.204 | 5.7 |
| Example 5 | 0.041 | 0.115 | 4.37 |
| Example 6 | 0.491 | 0.082 | — |
| Example 7 | 1.27 | 1.42 | — |
| Example 8 | 1.14 | 0.734 | — |
| Example 9 | 0.903 | 0.78 | 14.3 |
| Example 10 | 6.04 | — | — |
| Example 11 | 1.02 | 0.498 | 0.073 |
| Example 12 | 0.12 | 0.312 | — |
| Example 13 | 0.334 | 0.28 | — |
| Example 14 | 0.046 | 0.097 | 0.533 |
| Example 15 | 0.188 | 0.782 | 21.3 |
| Example 16 | 0.0924 | 2.87 | 14.2 |
| Example 17 | 2.22 | 4.09 | — |
| Example 18 | 1.47 | 3.04 | — |
| Example 19 | 2.77 | 2.47 | — |
| Example 20 | 16.6 | 3.103 | 0.579 |
| Example 21 | 2.08 | 0.049 | 0.022 |
| Example 22 | 1.96 | 1.3 | 2.07 |
| Example 23 | 4.19 | 1.56 | 0.453 |
| Example 24 | 7 | — | — |
| Example 25 | 0.649 | 1.28 | 1.9 |
| Example 26 | 0.713 | 0.998 | — |
| Example 27 | 11 | 16.5 | — |
| Example 29 | 0.57 | 0.981 | 0.484 |
| Example 30 | 1.05 | 0.024 | 0.016 |
| Example 31 | 0.517 | 0.0193 | 0.096 |
| Example 32 | 0.73 | 0.05 | 0.036 |
| Example 33 | — | — | 0.031 |
| Example 34 | 4.14 | 0.031 | 0.022 |
| Example 35 | 3.12 | — | — |
| Example 36 | 2.4 | 44 | — |
| Example 37 | 4.74 | — | — |
| Example 38 | 31.2 | 14.5 | 13.3 |
| Example 39 | 0.101 | 0.0759 | 0.00581 |
| Example 40 | 1.99 | 0.0105 | 0.037 |
| Example 41 | 0.014 | 0.0023 | 0.0028 |
| Example 42 | 0.0255 | 0.0054 | 0.00244 |
| Example 43 | 1.8 | 0.0023 | 0.00236 |
| Example 44 | 4 | 0.011 | 0.0202 |
| Example 45 | 1.01 | 0.017 | 0.0235 |
| Example 46 | 2.1 | 0.04 | 0.035 |
| Example 47 | 0.868 | 0.0853 | 0.0815 |
| Example 48 | 0.385 | 0.16 | 0.072 |
| Example 49 | 0.138 | 0.061 | 0.085 |
| Example 50 | 0.283 | 0.017 | 0.00606 |
| Example 51 | 0.084 | 0.023 | 0.0422 |
| Example 52 | 0.187 | 0.0011 | 0.0013 |
| Example 53 | 0.0105 | 0.00106 | 0.00069 |
| Example 54 | 0.7 | 0.07 | 0.076 |
| Example 55 | 1.9 | 0.211 | 0.75 |
| Example 56 | 2.3 | 0.34 | 0.925 |
| Example 57 | 0.075 | 0.0095 | 0.012 |
| Example 58 | 0.023 | 0.0029 | — |
| Example 59 | 0.23 | 0.011 | 0.0033 |
| Example 60 | 0.019 | 0.0123 | 0.018 |
| Example 62 | 0.369 | 0.31 | 55 |
| Example 63 | 0.058 | 0.032 | 1.5 |
| Example 64 | 0.107 | 0.049 | 0.735 |
| Example 65 | 1.05 | 0.227 | 0.51 |
| Example 66 | 0.39 | 0.75 | 4.7 |
| Example 67 | 0.216 | 0.036 | 5 |
| Example 68 | 0.35 | 0.16 | 1.46 |
| Example 69 | 0.214 | 0.498 | 1.2 |
| Example 70 | 0.194 | 0.0522 | 1.2 |
| Example 71 | — | — | 0.098 |
| Example 72 | 0.64 | 0.083 | 0.039 |
| Example 74 | 0.052 | 0.021 | 0.026 |
| Example 75 | 0.295 | 0.264 | 0.074 |
| Example 76 | 10.8 | 3.3 | 0.298 |
| Example 77 | 0.146 | 0.0319 | 0.0685 |
| Example 78 | 0.696 | 0.278 | 0.018 |
| Example 79 | 0.038 | 0.00177 | 0.339 |
| Example 81 | 0.273 | 1.4 | 5.6 |
| Example 82 | 0.379 | 0.878 | 2.4 |
| Example 83 | 0.107 | 0.58 | 17 |
| Example 84 | 1.73 | 3 | 0.385 |
| Example 85 | 0.116 | 0.031 | 0.084 |
| Example 86 | 0.102 | 0.046 | 0.647 |
| Example 87 | 0.091 | 0.00488 | 0.23 |
| Example 88 | 0.288 | 0.062 | 0.326 |
| Example 89 | 0.318 | 0.146 | 2.5 |
| Example 90 | 1.77 | 0.624 | 0.052 |
| Example 92 | 0.309 | 0.273 | 0.37 |
| Example 93 | 2.08 | 1.1 | 0.098 |
| Example 94 | 0.016 | 0.0012 | 0.0134 |
| Example 95 | 0.119 | 0.013 | 0.025 |
| Example 96 | 0.0087 | 0.00098 | 0.0127 |

In order to more fully illustrate the nature of the invention and the manner of practicing the same, the following experimental examples are presented, but they should not be taken as limiting.

EXAMPLE 1

Preparation of N-Hydroxy-3-(2-methylpropyl)-2-oxo-1-(2-phenylethyl)-3-pyrrolidineacetamide

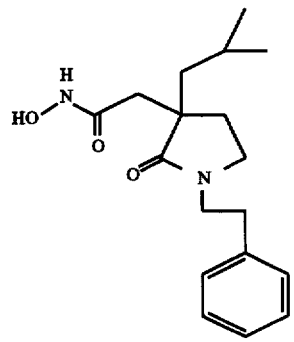

Step 1.

Preparation of 1-(2-Phenylethyl)-2-pyrrolidinone

Following the procedure of Boekelheide and Godfrey (J. Am. Chem. Soc. 1953, 75, 3679), γ-butyrolactene (50.0 mL, 650 mmol) and phenethylamine (85.0 mL, 677 mmol) are heated in a sealed reaction vessel from room temperature to 200° C. over 2.5 hours, at 280°–300° C. for 2 hours, and is allowed to cool to room temperature. The reaction mixture is distilled (1.5 mm, 130°–144° C.) to yield 107 g of the title compound which solidified upon standing (mp 50.5°–52.5° C.).

IR (mineral oil) 3334, 3079, 3022, 1671, 1634, 1498, 1493, 1433, 1425, 1328, 1280, 1248, 1156, 759, 707 cm$^{-1}$;

$^1$H NMR (300 MHz, CDCl$_3$) δ 7.10–7.35, 3.53, 3.25, 2.84, 2.35, 1.8–2.0;

MS (EI) m/z 189, 104, 98, 70.

Step 2.

Preparation of 3-(2-Methylpropyl)-1-(2-phenylethyl)-2-pyrrolidinone

A solution of 1-(2-phenylethyl)-2-pyrrolidinone (500 mg, 2.64 mmol) and THF (6 mL) is cooled to –78° C. Some precipitation occurred and 2 mL of THF is added. A solution of lithium diisopropylamide (LDA, 1.4 mL, 2.8 mmol, 2.0M in heptane/THF/ethylbenzene) is added and the mixture stirred at −78° C. for 40 minutes, giving a dark brown solution. To this solution is added 1-iodo-2-methylpropane (0.37 mL, 3.2 mmol). The solution is allowed to warm from −78° C. to 5° C. over 2.5 hours. After quenching with saturated aqueous ammonium chloride, aqueous workup (EtOAc, MgSO$_4$) and purification by column chromatography (20% EtOAc/hexane) to give 642 mg (99%) of the title compound as a white solid (mp 69°–71° C.).

IR (mineral oil) 3032, 3002, 1665, 1632, 1499, 1441, 1425, 1303, 1271, 1168, 772, 745, 704, 619 cm$^{-1}$;

$^1$H NMR (300 MHz, CDCl$_3$) δ 7.15–7.40, 3.40–3.65, 3.10–3.20, 2.84, 2.35–2.45, 2.05–2.2, 1.45–1.80, 1.10–1.25, 0.93, 0.89;

MS (EI) m/z 245, 189, 154, 126, 98, 54.

Step 3.

Preparation of tert-Butyl 3-(2-Methylpropyl)-2-oxo-1-(2-phenylethyl)-3-pyrrolidineacetate LDA (2.0M, 11.5 mL, 23.0 mmol) is added to a solution of 3-(2-methylpropyl)-1-(2-phenylethyl)-2-pyrrolidinone (4.70 g, 19.2 mmol) and THF (80 mL) at −78° C. The solution is stirred at −78° C. for 45 minutes, and tert-butyl bromoacetate (3.4 mL, 23 mmol) is added. The solution is allowed to warm to 0° C. over 2 hours and is allowed to stir overnight at room temperature. After quenching with saturated aqueous ammonium chloride, aqueous workup (EtOAc, MgSO$_4$) and purification by column chromatography (10% EtOAc/5% CH$_2$Cl$_2$/hexane) to give 4.67 g (68%) of the title compound as a colorless oil. An analytical sample is crystallized from hexane (mp 50° C.).

IR (liq.) 2957, 2930, 2870, 1728, 1688, 1497, 1455, 1444, 1429, 1367, 1347, 1278, 1258, 1156, 701 cm$^{-1}$;

$^1$H NMR (300 MHz, CDCl$_3$) δ 7.15–7.35, 3.6–3.75, 3.35–3.5, 3.15–3.25, 2.85, 2.43, 2.05–2.2, 1.9–2.0, 1.55–1.7, 1.35–1.5, 1.42, 0.88, 0.86;

MS (EI) m/z 359, 303, 286, 268, 247, 212, 184, 166, 156, 138, 105.

Step 4.

Preparation of 3-(2-Methylpropyl)-2-oxo-1-(2-phenylethyl)-3-pyrrolidineacetic Acid A solution of tert-butyl 3-(2-methylpropyl)-2-oxo-1-(2-phenylethyl)-3-pyrrolidineacetate (659 mg, 1.83 mmol), trifluoroacetic acid (6.5 mL) and CH$_2$Cl$_2$ (6.5 mL) is stirred at room temperature for 1 hour. The solution is concentrated from CH$_2$Cl$_2$ (3×50 mL), dissolved in 1N NaOH (10 ml), and the basic layer is extracted with Et$_2$O (2×25 mL). The pH of the basic layer is adjusted to pH 1 with 6N HCl. The acidic layer is extracted with CH$_2$Cl$_2$ (2×25 mL), the combined CH$_2$Cl$_2$ layers dried (MgSO$_4$), filtered and concentrated to give 511 mg (92%) of the title compound as a colorless oil.

IR (mineral oil) 3065, 3029, 1738, 1647, 1497, 1440, 1304, 1213, 1183, 1171, 1152, 1112, 756, 733, 701 cm$^{-1}$;

$^1$H NMR (300 MHz, CDCl$_3$) δ 7.10–7.35, 3.50–3.70, 3.15–3.35, 2.89, 2.55, 2.05–2.15, 1.60–1.85, 1.57, 1.36, 0.91, 0.87;

MS (EI) m/z 303, 247, 213, 212, 184, 166, 156, 138, 105, 104.

Step 5.

Preparation of N-Hydroxy-3-(2-methylpropyl)-2-oxo-1-(2-phenylethyl)-3-pyrrolidineacetamide Solid 1-(3-dimethylaminopropyl)-3-ethylcarbodiimide hydrochloride (EDC, 451 mg, 2.35 mmol) is added to a solution of 3-(2-methylpropyl)-2-oxo-1-(2-phenylethyl)-3-pyrrolidineacetic acid (595 mg, 1.96 mmol), 1-hydroxybenzotriazole hydrate (HOBT, 281 mg, 2.08 mmol) and 4-methylmorpholine (0.26 mL, 2.4 mmol) in CH$_2$Cl$_2$ (19 mL) and DMF (4 mL) at 0° C. The solution is stirred at 0° C. for 1 hour, and then a near solution of hydroxylamine hydrochloride (204 mg, 2.94 mmol) and 4-methylmorpholine (0.32 mL, 2.9 mmol) in DMF (2.7 mL) is added. After stirring at room temperature overnight, the mixture is concentrated under high vacuum, and purified by column chromatography (3% MeOH/CH$_2$Cl$_2$). Crystallization from Et$_2$O/hexane provided 193 mg (31%) of the title compound as a white solid (mp 123°–124° C.).

IR (mineral oil) 3205, 3071, 3026, 1664, 1638, 1496, 1353, 1316, 1296, 1283, 1271, 1078, 982, 751, 705 cm$^{-1}$;

$^1$H NMR (300 MHz, CDCl$_3$) δ 7.15–7.35, 3.55, 3.10–3.30, 2.84, 2.39, 1.85–2.20, 1.55–1.75, 1.50, 1.32, 0.88, 0.85;

MS (EI) m/z 318, 227, 211, 193, 182, 166, 154, 138, 110, 105.

EXAMPLE 2

Preparation of (3S)-N-Hydroxy-3-(2-methylpropyl)-2-oxo-1-(2-phenylethyl)-3-pyrrolidineacetamide

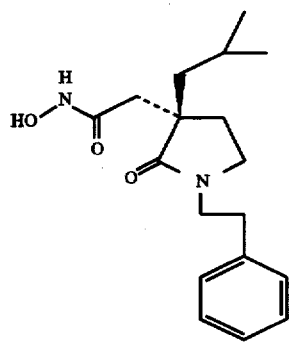

Resolution of tert-butyl 3-(2-methylpropyl)-2-oxo-1-(2-phenylethyl)-3-pyrrolidineacetate. A solution of 50 mg/mL of racemic tert-butyl 3-(2-methylpropyl)-2-oxo-1-(2-phenylethyl)-3-pyrrolidineacetate (EXAMPLE 1, step 3) is made in the mobile phase that consisted of 10% isopropanol in hexane (V/V). Aliquots of 3.5 mL (175 mg) are injected onto a 2.1×25 cm Chiralpak AD column (Chiral technologies, Inc.). The column is eluted at 10 mL/min and monitored at 220 nm. The two enantiomers are collected using a peak recognition program and fractions are pooled appropriately. Each enantiomer is obtained at >99% ee. Enantiomeric excess is determined on a 0.46×25 cm Chiralpak AD column (Chiral Technologies, Inc.), developed with the same solvent at 0.5 mL/min and the monitor set at 220 nm. The retention times here are 12.2 and 23.0 minutes (α=2.61).

Following the general procedure outlined in EXAMPLE 1 (steps 4–5), and making non-critical variations but starting with (S)-tert-butyl 3-(2-methylpropyl)-2-oxo-1-(2-phenylethyl)-3-pyrrolidineacetate (the faster eluting enantiomer described above), the title compound is obtained.

$^1$H NMR (300 MHz, CDCl$_3$) δ 7.10–7.35, 3.40–3.70, 3.10–3.30, 2.75–2.95, 2.38, 1.15–2.20, 0.75–1.00.

EXAMPLE 3

Preparation of N-Hydroxy-α-methyl-3-(2-methylpropyl)-2-oxo-1-(2-phenylethyl)-3-pyrrolidineacetamide

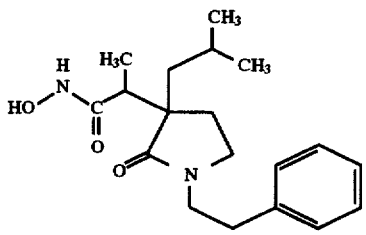

Step 1.

Preparation of tert-Butyl α-Methyl-3-(2-methylpropyl)-2-oxo-1-(2-phenylethyl)-3-pyrrolidineacetate LDA (1.5 mL, 3.0 mmol, 2.0M in heptane/THF/ethylbenzene) is added to a solution of tert-butyl 3-(2-methylpropyl)-2-oxo-1-(2-phenylethyl)-3-pyrrolidineacetate (967 mg, 2.69 mmol) and THF (11.0 mL) at −78° C. The solution is stirred at −78° C. for 30 minutes and then iodomethane (0.19 mL, 3.1 mmol) is added. The solution is stirred at −78° C. for 2 hours and then allowed to slowly warm to room temperature overnight. Aqueous workup (EtOAc, MgSO$_4$) and purification by flash chromatography (1:1 hexane:EtOAc) gives 791 mg (79%) of the title compound as an oil.

IR (liq.) 2975, 2956, 2931, 2869, 1724, 1686, 1497, 1455, 1429, 1367, 1279, 1257, 1153, 1114, 700, cm$^{-1}$;

$^1$H NMR (300 MHz, CDCl$_3$) δ 7.15–7.35, 3.60–3.75, 3.30–3.45, 3.25, 2.82, 2.65, 2.25–2.40, 1.50–1.80, 1.35–1.50, 1.40, 1.12, 0.86, 0.84;

MS (EI) m/z 373, 317, 300, 282, 261, 227, 226, 152, 105, 104, 57.

Step 2.

Preparation of α-Methyl-3-(2-methylpropyl)-2-oxo-1-(2-phenylethyl)-3-pyrrolidineacetic Acid TFA (10.0 mL) is added to a solution of tert-butyl α-methyl-3-(2-methylpropyl)-2-oxo-1-(2-phenylethyl)-3-pyrrolidineacetate (780 mg, 2.09 mmol) and CH$_2$Cl$_2$ (10 mL) at 0° C. The solution is stirred for 2.5 hours at 0° C. and 1.5 hours at room temperature. After concentration, the residue is partitioned between EtOAc and water. The organic layer is extracted several times with 10% NaOH, the combined basic layers acidified (4N HCl), and the acidic layers extracted several times with CH$_2$Cl$_2$. The CH$_2$Cl$_2$ layers are dried (MgSO$_4$), filtered, and concentrated to provide 79 mg (12%) of the title compound as a white solid (mp 94°–95° C.).

IR (mineral oil) 2400, 1731, 1616, 1505, 1497, 1488, 1443, 1354, 1326, 1289, 1266, 745, 736, 702, 607, cm$^{-1}$;

$^1$H NMR (300 MHz, CDCl$_3$) δ 7.15–7.35, 3.65–3.85, 3.45–3.60, 3.20–3.40, 2.90, 2.59, 1.50–2.10, 1.06, 0.89, 0.85;

MS (EI) m/z 317, 261, 227, 226, 216, 180, 152, 105, 104, 55.

Step 3.

Preparation of N-Benzyloxy-α-methyl-3-(2-methylpropyl)-2-oxo-1-(2-phenylethyl)-3-pyrrolidineacetamide CDI (39.7 mg, 0.245 mmol) is added to a solution of α-methyl-3-(2-methylpropyl)-2-oxo-1-(2-phenylethyl)-3-pyrrolidineacetic acid (74.0 mg, 0.233 mmol) and CH$_2$Cl$_2$ (2.0 mL). The solution is stirred for 1 hour at room temperature. To this is added O-benzylhydroxylamine.HCl (63.2 mg, 0.396 mmol) and N-methylmorpholine (44 μL, 0.40 mmol). The resultant solution is stirred for 16 hours at room temperature. Aqueous workup (CH$_2$Cl$_2$, MgSO$_4$) and purification by flash chromatography (2:1 EtOAc:hexane) gives 88.1 mg (89%) of the title compound as an oil.

IR (liq.) 3230, 3063, 3029, 2956, 2936, 2869, 1664, 1497, 1454, 1367, 1310, 1282, 1029, 748, 699 cm$^{-1}$;

$^1$H NMR (300 MHz, CDCl$_3$) δ 10.16, 7.10–7.45, 4.87, 3.35–3.60), 3.10–3.30, 2.81, 2.42, 2.10–2.30, 1.75–1.90, 1.35–1.70, 1.05, 0.85, 0.79;

MS (EI) m/z 422, 300, 225, 196, 152, 105, 104, 91, 77, 69, 55.

Step 4.

Preparation of N-Hydroxy-α-methyl-3-(2-methylpropyl)-2-oxo-1-(2-phenylethyl)-3-pyrrolidineacetamide An atmosphere of hydrogen is placed over a mixture of N-benzyloxy-α-methyl-3-(2-methylpropyl)-2-oxo-1-(2-phenylethyl)-3-pyrrolidineacetamide (80.0 mg, 0.189 mmol), MeOH (4.5 mL) and Pearlman's catalyst (15 mg). The mixture is stirred at room temperature for 4 hours. The mixture is filtered, the solids rinsed with MeOH (4×5 mL), and the filtrate concentrated to give 55.9 mg of an oil. Crystallization from hexane provided 46.9 mg (75%) of the title compound as a white solid (mp 107°–108° C.).

IR (mineral oil) 3227, 3044, 3026, 1658, 1641, 1498, 1436, 1294, 1262, 1031, 774, 735, 713, 695, 611 cm$^{-1}$;

MS (FAB) m/z 333, 332, 301, 300, 272, 105, 69, 55, 41.

EXAMPLE 4

Preparation of α-[2-(1,3-Dihydro-1,3-dioxo-2H-isoindol-2-yl)ethyl]-N-hydroxy-3-(2-methylpropyl)-2-oxo-1-(2-phenylethyl)-3-pyrrolidineacetamide

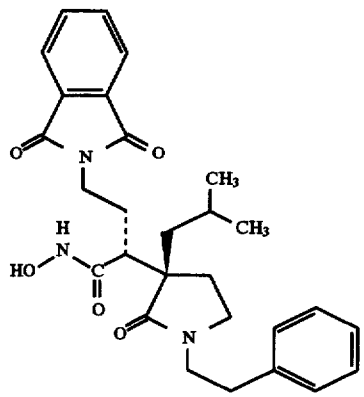

Step 1.

Preparation of tert-Butyl 3-(2-Methylpropyl)-2-oxo-1-(2-phenylethyl)-α-(propen-2-yl)-3-pyrrolidineacetate LDA (2.0M, 7.7 mL, 16 mmol) is added to a solution of tert-butyl 3-(2-methylpropyl)-2-oxo-1-(2-phenylethyl)-3-pyrrolidineacetate (EXAMPLE 1, step 3; 4.62 g, 12.9 mmol) and THF (45 mL) at −78° C. The solution is stirred at −78° C. for 45 minutes and allyl bromide (1.3 mL, 16 mmol) is added. The solution is allowed to warm to 0° C. over 2 hours, and is allowed to stir overnight at room temperature. After quenching with saturated aqueous ammonium chloride, aqueous workup (EtOAc, MgSO$_4$) and purification by column chromatography (2:1:17 v/v EtOAc:CH$_2$Cl$_2$:hexane) gives 4.43 g (86%) of the title compound as yellow oil which solidified upon standing (mp 54.5°–56° C.).

IR (mineral oil) 1712, 1686, 1641, 1497, 1432, 1298, 1281, 1270, 1250, 1237, 1205, 1155, 912, 752, 702, cm$^{-1}$;

$^1$H NMR (300 MHz, CDCl$_3$) δ 7.15–7.35, 5.65–5.8, 4.95–5.1, 3.55–3.7, 3.3–3.45, 3.15–3.25, 2.82, 2.53, 2.2–2.5, 1.7–1.85, 1.5–1.65, 1.35–1.45, 1.40, 0.87, 0.83;

MS (EI) m/z 399, 343, 326, 308, 253, 252, 234, 202, 105, 57.

Step 2.

Preparation of tert-Butyl α-(2-Hydroxyethyl)-3-(2-methylpropyl)-2-oxo-1-(2-phenylethyl)-3-pyrrolidineacetate Ozone is bubbled through a solution of tert-butyl 3-(2-methylpropyl)-2-oxo-1-(2-phenylethyl)-α-(propen-2-yl)-3-pyrrolidineacetate (555 mg, 1.39 mmol) and EtOH (12 mL) at −78° C. for 5 minutes. Nitrogen is then bubbled through the solution for 5 minutes. Sodium borohydride (79 mg, 2.1 mmol) is added and the mixture is allowed to warm slowly and to stir at room temperature overnight. The mixture is concentrated to near dryness, and aqueous workup (EtOAc, MgSO$_4$) to give 511 mg (91%) of the title compound as a colorless oil.

IR (liq.) 2957, 2931, 2870, 1720, 1672, 1671, 1497, 1455, 1392, 1367, 1282, 1257, 1152, 1055, 701 cm$^{-1}$;

$^1$H NMR (300 MHz, CDCl$_3$) δ 7.15–7.35, 3.55–3.75, 3.35–3.45, 3.15–3.25, 2.82, 2.61, 2.3–2.45, 1.85–2.0, 1.65–1.8, 1.35–1.60, 1.43, 0.87, 0.83;

MS (EI) m/z 403, 347, 330, 291, 270, 256, 238, 227, 202, 181, 105, 104.

Step 3.

Preparation of tert-Butyl α-[2-(1,3-Dihydro-1,3-dioxo-2H-isoindol-2-yl)ethyl]-3-(2-methylpropyl)-2-oxo-1-(2-phenylethyl)-3-pyrrolidineacetate Diethyl azodicarboxylate (182 uL, 1.16 mmol) is added to a mixture of tert-butyl α-(2-hydroxyethyl)-3-(2-methylpropyl)-2-oxo-1-(2-phenylethyl)-3-pyrrolidineacetate (468 mg, 1.16 mmol), triphenylphosphine (304 mg, 1.16 mmol), phthalimide (171 mg, 1.16 mmol) and THF (10 mL) at room temperature. The mixture is allowed to stir overnight and is concentrated. Purification by column chromatography (2 columns, 5% acetone/CH$_2$Cl$_2$ and 10% EtOAc/hexane) provided 327 mg (51%) of the title compound as a colorless oil.

IR (liq.) 2956, 2932, 1773, 1716, 1685, 1467, 1454, 1438, 1397, 1368, 1299, 1255, 1152, 720, 701 cm$^{-1}$;

$^1$H NMR (300 MHz, CDCl$_3$) δ 7.8–7.9, 7.65–7.75, 7.15–7.35, 3.55–3.8, 3.3–3.4, 3.15–3.25, 2.80, 2.51, 2.3–2.4, 2.0–2.15, 1.8–1.95, 1.6–1.8, 1.35–1.6, 1.46, 0.85, 0.82;

MS (EI) m/z 532, 476, 459, 441, 420, 385, 339, 311, 245, 202, 160, 105.

Step 4.

Preparation of α-[2-(1,3-Dihydro-1,3-dioxo-2H-isoindol-2-yl)ethyl]-3-(2-methylpropyl)-2-oxo-1-(2-phenylethyl)-3-pyrrolidineacetic Acid Trifluoroacetic acid (2.0 mL) is added to a solution of tert-butyl α-[2-(1,3-dihydro-1,3-dioxo-2H-isoindol-2-yl) ethyl]-3-(2-methylpropyl)-2-oxo-1-(2-phenylethyl)-3-pyrrolidineacetate (282 mg, 0.507 mmol) in CH$_2$Cl$_2$ (4.0 mL) at 0° C. The solution is stirred for 1 hour at 0° C. A second portion of trifluoroacetic acid (2.0 mL) is added, and the solution is stirred for 30 minutes at 0° C. and for 30 minutes at room temperature. Concentration and aqueous workup (CH$_2$Cl$_2$, MgSO$_4$) to give 217 mg (90%) of the title compound as a colorless oil.

IR (mineral oil) 1711, 1606, 1509, 1498, 1485, 1445, 1403, 1359, 1295, 1262, 244, 1111, 704 cm$^{-1}$;

$^1$H NMR (300 MHz, CDCl$_3$) δ 7.85–7.9, 7.7–7.8, 7.15, 6.9–7.0, 3.7–3.9, 3.55–3.65, 3.35–3.5, 3.25–3.35, 2.75–2.95, 2.49, 2.0–2.1, 1.80–1.95, 1.65–1.75, 1.5–1.65, 1.2–1.45, 0.91, 0.84;

MS (EI) m/z 476, 420, 385, 339, 311, 272, 258, 202, 160, 105.

Step 5.

Preparation of N-Benzyloxy-α-[2-(1,3-dihydro-1,3-dioxo-2H-isoindol-2-yl)ethyl]-3-(2-methylpropyl)-2-oxo-1-(2-phenylethyl)-3-pyrrolidineacetamide CDI (82 mg, 0.51 mmol) is added to a solution of α-[2-(1,3-dihydro-1,3-dioxo-2H-isoindol-2-yl)ethyl]-3-(2-methylpropyl)-2-oxo-1-(2-phenylethyl)-3-pyrrolidineacetic acid (202 mg, 0.424 mmol) and CH$_2$Cl$_2$ (3.2 mL) at room temperature, and the solution is stirred for 1 hour at room temperature. O-Benzylhydroxylamine hydrochloride (98 mg, 0.614 mmol) and 4-methylmorpholine (84 uL, 0.76 mmol) are added in succession, and the solution is allowed to stir overnight at room temperature. Aqueous workup (CH$_2$Cl$_2$, MgSO$_4$) and purification by column chromatography (2% acetene/CH$_2$Cl$_2$) gives 120 mg (49%) of the title compound as a colorless oil.

IR (mineral oil) 1773, 1715, 1683, 1663, 1662, 1497, 1398, 1340, 1301, 1270, 1038, 1030, 748, 699 cm$^{-1}$;

$^1$H NMR (300 MHz, CDCl$_3$) δ 7.8–7.9, 7.7–7.8, 7.05–7.55, 4.93, 3.55–3.8, 3.48, 3.1–3.2, 2.77, 2.15–2.3, 1.7–1.9, 1.35–1.65, 0.80, 0.73;

MS (FAB) m/z 582, 459, 431, 160, 105, 91.

Step 6.

Preparation of α-[2-(1,3-Dihydro-1,3-dioxo-2H-isoindol-2-yl)ethyl]-N-hydroxy-3-(2-methylpropyl)-2-oxo-1-(2-phenylethyl)-3-pyrrolidineacetamide A mixture of N-benzyloxy-α-[2-(1,3-dihydro-1,3-dioxo-2H-isoindol-2-yl)ethyl]-3-(2-methylpropyl)-2-oxo-1-(2-phenylethyl)-3-pyrrolidineacetamide (58 mg, 0.10 mmol) and 5% Pd/C (20 mg) is stirred for 1.5 hours at room temperature under an atmosphere of hydrogen. Palladium hydroxide on carbon (10 mg) is added and the mixture is stirred under hydrogen at room temperature for 6 hours. The mixture is filtered and the filtrate is concentrated. Purification by column chromatography (5% MeOH/EtOAc) gives 39 mg of an oil which is crystallized from EtOAc/hexane to give 29 mg (59%) of the title compound as a white solid (mp 158°–159° C.).

IR (mineral oil) 3212, 3101, 3087, 3005, 1773, 1711, 1659, 1495, 1444, 1401, 1310, 1292, 1040, 706 cm$^{-1}$;

$^1$H NMR (300 MHz, CDCl$_3$) δ 10.19, 7.8–7.9, 7.7–7.8, 7.05–7.35, 6.9–7.0, 3.3–3.8, 3.19, 2.79, 2.39, 2.1–2.3, 1.75–2.0, 1.35–1.7, 0.83, 0.76;

MS (EI) m/z 491, 459, 435, 419, 400, 375, 355, 327, 262, 261, 245, 202, 160, 105.

EXAMPLE 5

Preparation of (3S)-α-[2-(1,3-Dihydro-1,3-dioxo-2H-isoindol-2-yl)ethyl]-N-hydroxy-3-(2-methylpropyl)-2-oxo-1-(2-phenylethyl)-3-pyrrolidineacetamide

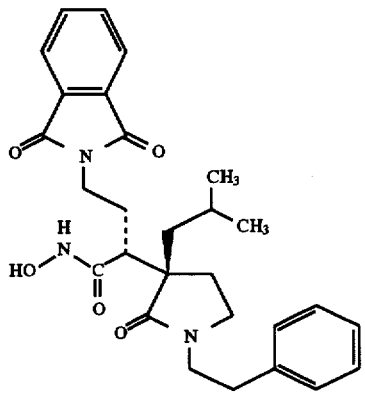

Following the general procedure outlined in EXAMPLE 4, and making non-critical variations but starting with (S)-tert-butyl 3-(2-methylpropyl)-2-oxo-1-(2-phenylethyl)-3-pyrrolidineacetate (EXAMPLE 2, faster eluting enantiomer), the title compound is obtained (mp 102°–105° C.).

IR (mineral oil) 3546, 3172, 3087, 3064, 3024, 1770, 1717, 1665, 1497, 1434, 1407, 1303, 746, 725, 703 cm$^{-1}$;

$^1$H NMR (300 MHz, CDCl$_3$) δ 7.80–7.90, 7.65–7.80, 7.05–7.35, 6.80, 3.25–3.80, 3.10–3.25, 2.79, 2.35–2.45, 2.10–2.30, 1.75–2.00, 1.30–1.75, 0.83, 0.76;

MS (EI) m/z 491, 459, 435, 431, 327, 262, 261, 244, 160, 105.

EXAMPLE 6

Preparation of α-[2-(1,3-Dihydro-1,3-dioxo-2H-naphthoisoindol-2-yl)ethyl]-N-hydroxy-3-(2-methylpropyl)-2-oxo-1-(2-phenylethyl)-3-pyrrolidineacetamide

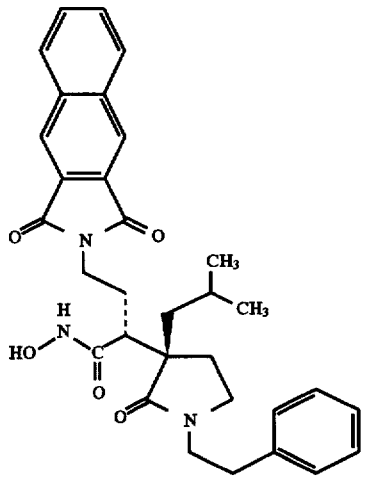

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and 2,3-naphthalenedicarboximide, the title compound is obtained (mp 203°–205° C.).

IR (mineral oil) 3216, 3061, 3028, 1767, 1703, 1662, 1515, 1497, 1437, 1394, 1343, 1131, 769, 765, 616 cm$^{-1}$;

$^1$H NMR (300 MHz, CDCl$_3$) δ 8.31, 7.95–8.10, 7.60–7.75, 6.90–7.35, 3.30–3.90, 3.18, 2.78, 2.35–2.50, 2.15–2.35, 1.75–2.10, 1.35–1.75, 0.82, 0.75;

MS (EI) m/z 541, 485, 262, 261, 245, 210, 202, 180, 154, 105, 56.

EXAMPLE 7

Preparation of N-Hydroxy-3-(2-methylpropyl)-2-oxo-1-(2-phenylethyl)-α-[2-(4,5,6,7-tetrafluoro-1,3-dihydro-1,3-dioxo-2H-isoindol-2-yl)ethyl]-3-pyrrolidineacetamide

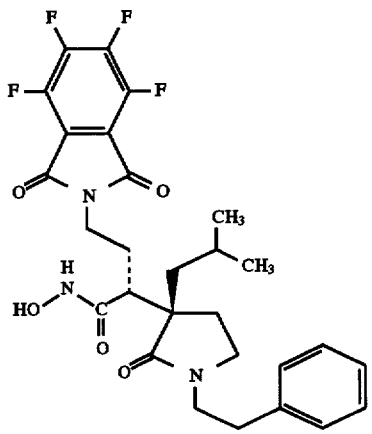

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and tetrafluorophthalimide, the title compound is obtained (mp 172.5°–173.5° C.).

IR (mineral oil) 3216, 1724, 1712, 1664, 1639, 1514, 1503, 1418, 1341, 1301, 1156, 1038, 948, 940, 754 cm$^{-1}$;

$^1$H NMR (300 MHz, CDCl$_3$) δ 8.89, 7.47, 6.95–7.35, 3.35–3.80, 3.10–3.35, 2.79, 2.38, 1.30–2.30, 0.85, 0.80;

MS (EI) m/z 563, 507, 454, 261, 245, 202, 154, 110, 105, 104, 55.

EXAMPLE 8

Preparation of α-[2-(5,6-Dichloro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide

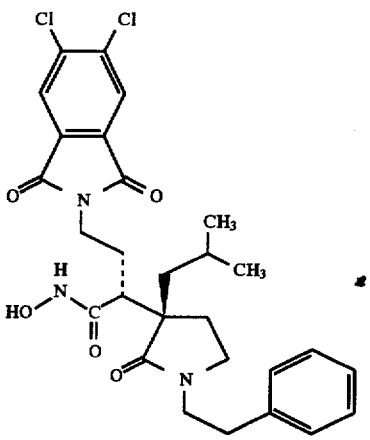

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and 4,5-dichlorophthalimide, the title compound is obtained (mp 207°–208° C.).

IR (mineral oil) 3173, 3070, 1775, 1709, 1667, 1630, 1441, 1434, 1401, 1330, 1278, 1033, 749, 706, 601 cm$^{-1}$;

$^1$H NMR (300 MHz, CDCl$_3$) δ 10.18, 8.91, 7.89, 7.42, 7.00–7.40, 3.35–3.80, 3.05–3.35, 2.78, 2.38, 2.05–2.30, 1.30–2.05, 0.83, 0.78;

MS (EI) m/z 559, 505, 503, 262, 261, 245, 244, 230, 228, 202, 105.

EXAMPLE 9

Preparation of α-[2-(5-Amino-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide

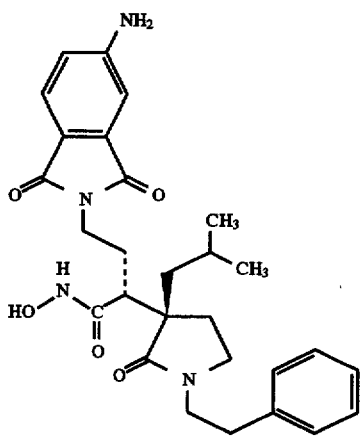

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and 4-aminophthalimide, the title compound is obtained (mp 187°–188° C.).

$^1$H NMR (300 MHz, CDCl$_3$) δ 7.56, 7.10–7.35, 7.01, 6.83, 3.30–3.70, 3.15–3.30, 2.80, 2.35–2.50, 2.15–2.30, 1.70–1.95, 1.20–1.60, 0.83, 0.75.

EXAMPLE 10

Preparation of N-Hydroxy-3-(2-methylpropyl)-α-[2-(4-nitro-1,3-dihydro-1,3-dioxo-2H-isoindol-2-yl)ethyl]-2-oxo-1-(2-phenylethyl)-3-pyrrolidineacetamide

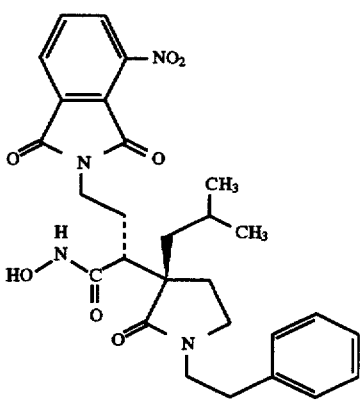

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and 3-nitrophthalimide, the title compound is obtained (mp 136°–138° C.):

IR (mineral oil) 3189, 3096, 3069, 1720, 1695, 1655, 1545, 1496, 1429, 1400, 1347, 1306, 1043, 749, 707 cm$^{-1}$;

$^1$H NMR (300 MHz, CDCl$_3$) δ 8.05–8.15, 7.85–7.95, 7.05–7.35, 3.35–3.85, 3.10–3.25, 2.79, 2.35–2.50, 2.10–2.25, 1.75–2.05, 1.35–1.70, 0.85, 0.79;

MS (FAB) m/z 537, 536, 523, 521, 505, 504, 476, 105, 104.

EXAMPLE 11

Preparation of N-Hydroxy-3-(2-methylpropyl)-α-[2-(5-nitro-1,3-dihydro-1,3-dioxo-2H-isoindol-2-yl)ethyl]-2-oxo-1-(2-phenylethyl)-3-pyrrolidineacetamide

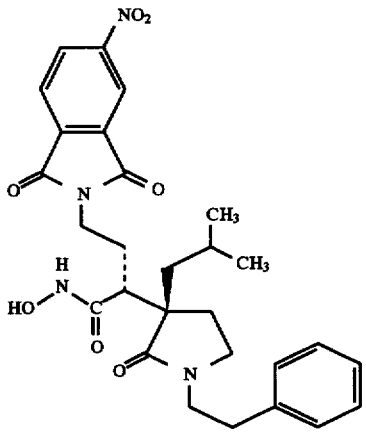

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and 4-nitrophthalimide, the title compound is obtained (mp 161°–162° C.).

IR (mineral oil) 3158, 3106, 3060, 3027, 1707, 1664, 1543, 1496, 1434, 1411, 1344, 1132, 725, 719, 700 cm$^{-1}$;

$^1$H NMR (300 MHz, CDCl$_3$) δ 8.65, 8.59, 8.04, 7.05–7.35, 3.35–3.90, 3.10–3.25, 2.79, 2.35–2.50, 2.10–2.30, 1.75–2.05, 1.35–1.75, 0.84, 0.79;

MS (FAB) m/z 537, 523, 522, 504, 476, 202, 105.

EXAMPLE 12

Preparation of α-[2-(4-Fluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide

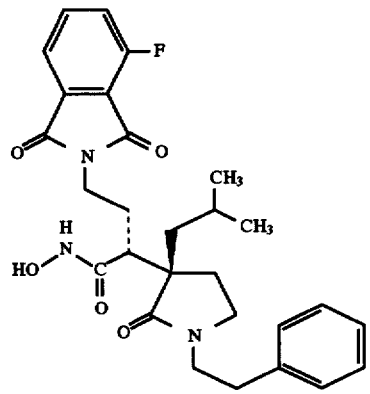

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and 3-fluorophthalimide, the title compound is obtained (mp 145°–146° C.).

IR (mineral oil) 3205, 3065, 3028, 1776, 1717, 1657, 1611, 1497, 1483, 1399, 1349, 1303, 1255, 746, 701 cm$^{-1}$;

$^1$H NMR (300 MHz, CDCl$_3$) δ 7.55–7.80, 7.36, 6.80–7.35, 3.35–3.85, 3.05–3.30, 2.79, 2.30–2.55, 2.05–2.30, 1.70–2.00, 1.35–1.70, 0.83, 0.78;

MS (EI) m/z 509, 477, 453, 449, 345, 262, 261, 178, 105, 104.

EXAMPLE 13

Preparation of α-[2-(4,7-Difluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide

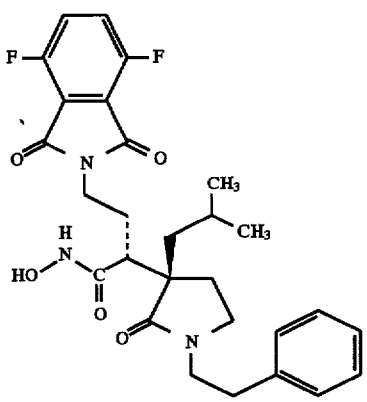

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and 3,6-difluorophthalimide, the title compound is obtained (mp 131°–132° C.).

IR (mineral oil) 3196, 3029, 1779, 1721, 1657, 1495, 1421, 1395, 1359, 1263, 1256, 911, 908, 753, 697 cm$^{-1}$;

$^1$H NMR (300 MHz, CDCl$_3$) δ 7.10–7.45, 6.94, 3.35–3.80, 3.15–3.30, 2.79, 2.30–2.50, 2.00–2.30, 1.75–2.00, 1.35–1.75, 0.85, 0.79;

MS (EI) m/z 527, 495, 471, 467, 363, 262, 261, 202, 196, 105, 104.

EXAMPLE 14

Preparation of α-[2-(5-Fluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide

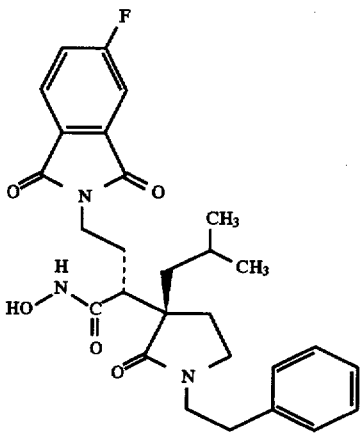

Following the general procedure of EXAMPLE 4 and making non-critical variations but starting with tert-butyl α-(2-hydroxyethyl)-3-(2-methylpropyl)-2-oxo-1-(2-phenylethyl)-3-pyrrolidineacetate and 4-fluorophthalimide, the title compound is obtained (mp 143°–144° C.).

IR (mineral oil) 3218, 3072, 3006, 1775, 1713, 1660, 1612, 1495, 1483, 1400, 1293, 1264, 1040, 747, 707 cm$^{-1}$;

$^1$H NMR (300 MHz, CDCl$_3$) δ 7.83, 7.50, 6.85–7.45, 3.35–3.80, 3.05–3.25, 2.79, 2.30–2.50, 2.05–2.30, 1.75–2.00, 1.30–1.70, 0.83, 0.77;

MS (EI) m/z 509, 477, 453, 449, 345, 262, 261, 178, 105, 104.

EXAMPLE 15

Preparation of α-[2-(1,3-Dihydro-1,3-dioxo-2H-isoindol-2-yl)propyl]-N-hydroxy-3-(2-methylpropyl)-2-oxo-1-(2-phenylethyl)-3-pyrrolidineacetamide

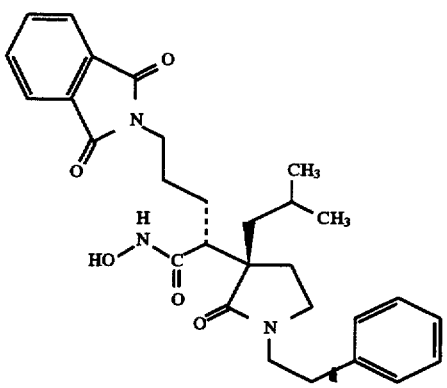

Following the general procedure of EXAMPLE 4 and making non-critical variations but starting with tert-butyl α-(3-hydroxypropyl)-3-(2-methylpropyl)-2-oxo-1-(2-phenylethyl)-3-pyrrolidineacetate (prepared similarly to that described in EXAMPLE 4, step 2) and phthalimide, the title compound is obtained (mp 113°–114° C.).

IR (mineral oil) 3241, 3087, 3058, 3026, 1773, 1715, 1663, 1498, 1399, 1352, 1320, 1298, 1067, 718, 604 cm$^{-1}$;

$^1$H NMR (300 MHz, CDCl$_3$) δ 10.66, 7.75–7.85, 7.60–7.55, 6.95–7.45, 3.35–3.80, 3.10–3.25, 2.80, 2.44, 2.10–2.30, 1.85–2.00, 1.30–1.85, 0.85, 0.79;

MS (EI) m/z 505, 473, 445, 261, 245, 244, 202, 160, 105, 104.

EXAMPLE 16

Preparation of α-[2-(1,3-Dihydro-1,3-dioxo-2H-isoindol-2-yl)methyl]-N-hydroxy-3-(2-methylpropyl)-2-oxo-1-(2-phenylethyl)-3-pyrrolidineacetamide

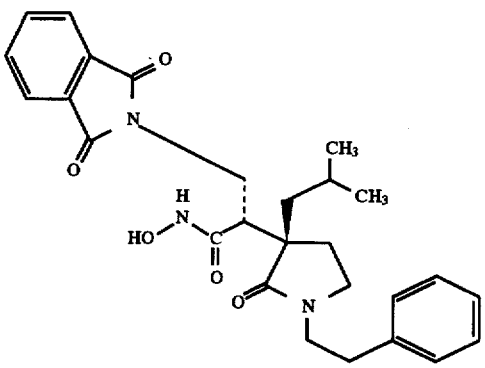

Step 1.

Preparation of tert-Butyl α-[2-(1,3-Dihydro-1,3-dioxo-2H-isoindol-2-yl)methyl]-3-(2-methylpropyl)-2-oxo-1-(2-phenylethyl)-3-pyrrolidineacetate LDA (1.50 mL, 3.0 mmol, 2.0M in heptane/THF/ethylbenzene) is added to a solution of tert-butyl 3-(2-methylpropyl)-2-oxo-1-(2-phenylethyl)-3-pyrrolidineacetate (EXAMPLE 1, step 3; 1.02 g, 2.84 mmol), HMPA (0.51 mL, 2.9 mmol), and THF (10 mL) at −78° C. The solution is stirred at −78° C. for 30 minutes and then a solution of N-(bromomethyl)phthalimide (0.887 g, 3.69 mmol) and THF (4.0 mL) is added. The solution is stirred at −78° C. for 1 hour and then allowed to warm slowly to room temperature overnight. Aqueous workup (EtOAc, MgSO$_4$) and purification by flash chromatography (3:1 hexane:EtOAc) gives 374 mg (25%) of the title compound as a white solid (mp 96°–98° C.).

IR (mineral oil) 1772, 1753, 1724, 1713, 1668, 1435, 1403, 1309, 1234, 1143, 1094, 737, 725, 714, 697 cm$^{-1}$;

$^1$H NMR (300 MHz, CDCl$_3$) δ 7.70–7.90, 7.15–7.35, 4.07, 3.86, 3.55–3.70, 3.35–3.50, 3.25–3.35, 3.11, 2.84, 2.50–2.65, 1.75–1.90, 1.60–1.75, 1.20, 0.85–0.95;

MS (FAB) m/z 519, 464, 463, 445, 159, 105, 57, 41, 29.

Step 2.

Preparation of α-[2-(1,3-Dihydro-1,3-dioxo-2H-isoindol-2-yl)methyl]-3-(2-methylpropyl)-2-oxo-1-(2-phenylethyl)-3-pyrrolidineacetic Acid TFA (5.0 mL) is added to a solution of tert-butyl α-[2-(1,3-dihydro-1,3-dioxo-2H-isoindol-2-yl)methyl]-3-(2-methylpropyl)-2-oxo-1-(2-phenylethyl)-3-pyrrolidineacetate (374 mg, 0.721 mmol) and CH$_2$Cl$_2$ (5.0 mL) at 0° C. The solution is stirred for 2 hours at 0° C. and 2 hours at room temperature. The solution is concentrated and recencentrated twice more from CH$_2$Cl$_2$ (2×30 mL). Aqueous workup (CH$_2$Cl$_2$, MgSO$_4$) provides 291 mg (87%) of the title compound as an oil which is carried on crude.

¹H NMR (300 MHz, CDCl₃) δ 7.65–7.95, 7.05–7.35, 3.90–4.05, 3.64, 3.35–3.55, 3.12, 2.80–3.05, 2.83, 2.10–2.40, 1.50–1.80, 0.90, 0.86.

Step 3.

Preparation of α-[2-(1,3-Dihydro-1,3-dioxo-2H-isoindol-2-yl)methyl]-N-hydroxy-3-(2-methylpropyl)-2-oxo-1-(2-phenylethyl)-3-pyrrolidineacetamide EDC (129 mg, 0.672 mmol) is added to a solution of α-[2-(1,3-dihydro-1,3-dioxo-2H-isoindol-2-yl)methyl]-3-(2-methylpropyl)-2-oxo-1-(2-phenylethyl)-3-pyrrolidineacetic acid (270 mg, 0.584 mmol), CH₂Cl₂ (5.7 mL), DMF (1.4 mL), HOBT (78.9 mg, 0.564 mmol), and N-methylmorpholine (74 µL, 0.67 mmol) at 0° C. The solution is stirred for 5 minutes at 0° C. and for 1 hour at room temperature. Hydroxylamine hydrochloride (80.9 mg, 1.16 mmol) and N-methylmorpholine (0.13 mL, 1.2 mmol) are added and the mixture stirred overnight at room temperature. Aqueous workup (CH₂Cl₂, MgSO₄) and purification by flash chromatography (EtOAc) provides 160 mg of the hydroxamate as a white foam which is crystallized from ether/hexane to give 129 mg (46%) of the title compound as a white crystalline material which is a 4.25:1 mixture of diastereomers (mp 170°–171° C.).

IR (mineral oil) 3194, 3105, 3050, 3028, 1773, 1709, 1665, 1644, 1496, 1434, 1409, 1393, 1309, 721, 701 cm⁻¹;

¹H NMR (300 MHz, CDCl₃) δ 10.97, 7.65–7.90, 7.10–7.35, 3.65–3.90, 3.20–3.55, 2.75–2.95, 2.35–2.50, 2.00–2.15, 1.50–1.85, 0.87;

MS (FAB) m/z 478 477, 445, 261, 202, 160, 105, 43.

EXAMPLE 17

Preparation of N-Hydroxy-3-(2-methylpropyl)-2-oxo-1-(2-phenylethyl)-α-[2-(2-thienylthio)ethyl]-3-pyrrolidineacetamide

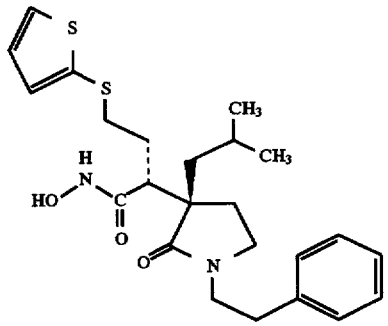

Step 1.

Preparation of tert-Butyl α-[2-(Methanesulfonyloxy)ethyl]-3-(2-methylpropyl)-2-oxo-1-(2-phenylethyl)-3-pyrrolidineacetate Methanesulfonyl chloride (0.29 mL, 3.7 mmol) is added to a solution of tert-butyl α-(2-hydroxyethyl)-3-(2-methylpropyl)-2-oxo-1-(2-phenylethyl)-3-pyrrolidineacetate (EXAMPLE 4, step 2; 1.36 g, 3.37 mmol), triethylamine (0.52 mL, 3.7 mmol) and CH₂Cl₂ (8 mL) at 0° C. The mixture is stirred for 2 hours, washed with saturated NaHCO₃ (2×10 mL), water (10 mL), dried (MgSO₄), filtered, and concentrated to give 1.22 g (75%) of the title compound as a light yellow oil.

¹H NMR (300 MHz, CDCl₃) δ 7.15–7.35, 4.10–4.30, 3.55–3.70, 3.35–3.50, 3.20–3.30, 3.01, 2.82, 2.55, 2.10–2.35, 1.85–2.05, 1.70–2.05, 1.40–1.65, 1.44, 0.87, 0.83.

Step 2.

Preparation of tert-Butyl 3-(2-Methylpropyl)-2-oxo-1-(2-phenylethyl)-α-[2-(2-thienylthio)ethyl]-3-pyrrolidineacetate Sodium hydride (60%, 41 mg, 1.0 mmol) is added to a solution of thiophenethiol (118 mg, 1.02 mmol), THF (25 mL) and DMF (25 mL) at 0° C. The mixture is stirred for 30 minutes at 0° C. and a solution of tert-butyl α-[2-(methanesulfonyloxy)ethyl]-3-(2-methylpropyl)-2-oxo-1-(2-phenylethyl)-3-pyrrolidineacetate (490 mg, 1.02 mmol) in THF (15 mL) is added. The solution is allowed to warm slowly and is stirred at room temperature overnight. Concentration, aqueous workup (EtOAc, MgSO₄), and purification by flash chromatography (25% EtOAc/hexane) gives 361 mg (71%) of title compound as a colorless oil.

IR (liq.) 2956, 2930, 2868, 1720, 1685, 1497, 1454, 1428, 1367, 1276, 1258, 1217, 1147, 847, 700 cm⁻¹;

¹H NMR (300 MHz, CDCl₃) δ 7.15–7.40, 7.10–7.15, 6.90–7.00, 3.55–3.65, 3.30–3.45, 3.15–3.25, 2.75–2.90, 2.60–2.75, 2.58, 2.25–2.40, 1.80–2.00, 1.65–1.80, 1.35–1.65, 1.39, 0.84, 0.80;

MS (EI) m/z 501, 428, 386, 331, 330, 303, 247, 246, 212, 105, 57.

Step 3.

Preparation of 3-(2-Methylpropyl)-2-oxo-1-(2-phenylethyl)-α-[2-(2-thienylthio)ethyl]-3-pyrrolidineacetic Acid A solution of tert-butyl 3-(2-methylpropyl)-2-oxo-1-(2-phenylethyl)-α-[2-(2-thienylthio)ethyl]-3-pyrrolidineacetate (338 mg, 0.674 mmol), trifluoroacetic acid (3 mL), and CH₂Cl₂ (3 mL) is stirred at 0° C. for 15 minutes and at room temperature for 1.5 hour. Concentration and aqueous workup (CH₂Cl₂, MgSO₄) gives 287 mg (96%) of the title compound as a colorless oil.

IR (liq.) 2958, 2931, 2870, 1736, 1683, 1620, 1498, 1480, 1465, 1454, 1444, 1263, 1216, 746, 700 cm⁻¹;

¹H NMR (300 MHz, CDCl₃) δ 13.75, 7.35–7.40, 7.05–7.35, 6.95–7.05, 3.70–3.85, 3.35–3.50, 3.15–3.35, 2.80–2.95, 2.55–2.80, 2.00–2.15, 1.35–1.90, 0.91, 0.84;

MS (EI) m/z 445, 331, 330, 258, 247, 246, 228, 212, 156, 105, 55.

Step 4.

Preparation of N-Hydroxy-3-(2-methylpropyl)-2-oxo-1-(2-phenylethyl)-α-[2-(2-thienylthio)ethyl]-3-pyrrolidineacetamide A solution of HOBT (83 mg, 0.62 mmol) in DMF (1.3 mL) is added to a solution of 3-(2-methylpropyl)-2-oxo-1-(2-phenylethyl)-α-[2-(2-thienylthio)ethyl]-3-pyrrolidineacetic acid (259 mg, 0.581 mmol) in CH₂Cl₂ (6 mL) at room temperature.

The solution is cooled to 0° C. To this is added 4-methylmorpholine (77 µL, 0.70 mmol) and EDC (134 mg, 0.697 mmol). The solution is stirred at 0° C. for 1 hour and then a mixture of hydroxylamine hydrochloride (57 mg, 0.87 mmol), 4-methylmorpholine (96 µL, 7.4 mmol), and DMF (0.8 mL) is added. The mixture is stirred overnight at room temperature and concentrated. Purification of the residue by flash chromatography (50% EtOAc/hexane) and crystallization (ether/hexane) gives 95 mg (36%) of the title compound as a white solid (mp 109°–110° C.).

IR (mineral oil) 3202, 3096, 3081, 3023, 1652, 1496, 1441, 1432, 1314, 1294, 1280, 1222, 751, 717, 702 cm$^{-1}$;

$^1$H NMR (300 MHz, CDCl$_3$) δ 10.55, 7.05–7.40, 6.90–7.00, 3.50–3.65, 3.05–3.25, 2.70–2.95, 2.50–2.70, 1.95–2.25, 1.35–1.95, 0.85, 0.80;

MS (EI) m/z 460 345, 284, 262, 261, 228, 105, 81, 79, 55.

EXAMPLE 18

Preparation of N-Hydroxy-3-(2-methylpropyl)-2-oxo-1-(2-phenylethyl)-α-[2-(2-thienylthio)propyl]-3-pyrrolidineacetamide

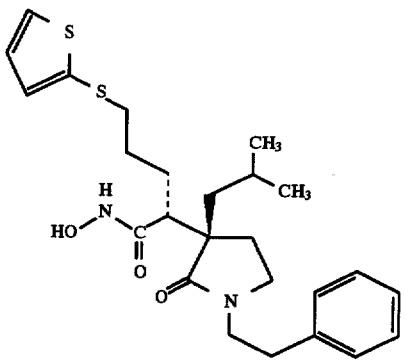

Following the general procedure of EXAMPLE 17 and making non-critical variations but starting with tert-butyl α-(3-hydroxypropyl)-3-(2-methylpropyl)-2-oxo-1-(2-phenylethyl)-3-pyrrolidineacetate, the title compound is obtained (mp 104°–105° C.).

IR (mineral oil) 3211, 3101, 3069, 3028, 1667, 1653, 1497, 1428, 1399, 1310, 1298, 1293, 1249, 760, 710 cm$^{-1}$;

$^1$H NMR (300 MHz, CDCl$_3$) δ 6.70–7.75, 3.05–3.95, 2.50–3.05, 1.15–2.50, 0.87, 0.82;

MS (EI) m/z 474, 442, 386, 359, 326, 298, 244, 202, 105, 55.

EXAMPLE 19

Preparation of N-Hydroxy-3-(2-methylpropyl)-2-oxo-1-(2-phenylethyl)-α-[2-(2-thienylthio)methyl]-3-pyrrolidineacetamide

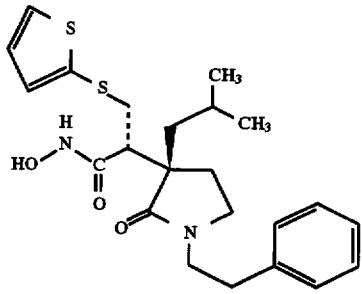

Following the general procedure of EXAMPLE 17 and making non-critical variations but starting with tert-butyl α-(1-hydroxymethyl)-3-(2-methylpropyl)-2-oxo-1-(2-phenylethyl)-3-pyrrolidineacetate, the title compound is obtained (mp 145°–146° C.).

IR (mineral oil) 3177, 3085, 3027, 1664, 1641, 1496, 1408, 1297, 1274, 1218, 1029, 1000, 845, 746, 702 cm$^{-1}$;

$^1$H NMR (300 MHz, CDCl$_3$) δ 7.68, 7.15–7.40, 6.90–7.15, 3.35–3.70, 2.55–3.30, 2.05–2.25, 1.65–1.70, 1.25–1.60, Major diastereomer peaks. 0.80, 0.71, Minor diastereomer peaks. 0.75, 0.61;

MS (EI) m/z 446, 246, 245, 203, 202, 154, 105.

EXAMPLE 20

Preparation of N$^3$-Hydroxy-N$^1$-methyl-3-(2-methylpropyl)-2-oxo-1,3-pyrrolidinediacetamide

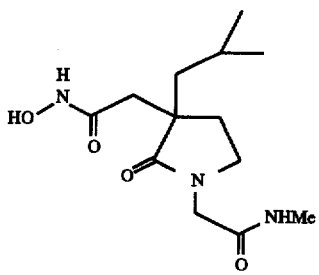

Step 1.

Preparation of 1-Trimethylsilyl-2-pyrrolidinone

Chlorotrimethylsilane (TMSCl, 56.0 mL, 441 mmol) is added dropwise to a solution of 2-pyrrolidinone (30.4 mL, 400 mmol), triethylamine (70.0 mL, 502 mmol) and toluene (400 mL) at room temperature. After stirring at room temperature with a mechanical stirrer for 20 minutes, the mixture is heated at 50° C. for 4 hours. After cooling, the mixture is diluted with hexane (300 mL) and stirred for 30 minutes at room temperature. The mixture is filtered and the filtrate concentrated. Distillation of the residue (1 mm, 68+–74° C.) gives 50.0 g (94%) of the title compound as an oil.

$^1$H NMR (300 MHz, d$_5$-pyridine) δ 3.17, 2.26, 1.70–1.85, 0.32.

Step 2.

Preparation of 3-(2-methylpropyl)-2-pyrrolidinone

A solution of LDA (2.0M, 111 mL, 222 mmol) and THF (300 mL) is cooled to –78° C. and a solution of 1-trimethylsilyl-2-pyrrolidinone (29.4 g, 221 mmol) in THF (145 mL) is added. After stirring for 45 minutes at –78° C., the enolate solution is added via cannula over 1 hour to a solution of 1-iodo-2-methylpropane (42.7 g, 232 mmol) in THF (200 mL) at –78° C. The solution is allowed to warm slowly and stirred at room temperature overnight. The reaction is quenched by the addition of 50 mL of acetic acid. Aqueous workup (EtOAc, MgSO$_4$) and purification by column chromatography (30→100% EtOAc/hexane) gives 12.8 g of the title compound as an oil.

$^1$H NMR (300 MHz, CDCl$_3$) δ 6.30, 3.10–3.30, 2.05–2.35, 1.45–1.80, 1.00–1.20, 0.81, 0.76.

Step 3.

Preparation of 3-(2-methylpropyl)-1-trimethylsilyl-2-pyrrolidinone

TMSCl (2.2 mL, 18 mmol) is added dropwise to a solution of 3-(2-methylpropyl)-2-pyrrolidinone (2.25 g, 15.9 mmol), triethylamine (2.7 mL, 19 mmol), and toluene (16 mL) at room temperature. The mixture is heated at 40° C. for 3 hours and diluted with hexane (50 mL). After stirring for 10 minutes at 0° C., the mixture is filtered and the filtrate concentrated. Distillation (1 mm, 62°–68° C.) of the residue gives 2.40 g (71%) of the title compound as an oil.

¹H NMR (300 MHz, CDCl₃) δ 3.05–3.30, 2.20–2.35, 2.05–2.20, 1.45–1.70, 1.05–1.15, 0.82, 0.78, 0.15.

Step 4.

Preparation of 3-(2-Methylpropyl)-3-(propen-2-yl)-2-pyrrolidinone

A solution of 3-(2-methylpropyl)-1-trimethylsilyl-2-pyrrolidinone (10.2 g, 47.8 mmol) and THF (153 mL) is cooled to −78° C., and LDA (2.0 M, 26.3 mL, 52.6 mmol) is added. The solution is stirred at −78° C. for 30 minutes and then allyl bromide (5.0 mL, 57 mmol) is added. The solution is allowed to warm to 5° C. over 2.5 hours, and is then stirred at 5° C. for 1 hour. After quenching with saturated aqueous ammonium chloride (25 mL), aqueous workup (EtOAc, MgSO₄) and purification by column chromatography (1:9:10 v/v CH₂Cl₂:EtOAc:hexane) provides 7.76 g (90%) of the title compound as an oil.

IR (liq.) 3241, 3077, 2957, 2929, 2902, 2873, 1708, 1693, 1640, 1440, 1284, 1277, 1264, 1251, 842 cm⁻¹;

¹H NMR (300 MHz, CDCl₃) δ 6.43, 5.65–5.85, 5.00–5.15, 3.15–3.35, 2.00–2.40, 1.65–1.85, 1.40–1.60, 0.92;

MS (EI) m/z 138, 125, 124, 98, 73, 60, 55, 45, 43, 41.

Step 5.

Preparation of Ethyl 3-(2-methylpropyl)-2-oxo-3-(propen-2-yl)-1-pyrrolidineacetate A solution of potassium bis(trimethylsilyl)amide (0.5M in toluene, 16.4 mL, 8.19 mmol) is cooled to 0° C., and a solution of 3-(2-methylpropyl)-3-(propen-2-yl)-2-pyrrolidinone (1.24 g, 6.82 mmol) in THF (10 mL) is added dropwise over 2 minutes After stirring at 0° C. for 40 minutes, ethyl bromoacetate (0.91 mL, 8.2 mmol) is added. The reaction is stirred at 0° C. for 3 hours and for 1 hour at room temperature. After quenching with saturated aqueous ammonium chloride (10 mL), aqueous workup (EtOAc, MgSO₄) and purification by column chromatography (1:9:10 v/v CH₂Cl₂:EtOAc:hexane) provided 1.66 g (91%) of the title compound as an oil.

IR (liq.) 2957, 2930, 2906, 2872, 1750, 1692, 1462, 1440, 1375, 1296, 1281, 1252, 1196, 1028, 916 cm⁻¹;

¹H NMR (300 MHz, CDCl₃) δ 5.50–5.75, 4.90–5.05, 4.00–4.15, 3.93, 3.15–3.30, 2.15–2.30, 2.00–2.15, 1.80–2.00, 1.55–1.75, 1.30–1.50, 1.16, 0.82, 0.77;

MS (EI) m/z 212, 211, 210, 194, 152, 138, 137, 110.

Step 6.

Preparation of N-Methyl-3-(2-methylpropyl)-2-oxo-3-(propen-2-yl)-1-pyrrolidineacetamide Ethyl 3-(2-methylpropyl)-2-oxo-3-(propen-2-yl)-1-pyrrolidineacetate (500 mg, 1.87 mmol) is stirred in a saturated solution of methylamine in EtOH (50 mL) at room temperature overnight. The solution is concentrated and purified by column chromatography (1:12:8 v/v CH₂Cl₂:EtOAc:hexane) to give 401 mg (85%) of the title compound as an oil.

IR (liq.) 3308, 2955, 2928, 2872, 1662, 1560, 1495, 1464, 1443, 1413, 1279, 1263, 1252, 915, 842 cm⁻¹;

¹H NMR (300 MHz, CDCl₃) δ 6.32, 5.50–5.75, 4.90–5.10, 3.79, 3.28, 2.67, 2.17, 1.85–2.10, 1.55–1.75, 1.30–1.55, 0.84, 0.77;

MS (EI) m/z 252, 221, 210, 209, 196, 194, 166, 165, 152, 138, 124, 110, 95, 73.

Step 7.

Preparation of 1-(N-Methylacetamide)-3-(2-methylpropyl)-2-oxo-3-pyrrolidineacetic Acid Ruthenium(IV) oxide hydrate (15 mg, 0.11 mmol) is added at room temperature to a mixture of sodium periodate (944 mg, 4.41 mmol) in acetonitrile (1.9 mL), carbon tetrachloride (0.9 mL) and water (2.0 mL). After stirring for 10 minutes, sodium bicarbonate (2.32 g, 27.6 mmol) is added, followed by a solution of N-methyl-3-(2-methylpropyl)-2-oxo-3-(propen-2-yl)-1-pyrrolidineacetamide (139 mg, 0.552 mmol) in acetonitrile (2.0 mL). Sodium periodate (approximately 150 mg) is added until the black mixture turnes light green. After 5 minutes the mixture is poured into 100 mL of water. The pH of the mixture is adjusted to pH 2 (pH paper) with concentrated HCl. The acidic solution is extracted with CH₂Cl₂ and EtOAc. The combined organic layers are dried (MgSO₄), filtered, and concentrated to provide 157 mg (100%) of the title compound as an oil.

¹H NMR (300 MHz, CDCl₃) δ 7.09, 4.30–4.45, 3.20–3.50, 2.67, 2.63, 1.95–2.25, 1.55–1.70, 1.30–1.45, 0.84, 0.78.

Step 8.

Preparation of N³-Hydroxy-N¹-methyl-3-(2-methylpropyl)-2-oxo-1,3-pyrrolidinediacetamide EDC (1.14 g, 5.95 mmol) is added to a solution of 1-(N-methylacetamide)-3-(2-methylpropyl)-2-oxo-3-pyrrolidineacetic acid (1.34 g, 4.96 mmol), HOBT (710 mg, 5.26 mmol) and 4-methylmorpholine (0.65 mL, 5.9 mmol) in CH₂Cl₂ (51 mL) and DMF (10 mL) at 0° C. The solution is stirred at 0° C. for 1 hour, and then a mixture of hydroxylamine hydrochloride (517 mg, 7.44 mmol) in DMF (7 mL) is added followed by 4-methylmorpholine (0.82 mL, 7.4 mmol). After stirring for 7 days at room temperature, the mixture is concentrated under high vacuum and purified by column chromatography (3% MeOH/CH₂Cl₂). Crystallization from Et₂O/hexane provides 211 mg (15%) of the title compound as a white solid (mp 145°–147° C.).

IR (mineral oil) 3259, 3199, 3097, 3017, 1662, 1564, 1522, 1501, 1412, 1405, 1313, 1297, 1275, 750, 724 cm⁻¹;

¹H NMR (300 MHz, CDCl₃/CD₃OD) δ 4.25–4.45, 3.05–3.50, 2.74, 2.32, 1.90–2.20, 1.55–1.75, 1.30–1.50, 0.87, 0.79;

MS (EI) m/z 285, 254, 229, 226, 194, 180, 169, 166, 152, 138, 124, 110, 55.

EXAMPLE 21

Preparation of N³-Hydroxy-N¹-methyl-3-(2-methylpropyl)-2-oxo-α¹-(phenylmethyl)-1,3-pyrrolidinediacetamide

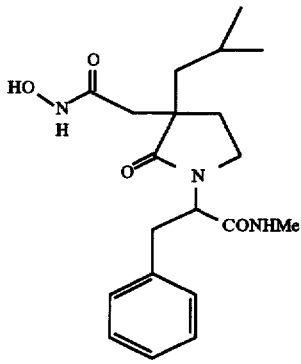

Step 1.

Preparation of Ethyl 3-(2-methylpropyl)-2-oxo-α-(phenylmethyl)-3-(propen-2-yl)-1-pyrrolidineacetate A solution of ethyl 3-(2-methylpropyl)-2-oxo-3-(propen-2-yl)-1-pyrrolidineacetate (Example 20, step 5; 1.63 g, 6.10 mmol) and THF (15 mL) is cooled to −78° C. and LDA (2.0M, 3.2 mL, 6.4 mmol) is added. The solution is stirred at −78° C. for 30 minutes and then benzyl bromide (0.80 mL, 6.7 mmol) is added. The solution is allowed to warm to 0° C. over 2 hours, and then stirred at 0° C. for 1 hour. After quenching with saturated aqueous ammonium chloride (10 mL), aqueous workup (EtOAc, MgSO₄) and purification by column chromatography (10% EtOAc/hexane) provided 1.94 g (89%) of the title compound as an oil in a 1:1 mixture of diastereomers.

IR (liq.) 2975, 2956, 2930, 2906, 1739, 1689, 1499, 1455, 1425, 1266, 1207, 1192, 1032, 915, 698 cm⁻¹;

¹H NMR (300 MHz, CDCl₃) δ 7.05–7.30, 5.55–5.75, 4.85–5.20, 4.65–4.85, 4.00– 4.20, 3.00–3.40, 2.80–2.95, 2.12, 1.50–1.95, 1.30–1.45, 1.15–1.30, 1.00–1.15, 0.83, 0.79, 0.66, 0.54;

MS (EI) m/z 357, 301, 238, 228, 284, 282, 267, 266, 210, 200, 176, 164, 125, 102, 91.

Step 2.

Preparation of N-Methyl-3-(2-methylpropyl)-2-oxo-α-(phenylmethyl)-3-(propen-2-yl)-1-pyrrolidineacetamide Methylamine gas is bubbled through a solution of ethyl 3-(2-methylpropyl)-2-oxo-α-(phenylmethyl)-3-(propen-2-yl)-1-pyrrolidineacetate (3.40 g, 9.51 mmol) in EtOH (120 mL) for 30 minutes at room temperature, and the solution is stirred at room temperature overnight. The solution is concentrated and purified by flash chromatography (1:6:11→1:10:9 v/v CH₂Cl₂:EtOAc:hexane) to give 3.01 g (92%) of the title compound as a solid (mp 91°–92° C.) which is a ca. 1:1 mixture of diastereomers.

IR (mineral oil) 3315, 1684, 1654, 1584, 1562, 1499, 1442, 1414, 1296, 1278, 1264, 1225, 913, 744, 708 cm⁻¹;

¹H NMR (300 MHz, CDCl₃) δ 7.10–7.30, 6.15–6.40, 5.50–5.70, 5.10–5.30, 4.95–5.10, 4.75–4.95, 3.15–3.35, 2.90–3.10, 2.72, 2.71, 1.95–2.20, 1.50–1.95, 1.15–1.50, 0.86, 0.78, 0.74, 0.64;

MS (EI) m/z 342, 300, 284, 267, 251, 242, 200, 162, 132, 105, 91, 81, 73, 67.

Step 3.

Preparation of N¹-Methylacetamide-3-(2-methylpropyl)-2-oxo-α¹-(phenylmethyl)-3-pyrrolidineacetic Acid Ruthenium(IV) oxide hydrate (29 mg, 0.22 mmol) is added to a mixture of sodium periodate (1.85 g, 8.65 mmol) in acetonitrile (3.8 mL), carbon tetrachloride (1.8 mL), and water (3.9 mL) at room temperature. After stirring for 10 minutes, sodium bicarbonate (4.55 g, 54.2 mmol) is added, followed by a solution of N-methyl-3-(2-methylpropyl)-2-oxo-α-(phenylmethyl)-3-(propen-2-yl)-1-pyrrolidineacetamide (371 mg, 1.08 mmol) in acetonitrile (4.0 mL). Sodium periodate (approximately 300 mg) is added until the black mixture turns light green. After 5 minutes, the mixture is poured into 100 mL of water. The mixture is extracted with EtOAc (2×50 mL). The pH of the aqueous mixture is adjusted to pH 2 (pH paper) with concentrated HCl. The acidic mixture is extracted with CH₂Cl₂ and EtOAc, and these layers are combined with the original EtOAc extracts, dried (MgSO₄), filtered, and concentrated to give 300 mg of the crude acid as a dark brown oil. This material is dissolved in 15% NaOH (10 mL) and extracted with Et₂O (3×20 mL). These Et₂O layers are discarded. The pH of the aqueous layer is adjusted to pH 2 (pH paper) with concentrated HCl. The acidic layer is extracted with EtOAc (3×30 mL), the combined EtOAc layers dried (MgSO₄), filtered, and concentrated to give 230 mg (59%) of the title compound as an oil as a 1:1 mixture of diastereomers.

IR (mineral oil) 3358, 3087, 3064, 3029, 1721, 1649, 1550, 1498, 1441, 1413, 1297, 1272, 1233, 1192, 700 cm⁻¹;

¹H NMR (300 MHz, CDCl₃) δ 7.05–7.40, 6.55–6.70, 5.10, 4.56, 3.64, 3.20–3.55, 2.70–3.05, 2.30–2.70, 1.75–2.20, 1.55–1.75, 1.49, 1.05–1.40, 0.80–1.00, 0.90, 0.83, 0.69, 0.66;

MS (EI) m/z 360, 336, 303, 302, 284, 269, 256, 246, 228, 200, 162, 161, 132, 105, 91.

Step 4.

Preparation of N³-Hydroxy-N¹-methyl-3-(2-methylpropyl)-2-oxo-α¹-(phenylmethyl)-1,3-pyrrolidinediacetamide EDC (1.08 g, 5.66 mmol) is added to a solution of N¹-methylacetamide-3-(2-methylpropyl)-2-oxo-α¹-(phenylmethyl)-3-pyrrolidineacetic acid (1.70 g, 4.72 mmol), HOBT (676 mg, 5.00 mmol) and 4-methylmorpholine (0.52 mL, 4.7 mmol) in CH₂Cl₂ (49 mL) and DMF (10 mL) at 0° C. The solution is stirred at 0° C. for 1 hour and then a mixture of hydroxylamine hydrochloride (491 mg, 7.08 mmol) in DMF (7 mL) is added, followed by 4-methylmorpholine (0.79 mL, 7.1 mmol). The mixture is stirred at room temperature overnight and concentrated under high vacuum. The residue is dissolved in 15% NaOH (13 mL) and extracted with EtOAc (3×20 mL). These EtOAc layers are discarded. The pH of the aqueous layer is adjusted to pH 2 (pH paper) with 6N HCl. The acidic layer is extracted with CH₂Cl₂ (3×30 mL), the combined CH₂Cl₂ layers dried (MgSO₄), filtered, and concentrated. Purification by column chromatography (5% MeOH/CH₂Cl₂) and crystallization from Et₂O/hexane provided 255 mg (14%) of the title compound as a white solid (mp 166°–168° C.) as a mixture of diastereomers.

IR (mineral oil) 3373, 3199, 3087, 3064, 3027, 1686, 1667, 1634, 1546, 1498, 1404, 1356, 1303, 742, 697 cm⁻¹;

¹H NMR (300 MHz, CDCl₃/CD₃OD) major diastereomer, key peaks: δ 4.48, 2.76, 0.89, 0.81. Minor diastereomer, key peaks: δ 5.05, 2.82, 0.69, 0.62;

MS (EI) m/z 375, 344, 317, 316, 285, 284, 256, 132, 91.

EXAMPLE 22

Preparation of α-[2-(1,3-Dihydro-1,3-dioxo-2H-isoindol-2-yl)ethyl]-N-hydroxy-3-(2-methylpropyl)-2-oxo-1-(phenylmethyl)-3-pyrrolidineacetamide

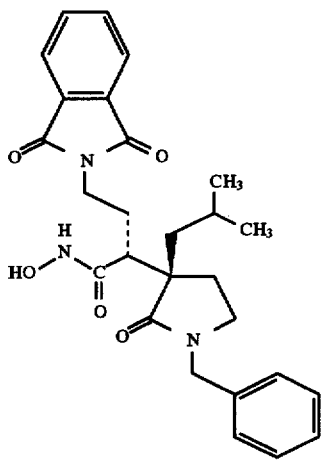

Step 1.

Preparation of N-tert-Butyloxycarbonyl-2-pyrrolidinone

A solution of di-tert-butyl dicarbonate (28.2 g, 129 mmol) in dry $CH_2Cl_2$ (80 mL) is added to a stirred solution of 2-pyrrolidinone (10.0 g, 117 mmol) and DMAP (200 mg, catalytic amount) in dry $CH_2Cl_2$ (230 ml,) over 10 minutes. After 16 hours, the solution is diluted with $H_2O$ (150 mL) and extracted with EtOAc (4×100 mL). The organic layers are combined, dried over anhydrous $Na_2SO_4$, filtered, and concentrated under reduced pressure to give a red oil. The oil is purified by silica gel chromatography (200 g SG, 40% EtOAc/hexane) to yield 20.1 g (93%) of the title compound as a gold oil.

IR (liq.) 2980, 1786, 1752, 1714, 1459, 1394, 1368, 1315, 1256, 1228, 1154, 1045, 1018, 858, 778 $cm^{-1}$;

$^1H$ NMR (300 MHz, $CDCl_3$) δ 3.74, 2.50, 1.90–2.05, 1.52; MS (FAB) m/z 186, 131, 130, 112, 86, 57, 41.

Step 2.

Preparation of N-tert-Butyloxycarbonyl-3-(2-methylpropen-2-yl)-2-pyrrolidinone

A solution of N-tert-butyloxycarbonyl-2-pyrrolidinone (10.0 g, 54.0 mmol) and HMPA (9.40 mL, 54.0 mmol) in dry THF (200 mL) is cooled to −78° C. and treated drop-wise over 6.5 minutes with lithium diisopropylamide (LDA, 29.7 mL, 59.4 mmol, 2M in heptane/THF/ethylbenzene). After 30 minutes at −78° C., 3-bromo-2-methylpropene (6.53 mL, 64.8 mmol) is added. The solution is maintained at −78° C. under $N_2$ for 6 hours, and is then quenched with saturated $NH_4Cl$ (100 mL). The solution is warmed to 0° C. and diluted with $H_2O$ (300 mL). The crude olefin is extracted into EtOAc (3×200 mL), dried over anhydrous $Na_2SO_4$, filtered, and concentrated under reduced pressure to give an oil. The oil is purified by silica gel chromatography (350 g gel; 20% EtOAc/hexane) to yield 7.75 g (60%) of the title compound as a golden oil.

IR (liq.) 2980, 2934, 2909, 1785, 1749, 1716, 1457, 1394, 1368, 1322, 1295, 1251, 1227, 1155, 779 $cm^{-1}$;

$^1H$ NMR (300 MHz, $CDCl_3$) δ 4.79, 4.71, 3.70–3.80, 3.50–3.65, 2.60–2.75, 1.95–2.20, 1.72, 1.55–1.75, 1.52;

MS (EI) m/z 239, 183, 166, 165, 139, 57.

Step 3.

Preparation of tert-Butyl N-tert-Butyloxycarbonyl-3-(2-methylpropen-2-yl)-2-oxo-3-pyrrolidineacetate A solution of N-tert-butyloxycarbonyl-3-(2-methylpropen-2-yl)-2-pyrrolidinone (7.39 g, 30.8 mmol) in dry THF (125 mL) is cooled to −78° C. and treated dropwise with LDA (17.0 mL, 33.9 mmol). After 30 minutes at −78° C., tert-butyl bromoacetate (5.46 mL, 37.0 mmol) is added. The solution is maintained at −78° C. for 6 hours and then quenched with saturated $NH_4Cl$ (50 mL). The solution is warmed to 0° C. and diluted with $H_2O$ (50 mL). The crude ester is extracted into EtOAc (3×100 mL), dried over anhydrous $Na_2SO_4$, filtered, and concentrated under reduced pressure to give an orange oil. The material is purified by silica gel chromatography (2 columns: 250 g, 100 g SG, 10% EtOAc/hexane) to yield 7.69 g (71%) of the title compound as a golden oil.

IR (liq.) 2980, 2934, 2918, 1786, 1748, 1718, 1457, 1394, 1369, 1315, 1258, 1208, 1155, 965, 853 $cm^{-1}$;

$^1H$ NMR (300 MHz, $CDCl_3$) δ 4.90, 4.78, 3.50–3.75, 2.53, 2.30, 2.05–2.20, 1.72, 1.51, 1.42;

MS (EI) m/z 353, 297, 280, 241, 224, 223, 196, 180, 57.

Step 4.

Preparation of tert-Butyl N-tert-Butyloxycarbonyl-3-(2-methylpropyl)-2-oxo-3-pyrrolidineacetate A solution of tert-butyl N-tert-butyloxycarbonyl-3-(2-methylpropen-2-yl)-2-oxo-3-pyrrolidineacetate (7.90 g, 22.4 mmol) in EtOH (150 mL) is treated with 10% palladium on carbon (1.98 g, 25% by weight) and hydrogenated in a Parr flask at 45 psi for 16 hours at room temperature. The mixture is filtered through celite; the residual cake is washed with EtOH (2×100 mL), MeOH (2×100 mL), and $CH_2Cl_2$ (100 mL). The filtrate is concentrated under reduced pressure to yield 7.86 g (99%) of the title compound as a thick, cloudy oil.

IR (liq.) 2978, 2934, 1786, 1749, 1717, 1476, 1458, 1393, 1369, 1317, 1258, 1207, 1155, 1117, 969 $cm^{-1}$;

$^1H$ NMR (300 MHz, $CDCl_3$) δ 3.55–3.80, 2.53, 2.05–2.20, 1.90–2.05, 1.60–1.80, 1.40–1.60, 1.52, 1.42, 0.91, 0.90;

MS (FAB) m/z 356, 300, 244, 226, 200, 182, 154, 57.

Step 5.

Preparation of tert-Butyl N-tert-Butyloxycarbonyl-3-(2-methylpropyl)-2-oxo-α-(propen-2-yl)-3-pyrrolidineacetate A solution of tert-butyl N-tert-butyloxycarbonyl-3-(2-methylpropyl)-2-oxo-3-pyrrolidineacetate (3.65 g, 10.3 mmol) in dry THF (45 mL) is cooled to −78° C. and treated drop-wise with LDA (5.70 mL, 11.3 mmol). After 30 minutes at −78° C., allyl bromide (1.10 mL, 12.4 mmol) is added. The solution is maintained at −78° C. for 3 hours, and is then allowed to slowly warm to room temperature under $N_2$. After 12 hours, the solution is quenched with saturated $NH_4Cl$ (10 mL) and diluted with $H_2O$ (50 mL). The crude lactam is extracted into EtOAc (3×100 mL). The organic extracts are combined, washed with brine (50 mL), dried over anhydrous $Na_2SO_4$, filtered, and concentrated under reduced pressure to give 4.72 g of gold oil. The oil is purified by silica gel chromatography (300 g SG, 5% EtOAc/hexane)

to yield 2.98 g (73%) of the title compound as a clear, pale gold oil as a mixture of diastereomers.

IR (liq.) 2979, 2961, 2934, 1785, 1748, 1719, 1457, 1393, 1369, 1315, 1257, 1207, 1156, 1125, 851 cm$^{-1}$;

$^1$H NMR (300 MHz, CDCl$_3$, key peaks of the major diastereomer): δ 5.60–5.85, 4.95–5.15, 3.55–3.75, 2.64, 2.20–2.50, 1.35–1.90, 1.52, 1.42, 0.91, 0.88;

MS (FAB) m/z 396, 340, 285, 284, 266, 222, 57, 41, 29.

Step 6.

Preparation of tert-Butyl 3-(2-Methylpropyl)-2-oxo-α-(propen-2-yl)-3-pyrrolidineacetate A solution of tert-butyl N-tert-butyloxycarbonyl-3-(2-methylpropyl)-2-oxo-α-(propen-2-yl)-3-pyrrolidineacetate (5.40 g, 13.7 mmol) in MeOH (70 mL) is treated with magnesium methoxide (74.7 mL, 68.5 mmol, 10.3 wt % in MeOH). The resultant solution is stirred under N$_2$ at room temperature for 16 hours. The solution is quenched with 1:1 glacial AcOH/H$_2$O (100 mL). The solution is reduced to a minimal volume under reduced pressure, and the unprotected lactam is extracted into CH$_2$Cl$_2$ (3×100 mL). The organic layers are combined, washed with saturated NH$_4$Cl (100 mL), brine (100 mL), dried over anhydrous Na$_2$SO$_4$, filtered, and concentrated under reduced pressure to give 4.75 g of a gold oil. The oil is purified by silica gel chromatography (100 g SG, 25% EtOAc/hexane) to yield 3.85 g (96%) of the title compound as an off-white, low-melting solid.

IR (mineral oil) 3206, 3105, 1720, 1701, 1352, 1299, 1268, 1255, 1231, 1162, 1153, 1125, 923 cm$^{-1}$;

$^1$H NMR (300 MHz, CDCl$_3$) δ 6.28, 5.65–5.85, 4.90–5.15, 3.20–3.40, 2.60, 2.20–2.60, 1.85–2.00, 1.65–1.80, 1.35–1.65, 1.41, 0.93, 0.91;

MS (FAB) m/z 296, 240, 222, 194, 57.

Step 7.

Preparation of tert-Butyl 3-(2-Methylpropyl)-2-oxo-1-(phenylmethyl)-α-(propen-2-yl)-3-pyrrolidineacetate A cold (0° C.) solution of tert-butyl 3-(2-methylpropyl)-2-oxo-α-(propen-2-yl)-3-pyrrolidineacetate (1.11 g, 3.76 mmol) in dry THF (25 mL) is treated with NaH (60% dispersion in mineral oil, 226 mg, 5.64 mmol) in one portion. After 30 minutes, benzyl bromide (537 μL, 4.51 mmol) is added. The solution is allowed to slowly warm to room temperature, stirring under N$_2$ overnight. The mixture is quenched with H$_2$O (25 mL) and extracted with EtOAc (3×25 mL). The organic extracts are combined, washed with brine (25 mL), dried over anhydrous Na$_2$SO$_4$, filtered, and concentrated under reduced pressure to yield 1.70 g of yellow oil. The oil is purified by silica gel chromatography (30 g SG, 10% EtOAc/hexane) to give 1.37 g (94%) of the title compound as a clear, colorless oil.

IR (liq.) 2977, 2957, 2930, 2870, 1721, 1687, 1496, 1454, 1440, 1367, 1287, 1260, 1238, 1153, 701 cm$^{-1}$;

$^1$H NMR (300 MHz, CDCl$_3$) δ 7.20–7.35, 5.65–5.85, 4.95–5.15, 4.41, 3.05–3.30, 2.62, 2.20–2.55, 1.50–1.85, 1.41, 0.89, 0.87;

MS (EI) m/z 385, 329, 312, 232, 231, 188, 91, 57.

Step 8.

Preparation of tert-Butyl α-(2-Hydroxyethyl)-3-(2-methylpropyl)-2-oxo-1-(phenylmethyl)-3-pyrrolidineacetate Ozone is bubbled through a cold (−78° C.) solution of tert-butyl 3-(2-methylpropyl)-2-oxo-1-(phenylmethyl)-α-(propen-2-yl)-3-pyrrolidineacetate (1.32 g, 3.42 mmol) in EtOH (30 mL). After purging the solution with N$_2$, sodium borohydride (195 mg, 5.14 mmol) is added in one portion (at −78° C.). The solution is allowed to slowly warm to room temperatuare under N$_2$ overnight. The reaction mixture is concentrated to a white solid, diluted with H$_2$O (10 mL) and extracted with EtOAc (3×25 mL). The organic extracts are combined, washed with brine (25 mL), dried over anhydrous Na$_2$SO$_4$, filtered, and concentrated under reduced pressure to yield 1.37 g of a clear, colorless oil. The oil is purified by silica gel chromatography (50 g SG, 20% EtOAc/hexane) to give 850 mg (64%) of the title compound as a clear, colorless oil, which is a single diastereomer.

IR (liq.) 2956, 2930, 2870, 1771, 1720, 1684, 1497, 1464, 1454, 1441, 1367, 1286, 1261, 1154, 701 cm$^{-1}$;

$^1$H NMR (300 MHz, CDCl$_3$) δ 7.20–7.40 4.42, 3.55–3.80, 3.10–3.30, 2.70, 2.35–2.50, 1.90–2.05, 1.50–1.90, 1.44, 0.88, 0.87;

MS (EI) m/z 389, 333, 287, 259, 258, 232, 230, 140, 119, 91.

Step 9.

Preparation of tert-Butyl α-[2-(1,3-Dihydro-1,3-dioxo-2H-isoindol-2-yl)ethyl]-3-(2-methylpropyl)-2-oxo-1-(phenylmethyl)-3-pyrrolidineacetate A solution of tert-butyl α-(2-hydroxyethyl)-3-(2-methylpropyl)-2-oxo-1-(phenylmethyl)-3-pyrrolidineacetate (435 mg, 1.12 mmol) in dry THF (10 mL) is treated with triphenylphosphine (323 mg, 1.23 mmol), diethylazodicarboxylate (194 μL, 1.23 mmol), and phthalimide (181 mg, 1.23 mmol). The solution is allowed to stir overnight at room temperature under N$_2$. The reaction mixture is concentrated and purified by silica gel chromatography (25 g SG, 20% EtOAc/hexane) to give 518 mg (89%) of the title compound as an off-white, amorphous solid.

IR (mineral oil) 1773, 1754, 1744, 1722, 1713, 1671, 1433, 1398, 1309, 1264, 1164, 1116, 706 cm$^{-1}$;

$^1$H NMR (300 MHz, CDCl$_3$) δ 7.80–7.90, 7.65–7.80, 7.20–7.35, 4.41, 3.60–3.85, 3.05–3.25, 2.59, 2.30–2.50, 2.00–2.20, 1.75–1.95, 1.40–1.75, 1.48, 0.87;

MS (FAB) m/z 519, 464, 463, 445, 417, 230, 91, 57.

Step 10.

Preparation of α-[2-(1,3-Dihydro-1,3-dioxo-2H-isoindol-2-yl)ethyl]-N-hydroxy-3-(2-methylpropyl)-2-oxo-1-(phenylmethyl)-3-pyrrolidineacetamide A cold (0° C.) solution of tert-butyl α-[2-(1,3-dihydro-1,3-dioxo-2H-isoindol-2-yl)ethyl]-3-(2-methylpropyl)-2-oxo-1-(phenylmethyl)-3-pyrrolidineacetate (500 mg, 0.964 mmol) in CH$_2$Cl$_2$ (2 ml) is treated with TFA (2 mL) and maintained at 0° C. for 1 hour, and then at room temperature for 1 hour. The solvent is removed in vacuo to give a quantitative yield of α-[2-(1,3-dihydro-1,3-dioxo-2H-isoindol-2-yl)ethyl]-3-(2-methylpropyl)-2-oxo-1-(phenylmethyl)-3-pyrrolidineacetic acid as a gelatinous solid.

IR (liq.) 2962, 1775, 1755, 1716, 1617, 1469, 1455, 1441, 1402, 1377, 1309, 721, 702 cm$^{-1}$;

$^1$H NMR (300 MHz, CDCl$_3$) δ 7.80–7.90, 7.70–7.80, 7.10–7.30, 4.44, 3.60–3.90, 3.32, 2.68, 1.80–2.25, 1.55–1.75, 0.91, 0.84;

MS (EI) m/z 462, 406, 302, 244, 232, 230, 188, 160, 91.

A cold (0° C.) solution of α-[2-(1,3-dihydro-1,3-dioxo-2H-isoindol-2-yl)ethyl]-3-(2-methylpropyl)-2-oxo-1-

(phenylmethyl)-3-pyrrolidineacetic acid (559 mg) in $CH_2Cl_2$/DMF (8 mL/2 mL) is treated with 1-hydroxybenzotriazole (158 mg, 1.17 mmol), 4-methylmorpholine (129 μL, 1.17 mmol), and EDC (224 mg, 1.17 mmol). After 1 hour, additional 4-methylmorpholine (159 μL, 1.45 mmol) and hydroxylamine HCl (101 mg, 1.45 mmol) are added. The solution is allowed to slowly warm to room temperature, stirring under $N_2$ overnight. The reaction mixture is diluted with $H_2O$ (25 mL) and extracted into $CH_2Cl_2$ (3×50 mL). The organic extracts are dried over anhydrous $Na_2SO_4$, filtered, concentrated under reduced pressure, and reconstituted in EtOAc (50 mL). The EtOAc layer is washed with more $H_2O$ (3×25 mL) and brine (25 mL). The organic layer is dried over anhydrous $Na_2SO_4$, filtered, and concentrated under reduced pressure to give 416 mg of white foam. The foam is purified by silica gel chromatography (50 g SG, 2% MeOH/CHCl$_3$) to yield 220 mg of white foam which is triturated with $Et_2O$ to give 181 mg (39%) of the title compound as a white solid (mp 162°–164° C.).

IR (mineral oil) 3167, 3059, 3033, 3022, 1776, 1710, 1666, 1653, 1498, 1396, 1265, 706, 696 cm$^{-1}$;

$^1$H NMR (300 MHz, CDCl$_3$) δ 7.80–7.90, 7.65–7.80, 7.05–7.40, 4.20–4.60, 3.60–4.00, 3.05–3.35, 1.40–2.75, 0.75–0.95;

MS (EI) m/z 477, 445, 421, 417, 248, 247, 188, 160, 91.

EXAMPLE 23

Preparation of N-Hydroxy-3-(2-methylpropyl)-2-oxo-1-(phenylmethyl)-3-pyrrolidineacetamide

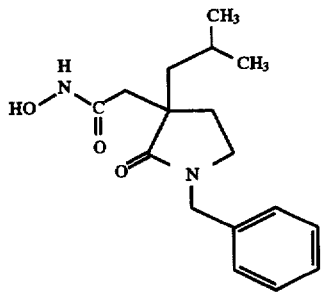

Following the general procedure in EXAMPLE 22 and making non-critical variations but starting with tert-butyl N-tert-butyloxycarbonyl-3-(2-methylpropyl)-2-oxo-3-pyrrolidineacetate (EXAMPLE 22, step 4), the title compound is obtained (mp 119°–120° C.).

IR (mineral oil) 3265, 3164, 3065, 3029, 3016, 1658, 1519, 1494, 1305, 1291, 1260, 1063, 701, 651, 617 cm$^{-1}$;

$^1$H NMR (300 MHz, CDCl$_3$) δ 10.13, 7.60–8.30, 7.10–7.40, 4.44, 3.10–3.30, 2.48, 2.15–2.30, 1.95–2.10, 1.35–1.85, 0.88, 0.87;

MS (EI) m/z 304, 272, 248, 215, 188, 187, 186, 92, 91, 65.

EXAMPLE 24

Preparation of N-Hydroxy-3-(2-methylpropyl)-2-oxo-1-(phenylmethyl)-α-[2-(4,5,6,7-tetrafluoro-1,3-dihydro-1,3-dioxo-2H-isoindol-2-yl)ethyl]-3-pyrrolidineacetamide

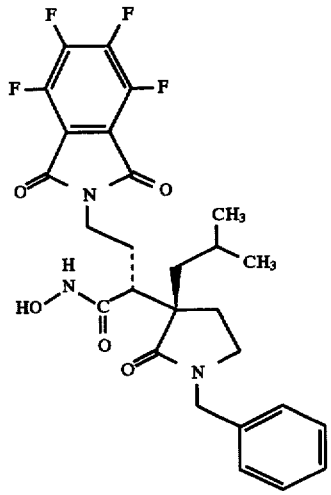

Following the general procedure in EXAMPLE 22 and making non-critical variations but starting with tert-butyl α-(2-hydroxyethyl)-3-(2-methylpropyl)-2-oxo-1-(phenylmethyl)-3-pyrrolidineacetate (EXAMPLE 22, step 8), the title compound is obtained (mp 183°–185° C.).

IR (mineral oil) 3221, 1724, 1713, 1694, 1672, 1629, 1513, 1503, 1418, 1262, 1155, 1033, 954, 941, 754 cm$^{-1}$;

$^1$H NMR (300 MHz, CDCl$_3$) δ 7.10–7.40, 4.25–4.55, 3.60–4.00, 3.10–3.35, 2.40–2.55, 1.40–1.35, 1.80–1.95;

MS (FAB) m/z 550, 534, 517, 489, 230, 91.

EXAMPLE 25

Preparation of 1-(3-Fluorophenyl)methyl)-α-[2-(1,3-dihydro-1,3-dioxo-2H-isoindol-2-yl)ethyl]-N-hydroxy-3-(2-methylpropyl)-2-oxo-3-pyrrolidineacetamide

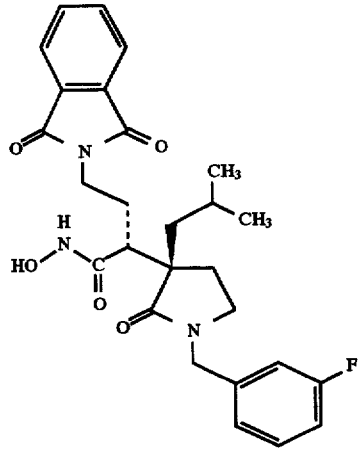

Following the general procedure in EXAMPLE 22 and making non-critical variations but starting with tert-butyl 3-(2-methylpropyl)-2-oxo-α-(propen-2-yl)-3-pyrrolidineacetate (EXAMPLE 22, step 6), the title compound is obtained (mp 162°–163° C).

IR (mineral oil) 3169, 3058, 3048, 1776, 1709, 1667, 1653, 1614, 1590, 1487, 1397, 1292, 1267 cm$^{-1}$;

$^1$H NMR (300 MHz, CDCl$_3$) δ 7.75–7.90, 7.65–7.75, 7.15–7.35, 6.80–7.00, 4.40, 3.60–3.85, 3.10–3.30, 2.30–2.65, 1.40–2.25, 0.85, 0.79;

MS (EI) m/z 495, 463, 435, 379, 322, 288, 248, 206, 160, 138, 109.

EXAMPLE 26

Preparation of α$^3$-[2-(1,3-Dihydro-1,3-dioxo-2H-isoindol-2-yl)ethyl]-N$^3$-hydroxy-N$^1$-methyl-3-(2-methylpropyl)-2-oxo-1,3-pyrrolidinediacetamide

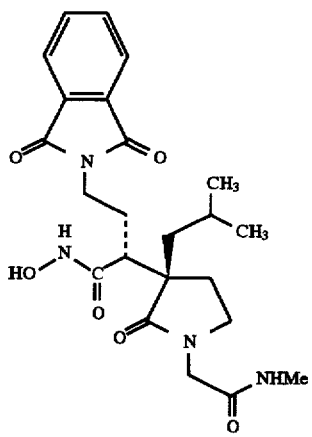

Following the general procedure in EXAMPLE 22 and making non-critical variations but starting with tert-butyl 3-(2-methylpropyl)-2-oxo-α-(propen-2-yl)-3-pyrrolidineacetate (EXAMPLE 22, step 6), the title compound is obtained (mp 120° C., dec).

IR (mineral oil) 3296, 3100, 3060, 1773, 1714, 1668, 1547, 1496, 1400, 1340, 1299, 1272, 1171, 1038 cm$^{-1}$;

$^1$H NMR (300 MHz, CDCl$_3$) δ 7.80–7.90, 7.65–7.80, 6.85, 4.33, 3.60–3.95, 3.25–3.55, 2.81, 2.65–2.85, 2.20–2.40, 1.70–2.20, 1.15–1.70, 0.75–0.95, 0.81, 0.68;

MS (EI) m/z 458, 402, 340, 339, 229, 212, 185, 169, 160, 138.

EXAMPLE 27

Preparation of N$^3$-Hydroxy-N$^1$-methyl-3-(2-methylpropyl)-2-oxo-α$^3$-[2-(4,5,6,7-tetrafluoro-1,3-dihydro-1,3-dioxo-2H-isoindol-2-yl)ethyl]-1,3-pyrrolidinediacetamide

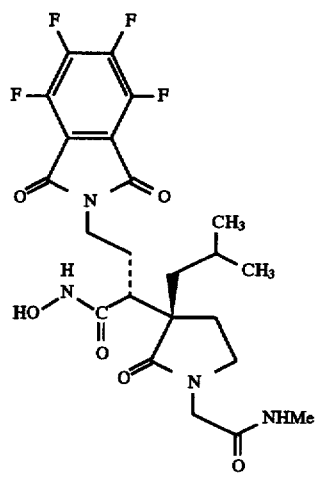

Following the general procedure in EXAMPLE 22 and making non-critical variations but starting with tert-butyl 3-(2-methylpropyl)-2-oxo-α-(propen-2-yl)-3-pyrrolidineacetate (EXAMPLE 22, step 6), the title compound is obtained (mp 130° C., dec).

IR (mineral oil) 3293, 1785, 1723, 1668, 1550, 1514, 1500, 1410, 1314, 1273, 1158, 1035, 944, 754 cm$^{-1}$;

$^1$H NMR (300 MHz, CDCl$_3$) δ 6.55, 4.30, 3.60–4.00, 3.20–3.55, 2.55–2.90, 1.30–1.40, 1.10–1.30, 0.89, 0.78;

MS (EI) m/z 530, 498, 474, 411, 232, 212, 180, 169, 154, 152, 138.

EXAMPLE 28

Preparation of [S-(R*,R*)]-N$^3$-Hydroxy-N$^1$-methyl-3-(2-methylpropyl)-2-oxo-α$^1$-(phenylmethyl)-1,3-pyrrolidinediacetamide

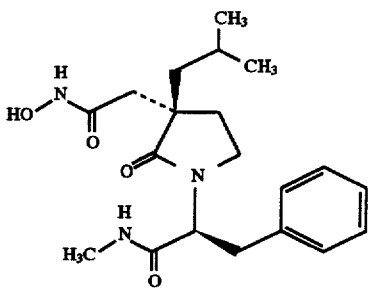

Step 1.

Resolution of tert-Butyl N-tert-Butyloxycarbonyl-3-(2-methylpropyl)-2-oxo-3-pyrrolidineacetate A 20 mg/mL solution of racemic tert-butyl N-tert-butyloxycarbonyl-3-(2-methylpropyl)-2-oxo-3-pyrrolidineacetate (EXAMPLE 22, step 4) is made in the mobile phase, 2% isopropanol in hexane (V/V). Aliquots of 53 mL (1.06 g) are injected onto a 5.1×50 cm Chiralcel OD column (Chiral Technologies, Inc., Extort, Pa. 19341) using a SepTech 140 HPLC (EM Separations, Inc., Wakefield, R.I. 02880) instrument in the automated peak shaving and recycling mode. The flow rate is 60 mL/min and the monitor is set at 213 nm. After four passes through the column with appropriate peak shaving, both peaks are obtained in nearly 100% yield at >99% ee for the earlier eluting enantiomer (enantiomer 1) and 96.4% ee for the later eluting enantiomer (enantiomer 2). Enantiomeric excess is determined on a 0.46×25 cm Chiralcel OD-H column (Chiral Technologies, Inc.) using 5% isopropanol in hexane (V/V) at 0.5 mL/min with the monitor set at 210 nm. Enantiomer 1 eluted at 8.8 minutes and enantiomer 2 eluted at 10.2 minutes ($\alpha=1.42$).

Step 2.

Preparation of (S)tert-Butyl 3-(2-methylpropyl)-2-oxo-3-pyrrolidineacetate

A solution of (S)-tert-butyl N-tert-butyloxycarbonyl-3-(2-methylpropyl)-2-oxo-3-pyrrolidineacetate (193 mg, 0.543 mmol), magnesium methoxide (3.0 mL, 6–10 wt. % in MeOH), and MeOH (2.7 mL) is stirred at room temperature for 16 hours. The solution is poured into water (15 mL) and the mixture acidified with acetic acid. The mixture is extracted several times with $CH_2Cl_2$, the combined filtrates dried ($MgSO_4$), filtered, and concentrated to give 124 mg (89%) of the title compound as an oil.

IR (mineral oil) 3209, 3100, 3001, 1728, 1691, 1496, 1318, 1302, 1281, 1261, 1208, 1163, 1132, 1079, 969 cm$^{-1}$;

$^1$H NMR (300 MHz, $CDCl_3$) δ 5.77, 3.25–3.40, 2.49, 2.20–2.40, 2.05–2.20, 1.65– 1.85, 1.35–1.60, 1.44, 1.42, 0.85–1.00;

MS (FAB) m/z 256, 201, 200, 182, 154, 57, 41.

Step 3.

Preparation of Methyl D-Phenyllactate

A mixture of D-phenyllactic acid (4.79 g, 28.8 mmol), iodomethane (1.80 mL, 28.9 mmol), $K_2CO_3$ (4.07 g, mmol), and DMF (80 mL) is stirred for 16 hours at room temperature. The solution is diluted with 500 mL of ether. The mixture washed with water (3×150 mL) and brine (150 mL). The organic layer is dried ($MgSO_4$), filtered, and concentrated to give 3.89 g (75%) of the title compound as a white solid.

$^1$H NMR (300 MHz, $CDCl_3$) δ 7.15–7.40, 4.40–4.55, 3.78, 3.13, 2.97, 2.68.

Step 4.

Preparation of the Triflate of Methyl D-Phenyllactate

Trifluoromethylsulfonic anhydride (1.37 mL, 8.14 mmol) is added to a solution of methyl D-phenyllactate (1.20 g, 6.66 mmol), $CCl_4$ (8.6 mL), and pyridine (0.70 mL, 8.7 mmol) at 0° C. The mixture is stirred for 1 hour at 0° C. and then diluted with pentane (35 mL). The mixture is allowed to warm to room temperature and is filtered. The solids are washed with pentane (35 mL) and the combined filtrates concentrated. Purification by flash chromatography (4:1 hexane:EtOAc) to give 1.39 g (55%) of the title compound as an oil.

$^1$H NMR (300 MHz, $CDCl_3$) δ 7.15–7.40, 5.25, 3.84, 3.35, 3.21.

Step 5.

Preparation of [S-(R*,R*)]$N^3$-tert-Butyl-$N^1$-methyl-3-(2-methylpropyl)-2-oxo-$\alpha^1$-(phenylmethyl)-1,3-pyrrolidinediacetate Sodium hydride (21.4 mg, 0.535 mmol, 60% mineral oil dispersion) is added to a solution of (S)tert-butyl 3-(2-methylpropyl)-2-oxo-3-pyrrolidineacetate (124 mg, 0.486 mmol) and THF (1.65 mL) at 0° C. The solution is stirred for 15 minutes at 0° C. and then a solution of the triflate (166 mg, 0.532 mmol) in 0.5 mL of pentane is added. The solution is stirred for 2 hours at 0° C. and 1 hour at room temperature. Aqueous workup (EtOAc, $MgSO_4$) and purification (4:1 hexane:EtOAc) provides 88.3 mg (44%) of the title compound as an oil.

IR (liq.) 2956, 2933, 1744, 1731, 1693, 1455, 1435, 1393, 1368, 1352, 1269, 1209, 1156, 1155, 700 cm$^{-1}$;

$^1$H NMR (300 MHz, $CDCl_3$) δ 7.15–7.35, 5.14, 3.70, 3.20–3.45, 3.00, 1.95–2.10, 2.08, 1.60–1.80, 1.45–1.55, 1.35–1.45, 1.40, 0.89, 0.86;

MS (EI) m/z 417, 361, 344, 305, 302, 271, 270, 214, 162, 132, 57.

Step 6.

Preparation of [S-(R*,R*)]3-(tert-Butylacetoxy)-3-(2-methylpropyl)-2-oxo-$\alpha^1$-(phenylmethyl)-1-pyrrolidineacetic Acid A mixture of [S-(R*,R*)]-$N^3$-tert-butyl-$N^1$-methyl-3-(2-methylpropyl)-2-oxo-$\alpha^1$-(phenylmethyl)-1,3-pyrrolidinediacetate (254 mg, 0.608 mmol), MeOH (12 mL), water (3.0 mL), and sodium hydroxide (98.4 mg, 2.46 mmol) is stirred at room temperature for 16 hours and then concentrated. The residue is diluted with water, acidified (10% HCl) and the aqueous layer extracted several times with $CH_2Cl_2$. The organic layers are dried ($MgSO_4$), filtered, and concentrated to give 233 mg (95%) of the title compound as an oil.

IR (liq.) 2958, 2933, 2872, 1730, 1693, 1651, 1456, 1443, 1393, 1368, 1273, 1258, 1207, 1155, 699 cm$^{-1}$;

$^1$H NMR (300 MHz, $CDCl_3$) δ 7.20–7.35, 4.67, 3.40, 3.20–3.35, 3.00–3.10, 2.29, 1.95–2.10, 1.80–1.95, 1.60–1.75, 1.52, 1.41, 1.31, 0.91, 0.87;

MS (EI) m/z 403, 347, 330, 303, 302, 291, 256, 200, 132, 57, 55.

Step 7.

[S-(R*,R*)]tert-Butyl $N^1$-Methylacetamide-3-(2-methylpropyl)-2-oxo-$\alpha^1$-(phenylmethyl)-3-pyrrolidineacetate CDI (94.3 mg, 0.582 mmol) is added to a solution of [S-(R*,R*)]3-(tert-butylacetoxy)-3-(2-methylpropyl)-2-oxo-$\alpha^1$-(phenylmethyl)-1-pyrrolidineacetic acid (224 mg, 0.555 mmol) and THF (2.5 mL). The solution is stirred for 1 hour at room temperature and then 0.27 mL of 40% aq methylamine is added. The solution is stirred at room temperature for 16 hours. Aqueous workup (EtOAc, 3% HCl, 10% NaOH and brine washes, $MgSO_4$) gives 259 mg of crude product which is purified by flash chromatography (1:1 hexane:EtOAc) to give 198 mg (86%) of the title compound as an oil.

IR (mineral oil) 3395, 1719, 1682, 1656, 1545, 1442, 1351, 1306, 1274, 1248, 1210, 1150, 1117, 747, 703 cm$^{-1}$;

$^1$H NMR (300 MHz, $CDCl_3$) δ 7.15–7.30, 6.90–7.05, 4.25, 3.41, 3.20–3.35, 2.95–3.10, 2.82, 2.43, 1.95–2.10, 1.75–1.90, 1.50–1.70, 1.43, 1.08, 0.88, 0.81;

MS (EI) m/z 416 (M$^+$) 360, 358, 343, 303, 302, 284, 269, 161, 132, 57.

Step 8.

Preparation of [S-(R*,R*)]$N^1$-Methylacetamide-3-(2-methylpropyl)-2-oxo-$\alpha^1$-(phenylmethyl)-3-pyrrolidineacetic Acid TFA (3.0 mL) is added to a solution of [S-(R*,R*)]tert-butyl $N^1$-methylacetamide-3-(2-methylpropyl)-2-oxo-$\alpha^1$-

(phenylmethyl)-3-pyrrolidineacetate (192 mg, 0.461 mmol) and $CH_2Cl_2$ (3.0 mL) at 0° C. The solution is stirred for 1 hour at 0° C. and for 3 hours at room temperature. The solution is concentrated which is repeated twice more from $CH_2Cl_2$ (2×30 mL). Aqueous workup ($CH_2Cl_2$, $MgSO_4$) provides 158 mg (95%) of the title compound as an oil.

$^1H$ NMR (300 MHz, $CDCl_3$) δ 7.15–7.35, 6.10–6.25, 4.66, 3.25–3.50, 3.17, 2.76, 2.38, 2.00–2.10, 1.60–1.85, 1.53, 1.25–1.40, 0.90, 0.84;

MS (EI) m/z 360, 303, 302, 284, 269, 161, 149, 132, 69, 57, 55.

Step 9.

Preparation of [S-(R*,R*)]-$N^3$-Hydroxy-$N^1$-methyl-3-(2-methylpropyl)-2-oxo-$α^1$-(phenylmethyl)-1,3-pyrrolidinediacetamide EDC (92.2 mg, 0.481 mmol) is added to a solution of [S-(R*,R*)]$N^1$-methylacetamide-3-(2-methylpropyl)-2-oxo-$α^1$-(phenylmethyl)-3-pyrrolidineacetic acid (151 mg, 0.419 mmol), $CH_2Cl_2$ (4.1 mL), DMF (1.0 mL), HOBT (56.4 mg, 0.417 mmol), and N-methylmorpholine (50 μL, 0.46 mmol) at 0° C. The solution is stirred for 5 minutes at 0° C. and 1 hour at room temperature. Hydroxylamine hydrochloride (57.8 mg, 0.832 mmol) and N-methylmorpholine (90 μL, 0.82 mmol) are added and the mixture stirred overnight at room temperature. Aqueous workup ($CH_2Cl_2$, $MgSO_4$) and purification by flash chromatography (20:1 $CH_2Cl_2$:MeOH) provided 74 mg of the hydroxamate as an oil which is crystallized from ether/EtOAc/hexane to give 50 mg (32%) of the title compound as a white crystalline material (mp 159°–184° C.): $[α]_D^{25}$ −84° (c 0.49, $CHCl_3$).

IR (mineral oil) 3372, 3196, 3028, 1687, 1669, 1635, 1605, 1543, 1441, 1404, 1355, 1302, 1287, 747, 703 $cm^{-1}$;

MS (EI) m/z 375, 317, 316, 302, 299, 284, 200, 132, 91, 58, 55.

EXAMPLE 29

Preparation of [R,R-(R*,R*)]-$α^3$-[2-(1,3-Dihydro-1,3-dioxo-2H-isoindol-2-yl)ethyl]-$N^3$-hydroxy-$N^1$-methyl-3-(2-methylpropyl)-2-oxo-$α^1$-(phenylmethyl)-1,3-pyrrolidinediacetamide

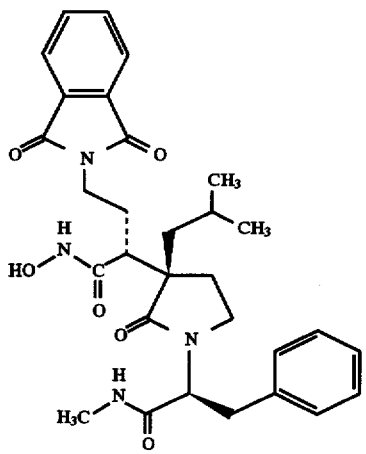

Step 1.

Preparation of (R)tert-Butylmethyl-3-(2-methylpropyl)-2-oxo-$α^1$-(phenylmethyl)-$α^3$-(propen-2-yl)-1,3-pyrrolidinediacetate Sodium hydride (129 mg, 3.23 mmol, 60% mineral oil dispersion) is added to a solution of tert-butyl 3-(2-methylpropyl)-2-oxo-α-(propen-2-yl)-3-pyrrolidineacetate (EXAMPLE 22, step 6; 862 mg, 2.92 mmol) and THF (10 mL) at 0° C. The solution is stirred for 20 minutes at 0° C. and then a solution of the triflate (EXAMPLE 28, step 4; 1.01 g, 3.23 mmol) in 2.0 mL of pentane is added. The solution is stirred for 2 hours at 0° C. and 1.5 hours at room temperature. Aqueous workup (EtOAc, $MgSO_4$) and purification (4:1 hexane:EtOAc) provided 922 mg (69%) of the title compound as an oil which is a mixture of diastereomers.

IR (liq.) 2975, 2956, 2934, 1745, 1724, 1690, 1455, 1435, 1425, 1368, 1288, 1267, 1237, 1210, 1153, $cm^{-1}$;

$^1H$ NMR (300 MHz, $CDCl_3$) major peaks only δ 3.71, 3.70, 1.40, 1.38, 0.89, 0.83, 0.69, 0.56;

MS (EI) m/z 457, 401, 342, 310, 304, 303, 260, 200, 162, 91, 57.

Step 2.

Preparation of (R)3-(tert-Butylacetoxy)-3-(2-methylpropyl)-2-oxo-$α^1$-1-(phenylmethyl)-$α^3$-(propen-2-yl)-1-pyrrolidineacetic Acid A mixture of (R)tert-butylmethyl-3-(2-methylpropyl)-2-oxo-$α^1$-(phenylmethyl)-$α^3$-(propen-2-yl)-1,3-pyrrolidinediacetate (913 mg, 2.00 mmol), MeOH (32 mL), water (8.0 mL), and sodium hydroxide (362 mg, 9.05 mmol) is stirred at room temperature for 16 hours and then concentrated. The residue is diluted with water, acidified (10% HCl), and the aqueous layer extracted several times with $CH_2Cl_2$. The organic layers are dried ($MgSO_4$), filtered, and concentrated to give 829 mg (93%) of the title compound as an oil.

IR (liq.) 3003, 2974, 2959, 2932, 1725, 1692, 1652, 1643, 1455, 1368, 1284, 1272, 1255, 1206, 1153 $cm^{-1}$;

$^1H$ NMR (300 MHz, $CDCl_3$) major peaks only δ 3.57, 2.99, 2.69, 1.40, 1.38, 0.89, 0.85, 0.61, 0.59;

MS (EI) m/z 443, 387, 342, 296, 290, 289, 252, 246, 200, 91, 57.

Step 3.

Preparation of [R,R-(R*,R*)]and [S,R-(S*,S*)]tert-Butyl $N^1$-Methylacetamide-3-(2-methylpropyl)-2-oxo-$α^1$-1-(phenylmethyl)-$α^3$-(propen-2-yl)-3-pyrrolidineacetate CDI (314 mg, 1.94 mmol) is added to a solution of (R)3-(tert-butylacetoxy)-3-(2-methylpropyl)-2-oxo-$α^1$-1-(phenylmethyl)-$α^3$-(propen-2-yl)-1-pyrrolidineacetic acid (821 mg, 1.85 mmol) and THF (8.0 mL). The solution is stirred for 1 hour at room temperature and then 1.1 mL of 40% aq methylamine is added. The solution is stirred at room temperature for 16 hours. Aqueous workup (EtOAc, 3% HCl, 10% NaOH and brine washes, $MgSO_4$) gives 921 mg of crude product which is purified by flash chromatography (1:1 hexane:EtOAc) to give 126 mg of diastereomer A. Further elution provided diastereomer B contaminated by diastereomer A and two minor diastereomers. Repurification of the mixture by flash chromatography (two collures; 1:1 hexane EtOAc) provides an additional 174 mg of diastereomer A (total 300 mg, 36%) as an oil.

IR (mineral oil) 3376, 1702, 1685, 1667, 1538, 1501, 1443, 1433, 1277, 1267, 1249, 1232, 1156, 742, 697 $cm^{-1}$;

MS (EI) m/z 456, 400, 399, 398, 343, 342, 324, 309, 200, 132, 57.

Further elution provided 209 mg (25%) of impure diastereomer B:

IR (liq.) 3328, 2975, 2957, 2934, 1724, 1663, 1554, 1498, 1455, 1438, 1368, 1292, 1266, 1152, 699 $cm^{-1}$;

¹H NMR (300 MHz, CDCl₃) δ 7.10–7.30, 6.25–6.35, 5.50–5.70, 4.90–5.10, 4.64, 3.30–3.45, 3.08, 2.80, 2.71, 2.10–2.40, 1.70–1.90, 1.30–1.65, 0.86, 0.79;

MS (EI) m/z 456, 400, 398, 343, 342, 324, 309, 259, 200, 132, 57.

Step 4.

Preparation of [R,R-(R*,R*)]-tert-Butyl α³-(2-Hydroxyethyl)-N¹-methylacetamide-3-(2-methylpropyl)-2-oxo-α¹-1-(phenylmethyl)-3-pyrrolidineacetate Ozone is passed through a solution of [R,R-(R*,R*)]-tert-butyl N¹-methylacetamide-3-(2-methylpropyl)-2-oxo-α¹-1-(phenylmethyl)-α³-(propen-2-yl)-3-pyrrolidineacetate (EXAMPLE 29, step 3, diastereomer B; 203 mg, 0.445 mmol) and EtOH (4.4 mL) at –78° C. for 4 minutes. After purging with oxygen, sodium borohydride (27 mg, 0.71 mmol) is added. The mixture is stirred at –78° C. for 1 hour and then allowed to slowly warm to room temperature over 1 hour. After 1 hour at room temperature, sodium borohydride (14 mg, 0.37 mmol) is added and the mixture stirred an additional 2 hours at room temperature. Concentration and aqueous workup (EtOAc, MgSO₄) provided 198 mg (97%) of the title compound as an oil which is carried on crude.

IR (liq.) 3320, 2957, 2934, 1722, 1659, 1455, 1437, 1414, 1392, 1368, 1260, 1152, 1057, 734, 699 cm⁻¹;

¹H NMR (300 MHz, CDCl₃) δ 7.10–7.35, 6.15–6.25, 4.64, 2.70, 1.44, 0.86, 0.79;

MS (EI) m/z 460, 346, 328, 132, 105, 91, 81, 69, 58, 57, 55.

Step 5.

Preparation of [R,R-(R*,R*)]-tert-Butyl α³-[2-(1,3-Dihydro-1,3-dioxo-2H-isoindol-2-yl)ethyl]-N¹-methylacetamide-3-(2-methylpropyl)-2-oxo-α¹-1-(phenylmethyl)-3-pyrrolidineacetate DEAD (73.4 uL, 0.446 mmol) is added to a solution of [R,R-(R*,R*)]-tert-butyl α³-(2-hydroxyethyl)-N¹-methylacetamide-3-(2-methylpropyl)-2-oxo-α¹-1-(phenylmethyl)-3-pyrrolidineacetate (195 mg, 0.423 mmol), triphenylphosphine (122 mg, 0.465 mmol), phthalimide (68.1 mg, 0.463 mmol) and THF (5.0 mL). The solution is stirred for 16 hours at room temperature. Concentration and purification by flash chromatography (two collures; 1:1 hexane:EtOAc) give 144 mg (58%) of the title compound as an oil.

¹H NMR (300 MHz, CDCl₃) major peaks δ 7.78–7.90, 7.65–7.75, 7.10–7.35, 6.30–6.40, 4.59, 2.71, 1.49, 0.83, 0.78.

Step 6.

Preparation of [R,R-(R*,R*)]-α³-[2-(1,3-Dihydro-1,3-dioxo-2H-isoindol-2-yl)ethyl]-N³-hydroxy-N¹-methyl-3-(2-methylpropyl)-2-oxo-α¹-1-(phenylmethyl)-1,3-pyrrolidinediacetamide TFA (2.0 mL) is added to a solution of [R,R-(R*,R*)]-tert-butyl α³-[2-(1,3-dihydro-1,3-dioxo-2H-isoindol-2-yl)ethyl]-N¹-methylacetamide-3-(2-methylpropyl)-2-oxo-α¹-1-(phenylmethyl)-3-pyrrolidineacetate (144 mg, 0.244 mmol) and CH₂Cl₂ (2.0 mL) at 0° C. The solution is stirred for 0.5 hours at 0° C. and for 1.5 hours at room temperature. The solution is concentrated which is repeated twice more from CH₂Cl₂ (2×40 mL). Aqueous workup (CH₂Cl₂, MgSO₄) provides 127 mg (97%) of the acid intemediate as an oil.

EDC (52.7 mg, 0.275 mmol) is added to a solution of the crude acid (127 mg, 0.238 mmol), CH₂Cl₂ (2.4 mL), DMF (0.6 mL), HOBT (32.2 mg, 0.238 mmol), and N-methylmorpholine (28.5 μL, 0.259 mmol) at 0° C. The solution is stirred for 5 minutes at 0° C. and 1 hour at room temperature. Hydroxylamine hydrochloride (33.2 mg, 0.478 mmol) and N-methylmorpholine (51 μL, 0.46 mmol) are added and the mixture stirred overnight at room temperature. Aqueous workup (CH₂Cl₂, MgSO₄) and purification by flash chromatography (40:1 EtOAc:MeOH) provides 65.9 mg of the title compound as an oil which is crystallized from ether/hexane to give 45 mg (34%) of the product as a white powder material (mp 176°–180° C.).

IR (mineral oil) 1714, 1672, 1634, 1401 cm⁻¹;

¹H NMR (300 MHz, CDCl₃) δ 7.70–7.90, 7.05–7.35, 6.85–7.00, 6.10–6.20, 4.68, 3.35–3.75, 3.41, 3.23, 2.90–3.10, 2.70, 2.32, 2.10–2.35, 1.30–1.95, 0.82, 0.73;

MS (EI) m/z 548, 430, 429, 302, 259, 244, 200, 185, 160, 130, 56.

EXAMPLE 30

Preparation of [S-(R*,R*)]-N³-Hydroxy-N¹-methyl-3-(2-methylpropyl)-2-oxo-α¹-(phenylmethyl)-1,3-pyrrolidinediacetamide

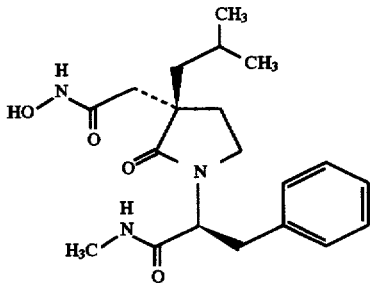

Step 1.

Preparation of (γS)-α-(2-Methylpropen-2-yl)-γ-trityloxymethyl-γ-butyrolactone

Lithium diisopropylamide (10.6 mL, 21.2 mmol, 2.0M, heptane/THF/ethylbenzene) is added to a solution of S-(+)-γ-trityloxymethyl-γ-butyrolactone (6.36 g, 17.6 mmol), THF (51 mL), and HMPA (3.8 mL) at –78° C. After stirring for 30 minutes at –78° C., a solution of 3-bromo-2-methylpropene (1.96 mL, 19.4 mmol) and THF (10.0 mL) is added. The solution is allowed to stir for 4 hours at –78° C. and is then quenched with aqueous ammonium chloride (50 mL). After warming to room temperature, aqueous workup (EtOAc, MgSO₄) provides an oil which is crystallized from hexane/EtOAc (4:1) to give 3.89 g of the title compound as a white solid (mp 134°–135.5° C.). The filtrate is concentrated and purified by flash chromatography (4:1 hexane:EtOAc) to give additional title compound (6.11 g total, 84%):

IR (mineral oil) 1764, 1489, 1216, 1179, 1151, 1102, 1041, 1029, 962, 902, 771, 749, 707, 694, 636 cm⁻¹;

¹H NMR (300 MHz, CDCl₃) δ 7.15–7.50, 4.81, 4.72, 4.50–4.65, 3.45, 3.13, 2.95–3.15, 2.60–2.70, 1.85–2.25, 1.73;

MS (EI) m/z 412, 335, 259, 258, 244, 243, 165, 105, 93, 77, 55.

Step 2.

Preparation of (γS)-α-(2-Methylpropyl)-γ-trityloxymethyl-γ-butyrolactone

A mixture of (γS)-α-(2-methylpropen-2-yl)-γ-trityloxymethyl-γ-butyrolactone (6.10 g, 14.8 mmol), 10%

Pd/C (800 mg) and EtOAc (250 mL) is hydrogenated (42 psi) in a Parr flask at room temperature for 18 hours. The mixture is filtered and the residue washed with EtOAc, $CH_2Cl_2$, and EtOAc. The filtrate is dried ($MgSO_4$), filtered, and concentrated to give 5.67 g (92%) of the title compound as an oil which is a mixture of diastereomers.

IR (liq.) 2956, 2930, 2871, 1773, 1490, 1449, 1227, 1172, 1093, 1033, 974, 767, 747, 706, 633 $cm^{-1}$;

$^1$H NMR (300 MHz, $CDCl_3$) δ 7.15–7.50, 4.50–4.65, 3.44, 3.12, 2.80–2.95, 2.15–2.30, 1.85–2.00, 1.60–1.85, 1.20–1.40, 0.95, 0.91;

MS (EI) m/z 414, 337, 259, 258, 244, 243, 165, 109, 105, 77, 69.

Step 3.

Preparation of [S-(R*,R*)]-α-(2-Methylpropyl)-α-(propen-2-yl)-γ-trityloxymethyl-γ-butyrolactone Lithium diisopropylamide (8.3 mL, 16.6 mmol, 2.0M, heptane/THF/ethylbenzene) is added to a solution of (γS)-α-(2-methylpropyl)-γ-trityloxymethyl-γ-butyrolactone (5.67 g, 13.7 mmol), THF (50 mL), and HMPA (2.9 mL) at −78° C. After stirring for 30 minutes at −78° C., a solution of allyl bromide (1.46 mL, 16.9 mmol) and THF (8.0 mL) is added. The solution is allowed to stir for 4 hours at −78° C. and is then quenched with aqueous ammonium chloride (50 mL). After warming to room temperature, aqueous workup (EtOAc, $MgSO_4$) and purification by flash chromatography (6:1 hexane:EtOAc) to give 5.12 g of the title compound (82%) as a white powder (mp 84°–85° C.).

IR (mineral oil) 1770, 1489, 1184, 1119, 1089, 1070, 1034, 1027, 1002, 991, 775, 754, 704, 632 $cm^{-1}$;

$^1$H NMR (300 MHz, $CDCl_3$) δ 7.15–7.50, 5.65–5.85, 5.10–5.20, 4.40–4.55, 3.15–3.35, 2.20–2.40, 1.90–2.15, 1.45–1.80, 0.92, 0.85;

MS (EI) m/z 454, 377, 259, 258, 244, 243, 165, 109, 105, 77, 55.

Step 4.

Preparation of [S-(R*,R*)]-α-(2-Methylpropyl)-α-(propen-2-yl)-γ-hydroxymethyl-γ-butyrolactone TFA (15.0 mL) is added to a solution of [S-(R*,R*)]-α-(2-methylpropyl)-α-(propen-2-yl)-γ-trityloxymethyl-γ-butyrolactone (2.09 g, 4.60 mmol) and $CH_2Cl_2$ (30.0 mL) at 0° C. The solution is stirred for 75 minutes at 0° C. and is concentrated. Aqueous workup ($CH_2Cl_2$, $MgSO_4$) and purification by flash chromatography (1:1 hexane:EtOAc) provides 684 mg (70%) of the title compound as an oil.

IR (liq.) 3434, 2958, 2932, 2872, 1767, 1368, 1191, 1140, 1101, 1075, 1058, 1034, 998, 923, 622 $cm^{-1}$;

$^1$H NMR (300 MHz, $CDCl_3$) δ 5.70–5.90, 5.10–5.25, 4.45–4.55, 3.89, 3.60, 2.00– 2.50, 1.60–1.90, 1.52, 0.96, 0.89;

MS (EI) m/z 212, 156, 111, 109, 93, 81, 69, 67, 55, 43, 41.

Step 5.

Preparation of [R*,R*]α-(2-Methylpropyl)-α-(propen-2-yl)-γ-hydroxy-γ-butyrolactone A mixture of [S-(R*,R*)]-α-(2-methylpropyl)-α-(propen-2-yl)-γ-hydroxymethyl-γ-butyrolactone (682 mg, 3.21 mmol), NaOH (350 mg, 8.75 mmol), THF (40 mL), and $H_2O$ (10 mL) is stirred for 19 hours at room temperature. Additional NaOH (114 mg, 2.85 mmol) is added after 16 hours. The mixture is concentrated and the residue taken up into MeOH (43 mL). A solution of sodium periodate (862 mg, 4.03 mmol) and $H_2O$ (4.3 mL) is added and the mixture stirred at room temperature for 3 hours. After concentration, the aqueous residue is acidified (HCl) and extracted with $CH_2Cl_2$ (3×40 mL). The organic layers are dried ($MgSO_4$), filtered, and concentrated to provide 625 mg (98%) of the title compound as a semi-solid.

IR (liq.) 3389, 2959, 2933, 2873, 1769, 1747, 1746, 1369, 1186, 1170, 1129, 988, 963, 944, 926 $cm^{-1}$;

$^1$H NMR (300 MHz, $CDCl_3$) δ 5.60–5.90, 5.10–5.25, 3.30–3.50, 1.45–2.55, 0.85–1.00;

MS (EI) m/z 142, 113, 97, 95, 67, 57, 55, 43, 41, 39.

Step 6.

Preparation of L-Phenylalanine Methyl Amide

CDI (545 mg, 3.36 mmol) is added to a solution of CBZ-L-phenylalanine (1.00 g, 3.34 mmol) and THF (12.5 mL). The solution is stirred for 1 hour at room temperature and then 40% aqueous methylamine (1.5 mL) is added. The solution is stirred for 16 hours at room temperature. The solution is diluted with EtOAc and is washed with $NaHCO_3$, 10% HCl, $NaHCO_3$, and brine. The organic layer is dried ($MgSO_4$), filtered, and concentrated to give 983 mg (94%) of the carbamate intermediate as a white solid.

$^1$H NMR (300 MHz, $CDCl_3$) δ 7.10–7.40, 5.50–5.65, 5.25–5.40, 5.07, 4.33, 2.95–3.20, 2.70.

Ammonium formate (644 mg, 10.2 mmol) is added to a mixture of the carbamate (980 mg, 3.14 mmol), MeOH (21 mL), and 10% Pd/C (104 mg). The mixture is stirred for 1 hour at room temperature and is filtered. The residue is washed with MeOH, $CH_2Cl_2$, and is concentrated. The residue is diluted with 30:1 $CH_2Cl_2$:MeOH (30 mL), dried ($MgSO_4$), filtered, and concentrated to provide 504 mg (90%) of the title compound as a foam which is carried on crude.

$^1$H NMR (300 MHz, $CDCl_3$) δ 8.12, 7.15–7.40, 4.07, 3.72, 3.26, 2.65–2.85, 2.78.

Step 7.

Preparation of [S-(R*,R*)]Methyl-3-(2-methylpropyl)-2-oxo-α-(phenylmethyl)-3-(propen-2-yl)-1-pyrrolidineacetamide A solution of L-phenylalanine methyl amide (EXAMPLE 30, step 6; 210 mg, 1.18 mmol) and MeOH (8.5 mL) is added to [R*,R*]α-(2-methylpropyl)-α-(propen-2-yl)-γ-hydroxy-γ-butyrolactone (EXAMPLE 30, step 5; 200 mg, 1.01 mmol). Sodium cyanoborohydride (85.0 mg, 1.35 mmol) is added and the solution stirred for 16 hours at room temperature. Concentration and aqueous workup (20:1 $CHCl_3$:MeOH, $MgSO_4$) provided 397 mg of the uncyclized intermediate as an oil. A mixture of the crude residue, toluene (24 mL), MeOH (8.0 mL), and silica gel (800 mg) is slowly heated to reflux allowing the MeOH to boil off. The mixture is then maintained at reflux for 3 hours and is allowed to cool to room temperature. The mixture is filtered, the solids washed with 20:1 $CH_2Cl_2$:MeOH (3×40 mL), and the filtrate concentrated. Purification by flash chromatography (EtOAc) provided 218 mg (63%) of the title compound as an oil.

IR (liq.) 3314, 2955, 2929, 2871, 1661, 1660, 1558, 1498, 1455, 1439, 1413, 1296, 1267, 741, 698 $cm^{-1}$;

$^1$H NMR (300 MHz, $CDCl_3$) δ 7.15–7.35, 6.15–6.30, 5.10–5.35, 4.75–5.00, 3.15–3.40, 3.07, 2.74, 2.00–2.15, 1.55–2.00, 1.35–1.55, 0.90, 0.81;

MS (EI) m/z 342, 311, 299, 285, 284, 162, 132, 105, 91, 81, 67, 58, 55.

Step 8.

Preparation of [S-(R*,R*)]N¹-Methylacetamide-3-(2-methylpropyl)-2-oxo-α¹-(phenylmethyl)-3-pyrrolidineacetic Acid Ruthenium(IV) oxide hydrate (17.3 mg, 0.130 mmol) is added to a mixture of sodium periodate (1.07 g, 5.00 mmol), $H_2O$ (14.0 mL), $CH_3CN$ (14.0 mL), and $CCl_4$ (14.0 mL). The mixture is stirred for 20 minutes at room temperature and then $NaHCO_3$ (1.32 g, 15.7 mmol) and $H_2O$ (7.0 mL) are added. After stirring an additional 5 minutes, a solution of [S-(R*,R*)]-methyl-3-(2-methylpropyl)-2-oxo-α-(phenylmethyl)-3-(propen-2-yl)-1-pyrrolidineacetamide (215 mg, 0.628 mmol) and $CH_3CN$ (6.0 mL) is added. After stirring for 8 minutes at room temperature, the residue is poured into a mixture of $H_2O$ (40 mL) and EtOAc (100 mL). The aqueous layer is removed and the organic layer extracted with 10% NaOH (2×15 mL). The combined basic layers are acidified (4N HCl) and extracted with $CH_2Cl_2$ (3×50 mL). The $CH_2Cl_2$ layers are dried ($MgSO_4$), filtered, and concentrated to provide 109 mg (48%) of the title compound as an oil.

IR (liq.) 3347, 3029, 2957, 2872, 1724, 1657, 1552, 1498, 1455, 1440, 1413, 1296, 1271, 1193, 700 $cm^{-1}$;

$^1H$ NMR (300 MHz, $CDCl_3$) δ 7.10–7.40, 6.81, 4.54, 3.15–3.50, 2.73, 2.45, 1.80– 2.05, 1.55–1.75, 1.40–1.55, 1.24, 0.89, 0.82;

MS (EI) m/z 360, 303, 302, 284, 269, 244, 200, 161, 132, 91, 55.

Step 9.

Preparation of [S-(R*,R*)]-N³-Benzyloxy-N¹-methyl-3-(2-methylpropyl)-2-oxo-α¹-(phenylmethyl)-1,3-pyrrolidinediacetamide CDI (59.0 mg, 0.364 mmol) is added to a solution of [S-(R*,R*)]N¹-methylacetamide-3-(2-methylpropyl)-2-oxo-α¹(phenylmethyl)-3-pyrrolidineacetic acid (109 mg, 0.302 mmol) and $CH_2Cl_2$ (2.3 mL). The solution is stirred for 1 hour at room temperature and then O-benzylhydroxylamine hydrochloride (70.0 mg, 0.439 mmol) and N-methylmorpholine (0.06 mL, 5.5 mmol) are added. The solution is stirred for 16 hours at room temperature. Aqueous workup ($CH_2Cl_2$, $MgSO_4$) and purification by flash chromatography (EtOAc) provides 82.4 mg (59%) of the title compound as an oil.

IR (liq.) 3213, 3031, 2957, 2872, 1662, 1545, 1498, 1455, 1441, 1412, 1368, 1295, 1280, 750, 699 $cm^{-1}$;

$^1H$ NMR (300 MHz, $CDCl_3$) δ 8.85–9.00, 7.10–7.50, 6.40–6.55, 4.75–5.00, 4.40–4.55, 3.10–3.45, 2.75, 2.15–2.30, 1.80–2.15, 1.40–1.65, 1.10–1.30, 0.87, 0.79;

MS (EI) m/z 465, 407, 284, 132, 105, 92, 91, 77, 69, 58, 55.

Step 10.

Preparation of [S-(R*,R*)]-N³-Hydroxy-N¹-methyl-3-(2-methylpropyl)-2-oxo-α¹-(phenylmethyl)-1,3-pyrrolidinediacetamide An atmosphere of hydrogen is placed over a mixture of [S-(R*,R*)]-N³-benzyloxy-N¹-methyl-3-(2-methylpropyl)-2-oxo-α¹-(phenylmethyl)-1,3-pyrrolidinediacetamide (79.2 mg, 0.170 mmol), MeOH (4.0 mL) and 10% Pd/C (15 mg). After stirring for 4 hours at room temperature, the mixture is filtered, the solids washed with MeOH (4×5 mL) and $CH_2Cl_2$ (5 mL), and the combined filtrate concentrated to provide 41 mg of the desired product as an oil. Trituration (ether/hexane) provides 39.4 mg (62%) of the title compound as a white powder (mp 162°–165° C.): $[α]_D^{25}$ –96° (c 0.26, $CHCl_3$).

IR (mineral oil) 3372, 3195, 3028, 1687, 1669, 1636, 1605, 1542, 1441, 1405, 1355, 1302, 1287, 747, 704 $cm^{-1}$;

$^1H$ NMR (300 MHz, $CDCl_3$) δ 7.15–7.40, 6.50–6.65, 4.50–4.65, 3.10–3.50, 2.78, 2.32, 1.90–2.15, 1.45–1.80, 1.20–1.35, 0.90, 0.83;

MS (EI) m/z 375, 317, 302, 301, 299, 284, 244, 200, 132, 91, 55.

EXAMPLE 31

Preparation of [S-(R*,R*)]-N³-Hydroxy-3-(2-methylpropyl)-2-oxo-N¹-(2-phenethyl)-α¹-(phenylmethyl)-1,3-pyrrolidinediacetamide

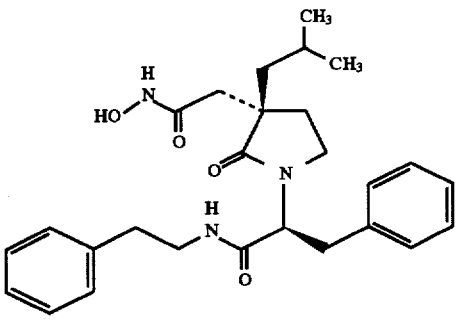

Following the general procedure of EXAMPLE 30 and making non-critical variations but starting with [R*,R*]α-(2-methylpropyl)-α-(propen-2-yl)-γ-hydroxy-γ-butyrolactone (EXAMPLE 30, Step 5) and L-phenylalanine phenethyl amide (prepared similarly to that described in EXAMPLE 30, Step 6), the title compound is obtained (mp 158°–159° C.).

$[α]_D^{25}$ –83° (c 0.35, $CHCl_3$);

IR (mineral oil) 3219, 3087, 3063, 3029, 1668, 1644, 1558, 1498, 1354, 1311, 1297, 1283, 749, 743, 701 $cm^{-1}$;

$^1H$ NMR (300 MHz, $CDCl_3$) δ 9.63, 7.00–7.40, 6.31, 4.59, 3.30–3.60, 3.00–3.20, 2.65–2.85, 2.14, 1.85–2.10, 1.40–1.75, 1.25, 0.87, 0.80;

MS (EI) m/z 465, 318, 317, 316, 284, 200, 132, 105, 91, 55.

EXAMPLE 32

Preparation of [S-(R*,R*)]-N³-Hydroxy-N¹-methyl-α¹,3-bis(2-methylpropyl)-2-oxo-1,3-pyrrolidinediacetamide

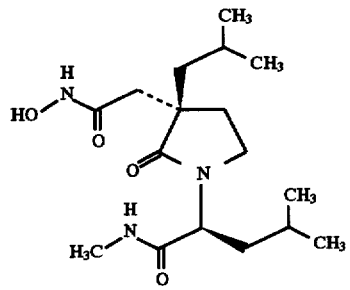

Following the general procedure of EXAMPLE 30 and making non-critical variations but starting with [R*,R*]α-

(2-methylpropyl)-α-(propen-2-yl)-γ-hydroxy-γ-butyrolactone (EXAMPLE 30, Step 5) and L-leucine methyl amide (prepared similarly to that described in EXAMPLE 30, Step 6), the title compound is obtained (mp 138°–139° C.).

$[\alpha]_D^{25}$ +117° (c 0.28, CHCl₃);

IR (mineral oil) 3376, 3198, 3023, 1689, 1676, 1639, 1543, 1493, 1406, 1355, 1304, 1281, 1195, 1166 cm⁻¹;

¹H NMR (300 MHz, CDCl₃) δ 9.91, 6.31, 4.35–4.50, 3.30–3.55, 2.76, 2.44, 2.20–2.40, 2.00–2.15, 1.35–1.90, 0.75–1.00;

MS (EI) m/z 341, 310, 284, 283, 282, 251, 250, 222, 98, 86, 55.

EXAMPLE 33

Preparation of [S-(R*,R*)]-α¹-(Cyclohexylmethyl)-N³-hydroxy-N¹-methyl-3-(2-methylpropyl)-2-oxo-1,3-pyrrolidinediacetamide

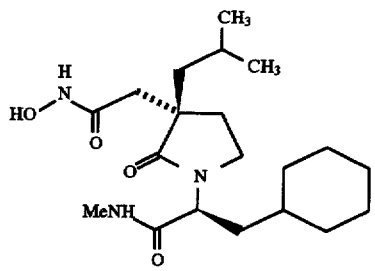

Following the general procedure of EXAMPLE 30 and making non-critical variations but starting with [R*,R*]α-(2-methylpropyl)-α-(propen-2-yl)-γ-hydroxy-γ-butyrolactone (EXAMPLE 30, Step 5) and β-cyclohexyl-L-alanine methyl amide (prepared similarly to that described in EXAMPLE 30 Step 6), the title compound is obtained (mp 150°–152° C.).

IR (mineral oil) 3253, 3194, 3058, 1678, 1643, 1544, 1502, 1409, 1285, 1268, 1259, 1228, 1048, 738, 647 cm⁻¹;

¹H NMR (300 MHz, CDCl₃) δ 6.52, 4.42, 3.30–3.55, 2.77, 2.44, 2.20–2.35, 1.95–2.15, 1.98, 1.35–1.90, 0.75–1.35, 0.92, 0.86;

MS (EI) m/z 381, 324, 323, 322, 290, 208, 86, 67.

EXAMPLE 34

Preparation of [S-(R*,R*)]-N³-Hydroxy-N¹-methyl-3-(3-methylbutyl)-2-oxo-α¹-(phenylmethyl)-1,3-pyrrolidinediacetamide

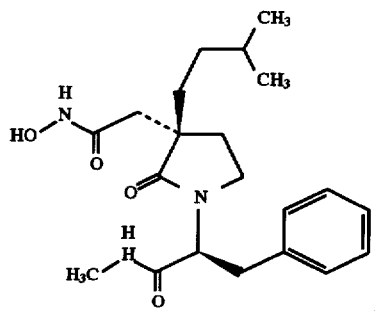

Following the general procedure of EXAMPLE 30 and making non-critical variations but starting with [R*,R*]α-(3-methylbutyl)-α-(propen-2-yl)-γ-hydroxy-γ-butyrolactone (prepared similarly to that described in EXAMPLE 30, Steps 1–5) and L-phenylalanine methyl amide (EXAMPLE 30, step 6), the title compound is obtained (mp 167°–168° C.).

$[\alpha]_D^{25}$ −104° (c 0.43, CHCl₃);

IR (mineral oil) 3372, 3195, 3064, 3029, 1687, 1670, 1635, 1545, 1497, 1443, 1405, 1297, 1287, 745, 701 cm⁻¹;

¹H NMR (300 MHz, CDCl₃) δ 9.50–9.80, 7.10–7.40, 6.92, 4.40–4.50, 3.10–3.45, 2.79, 2.23, 1.90–2.20, 1.70–1.90, 1.05–1.55, 0.75–1.00;

MS (FAB) m/z 390, 389, 374, 357, 331, 298, 132.

EXAMPLE 35

Preparation of N-Hydroxy-3-(2-methylpropyl)-2,5-dioxo-1-(2-phenylethyl)-3-pyrrolidineacetamide

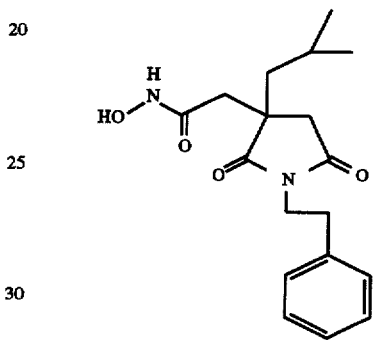

Step 1.

Preparation of Ethyl 3-(2-Methylpropyl)-2,5-dioxo-1-(2-phenylethyl)-3-pyrrolidineacetate Ruthenium(IV) oxide hydrate (27 mg, 0.20 mmol) is added to a mixture of ethyl 3-(2-methylpropyl)-2-oxo-1-(2-phenylethyl)-3-pyrrolidineacetate (prepared similarly to that described in EXAMPLE 1, steps 1–3; 900 mg, 2.71 mmol), sodium periodate (2.71 g, 12.7 mmol), water (27 mL), and CCl₄ (27 mL) at room temperature. After stirring overnight at room temperature, aqueous workup (CH₂Cl₂, MgSO₄) and purification by column chromatography (20% EtOAc/hexane) gives 611 mg of the title compound (65%) as a colorless oil.

IR (liq.) 2959, 1775, 1733, 1704, 1455, 1438, 1403, 1368, 1346, 1255, 1218, 1193, 1165, 1030, 699 cm⁻¹;

¹H NMR (300 MHz, CDCl₃) δ 7.15–7.35, 4.09, 3.65–3.85, 2.50–3.00, 1.35–1.80, 1.22, 0.91, 0.85;

MS (EI) m/z 345, 300, 289, 259, 203, 105, 104.

Step 2.

Preparation of 3-(2-Methylpropyl)-2,5-dioxo-1-(2-phenylethyl)-3-pyrrolidineacetic Acid Sodium hydroxide (283 mg, 7.08 mmol) is added to a mixture of ethyl 3-(2-methylpropyl)-2,5-dioxo-1-(2-phenylethyl)-3-pyrrolidineacetate (611 mg, 1.77 mmol), methanol (10 mL), and water (5 mL), and the mixture is allowed to stir overnight at room temperature. The mixture is partitioned with 10 ml of water and 10 mL of Et₂O. The layers are separated and the pH of the aqueous layer was adjusted to pH 2 (pH meter) with 1.2N HCl. The aqueous layer is extracted with EtOAc (2×10 mL) and CH₂Cl₂ (2×10 mL), and the combined organic layers are dried (MgSO₄), filtered and concentrated to give 500 mg (89%) of the title compound as a white foam which is carried on crude.

$^1$H NMR (300 MHz, CDCl$_3$) δ 7.10–7.40, 3.30–3.85, 2.50–2.95, 1.10–1.85, 0.75–1.00.

Step 3.

Preparation of N-Benzyloxy-3-(2-methylpropyl)-2,5-dioxo-1-(2-phenylethyl)-3-pyrrolidineacetamide CDI (153 mg, 0.945 mmol) is added to a mixture of 3-(2-methylpropyl)-2,5-dioxo-1-(2-phenylethyl)-3-pyrrolidineacetic acid (300 mg, 0.945 mmol) and CH$_2$Cl$_2$ (7.5 mL) at room temperature. Afar stirring at room temperature for 1 hour, O-benzylhydroxylamine hydrochloride (181 mg, 1.13 mmol) and 4-methylmorpholine (124 μL, 1.13 mmol) are added to the solution. The mixture is allowed to stir overnight at room temperature. Basic workup (CH$_2$Cl$_2$, NaHCO$_3$, MgSO$_4$) and purification by column chromatography (1.5% MeOH/CHCl$_3$) affordes 70 mg (18%) of the title compound as a white solid (mp 115°–117° C.).

IR (mineral oil) 3195, 1705, 1677, 1659, 1409, 1357, 1182, 1169, 1018, 773, 752, 707, 700, 693, 627 cm$^{-1}$;

$^1$H NMR (300 MHz, CDCl$_3$) δ 8.53, 8.10–8.30, 7.10–7.45, 4.704.90, 3.60–3.80, 2.65–2.95, 2.10–2.65, 1.25–1.60, 0.86, 0.79;

MS (EI) m/z 422, 389, 366, 300, 260, 229, 194, 179, 125, 105, 104, 91.

Step 4.

Preparation of N-Hydroxy-3-(2-methylpropyl)-2,5-dioxo-1-(2-phenylethyl)-3-pyrrolidineacetamide A mixture of N-benzyloxy-3-(2-methylpropyl)-2,5-dioxo-1-(2-phenylethyl)-3-pyrrolidineacetamide (80 mg, 0.19 mmol), Pd/C (10%, 5 mg), ammonium formate (59 mg, 0.95 mmol) and EtOH (2.5 mL) is stirred at room temperature. After 2 hours, a second portion of ammonium formate (35 mg, 0.56 mmol) is added and the mixture is allowed to stir overnight at room temperature. The mixture is filtered, and the filter cake washed with MeOH (3×15 mL) and CHCl$_3$ (3×15 mL). The filtrate is concentrated, reconstituted in 100 mL of 5% MeOH/CHCl$_3$, dried (MgSO$_4$), filtered and concentrated to an oil. Crystallization from CH$_2$Cl$_2$/Et$_2$O/ hexane gives 19 mg (31%) of the title compound as a white solid (mp 136°–137° C.).

IR (mineral oil) 3316, 3087, 3065, 3027, 1702, 1634, 1563, 1498, 1420, 1229, 1213, 1164, 1083, 1048, 698 cm$^{-1}$;

$^1$H NMR (300 MHz, CDCl$_3$) δ 7.10–7.40, 5.63, 3.50, 2.65–2.90, 2.71, 2.54, 1.45–1.90, 0.92, 0.87;

MS (EI) m/z 332, 300, 276, 259, 241, 212, 196, 184, 142, 109, 105, 104, 103, 91.

EXAMPLE 36

Preparation of N-Hydroxy-3-methyl-4-(2-methylpropyl)-2,5-dioxo-1-(2-phenylethyl)-4-imidazolidineacetamide

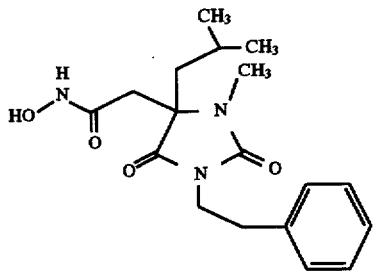

Step 1.

Preparation of 3-Methyl-1-(2-phenylethyl)hydantoin

Sodium hydride (921 mg, 23.0 mmol, 60% mineral oil dispersion) is added to a solution of 1-methylhydantoin (2.19 g, 19.2 mmol) and DMF (40 mL) at 0° C. The mixture was stirred for 1 hour and then (2-bromoethyl)benzene (3.14 mL, 23.0 mmol) is added. The mixture is stirred at 0° C. for 1 hour and 16 hours at room temperature. Aqueous workup (EtOAc, MgSO$_4$) and trituration with ether provides 2.21 g (53%) of the title compound as a white solid (mp 113°–114° C.).

IR (mineral oil) 1768, 1758, 1748, 1713, 1488, 1441, 1403, 1340, 1290, 1243, 1134, 995, 989, 748, 704 cm$^{-1}$;

$^1$H NMR (300 MHz, CDCl$_3$) δ 7.15–7.35, 3.82, 3.70–3.80, 2.99, 2.85–3.00;

MS (EI) m/z 218, 105, 104, 99, 91, 78, 65, 57, 56, 51.

Step 2.

Preparation of 3-Methyl-4-(2-methylpropyl)-1-(2-phenylethyl)hydantoin

Lithium diisopropylamide (3.45 mL, 6.90 mmol, 2.0M, heptane/THF/ethylbenzene) is added to a mixture of 3-methyl-1-(2-phenylethyl)hydantoin (1.50 g, 6.87 mmol) and THF (27 mL) at −78° C. After stirring for 30 minutes at −78° C., 1-iodo-2-methylpropane (0.93 mL, 8.08 mmol) is added. The mixture is stirred at −78° C. for 30 minutes and is allowed to gradually warm to room temperature. After stirring at room temperature for 1 hour, aqueous workup (EtOAc, MgSO$_4$) and purification by flash chromatography (1:1 hexane:EtOAc) gives 467 mg of the title compound (25%) as an oil. Further elution provides 704 mg of recovered starting material (47% of product based on recovered starting material). Spectral data for the title compound.

IR (liq.) 2958, 2936, 2871, 1771, 1712, 1498, 1454, 1429, 1412, 1389, 1368, 1142, 1030, 753, 701 cm$^{-1}$;

$^1$H NMR (300 MHz, CDCl$_3$) δ 7.15–7.35, 3.65–3.85, 2.85–3.00, 2.93, 1.50–1.90, 0.91;

MS (EI) m/z 274, 218, 127, 114, 105, 104, 91, 43, 41.

Step 3.

Preparation of 3-Methyl-4-(2-methylpropyl)-2,5-dioxo-1-(2-phenylethyl)-4-imidazolidineacetic Acid Lithium diisopropylamide (0.84 mL, 1.7 mmol, 2.0M, heptane/THF/ethylbenzene) is added to a solution of 3-methyl-4-(2-methylpropyl)-1-(2-phenylethyl)hydantoin (464 mg, 1.69 mmol) and THF (7.0 mL) at −78° C. After stirring the partial solution for 30 minutes at −78° C., ethyl bromoacetate (0.23 mL, 2.1 mmol) is added. The mixture is stirred for 1 hour at −78° C. and is then allowed to warm to room temperature. After stirring at room temperature for 1 hour, aqueous workup (EtOAc, MgSO$_4$) and purification by flash chromatography (3:1 hexane:EtOAc) gives 407 mg of a 1.25:1 mixture of starting material and the ester intermediate. The mixture could not be purified by chromatography and is carried on crude. Key spectral features for the ester intermediate: $^1$H NMR (300 MHz, CDCl$_3$) δ 4.00–4.15, 2.84, 1.19, 0.81.

A mixture of the crude ester (407 mg), MeOH (12 mL), H$_2$O (2.5 mL) and NaOH (213 mg, 5.33 mmol) is stirred at room temperature for 16 hours and is concentrated. The residue is partitioned between EtOAc and 10% NaOH. The organic layer is dried (MgSO$_4$), filtered, and concentrated to give 250 mg of starting material. The basic layer is acidified (10% HCl) and extracted several times with CH$_2$Cl$_2$. The CH$_2$Cl$_2$ layers are dried (MgSO$_4$), filtered, and concentrated to give 117 mg (21%, 45% based on recovered starting material) of the title compound as a white solid (mp 64°–67° C.).

IR (mineral oil) 3505, 3374, 1761, 1699, 1499, 1414, 1404, 1336, 1325, 1230, 1136, 1036, 1031, 736, 697 cm$^{-1}$;

$^1$H NMR (300 MHz, CDCl$_3$) δ 7.15–7.35, 3.70–3.80, 2.80–3.00, 2.85, 2.78, 1.73, 1.55, 1.20–1.40, 0.84, 0.78;

MS (EI) m/z 332, 276, 275, 273, 241, 231, 105, 104, 91, 56.

Step 4.

Preparation of N-Benzyloxy-3-methyl-4-(2-methylpropyl)-2,5-dioxo-1-(2-phenylethyl)-4-imidazolidineacetamide CDI (57.0 mg, 0.352 mmol) is added to a solution of 3-methyl-4-(2-methylpropyl)-2,5-dioxo-1-(2-phenylethyl)-4-imidazolidineacetic acid (113 mg, 0.340 mmol) and CH$_2$Cl$_2$ (2.5 mL). The solution is stirred for 1 hour at room temperature and then O-benzyl hydroxylaminehydrochloride (67.0 mg, 0.420 mmol) and N-methylmorpholine (46 μL, 0.42 mmol) are added. The solution is stirred for 60 hours at room temperature. Basic workup (CH$_2$Cl$_2$, NaHCO$_3$, MgSO$_4$) and purification by flash chromatography (1:1 hexane:EtOAc) provides 94.8 mg (64%) of the title compound as a white solid.

IR (mineral oil) 3198, 3012, 1771, 1713, 1681, 1653, 1522, 1498, 1432, 1414, 1394, 1359, 758, 738, 696 cm$^{-1}$;

$^1$H NMR (300 MHz, CDCl$_3$) δ 8.35–8.55, 7.15–7.50, 4.70–4.90, 3.74, 2.96, 2.84, 2.60–2.90, 2.38, 1.69, 1.45–1.65, 1.20–1.40, 0.80, 0.65–0.85;

MS (EI) m/z 437, 363, 273, 231, 169, 105, 104, 92, 91, 56.

Step 5.

Preparation of N-Hydroxy-3-methyl-4-(2-methylpropyl)-2,5-dioxo-1-(2-phenylethyl)-4-imidazolidineacetamide Ammonium formate (59.0 mg, 0.936 mmol) is added to a mixture of N-benzyloxy-3-methyl-4-(2-methylpropyl)-2,5-dioxo-1-(2-phenylethyl)-4-imidazolidineacetamide (91.0 mg, 0.208 mmol), EtOH (2.5 mL), and 10% Pd/C (15 mg). The mixture is stirred at room temperature for 5.5 hours. Additional ammonium formate (35.0 mg, 0.555 mmol) is added after 2.5 hours. The mixture is filtered, the solids washed with MeOH (3×15 mL) and CHCl$_3$ (3×15 mL), and the filtrate concentrated. The residue was taken up into CHCl$_3$ (40 mL), dried (MgSO$_4$), filtered, and concentrated to give 64.7 mg (90%) of the title compound as an oil. Crystallization from ether/hexane provided 46.4 mg (64%) of the title compound as a white powder (mp 127°–129° C.).

IR (mineral oil) 3223, 3025, 1771, 1701, 1690, 1661, 1497, 1416, 1394, 1359, 1136, 1027, 742, 737, 698 cm$^{-1}$;

$^1$H NMR (300 MHz, CDCl$_3$) δ 9.55, 7.10–7.30, 3.60–3.85, 2.92, 2.81, 2.55, 1.45–1.75, 1.15–1.35, 0.76, 0.73;

MS (EI) m/z 347, 274, 273, 231, 169, 105, 104, 56.

EXAMPLE 37

Preparation of N-Hydroxy-4-(2-methylpropyl)-2,5-dioxo-1-(2-phenylethyl)-4-imidazolidineacetamide

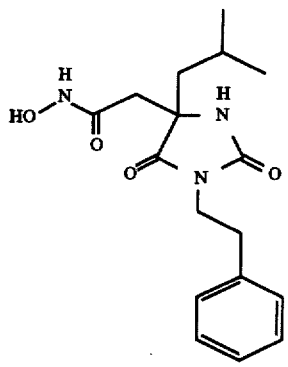

Step 1.

Preparation of 4-(2-Methylpropyl)-2,5-dioxo-1-(2-phenylethyl)-4-imidazolidineacetic Acid Sodium hydroxide (300 mg, 7.50 mmol) is added to a solution of 2-(2-methylpropyl)-2-(propen-2-yl)glycine trifluoroacetic acid (856 mg, 3.00 mmol) which is prepared by the method described in J. Org. Chem., 1988, Vol. 53, p. 5607 and H$_2$O (10 mL). Phenethyl isocyanate (541 mg, 3.00 mmol) is added after 5 minutes and the mixture stirred for 1 hour at room temperature under N$_2$. The solution is diluted with more H$_2$O (5 mL) and acidified with 6N HCl. The resultant solution is heated at reflux for 2 hours. Upon cooling to room temperature, the desired product is extracted into CH$_2$Cl$_2$ (3×50 mL) and EtOAc (2×50 mL). The combined organic layers are dried over anhydrous Na$_2$SO$_4$, filtered, and concentrated under reduced pressure to yield 619 mg of a golden oil. The oil is purified by silica gel chromatography (50 g SG, packed and eluted with a gradient of 0–40% EtOAc/hexane) to give 162 mg (18%) of the hydantoin intermediate as an oil. The material is sufficiently pure to be carried on: $^1$H NMR (300 MHz, CDCl$_3$) δ 7.90–8.60, 7.20–7.40, 5.75–5.95, 5.25–5.40, 3.15–3.30, 3.05–3.15, 2.60–2.90, 1.80–2.00, 0.90–1.05.

Sodium periodate (NaIO$_4$, 883 mg, 4.13 mmol) is added to a mixture of H$_2$O/CH$_3$CN/CCl$_4$ (3/3/2 mL, respectively) and treated with ruthenium oxide monohydrate (14 mg, 20 mole %). Once the black solution has turned green, NaHCO$_3$ (2.17 g, 25.8 mmol) is added, followed by the further addition of NaIO$_4$ until the solution became green again. A solution of the hydantoin intermediate (155 mg, 0.516 mmol) in 3 mL CH$_3$CN is added to the green mixture. After 5 minutes, the reaction mixture is quenched with H$_2$O and extracted with EtOAc several times. The aqueous layer is acidified with 6N HCl and then extracted twice with CH$_2$Cl$_2$ (2×) and EtOAc (2×). The organic layers are combined, washed again with brine, dried over anhydrous Na₂SO₄, filtered, and concentrated under reduced pressure to yield 79 mg of the title compound as a solid. Additional title compound is recovered by washing the original EtOAc extracts with 10% NaOH, acidifying the aqueous with 6N HCl, and re-extracting with CH₂Cl₂ (3×). These extracts are also combined, washed again with brine, dried over anhydrous Na₂SO₄, filtered, and concentrated under reduced pressure to yield an additional 64 mg of the title compound. Both crops are dissolved in CH₂Cl₂, combined, filtered through a fine frit, and concentrated under reduced pressure to give a total of 143 mg (87%) of the title compound as a solid.

¹H NMR (300 MHz, CDCl₃) δ 7.10–7.35, 3.70–3.80, 2.95, 2.66, 1.65–1.80, 1.40–1.55, 0.88, 0.80.

Step 2.

Preparation of N-Benzyloxy-4-(2-methylpropyl)-2,5-dioxo-1-(2-phenylethyl)-4-imidazolidineacetamide A solution of 4-(2-methylpropyl)-2,5-dioxo-1-(2-phenylethyl)-4-imidazolidineacetic acid (126 mg, 0.379 mmol) in dry THF (5 mL) is treated with CDI (74.0 mg, 0.455 mmol). After 1 hour, 4-methylmorpholine (417 µL, 3.79 mmol) and O-benzylhydroxylamine hydrochloride (91.0 mg, 0.569 mmol) are added. The mixture is stirred for 12 hours at room temperature and is diluted with EtOAc. The solution is washed with saturated NaHCO₃, 1N HCl, saturated NaHCO₃, and brine. The organic layer is dried over anhydrous Na₂SO₄, filtered, and concentrated under reduced pressure to yield 156 mg of a black oil. The oil is purified by silica gel chromatography (25 g SG, packed with hexane, eluted with 50% EtOAc/hexane) to give 47 mg (28%) of the title compound as an amorphous white solid.

¹H NMR (300 MHz, CDCl₃) δ 8.89, 7.15–7.45, 6.67, 4.70–5.00, 3.60–3.90, 2.95, 2.15–2.40, 1.50–1.70, 1.35–1.50, 0.84, 0.75;

MS (FAB) m/z 424, 334, 318, 259, 105, 91.

Step 3.

Preparation of N-Hydroxy-4-(2-methylpropyl)-2,5-dioxo-1-(2-phenylethyl)-4-imidazolidineacetamide A solution of N-benzyloxy-4-(2-methylpropyl)-2,5-dioxo-1-(2-phenylethyl)-4-imidazolidineacetamide (85.0 mg, 0.201 mmol) in 25% MeOH/EtOAc is purged with N₂, treated with palladium hydroxide on carbon (17 mg, 20% by weight), and placed under a H₂ atmosphere (balloon). After 2.5 hours, the reaction mixture is filtered through celite and concentrated under reduced pressure to yield 70 mg of an off-white foam. The material is recrystallized from hot EtOAc/hexane to give 36 mg (54%) of the title compound as a white, powdery solid (mp 145°–147° C.).

IR (mineral oil) 3284, 3227, 1762, 1719, 1707, 1662, 1655, 1424, 1365, 699 cm⁻¹;

¹H NMR (300 MHz, CDCl₃) δ 7.84, 7.15–7.40, 3.60–3.85, 2.65–3.10, 2.35–2.55, 1.45–1.75, 0.90, 0.83;

MS (EI) m/z 333, 277, 259, 243, 229, 217, 155, 105, 104, 91.

EXAMPLE 38

Preparation of N-Hydroxyl-4-(2-methylpropyl)-5-oxo-1-(2-phenylethyl)-4-pyrazolidineacetamide monohydrochloride

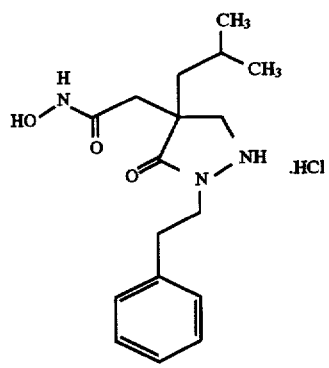

Step 1.

Preparation of 1-(Benzyloxycarbonyl)-2-(2-phenylethyl)pyrazolidin-3-one

Sodium hydride (562 mg, 14.1 mmol, 60% mineral oil dispersion) is added to a solution of 1-(benzyloxycarbonyl)pyrazolidin-3-one (2.81 g, 12.8 mmol, prepared similarly to that described in J. Org. Chem. 1990, 55, 6037) and DMF (37 mL) at 0° C. The solution is stirred for 30 minutes and then (2-bromoethyl)benzene (1.90 mL, 13.9 mmol) is added. The solution is stirred at 0° C. for 1 hour and 16 hours at room temperature. Aqueous workup (EtOAc, brine, MgSO₄) and purification by flash chromatography (2:1→1:1 hexane:EtOAc) gives 1.58 g (38%) of the title compound as an oil.

IR (liq.) 3029, 2954, 1709, 1498, 1455, 1412, 1378, 1314, 1214, 1184, 1110, 1086, 1027, 748, 699 cm⁻¹;

¹H NMR (300 MHz, CDCl₃) δ 7.38, 7.10–7.30, 5.23, 4.02, 3.80, 2.87, 2.44;

MS (EI) m/z 324, 190, 189, 106, 105, 104, 92, 91, 79, 77, 65.

Step 2.

Preparation of 1-(Benzyloxycarbonyl)-4-(2-methylpropen-2-yl)-2-(2-phenylethyl)pyrazolidin-3-one Lithium diisopropylamide (2.92 mL, 5.84 mmol, 2.0M, heptane/THF/ethylbenzene) is added to a solution of 1-(benzyloxycarbonyl)-2-(2-phenylethyl)pyrazolidin-3-one (1.58 g, 4.87 mmol), THF (15 mL), and HMPA (1.04 mL) at −78° C. After stirring for 35 minutes at −78° C., a solution of 3-bromo-2-methylpropene (0.54 mL, 5.4 mmol) and THF (2.6 mL) is added. The solution is allowed to stir for 6 hours at −78° C. and is then quenched with aqueous ammonium chloride (25 mL). After warming to room temperature, aqueous workup (EtOAc, MgSO₄) and purification by flash chromatography (3:1 hexane:EtOAc) gives 1.21 g of the title compound (66%) as an oil. Further elution provides 201 mg of recovered starting material (75% of product based on recovered sm). Spectral data for the title compound:

IR (liq.) 2945, 1710, 1498, 1455, 1416, 1377, 1318, 1232, 1206, 1172, 1121, 1028, 897, 748, 698 cm⁻¹;

¹H NMR (300 MHz, CDCl₃) δ 7.38, 7.10–7.40, 5.23, 4.71, 4.53, 4.10–4.30, 4.01, 3.80–3.95, 3.09, 2.75–2.95, 2.60–2.80, 2.35–2.45, 1.63, 1.53;

MS (EI) m/z 378, 244, 243, 105, 104, 92, 91, 79, 77, 65.
Step 3.

Preparation of tert-Butyl 2-(Benzyloxycarbonyl)-4-(2-methylpropen-2-yl)-5-oxo-1-(2-phenylethyl)-4-pyrazolidinacetate Lithium diisopropylamide (1.70 mL, 3.40 mmol, 2.0M, heptane/THF/ethylbenzene) is added to a solution of 1-(benzyloxycarbonyl)-4-(2-methylpropen-2-yl)-2-(2-phenylethyl)pyrazolidin-3-one (1.20 g, 3.17 mmol), THF (15.6 mL), and HMPA (0.69 mL) at −78° C. After stirring for 30 minutes at −78° C., a solution of tert-butyl bromoacetate (0.57 mL, 3.5 mmol) and THF (1.5 mL) is added. The solution is allowed to stir for 6 hours at −78° C. and is then quenched with aqueous ammonium chloride (25 mL). After warming to room temperature, aqueous workup (EtOAc, $MgSO_4$) and purification by flash chromatography (4:1→3:1 hexane:EtOAc) gives 410 mg of the title compound (26%) as an oil. Further elution provides 624 mg of recovered starting material (55% of product based on recovered sm). Spectral data for the title compound.

IR (neat) 1723, 1696, 1320, 1286, 1263, 1242, 1201, 1186, 1165, 1123, 906, 764, 749, 697, 604 $cm^{-1}$;

$^1$H NMR (300 MHz, $CDCl_3$) δ 7.35–7.45, 7.10–7.30, 5.19, 4.74, 4.68, 4.15–4.30, 3.88, 3.75–3.95, 2.80–2.95, 2.19, 2.17, 1.62, 1.41;

MS (EI) m/z 492, 302, 301, 283, 255, 105, 92, 91, 57.
Step 4.

Preparation of 2-(Benzyloxycarbonyl)-4-(2-methylpropen-2-yl)-5-oxo-1-(2-phenylethyl)-4-pyrazolidineacetic Acid TFA (8.0 mL) is added to a solution of tert-butyl 2-(benzyloxycarbonyl)-4-(2-methylpropen-2-yl)-5-oxo-1-(2-phenylethyl)-4-pyrazolidinacetate (546 mg, 1.11 mmol) and $CH_2Cl_2$ (20 mL) at 0° C. The solution is stirred for 1.5 hours at 0° C. and is concentrated. Aqueous workup ($CH_2Cl_2$, $MgSO_4$) provides 456 mg (94%) of the title compound which is isolated as an oil.

IR (mineral oil) 3069, 3061, 3031, 1719, 1651, 1422, 1405, 1329, 1238, 1207, 1134, 1027, 905, 755, 699, $cm^{-1}$;

$^1$H NMR (300 MHz, $CDCl_3$) δ 7.39, 7.10–7.30, 5.19, 4.75, 4.68, 4.20–4.35, 3.80–3.95, 3.77, 2.75–3.00, 2.10–2.40, 1.61;

MS (EI) m/z 436, 301, 255, 105, 104, 92, 91, 79, 77, 65, 57.
Step 5.

Preparation of N-Benzyloxy-2-(benzyloxycarbonyl)-4-(2-methylpropen-2-yl)-5-oxo-1-(2-phenylethyl)-4-pyrazolidineacetamide CDI (204 mg, 1.26 mmol) is added to a solution of 2-(benzyloxycarbonyl)-4-(2-methylpropen-2-yl)-5-oxo-1-(2-phenylethyl)-4-pyrazolidineacetic acid (453 mg, 1.04 mmol) and $CH_2Cl_2$ (10 mL). The solution is stirred for 1 hour at room temperature and then O-benzylhydroxylamine hydrochloride (293 mg, 1.84 mmol) and N-methylmorpholine (0.23 mL, 2.1 mmol) are added. The solution is stirred for 60 hours at room temperature. Aqueous workup ($CH_2Cl_2$, $MgSO_4$) and purification by flash chromatography (1:1 hexane:EtOAc) provides 468 mg (83%) of the title compound as an oil.

IR (liq.) 3031, 1724, 1701, 1498, 1455, 1379, 1320, 1217, 1182, 1134, 1044, 1028, 749, 698, $cm^{-1}$;

$^1$H NMR (300 MHz, $CDCl_3$) δ 8.72, 7.05–7.45, 5.18, 4.88, 4.73, 4.66, 4.05–4.30, 3.80–3.95, 3.57, 2.75–2.95, 1.95–2.20, 1.78, 1.57;

MS (EI) m/z 541, 407, 406, 106, 105, 104, 92, 91, 79, 77, 65.

Step 6.

Preparation of N-Hydroxyl-4-(2-methylpropyl)-5-oxo-1-(2-phenylethyl)-4-pyrazolidineacetamide monohydrochloride An atmosphere of hydrogen is placed over a mixture of N-benzyloxy-2-(benzyloxycarbonyl)-4-(2-methylpropen-2-yl)-5-oxo-1-(2-phenylethyl)-4-pyrazolidineacetamide (462 mg, 0.853 mmol), MeOH (34 mL) and Pearlman's catalyst (85 mg). After stirring for 8 hours at room temperature, the mixture is filtered, the solids washed with MeOH (3×10 mL), $CH_2Cl_2$ (10 mL), and the filtrates concentrated to provide 220 mg (81%) of the title compound as an oil.

$^1$H NMR (300 MHz, $CDCl_3$) δ 10.3–10.5, 7.10–7.40, 3.45–3.80, 3.37, 2.80–3.00, 2.35, 1.45–1.90, 1.10–1.30, 0.88, 0.82.

The hydrochloride salt is formed (EtOAc/MeOH) and triturated with ether to provide the hydrochloride salt of the title compound as a solid (mp 51°–54° C.).

IR (mineral oil) 3172, 3061, 3028, 2724, 1714, 1655, 1604, 1585, 1556, 1498, 1414, 1282, 1227, 750, 701 $cm^{-1}$;

MS (EI) m/z 319, 263, 245, 228, 172, 105, 104, 91, 57, 55.

Following the general procedures outlined in EXAMPLES 28,29 and making non-critical variations, the following compounds are prepared.

EXAMPLE 39

Preparation of [S-(R*,R*)]-$N^3$-Hydroxy-3-(2-methylpropyl)-2-oxo-$N^1$-phenyl-$α^1$-(phenylmethyl)-1,3-pyrrolidinediacetamide

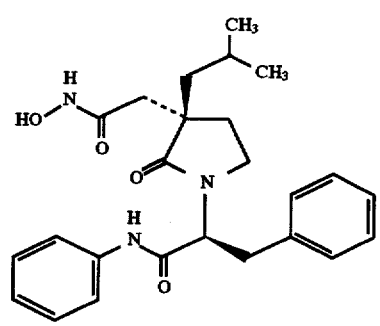

mp 169°–172° C.;

[α]$_D^{25}$ −43° (c 0.54, MeOH);

IR (mull) 3246, 3193, 3135, 3059, 3029, 1658, 1600, 1547, 1493, 1444, 1358, 1322, 1311, 759, 698 $cm^{-1}$;

$^1$H NMR (300 MHz, $CDCl_3$) δ 7.48, 7.10–7.35, 7.06, 4.74, 3.30–3.55, 3.05–3.25, 1.90–2.40, 1.40–1.65, 1.20–1.35, 0.83, 0.75;

MS (EI) m/e 364, 321, 273, 244, 228, 200, 132.

EXAMPLE 40

Preparation of [S-(R*,R*)]-N³-Hydroxy-3-(2-methylpropyl)-2-oxo-α¹-(phenylmethyl)-N¹-(2-pyridinylmethyl)-1,3-pyrrolidinediacetamide

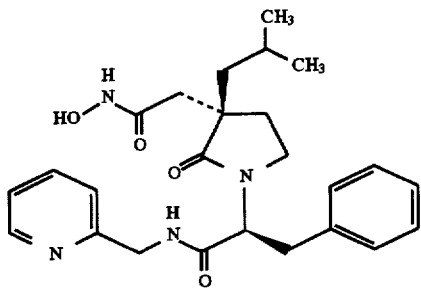

mp 68°–71° C.;

IR (mull) 3244, 3062, 3027, 1658, 1598, 1572, 1540, 1497, 1439, 1354, 1296, 1271, 751, 701, 620 cm$^{-1}$;

$^1$H NMR (300 MHz, CDCl$_3$) δ 8.40–8.55, 7.90–8.00, 7.75, 7.50, 7.05–7.35, 4.35–4.70, 4.10–4.25, 3.25–3.50, 2.75–2.90, 2.15–2.40, 1.75–1.90, 1.40–1.65, 1.00–1.15, 0.86, 0.81;

MS (EI) m/z 436, 379, 336, 301, 244, 200, 147, 135, 92.

EXAMPLE 41

Preparation of [S-(R*,R*)]-N³-Hydroxy-3-(2-methylpropyl)-2-oxo-α¹-(phenylmethyl)-N¹-(4-pyridinyl)-1,3-pyrrolidinediacetamide

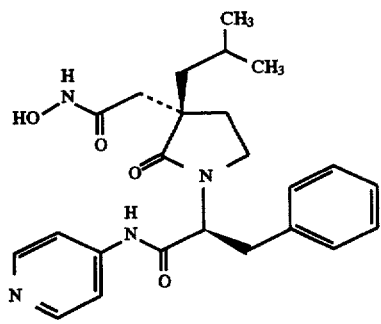

mp 121°–123° C.;

IR (mull) 3240, 3178, 3086, 3064, 3028, 1664, 1593, 1512, 1498, 1422, 1331, 1294, 1210, 749, 701 cm$^{-1}$;

$^1$H NMR (300 MHz, CDCl$_3$) δ 9.98, 8.25, 7.65–7.85, 7.15–7.35, 4.15–4.25, 3.25–3.65, 2.65–2.85, 2.37, 1.70–1.85, 1.45–1.70, 1.10–1.20, 0.90, 0.84;

MS (EI) m/z 438 (M$^+$) 317, 316, 301, 284, 200, 132, 105, 95, 91, 55.

EXAMPLE 42

Preparation of [S-(R*,R*)]-N¹-(4-Fluorophenyl)-N³-hydroxy-3-(2-methylpropyl)-2-oxo-α¹-(phenylmethyl)-1,3-pyrrolidinediacetamide

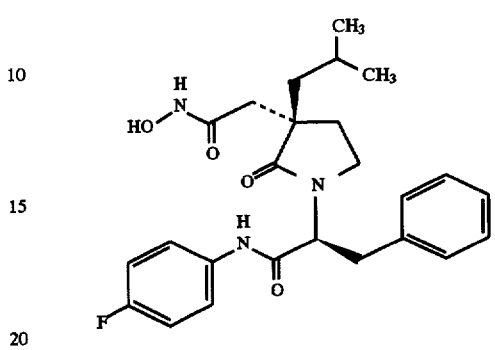

mp 181–182.5;

IR (mull) 3254, 3154, 3066, 1658, 1614, 1552, 1511, 1499, 1409, 1309, 1299, 1230, 1213, 836, 699 cm$^{-1}$;

$^1$H NMR (300 MHz, CDCl$_3$) δ 8.20–8.50, 7.46, 7.15–7.40, 6.90–7.05, 4.65–4.80, 3.15–3.50, 1.90–2.45, 1.40–1.70, 1.20–1.35, 0.87, 0.79;

MS (EI) m/z 455 (M$^+$) 345, 344, 317, 316, 284, 200, 132, 131, 91, 55.

EXAMPLE 43

Preparation of [S-(R*,R*)]-N³-Hydroxy-3-(2-methylpropyl)-2-oxo-α¹-(phenylmethyl)-N¹-[1-(phenylmethyl)-4-piperdinyl]-1,3-pyrrolidinediacetamide

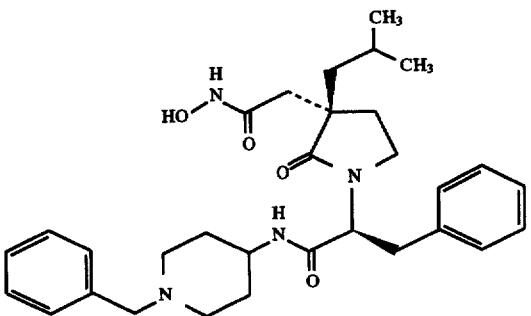

mp 108°–110° C.;

IR (mull) 3276, 3107, 3085, 3062, 3027, 2764, 1658, 1540, 1496, 1296, 1271, 744, 721, 700 cm$^{-1}$; MS (FAB) m/z 535 (MH$^+$), 534, 533, 519, 172, 91, 82.

EXAMPLE 44

Preparation of [S-(R*,R*)]-N³-Hydroxy-3-(2-methylpropyl)-2-oxo-α¹-(phenylmethyl)-N¹-(4-piperdinyl)-1,3-pyrrolidinediacetamide

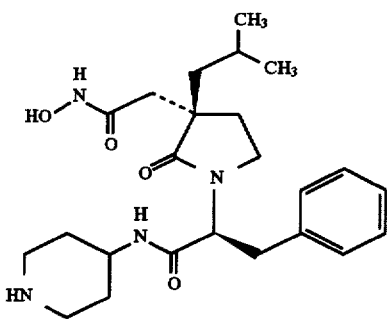

mp 160°–165° C.;

IR (mull) 3283, 3085, 3062, 3028, 1661, 1584, 1544, 1497, 1311, 1297, 1271, 1213, 1154, 748, 700 cm⁻¹; MS (EI) m/z 444 (M⁺), 302, 301, 264, 132, 91, 84, 83, 82, 56, 55.

EXAMPLE 45

Preparation of [S-(R*,R*)]-N³-Hydroxy-3-(2-methylpropyl)-2-oxo-α¹-(phenylmethyl)-N¹-(4-pyridinylmethyl)-1,3-pyrrolidinediacetamide

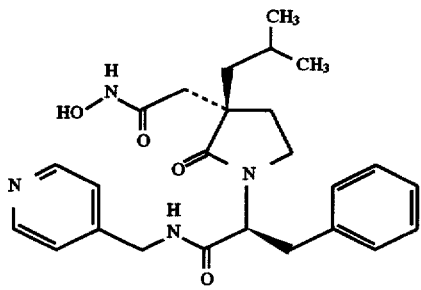

mp 140.5°–142° C.

¹H NMR (300 MHz, CDCl₃) δ 8.49, 8.35, 7.95–8.10, 7.10–7.35, 4.50–4.60, 4.20–4.45, 3.25–3.55, 2.80–3.10, 2.15–2.60, 1.95–2.10, 1.75–1.90, 1.40–1.70, 1.05–1.35, 0.89, 0.83;

MS (FAB) m/z 453 (MH⁺), 452, 437, 284, 132, 105, 93, 91.

EXAMPLE 46

Preparation of [S-(R*,R*)]-N¹-(4-Fluorophenylmethyl)-N³-hydroxy-3-(2-methylpropyl)-2-oxo-α¹-(phenylmethyl)-1,3-pyrrolidinediacetamide

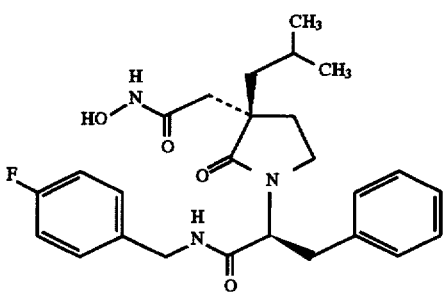

mp 64°–66° C.

¹H NMR (300 MHz, CDCl₃) δ 7.05–7.35, 6.90–7.05, 4.50–4.70, 4.20–4.45, 3.10–3.45, 2.29, 1.80–2.10, 1.40–1.70, 1.10–1.30, 0.86, 0.80.

EXAMPLE 47

Preparation of [S-(R*,R*)]-N³-Hydroxy-N¹-methyl-3-(2-methylpropyl)-2-oxo-α¹-(2-phenylethyl)-1,3-pyrrolidinediacetamide

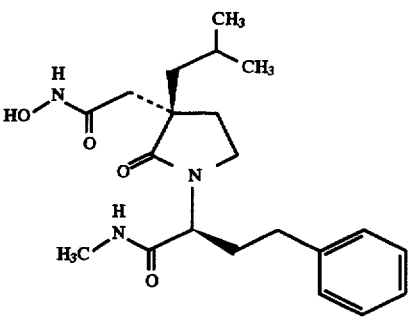

mp 148°–148.5° C.;

[α]$_D^{25}$ –31° (c 0.68, MeOH);

IR (mull) 3227, 3092, 3084, 3024, 1678, 1667, 1658, 1644, 1569, 1503, 1496, 1297, 1282, 1206, 703 cm⁻¹;

¹H NMR (300 MHz, CDCl₃) δ 7.10–7.35, 6.29, 4.30, 3.35–3.50, 2.75, 2.45–2.65, 2.35, 2.00–2.30, 1.60–1.80, 1.35–1.60, 0.91, 0.86;

MS (EI) m/e 316, 273, 258, 91, 44.

EXAMPLE 48

Preparation of [S-(R*,R*)]-N³-Hydroxy-3-(2-methylpropyl)-2-oxo-α¹-(2-phenylethyl)-N¹-(phenylmethyl)-1,3-pyrrolidinediacetamide

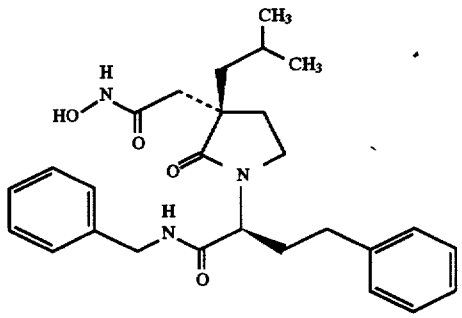

mp 59°–61° C.;

[α]$_D^{25}$ −57° (c 0.39, CHCl₃);

IR (mull) 3234, 3086, 3062, 3027, 1652, 1605, 1585, 1540, 1497, 1295, 1269, 1213, 1030, 739, 699 cm⁻¹;

¹H NMR (300 MHz, CDCl₃) δ 7.10–7.40, 6.40–6.55, 4.25–4.50, 3.25–3.50, 2.00–2.70, 1.25–1.75, 0.87, 0.83; MS (EI) m/z 465 (M⁺) 361, 332, 331, 330, 316, 298, 182, 117, 91.

EXAMPLE 49

Preparation of [S-(R*,R*)]-N³-Hydroxy-α¹,3-bis(2-methylpropyl)-2-oxo-N¹-2-pyridinyl-1,3-pyrrolidinediacetamide

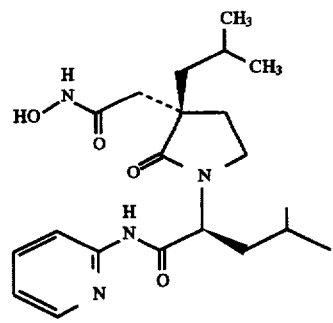

mp 73°–75° C.;

IR (mull) 3203, 2728, 1663, 1600, 1579, 1532, 1494, 1435, 1298, 1279, 1181, 1152, 780, 741 cm⁻¹;

¹H NMR (300 MHz, CDCl₃) δ 8.10–8.35, 7.72, 7.05, 4.25–4.40, 3.30–3.65, 2.35–2.60, 2.00–2.20, 1.35–1.95, 1.20–1.35, 0.75–1.10;

MS (EI) m/z 404 (M⁺), 284, 283, 267, 250, 208, 149, 98, 56, 55.

EXAMPLE 50

Preparation of [S-(R*,R*)]-α¹-Cyclohexyl-N³-hydroxy-N¹-methyl-3-(2-methylpropyl)-2-oxo-1,3-pyrrolidinediacetamide

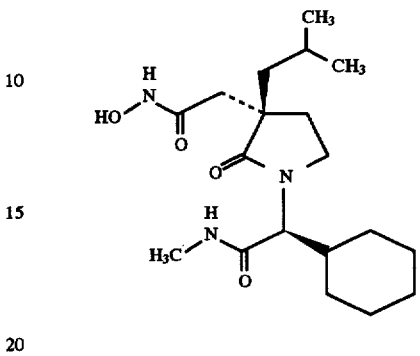

mp 199°–200° C.;

IR (mull) 3310, 3232, 3105, 1647, 1565, 1536, 1498, 1415, 1297, 1277, 1258, 1236, 1223, 1047, 722 cm⁻¹;

¹H NMR (300 MHz, CDCl₃) δ 6.15–6.35, 4.01, 3.30–3.60, 2.76, 2.44, 2.20–2.40, 1.90–2.15, 1.10–1.80, 0.90, 0.83;

MS (EI) m/z 367 (M⁺) 336, 310, 309, 308, 277, 276, 154, 95, 58, 55.

EXAMPLE 51

Preparation of [S-(R*,R*)]-α¹-Cyclohexyl-N³-hydroxy-3-(2-methylpropyl)-2-oxo-N¹-2-pyridinyl-1,3-pyrrolidinediacetamide

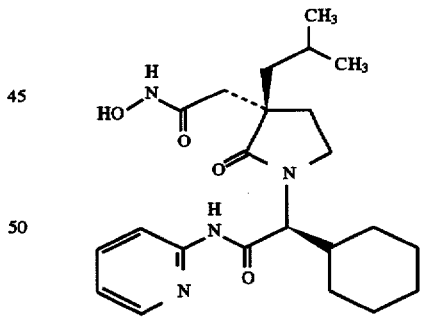

mp 119°–121° C.;

IR (mull) 3254, 1665, 1596, 1579, 1532, 1497, 1434, 1301, 1279, 1270, 1186, 1172, 1151, 779, 740 cm⁻¹;

¹H NMR (300 MHz, CDCl₃) δ 8.25–8.35, 8.17, 7.65–7.80, 7.00–7.15, 4.20–4.35, 3.35–3.60, 2.00–2.75, 0.70–1.85;

MS (EI) m/z 430 (M⁺), 309, 294, 293, 276, 218, 154, 95, 78, 67, 55.

EXAMPLE 52

Preparation of [S-(R*,R*)]-3-(Cyclopentylmethyl)-N³-hydroxy-N¹-methyl-2-oxo-α¹-(phenylmethyl)-1,3-pyrrolidinediacetamide

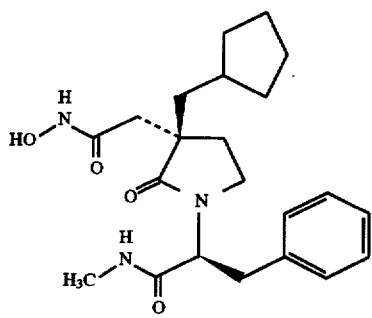

mp 180°–181.5° C.;

¹H NMR (300 MHz, CDCl₃) δ 7.10–7.40, 4.41, 3.10–3.45, 2.75, 2.70–3.05, 2.00–2.35, 1.85–2.00, 1.30–1.85, 0.85–1.15;

MS (EI) m/z 401, 343, 342, 328, 310, 200, 132, 91, 58.

EXAMPLE 53

Preparation of [3S-[1(R*),3R*(R*)]]-α³-[2-(Benzoylamino)ethyl]-N³-hydroxy-N¹-methyl-3-(2-methylpropyl)-2-oxo-α¹-(phenylmethyl)-1,3-pyrrolidinediacetamide

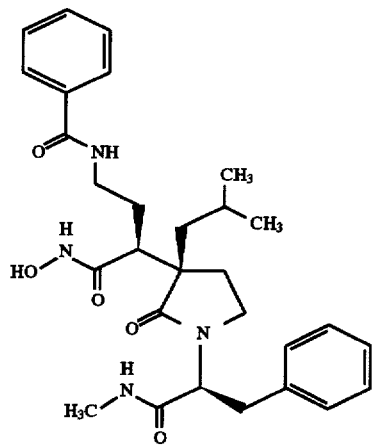

¹H NMR (300 MHz, CDCl₃) δ 7.70–7.85, 7.35–7.55, 7.05–7.35, 6.40, 4.80–5.00, 3.10–3.50, 2.76, 2.20–2.40, 1.20–2.00, 0.70–1.00, 0.30–0.45;

MS (FAB) m/z 523 (MH⁺), 522, 391, 371, 129, 105, 71, 57, 43.

EXAMPLE 54

Preparation of [S-(R*,R*)]-N³-Hydroxy-3-(2-methylpropyl)-N¹-[2-(4-morpholinyl)ethyl]-2-oxo-α¹-(phenylmethyl)-1,3-pyrrolidinediacetamide

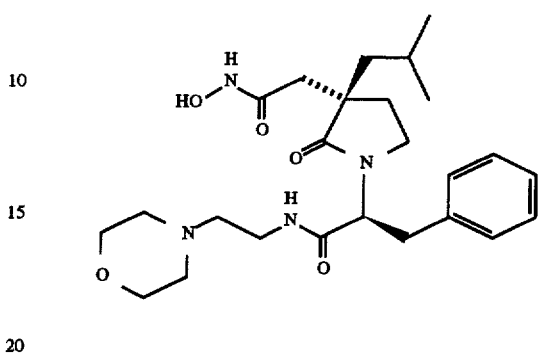

mp 66° C.;

[α]$_D$=−56° (c, 0.58; CHCl₃);

IR (mull) 3223, 3086, 3063, 3027, 1653, 1547, 1497, 1297, 1271, 1239, 1146, 1118, 1071, 748, 700 cm⁻¹;

¹H NMR (300 MHz, CDCl₃) δ 7.45–7.15, 3.80–3.60, 3.50–3.00, 2.70–2.00, 1.95–1.80, 1.75–1.45, 1.35–1.15, 0.88;

MS (EI) m/z 474 (M⁺), 418, 358, 345, 244, 200, 113, 100.

EXAMPLE 55

Preparation of [S-(R*,R*)]-N-Hydroxy-3-(2-methylpropyl)-1-[2-(4-morpholinyl)-2-oxo-1-(phenylmethyl)ethyl]-2-oxo-3-pyrrolidineacetamide

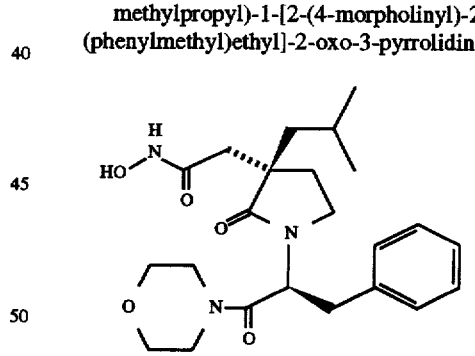

mp 52°–56° C.);

[α]$_D$=−82° (c, 0.70; CHCl₃);

IR (mull) 3237, 3085, 3061, 3025, 1648, 1494, 1299, 1268, 1239, 1213, 1115, 1039, 1029, 751, 702 cm⁻¹;

MS (EI) m/z 431 (M⁺), 399, 375, 357, 344, 340, 317, 284, 114, 91;

¹H NMR (CDCl₃) δ 7.35–7.15, 5.30, 3.70–3.10, 3.10–2.90, 2.40–1.95, 1.85–1.15, 0.86;

HRMS (EI) 431.2436.

EXAMPLE 56

Preparation of [1(1S)-[1[R*(R*)],3α,5α]]-1-[2-(3,5-Dimethyl-1-piperazinyl)-2-oxo-1-(phenylmethyl)ethyl]-N-hydroxy-3-(2-methylpropyl)-2-oxo-3-pyrrolidineacetamide

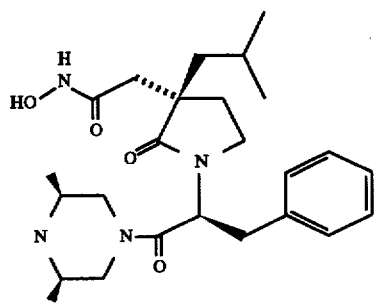

mp 106° C.;

[α]_D=-77° (c, 0.6082; CHCl_3);

IR (mull) 3252, 3087, 3062, 3027, 1649, 1493, 1323, 1263, 1193, 1157, 1110, 1084, 1033, 751, 702 cm$^{-1}$;

$^1$H NMR (300 MHz, CDCl_3) δ 7.35–7.10, 5.40–5.25, 4.50–4.35, 3.95–3.65, 3.55–3.30, 3.30–2.95, 2.75–0.75;

MS (EI) m/z 458 (M$^+$), 402, 317, 113, 84.

EXAMPLE 57

Preparation of [S-(R*,R*)]-N$^3$-Hydroxy-3-(2-methylpropyl)-2-oxo-α$^1$-(phenylmethyl)-N$^1$-2-pyridinyl-1,3-pyrrolidinediacetamide

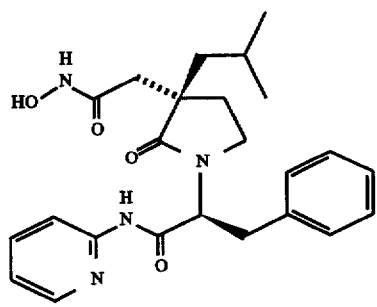

mp 171°–174° C.;

[a]_D=-14° (c, 0.67; CHCl_3);

IR (mull) 3057, 3030, 3010, 1706, 1661, 1642, 1614, 1586, 1558, 1315, 1282, 1205, 786, 753, 704 cm$^{-1}$;

$^1$H NMR (300 MHz, CDCl_3) δ 8.40–8.30, 8.25–8.15, 7.85–7.75, 7.40–7.20, 7.20–7.05, 4.26, 3.60–3.35, 2.80–2.65, 2.55–2.25, 1.90–1.40, 1.10–1.95, 0.87;

MS (EI) m/z 438 (M$^+$), 406, 382, 364, 347, 317, 284, 226, 200, 132, 91.

EXAMPLE 58

Preparation of [3S-[1(R*),3R*(R*)]]-α$^3$-[2-(1,3-Dihydro-1,3-dioxo-2H-isoindol-2-yl)ethyl]-N$^3$-hydroxy-N$^1$-methyl-3-(2-methylpropyl)-2-oxo-α$^1$-(phenylmethyl)-1,3-pyrrolidinediacetamide

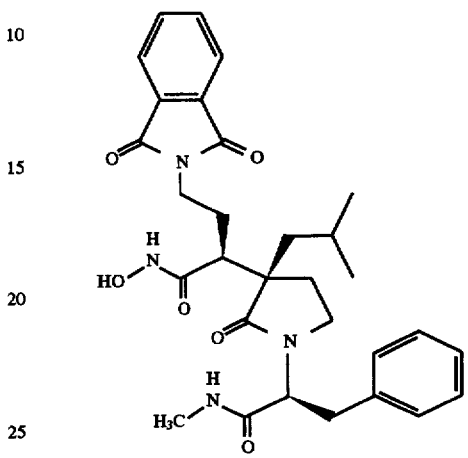

$^1$H NMR (300 MHz, CDCl_3) δ 7.65–7.95, 7.10–7.40, 6.20, 4.55–4.70, 3.05–3.75, 2.67, 1.15–2.30, 0.77, 0.68;

MS (FAB) m/z 549 (MH$^+$), 550, 549, 517, 516, 429, 160, 69, 57, 55, 43.

EXAMPLE 59

Preparation of [S-(R*,R*)]-α$^1$-Cyclohexyl-N$^1$-cyclopropylmethyl-N$^3$-hydroxy-3-(2-methylpropyl)-2-oxo-1,3-pyrrolidinediacetamide

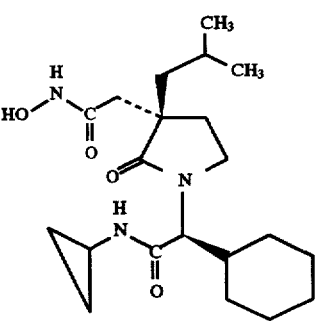

mp 140°–144° C.;

$^1$H NMR (300 MHz, CDCl_3) δ 6.40, 3.97, 3.50–3.65, 3.30–3.45, 2.50–2.70, 2.20–2.40, 1.90–2.15, 1.10–1.90, 0.65–1.00, 0.40–0.60.

EXAMPLE 60

Preparation of [S-(R*,R*)]-α¹-Cyclohexyl-N¹-(4-fluorophenyl)-N³-hydroxy-3-(2-methylpropyl)-2-oxo-1,3-pyrrolidinediacetamide

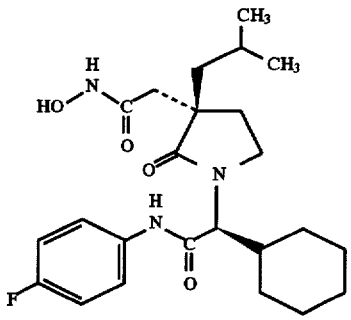

mp 132°–135° C.;

¹H NMR (300 MHz, CDCl₃) δ 8.47, 7.40–7.50, 6.99, 4.15, 3.35–3.65, 2.57, 2.30–2.45, 2.00–2.20, 0.95–1.85, 0.86, 0.77.

Following the general procedures outlined in EXAMPLES 30–34 and making non-critical variations, the following compounds are prepared.

EXAMPLE 61

Preparation of [S-(R*,R*)]-α¹-tert-Butyl-N³-hydroxy-N¹-methyl-3-(2-methylpropyl)-2-oxo-1,3-pyrrolidinediacetamide

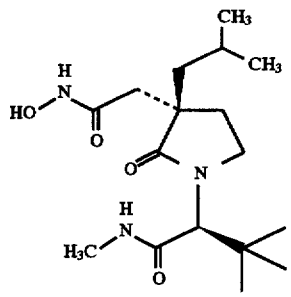

mp 108°–110° C.;

¹H NMR (300 MHz, CDCl₃) δ 5.80–6.00, 4.23, 4.15–4.35, 2.70–2.80, 2.45–2.70, 2.30–2.45, 1.85–2.30, 1.35–1.85, 1.05, 0.75–1.00;

MS (ESI) 340 (MH⁻).

Following the general procedures outlined in EXAMPLES 4–14 and making non-critical variations, the following compounds are prepared.

EXAMPLE 62

Preparation of N-Hydroxy-3-(2-methylpropyl)-2-oxo-1-(2-phenylethyl)-α-[2-(5-propyloxy-1,3-dihydro-1,3-dioxo-2H-isoindol-2-yl)ethyl]-3-pyrrolidineacetamide

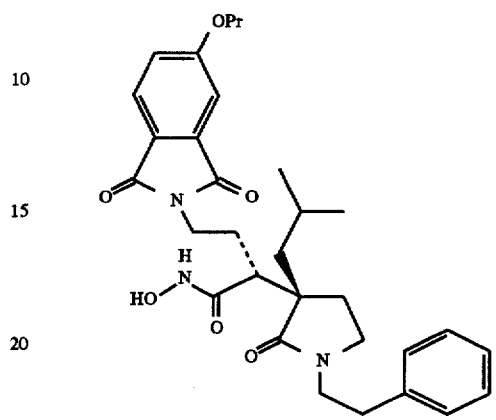

mp 137°–138° C.;

IR (mineral oil) 3211, 3085, 3028, 1772, 1712, 1660, 1620, 1491, 1400, 1346, 1292, 1249, 1234, 749, 705 cm⁻¹;

¹H NMR (300 MHz, CDCl₃) δ 7.72, 7.05–7.40, 4.02, 3.35–3.80, 3.10–3.25, 2.78, 2.30–2.45, 2.05–2.30, 1.75–2.00, 1.35–1.70, 1.06, 0.83, 0.76;

MS (EI) m/z 549 (M⁺), 493, 489, 262, 261, 245, 244, 218, 202, 176, 105.

EXAMPLE 63

Preparation of [R-(R*,S*)]-5-Fluoro-1,3-dihydro-N-hydroxy-α-[3-(2-methylpropyl)-2-oxo-1-(2-phenylethyl)-3-pyrrolidinyl]-1,3-dioxo-2H-isoindole-2-butanamide

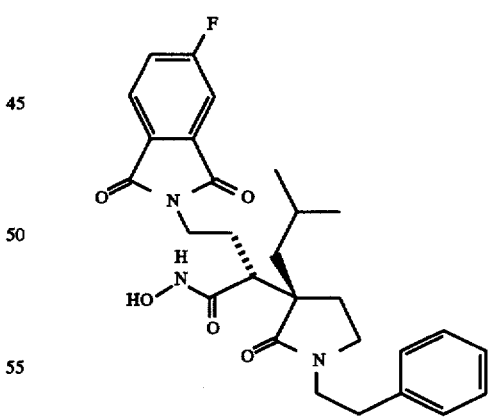

IR (mull) 3205, 3063, 3027, 1775, 1717, 1664, 1616, 1497, 1481, 1399, 1302, 1263, 1229, 747, 701 cm⁻¹;

¹H NMR (300 MHz, CDCl₃) δ 8.92, 7.83, 7.50, 7.00–7.45, 3.35–3.80, 3.25–3.35, 3.10–3.25, 2.79, 2.55–2.70, 2.30–2.50, 2.10–2.30, 1.70–2.00, 1.35–1.65, 0.70–1.00;

MS (EI) m/z 509 (M⁺), 477, 453, 449, 345, 262, 261, 178, 105, 104.

EXAMPLE 64

Preparation of α-[2-(5,6-Difluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide

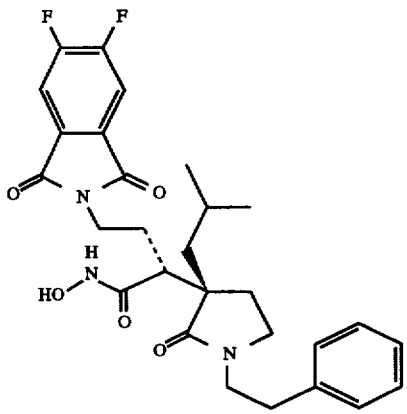

IR (mull) 3340, 3187, 3062, 3028, 1777, 1720, 1678, 1654, 1505, 1406, 1354, 1277, 1261, 746, 704 cm$^{-1}$;

$^1$H NMR (300 MHz, CDCl$_3$) δ 7.55–7.70, 7.40–7.55, 7.05–7.40, 3.35–3.80, 3.10–3.35, 2.70–2.85, 2.55–2.70, 2.30–2.55, 2.05–2.30, 1.70–2.05, 1.35–1.70, 0.85, 0.79;

MS (EI) m/z 527 (M$^+$), 471, 467, 363, 262, 261, 202, 196, 105, 104.

EXAMPLE 65

Preparation of N-Hydroxy-3-(2-methylpropyl)-2-oxo-1-(2-phenylethyl)-α-[2-(5-trifluoromethyl-1,3-dihydro-1,3-dioxo-2H-isoindol-2-yl)ethyl]-3-pyrrolidineacetamide

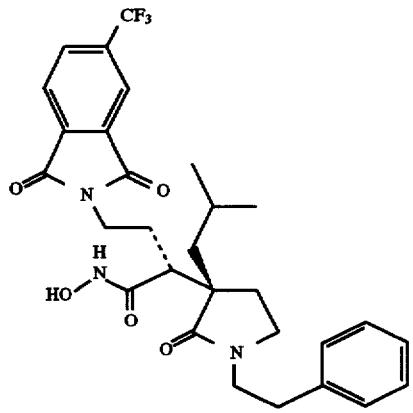

mp 137°–138° C.;

IR (mull) 1715, 1659, 1494, 1444, 1398, 1348, 1323, 1307, 1295, 1266, 1184, 1140, 1101, 750, 694 cm$^{-1}$;

$^1$H NMR (CDCl$_3$) δ 8.91, 8.05–8.15, 7.90–8.05, 7.37, 7.05–7.35, 3.35–3.85, 3.25–3.35, 3.10–3.25, 2.79, 2.55–2.70, 2.35–2.55, 2.10–2.35, 1.75–2.05, 1.30–1.70, 0.84, 0.78;

MS (EI) m/z 559 (M$^+$), 527, 503, 499, 395, 262, 261, 228, 105, 104.

EXAMPLE 66

Preparation of α-[2-(1,3,4,5,6,7-Hexahydro-1,3-dioxo-2H-isoindol-2-yl)ethyl]-N-hydroxy-3-(2-methylpropyl)-2-oxo-1-(2-phenylethyl)-3-pyrrolidineacetamide

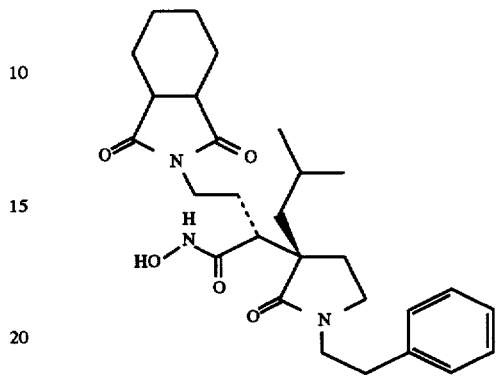

mp 118°–119° C.;

IR (mull) 3167, 3088, 3065, 3028, 1703, 1668, 1497, 1443, 1393, 1346, 1331, 1306, 1296, 1279, 701 cm$^{-1}$;

$^1$H NMR (300 MHz, CDCl$_3$) δ 8.80, 7.45, 7.10–7.40, 3.35–3.65, 3.10–3.35, 2.70–2.95, 2.50–2.70, 2.10–2.50, 1.25–2.10, 0.85, 0.79;

MS (EI) m/z 497 (M$^+$), 465, 441, 437, 262, 261, 244, 105, 104, 81.

EXAMPLE 67

Preparation of α-[2-(1,3-Dihydro-1,3-dioxo-2H-isoindol-2-yl)ethyl]-N-hydroxy-3-(2-methylpropyl)-2-oxo-1-(3-phenylpropyl)-3-pyrrolidineacetamide

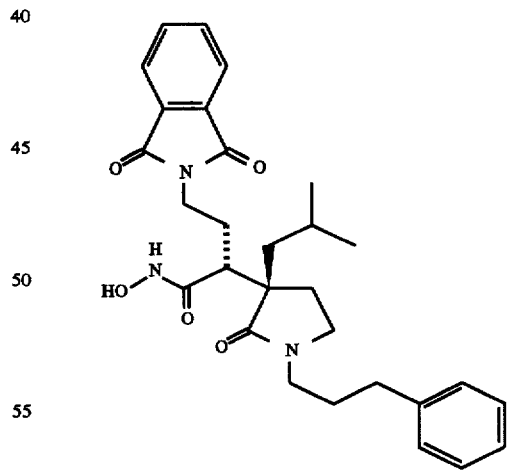

mp 163°–165° C.):

IR (mineral oil) 3231, 3107, 3088, 3051, 3034, 1771, 1712, 1683, 1663, 1499, 1442, 1400, 1298 cm$^{-1}$; $^1$H NMR (300 MHz, CDCl$_3$) δ 7.75–7.90, 7.65–7.75, 7.10–7.30, 3.60–3.85, 3.10–3.40, 2.56, 1.35–2.45, 0.87, 0.80;

MS (EI) m/z 505 (M$^+$), 387, 386, 276, 259, 258, 216, 185, 130, 91, 56.

EXAMPLE 68

Preparation of 1-[2-(4-Fluorophenyl)ethyl]-α-[2-(1,3-dihydro-1,3-dioxo-2H-isoindol-2-yl)ethyl]-N-hydroxy-3-(2-methylpropyl)-2-oxo-3-pyrrolidineacetamide

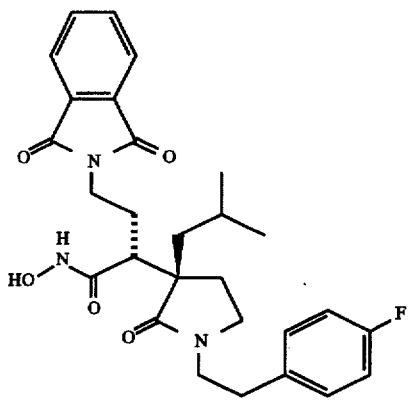

mp 142.5°–144° C.;

IR (mineral oil) 3212, 3067, 1773, 1712, 1673, 1657, 1510, 1495, 1438, 1398, 1341, 1301, 1219, 1034 cm$^{-1}$;

$^1$H NMR (300 MHz, CDCl$_3$) δ 7.60–7.95, 7.05–7.25, 6.85–7.05, 3.20–3.85, 3.10–3.25, 2.76, 1.30–2.50, 1.21, 0.82, 0.75;

MS (EI) m/z 509 (M$^+$), 477, 453, 449, 400, 220, 160, 123.

EXAMPLE 69

Preparation of α-[2-(o-benzoic sulfimide)ethyl]-N-hydroxy-3-(2-methylpropyl)-2-oxo-1-(2-phenylethyl)3-pyrrolidineacetamide

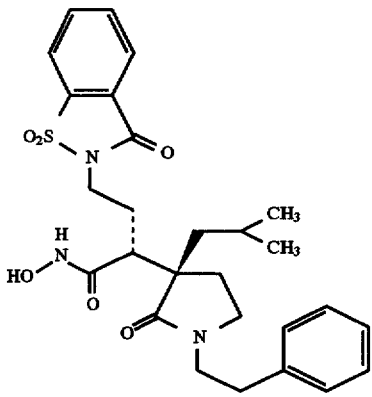

mp 144°–144.5° C.;

IR (mull) 3257, 1739, 1656, 1492, 1334, 1326, 1298, 1279, 1264, 1181, 1178, 1163, 1126, 752, 674 cm$^{-1}$;

$^1$H NMR (300 MHz, CDCl$_3$) δ 7.75–8.15, 7.00–7.40, 3.35–4.05, 3.10–3.30, 2.70–2.90, 2.40–2.60, 1.20–2.35, 0.65–1.00;

MS (EI) m/z 527 (M$^+$) 495, 471, 261, 245, 244, 202, 105, 104, 81, 56.

EXAMPLE 70

Preparation of Ethyl Phenylmethyl[4-(hydroxyamino)-3-[3-(2-methylpropyl)-2-oxo-1-(2-phenylethyl)-3-pyrrolidinyl]-4-oxobutyl]imidodicarbonate

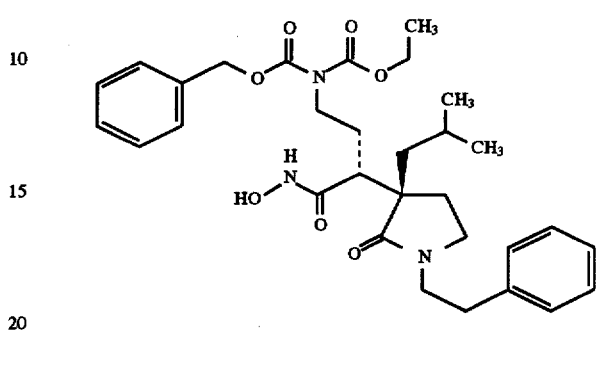

MS (EI) m/e 568.

Following the general procedures outlined in EXAMPLES 4–14 and making non-critical variations, but starting with the diastereomer of tert-butyl α-(2-hydroxyethyl)-3-(2-methylpropyl)-2-oxo-1-(2-phenylethyl)-3-pyrrolidineacetate (EXAMPLE 4, step 2), the following compounds are prepared.

EXAMPLE 71

Preparation of [S-(R*,R*)]-1,3-Dihydro-N-hydroxy-α-[3-(2-methylpropyl)-2-oxo-1-(2-phenylethyl)-3-pyrrolidinyl]-1,3-dioxo-2H-isoindole-2-butanamide

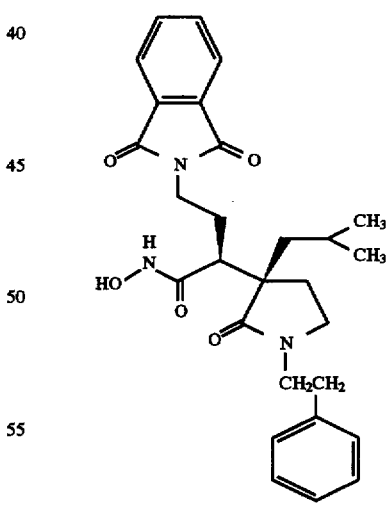

IR (mull) 1716, 1660, 1644, 1401 cm$^{-1}$;

$^1$H NMR (300 MHz, CDCl$_3$) δ 9.84, 7.80–7.90, 7.65–7.80, 7.15–7.35, 3.70–3.80, 3.35–3.70, 3.05–3.25, 2.80, 2.40–2.55, 2.34, 1.85–2.10, 1.30–1.65, 0.79, 0.71;

MS (EI) m/e 491, 459, 373, 245, 202, 185, 105.

EXAMPLE 72

Preparation of 1,3-Dihydro-N-hydroxy-α-[3-(2-methylpropyl)-2-oxo-1-[2-(4-fluorophenyl)ethyl]-3-pyrrolidinyl]-1,3-dioxo-2H-isoindole-2-butanamide

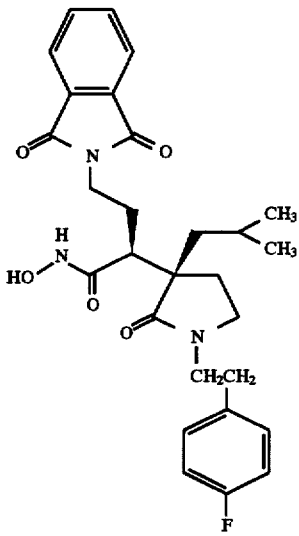

IR (mull) 3223, 1716, 1675, 1648, 1510, 1444, 1397, 1367, 1218, 722 cm$^{-1}$;

MS (EI) m/e 509, 477, 453, 449, 400, 262, 220, 160, 123.

EXAMPLE 73

Preparation of α-[2-[(3,4-Difluorobenzoyl)amino]ethyl]-N-hydroxy-3-(2-methylpropyl)-2-oxo-1-(2-phenylethyl)-3-pyrrolidineacetamide

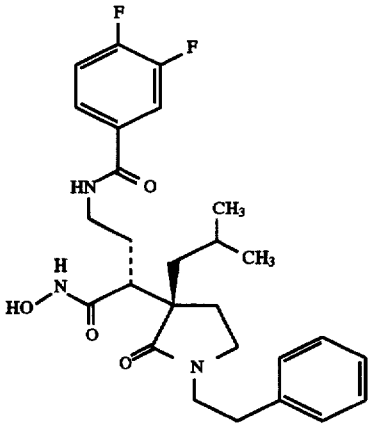

Step 1.

Preparation of tert-Butyl α-(2-Aminoethyl)-3-(2-methylpropyl)-2-oxo-1-(2-phenylethyl)-3-pyrrolidineacetate DEAD (1.18 mL) is added to a solution of tert-butyl α-(2-hydroxyethyl)-3-(2-methylpropyl)-2-oxo-1-(2-phenylethyl)-3-pyrrolidineacetate (EXAMPLE 4, step 2; 2.74 g, 6.79 mmol), dibenzyl iminodicarboxylate (2.14 g), triphenylphosphine (1.96 g) and THF (43 mL). The mixture is stirred for 16 hours at room temperature. The solution is concentrated and purified by flash chromatography (3:1 hexane EtOAc) to give 3.09 g (68%) of the imide as an oil:

IR (neat) 2957, 1799, 1751, 1723, 1686, 1498, 1455, 1387, 1367, 1335, 1331, 1287, 1213, 1188, 1153, 1108, 1092, 698 cm$^{-1}$;

$^1$H NMR (300 MHz, CDCl$_3$) δ 7.15–7.40, 5.23, 3.55–3.90, 3.25–3.40, 3.19, 2.79, 2.47, 2.30–2.45, 1.75–1.95, 1.50–1.70, 1.39, 0.82, 0.79;

MS (FAB) m/z 671 (MH$^+$), 616, 572, 420, 419, 105, 92, 91, 57.

A mixture of the imide (1.01 g, 1.51 mmol), EtOH (100 mL), and 10% Pd/C (250 mg) is hydrogenated at 32 psi for 16 hours. The mixture is filtered, the solids washed with EtOH (20 mL), CH$_2$Cl$_2$ (20 mL), and EtOH (20 mL). The combined filtrates are concentrated to provide 549 mg (91%) of the title compound as an oil:

$^1$H NMR (300 MHz, CDCl$_3$) δ 7.15–7.35, 3.55–3.70, 3.30–3.45, 3.15–3.30, 2.30–2.90, 1.92, 1.35–1.85, 0.87, 0.83.

Step 2.

Preparation of tert-Butyl α-[2-[(3,4-Difluorobenzoyl)amino]ethyl]-3-(2-methylpropyl)-2-oxo-1-(2-phenylethyl)-3-pyrrolidineacetate To a solution of tert-butyl α-(2-aminoethyl)-3-(2-methylpropyl)-2-oxo-1-(2-phenylethyl)-3-pyrrolidineacetate (549 mg, 1.36 mmol), CH$_2$Cl$_2$ (8.4 mL), and diisopropylethylamine (0.29 ml, 1.6 mmol) at 0° C. is added 3,4-difluorobenzoyl chloride (0.21 mL, 1.6 mmol). The solution is stirred at 0° C. for 1 hour and 16 hours at room temperature. Basic workup (CH$_2$Cl$_2$, NaHCO$_3$, MgSO$_4$) and purification by flash chromatography (1:1 hexane:EtOAc) gives 477 mg (64%) of the title compound as a white solid (mp 147°–148° C.):

IR (mull) 3365, 1717, 1657, 1606, 1549, 1509, 1497, 1319, 1295, 1282, 1229, 1199, 1152, 832, 774 cm$^{-1}$;

$^1$H NMR (300 MHz, CDCl$_3$) δ 7.65–7.80, 7.50–7.60, 7.15–7.40, 6.55–6.70, 3.55–3.70, 3.20–3.50, 2.81, 2.50–2.60, 2.10–2.40, 1.75–1.90, 1.40–1.65, 1.43, 0.85, 0.79;

MS (EI) m/z 542 (M$^+$) 486, 396, 395, 260, 245, 202, 141, 105, 104, 57.

Step 3.

Preparation of α-[2-[(3,4-Difluorobenzoyl)amino]ethyl]-3-(2-methylpropyl)-2-oxo-1-(2-phenylethyl)-3-pyrrolidineacetic Acid A solution of tert-butyl α-[2-[(3,4-difluorobenzoyl)amino]ethyl]-3-(2-methylpropyl)-2-oxo-1-(2-phenylethyl)-3-pyrrolidineacetate (473 mg, 0.872 mmol), CH$_2$Cl$_2$ (5.0 mL), and TFA (5.0 mL) is stirred for 1 hour at 0° C. and 2 hours at room temperature. The solution is concentrated and the residue resuspended in CH$_2$Cl$_2$ and reconcentrated two additional times (2×20 mL). Aqueous workup (CH$_2$C$_2$, MgSO$_4$) provides 420 mg (99%) of the title compound as an oil:

IR (liq.) 2959, 1728, 1661, 1618, 1607, 1553, 1510, 1467, 1454, 1443, 1442, 1314, 1297, 1283, 1203 cm$^{-1}$;

$^1$H NMR (300 MHz, CDCl$_3$) δ 7.65–7.75, 7.50–7.60, 7.15–7.40, 6.75–6.90, 3.70–3.90, 3.60–3.70, 3.40–3.55, 3.20–3.40, 2.80–3.00, 2.52, 1.95–2.10, 1.50–1.90, 1.15–1.35, 0.91, 0.83;

MS (EI) m/z 486 (M$^+$), 395, 272, 259, 258, 247, 141, 113, 105, 104.

Step 4.

Preparation of α-[2-[(3,4-Difluorobenzoyl)amino]ethyl]-N-hydroxy-3-(2-methylpropyl)-2-oxo-1-(2-phenylethyl)-3-pyrrolidineacetamide EDC (193 mg) is added to a solution of α-[2-[(3,4-difluorebenzoyl)amino]ethyl]-3-(2-methylpropyl)-2-oxo-1-

(2-phenylethyl)-3-pyrrolidineacetic acid (411 mg, 0.865 mmol), CH$_2$Cl$_2$ (8.7 mL), DMF (2.1 mL), HOBT (118 mg), and 4-methylmorpholine (0.11 ml) at 0° C. The solution was stirred for 5 min at 0° C. and 50 min at room temperature. Hydroxylamine hydrochloride (121 mg) and 4-methylmorpholine (0.19 mL) are added and the solution stirred for 16 hours at room temperature. The solution is diluted with 20 mL of water and the mixture acidified to pH 5 with 1N HCl. The mixture is extracted several times with CH$_2$Cl$_2$ (3×20 mL), the combined organic layers dried (MgSO$_4$), filtered, and concentrated. The residue is purified by flash chromatography (10:1 CH$_2$Cl$_2$:MeOH) to give 273 mg of an oil which is crystallized from EtOAc/hexane to give 164 mg (38%) of the title compound as a white powder (mp 132.5°–134° C.):

IR (mull) 3264, 1674, 1666, 1649, 1512, 1497 cm$^{-1}$; $^1$H NMR (300 MHz, CDCl$_3$) δ 7.60–7.80, 7.50–7.60, 7.05–7.35, 3.15–3.65, 2.81, 2.48, 1.85–2.20, 1.40–1.75, 0.85, 0.79;

MS (EI) m/e 501, 469, 262, 245, 202, 141, 105.

Following the general procedures outlined in EXAMPLE 73 and making non-critical variations, the following compounds were prepared.

EXAMPLE 74

Preparation of [R-(R*,S*)-α-[2-[(3-Fluorobenzoyl)amino]ethyl]-N-hydroxy-3-(2-methylpropyl)-2-oxo-1-(2-phenylethyl)-3-pyrrolidineacetamide

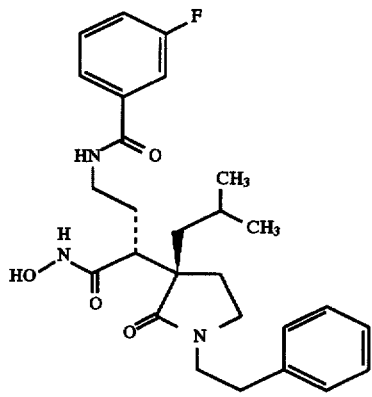

mp 144°–145° C.;

[α]$_D^{25}$ +13° (c 0.75, CHCl$_3$);

IR (mull) 3290, 3216, 3062, 3029, 1673, 1662, 1643, 1585, 1555, 1496, 1486, 1323, 1301, 1227, 698 cm$^{-1}$;

$^1$H NMR (300 MHz, CDCl$_3$) δ 7.45–7.60, 7.10–7.45, 6.97, 3.35–3.70, 3.15–3.30, 2.83, 2.40–2.55, 1.80–2.05, 1.40–1.70, 0.87, 0.80;

MS (EI) m/z 483 (M$^+$), 451, 262, 245, 202, 154, 123, 105, 104, 95, 56.

EXAMPLE 75

Preparation of α-[2-[(4-Fluorobenzoyl)amino]ethyl]-N-hydroxy-3-(2-methylpropyl)-2-oxo-1-(2-phenylethyl)-3-pyrrolidineacetamide

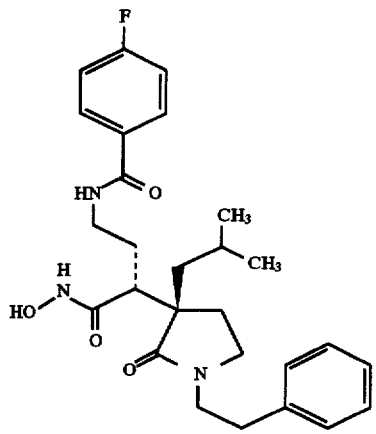

IR (mull) 2950, 2932, 1718, 1661, 1604, 1547, 1504, 1466, 1454, 1234 cm$^{-1}$.

EXAMPLE 76

Preparation of N-Hydroxy-3-(2-methylpropyl)-α-[2-[(3-nitrobenzoyl)amino]ethyl]-2-oxo-1-(2-phenylethyl)-3-pyrrolidineacetamide

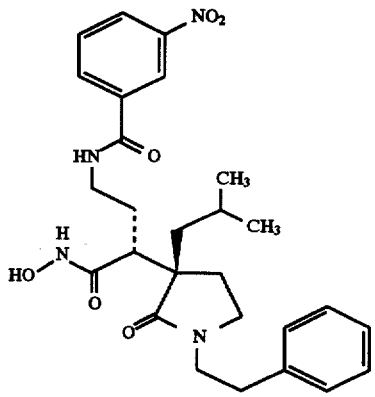

IR (mull) 3270, 1664, 1633, 1556, 1532, 1454, 1447, 1351, 1310, 698 cm$^{-1}$;

MS (EI) m/e 510.

EXAMPLE 77

Preparation of α-[2-[(3-Fluorobenzoyl)amino]ethyl]-N-hydroxy-3-(2-methylpropyl)-2-oxo-1-(2-phenylethyl)-3-pyrrolidineacetamide

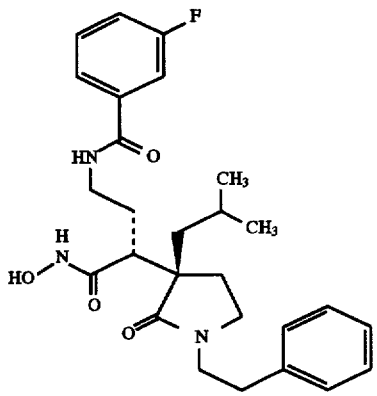

mp 157°–159° C.;

IR (mull) 2954, 2925, 2868, 2855, 1645, 1624, 1586, 1552, 1465, 1455 cm$^{-1}$;

MS (EI) m/e 403.

EXAMPLE 78

Preparation of α-[2-[(3-Fluorobenzoyl)amino]ethyl]-1-[2-(4-fluorophenyl)ethyl]-N-hydroxy-3-(2-methylpropyl)-2-oxo-3-pyrrolidineacetamide

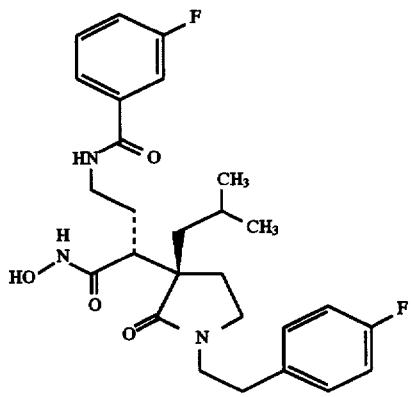

IR (mull) 2954, 2924, 2855, 1662, 1586, 1544, 1510, 1484, 1462, 1224 cm$^{-1}$.

EXAMPLE 79

Preparation of α-[2-[(4-Biphenylcarbonyl)amino]ethyl]-N-hydroxy-3-(2-methylpropyl)-2-oxo-1-(2-phenylethyl)-3-pyrrolidineacetamide

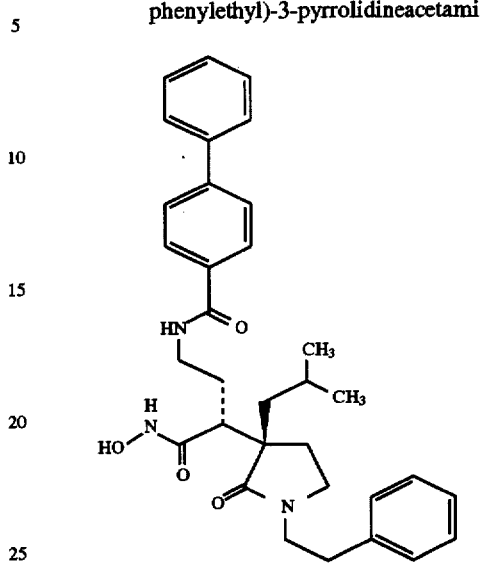

MS (EI) m/e MH$^+$ 542.

EXAMPLE 80

Preparation of N-Hydroxy-α-[2-[[(4-methylphenyl)sulfonyl]amino]ethyl]-3-(2-methylpropyl)-2-oxo-(2-phenylethyl)-3-pyrrolidineacetamide

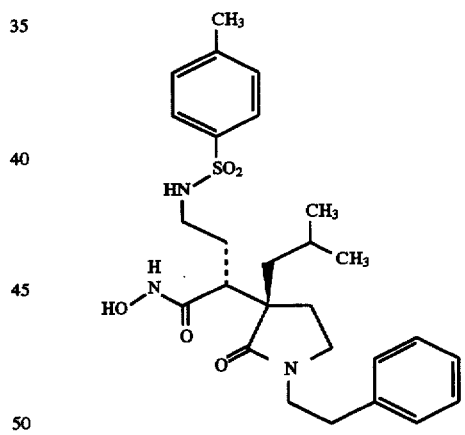

Step 1.

Preparation of tert-Butyl α-[2-[[(4-Methylphenyl)sulfonyl]amino]ethyl]-3-(2-methylpropyl)-2-oxo-1-(2-phenylethyl)-3-pyrrolidineacetate Toluenesulfonyl chloride (372 mg) is added to a solution of tert-butyl α-(2-aminoethyl)-3-(2-methylpropyl)-2-oxo-1-(2-phenylethyl)-3-pyrrolidineacetate (EXAMPLE 73, step 1; 654 mg, 1.62 mmol), CH$_2$Cl$_2$ (10.0 mL), and diisopropylethylamine (0.34 mL) at 0° C. The solution is stirred at 0° C. for 1 hour and at room temperature for 16 hours. Basic workup (CH$_2$Cl$_2$, NaHCO$_3$, MgSO$_4$) and purification by flash chromatography gives 634 nag (70%) of the title compound as a white solid (mp 136°–138° C.):

IR (mineral oil) 1710, 1674, 1366, 1329, 1303, 1156, 1101 cm$^{-1}$;

¹H NMR (300 MHz, CDCl₃) δ 7.73, 7.15–7.35, 4.45–4.55, 3.50–3.70, 3.30–3.45, 3.15–3.30, 2.75–3.10, 2.42, 2.20–2.35, 1.80–1.95, 1.60–1.80, 1.30–1.60, 1.38, 0.84, 0.79;

MS (FAB) m/z 557 (MH⁺), 503, 502, 501, 484, 483, 105, 91, 57.
Step 2.

Preparation of α-[2-[[(4-Methylphenyl)sulfonyl]amino]ethyl]-3-(2-methylpropyl)-2-oxo-1-(2-phenylethyl)-3-pyrrolidineacetic Acid TFA (7.0 mL) is added to a solution of tert-butyl α-[2-[[(4-methylphenyl)sulfonyl]amino]ethyl]-3-(2-methylpropyl)-2-oxo-1-(2-phenylethyl)-3-pyrrolidineacetate (616 mg, 1.11 mmol) and CH₂Cl₂ (7.0 mL) at 0° C. The solution is stirred for 1 h at 0° C. and for 2 hours at room temperature. The solution is concentrated which is repeated twice more from CH₂Cl₂ (2×20 mL). Aqueous workup (CH₂Cl₂, MgSO₄) provides 463 mg (84%) of the title compound as a white foam:

IR (mineral oil) 1733, 1615, 1503, 1498, 1481, 1330, 1305, 1288, 1160, 1094, 701 cm⁻¹; ¹H NMR (300 MHz, CDCl₃) δ 7.70–7.80, 7.15–7.40, 4.80–5.00, 3.70–3.90, 3.20–3.50, 2.65–3.10, 2.50–2.65, 2.42, 1.95–2.10, 1.80–1.95, 1.50–1.80, 1.00–1.20, 0.92, 0.85;

MS (EI) m/z 500 (M⁺), 426, 392, 391, 334, 327, 244, 155, 105, 104, 91.
Step 3.

Preparation of N-Benzyloxy-α-[2-[[(4-methylphenyl)sulfonyl]amino]ethyl]-3-(2-methylpropyl)-2-oxo-1-(2-phenylethyl)-3-pyrrolidineacetamide CDI (162 mg) is added to a solution of α-[2-[[(4-methylphenyl)sulfonyl]amino]ethyl]-3-(2-methylpropyl)-2-oxo-1-(2-phenylethyl)-3-pyrrolidineacetic acid (453 mg) and CH₂Cl₂ (5.0 mL). The solution is stirred for 1 hour at room temperature and then O-benzylhydroxylamine hydrochloride (192 mg) and 4-methylmorpholine (0.13 mL) are added. The solution is stirred for 16 h at room temperature. The solution is diluted with 60 mL of EtOAc which is washed with 10% HCl, brine, dried (MgSO₄), filtered, and concentrated. Purification by flash chromatography (1:1 hexane:EtOAc) provides a lactam intermediate with no evidence of O-benzylhydroxylamine incorporation:

¹H NMR (300 MHz, CDCl₃) δ 7.86, 7.15–7.45, 3.85–4.00, 3.45–3.70, 3.18, 2.85, 2.60–2.80, 2.43, 1.80–2.15, 1.35–1.55, 0.70–0.95.

A solution of the bis-lactam intermediate (317 mg, 0.657 mmol), O-benzylhydroxylamine (500 mg) and THF (4.0 mL) is heated at reflux for 72 hours and then allowed to cool to room temperature. The residue is diluted with EtOAc which is washed with 10% HCl (2×10 mL) and brine (10 mL). The organic layer is dried (MgSO₄), filtered, and concentrated. Purification by flash chromatography (1:1 hexane:EtOAc) and crystallization from ether provides 139 mg (35%) of the title compound as a white crystalline material (mp 155°–157° C.):

IR (mull) 3162, 1664, 1650, 1332, 1154, 704 cm⁻¹;

¹H NMR (300 MHz, CDCl₃) δ 7.71, 7.15–7.40, 4.97, 4.81, 3.35–3.65, 3.17, 2.75–3.00, 2.55–2.75, 2.30–2.45, 2.39, 1.80–2.05, 1.35–1.70, 0.84, 0.77;

MS(EI) m/e 605, 483, 433, 327, 245, 202.
Step 4.

Preparation of N-Hydroxy-α-[2-[[(4-methylphenyl)sulfonyl]amino]ethyl]-3-(2-methylpropyl)-2-oxo-1-(2-phenylethyl)-3-pyrrolidineacetamide A mixture of N-benzyloxy-α-[2-[[(4-methylphenyl)sulfonyl]amino]ethyl]-3-(2-methylpropyl)-2-oxo-1-(2-phenylethyl)-3-pyrrolidineacetamide (133 mg, 0.220 mmol), MeOH (8.0 mL), and Pearlman's cat (25 mg) is hydrogenated (1 atm) for 8 h at room temperature. The mixture is filtered, the solids washed with MeOH (2×5 mL), CH₂Cl₂ (5 mL), and MeOH (5 mL). The combined filtrates are concentrated and the residue crystallized from EtOAc/hexane to give 84 mg (74%) of the title compound as a white solid (mp 166.5°–167° C.):

IR (mull) 3278, 3202, 3028, 1659, 1636, 1496, 1329, 1298, 1291, 1160, 1093, 1061, 816, 702, 656 cm⁻¹;

¹H NMR (300 MHz, CDCl₃) δ 7.72, 7.30–7.60, 7.15–7.35, 5.82, 3.40–3.70, 3.15–3.35, 2.95–3.10, 2.70–2.95, 2.81, 2.57, 2.40, 2.10–2.25, 1.80–2.00, 1.30–1.75, 0.86, 0.80;

MS (EI) m/z 515 (M⁺), 483, 391, 343, 245, 244, 202, 155, 105, 104, 91.

Following the general procedures outlined in EXAMPLE 80 and making non-critical variations, the following compounds are prepared.

EXAMPLE 81

Preparation of α-[2-[[(4-Fluorophenyl)sulfonyl]amino]ethyl]-N-hydroxy-3-(2-methylpropyl)-2-oxo-1-(2-phenylethyl)-3-pyrrolidineacetamide

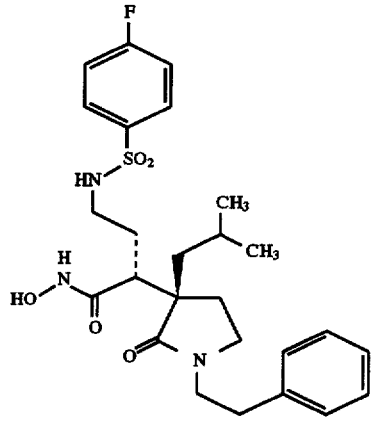

IR (mull) 3195, 3026, 1661, 1634, 1593, 1496, 1333, 1259, 1238, 1166, 1157, 1095, 1060, 844, 702 cm⁻¹;

¹H NMR (300 MHz, CDCl₃) δ 8.79, 7.75–7.90, 7.50–7.70, 7.43, 7.10–7.30, 3.10–3.50, 2.68, 2.40–2.75, 2.05–2.20, 1.85–2.00, 1.50–1.70, 1.30–1.50, 1.15–1.30, 0.75, 0.66;

MS (EI) m/z 519 (M⁺), 395, 245, 202, 159, 154, 110, 105, 104, 95, 56.

EXAMPLE 82

Preparation of N-Hydroxy-α-[2-[[(4-methoxyphenyl)sulfonyl]amino]ethyl]-3-(2-methylpropyl)-2-oxo-1-(2-phenylethyl)-3-pyrrolidineacetamide

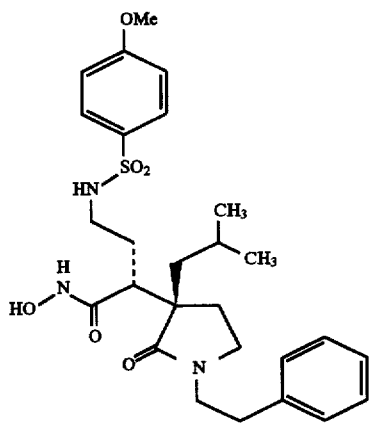

MS (EI) m/e 532 (MH⁺).

EXAMPLE 83

Preparation of N-Hydroxy-3-(2-methylpropyl)-2-oxo-1-(2-phenylethyl)-α-[2-[(phenylsulfonyl)amino]ethyl]-3-pyrrolidineacetamide

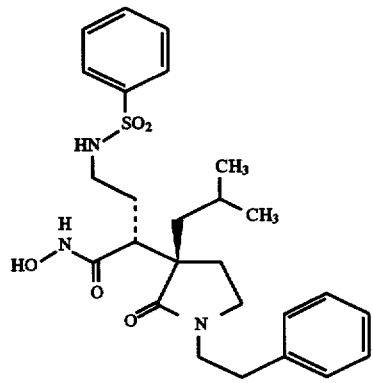

IR (mull) 2954, 2924, 2862, 2855, 1663, 1610, 1569, 1453, 1446, 1429 cm⁻¹;

MS (EI) m/e 502 (MH⁺).

EXAMPLE 84

Preparation of [R-(R*,S*)]-α-[2-[[(4-Fluorophenyl)sulfonyl]amino]ethyl]-N-hydroxy-3-(2-methylpropyl)-2-oxo-1-(2-phenylethyl)-3-pyrrolidineacetamide

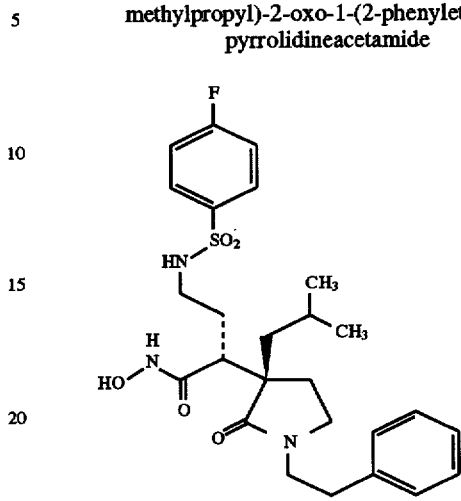

mp 67°–70° C.;

IR (mull) 3196, 3107, 3065, 3027, 1662, 1592, 1495, 1332, 1292, 1237, 1166, 1154, 1093, 839, 701 cm⁻¹;

¹H NMR (300 MHz, CDCl₃) δ 7.80–7.95, 7.40–7.70, 7.10–7.40, 5.90, 3.10–3.70, 3.00–3.15, 2.70–3.00, 2.55, 2.05–2.20, 1.80–2.00, 1.20–1.80, 0.85, 0.80;

MS (FAB) m/z 520 (MH⁺), 519, 504, 488, 487, 343, 202, 105.

EXAMPLE 85

Preparation of 5,6-Difluoro-1,3-dihydro-N-hydroxy-α-[3-(2-methylpropyl)-2-oxo-1-(2-phenylethyl)-3-pyrrolidinyl]-1-oxo-2H-isoindole-2-butanamide

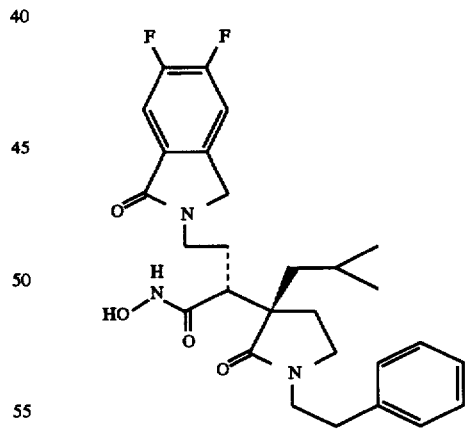

Step 1.

Preparation of tert-Butyl α-[2-(3-Acetoxy-5,6-difluoro-1,3-dihydro-1-oxo-2H-isoindol-2-yl)ethyl]-3-(2-methylpropyl)-2-oxo-1-(2-phenylethyl)-3-pyrrolidineacetate Sodium borohydride (26 mg, 0.68 mmol) is added to a solution of tert-butyl α-[2-(5,6-difluoro-1,3-dihydro-1,3-dioxo-2H-isoindol-2-yl)ethyl]-3-(2-methylpropyl)-2-oxo-1-(2-phenylethyl)-3-pyrrolidineacetate (EXAMPLE 64; 384 mg, 0.675 mmol) and methanol (2.4 mL) at room temperature. The solution is stirred overnight at room temperature. Aqueous workup (EtOAc, MgSO$_4$) provides 386 mg (100%) of the diastereomeric mixture as a white foam. Solid 4-dimethylaminopyridine (14 mg, 0.12 mmol) is added to a solution of the crude alcohol (336 mg, 0.590 mmol), triethylamine (0.49 mL, 3.5 mmol), acetic anhydride (0.28 mL, 3.0 mmol) and CH$_2$Cl$_2$ (6.0 mL). The solution is stirred at room temperature for 2 hours. The reaction mixture was diluted with ether and the ether is washed with 10% HCl, saturated NaHCO$_3$, dried over MgSO$_4$, filtered, and concentrated. Column chromatography (20→50% EtOAc/hexane) provides 273 mg (76%) of the title compound as a diastereomeric mixture as an oil:

MS (EI) m/z 612 (M$^+$) 497, 496, 440, 406, 405, 245, 236, 202, 105, 57.

Step 2.

Preparation of tert-Butyl 5,6-Difluoro-1,3-dihydro-α-[3-(2-methylpropyl)-2-oxo-1-(2-phenylethyl)-3-pyrrolidinyl]-1-oxo-2H-isoindole-2-butyrate A mixture of tert-butyl α-[2-(3-acetoxy-5,6-difluoro-1,3-dihydro-1-oxo-2H-isoindol-2-yl)ethyl]-3-(2-methylpropyl)-2-oxo-1-(2-phenylethyl)-3-pyrrolidineacetate (236 mg, 0.386 mmol), palladium on carbon (10%, 60 mg) and acetonitrile (30 mL) is hydrogenated at 35 psi for 2 hours. The mixture was filtered and concentrated. Aqueous workup (EtOAc, MgSO$_4$) gave 200 mg (93%) of the title compound as an oil:

MS (EI) m/z 554 (M$^+$) 499, 498, 481, 408, 407, 247, 202, 182, 105, 57.

Step 3.

Following the general procedure outlined in EXAMPLE 1, steps 4 and 5, and making non-critical variations, but starting with tert-butyl 5,6-difluoro-1,3-dihydro-α-[3-(2-methylpropyl)-2-oxo-1-(2-phenylethyl)-3-pyrrolidinyl]-1-oxo-2H-isoindole-2-butyrate, the title compound is obtained: (mp 175°–176° C.):

IR (mull) 3186, 3060, 3022, 1702, 1659, 1511, 1436, 1307, 1290, 1265, 1219, 762, 757, 707, 699 cm$^{-1}$;

$^1$H NMR (300 MHz, CDCl$_3$) δ 8.80, 7.45–7.60, 7.05–7.35, 4.30-4.60, 3.05–3.75, 2.60–2.80, 1.30–2.60, 0.87, 0.78;

MS (EI) m/z 513 (M$^+$) 514, 513, 480, 423, 262, 244, 236, 202, 182, 105.

Following the general procedures outlined in EXAMPLE 85 and making non-critical variations, the following compounds are prepared.

EXAMPLE 86

Preparation of 1,3-Dihydro-N-hydroxy-α-[8-(2-methylpropyl)-2-oxo-1-(2-phenylethyl)-3-pyrrolidinyl]-1-oxo-2H-isoindole-2-butanamide

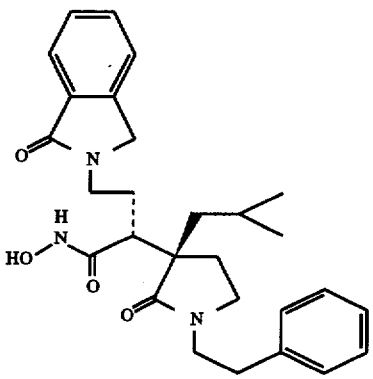

mp 140°–144° C.;

IR (mull) 3165, 3085, 3058, 3020, 1683, 1669, 1653, 1616, 1487, 1424, 1349, 1335, 1295, 738, 699 cm$^{-1}$;

$^1$H NMR (300 MHz, CDCl$_3$) δ 7.80, 7.35–7.55, 7.00–7.35, 4.30–4.55, 3.10–3.85, 2.60–2.80, 1.90–2.40, 1.45–1.85, 0.87, 0.76;

MS (EI) m/z 477 (M$^+$), 202, 200, 189, 146, 134, 105, 104, 91, 56.

EXAMPLE 87

Preparation of [R-(R*,S*)]-6-Fluoro-1,3-dihydro-N-hydroxy-α-[3-(2-methylpropyl)-2-oxo-1-(2-phenylethyl)-3-pyrrolidinyl]-1-oxo-2H-isoindole-2-butanamide

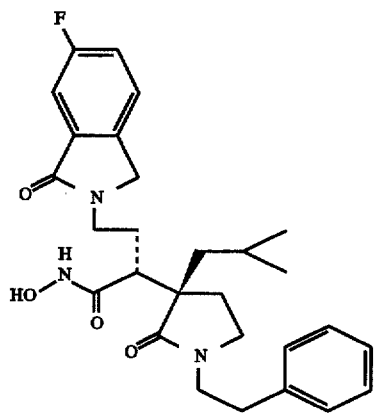

mp 167°–170° C.;

$^1$H NMR (300 MHz, CDCl$_3$) δ 7.48, 7.35–7.45, 7.05–7.35, 4.30–4.50, 3.10–3.80, 2.55–2.95, 1.15–2.55, 0.87, 0.77;

MS (ESI) 496 (MH$^+$).

EXAMPLE 88

Preparation of [R-(R*,S*)]-5-Fluoro-1,3-dihydro-N-hydroxy-α-[3-(2-methylpropyl)-2-oxo-1-(2-phenylethyl)-3-pyrrolidinyl]-1-oxo-2H-isoindole-2-butanamide

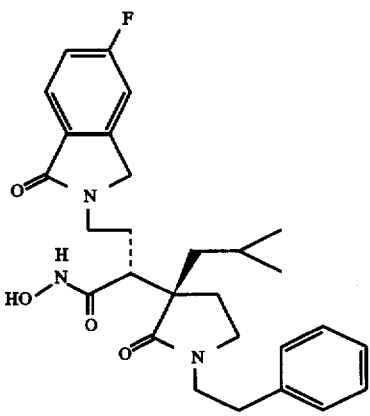

mp 135°–136° C.;

¹H NMR (300 MHz, CDCl₃) δ 7.70–7.85, 7.44, 7.00–7.35, 4.30–4.55, 3.05–3.80; 2.55–2.80, 2.35–2.55, 1.85–2.35, 0.87, 0.76;

MS (ESI) 496 (MH⁺).

EXAMPLE 89

Preparation of [R-(R*,S*)]-5,6-Difluoro-1,3-dihydro-N-hydroxy-α-[3-(2-methylpropyl)-2-oxo-1-(2-phenylethyl)-3-pyrrolidinyl]-1-oxo-2H-isoindole-2-butanamide

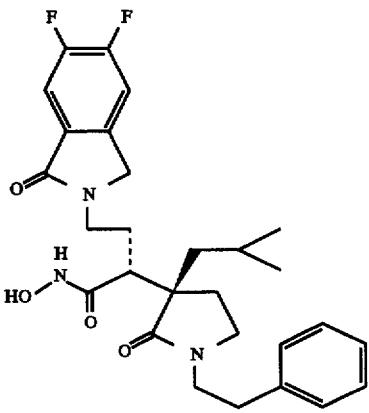

mp 153.5°–155° C.;

¹H NMR (300 MHz, CDCl₃) δ 8.98, 7.50–7.65, 7.43, 7.00–7.35, 4.50, 3.10–3.75, 2.60–2.80, 2.45–2.60, 2.25–2.45, 1.85–2.25, 1.40–1.85, 0.87, 0.79;

MS (ESI) 514 (MH⁺).

EXAMPLE 90

Preparation of N-Hydroxy-α-[[[(4-methoxyphenyl)sulfonyl]amino]methyl]-3-(2-methylpropyl)-2-oxo-1-(2-phenylethyl)-3-pyrrolidineacetamide (αR-diastereomer)

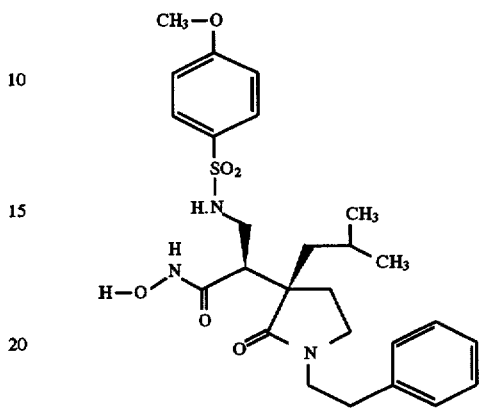

Step 1.

Preparation of tert-Butyl α-(1-Hydroxymethyl)-3-(2-methylpropyl)-2-oxo-1-(2-phenylethyl)-3-pyrrolidineacetate (αS-diastereomer)

A cold (−78° C.) solution of tert-butyl 3-(2-methylpropyl)-2-oxo-1-(2-phenylethyl)-3-pyrrolidineacetate (EXAMPLE 1, step 3; 2.00 g, 5.56 mmol) in dry THF (20 mL) is treated with the dropwise addition of LDA (3.20 mL, 6.40 mmol, 2.0N). The solution is maintained at −78° C. for 30 min and then warmed to −30° C. Gaseous formaldehyde (generated by heating 834 mg of paraformaldehyde at 160° C. to provide approximately 28 mmol) is bubbled through the enolate solution. The solution is maintained at −30° C. for 1 hour and then quenched with saturated aqueous NH₄Cl (5 mL) and diluted with H₂O (20 mL). The product is extracted into EtOAc (3×50 mL), dried over anhydrous MgSO₄, filtered, and concentrated under reduced pressure to provide 2.52 g of a yellow solid which is purified by silica gel chromatography (100 g SG; 25% EtOAc/hexane) to give 1.43 g (83%) of the title compound as a golden oil. Another fraction containing 375 mg of a mix of both diastereomers is also recovered. Spectral data for the title compound:

IR (liq.) 3417, 2957, 2931, 2869, 1722, 1669, 1497, 1465, 1455, 1392, 1368, 1274, 1252, 1155, 701 cm⁻¹;

¹H NMR (300 MHz, CDCl₃) δ 7.15–7.40, 3.90–4.05, 3.70–3.80, 3.55–3.70, 3.40–3.55, 3.20–3.30, 2.85, 2.75, 2.69, 2.00–2.20, 1.90–2.00, 1.65–1.70, 1.50–1.60, 1.44, 0.90, 0.84;

MS (EI) m/z 389 (M⁺), 333, 316, 298, 277, 243, 242, 202, 105, 104, 57.

Step 2.

Preparation of tert-Butyl α-(1-Hydroxymethyl)-3-(2-methylpropyl)-2-oxo-1-(2-phenylethyl)-3-pyrrolidineacetate (αR-diastereomer)

A cold (−78° C.) solution of oxalyl chloride (1.02 mL, 11.7 mmol) in dry CH₂Cl₂ (30 mL) is treated with DMSO (1.66 mL, 23.4 mmol, in 5 mL CH₂Cl₂). After 5 min, tert-butyl α-(1-hydroxymethyl)-3-(2-methylpropyl)-2-oxo-1-(2-phenylethyl)-3-pyrrolidineacetate (S-isomer) (3.80 g, 9.76 mmol) is added. The solution is stirred for an additional 15 min and then quenched with triethylamine (6.8 mL, 48.8 mmol). The solution is maintained at −78° C. for 30 min and then allowed to warm to room temperature under $N_2$. After 2.5 hours, the solution is diluted with $H_2O$ (50 mL) and extracted into EtOAc (3×100 mL). The extracts are combined, dried over anhydrous $MgSO_4$, filtered, and concentrated under reduced pressure to provide a quantitative yield of the desired aldehyde as a ca. 1:2 mixture in favor of the R diastereomer. Key peaks of the NMR of the crude mixture:

$^1$H NMR (300 MHz, $CDCl_3$) δ 9.75, 9.48.

A cold (0° C.) solution of the aldehyde mixture (1.68 g, 4.34 mmol) in MeOH (30 mL) is treated with sodium borohydride (246 mg, 6.51 mmol). The solution is maintained at 0° C. for 1 h, and then allowed to warm to room temperature. After 3 hours, the solution is concentrated to a yellow foam. The foam is diluted with $H_2O$ (25 mL) and extracted with EtOAc (3×50 mL). The extracts are combined, dried over anhydrous $MgSO_4$, filtered, and concentrated under reduced pressure. The material, 1.69 g, is purified by silica gel chromatography (100 g SG; 20% EtOAc/hexane) to provide 562 mg (33%) of the title compound, 467 mg (28%) of the S diastereomer and 331 mg of the unreduced aldehyde. Spectral data for the title compound:

IR (mineral oil) 3542, 3006, 1704, 1672, 1499, 1396, 1313, 1265, 1160, 1124, 1066, 1059, 1036, 738, 697 cm$^{-1}$;
$^1$H NMR (300 MHz, $CDCl_3$) δ 7.15–7.35, 3.95, 3.75, 3.60–3.75, 3.40–3.65, 3.24, 2.87, 2.69, 1.80–2.15, 1.40–1.70, 1.45, 0.89, 0.87;
MS (FAB) m/z 390 (MH$^+$), 335, 334, 332, 316, 298, 242, 105, 57.

Step 3.

Preparation of tert-Butyl α-(1-Azidomethyl)-3-(2-methylpropyl)-2-oxo-1-(2-phenylethyl)-3-pyrrolidineacetate Methanesulfonyl chloride (0.058 mL, 0.751 mmol) is added dropwise to a solution of tert-butyl α-(1-hydroxymethyl)-3-(2-methylpropyl)-2-oxo-1-(2-phenylethyl)-3-pyrrolidineacetate (αR-diastereomer) (225 mg, 0.578 mmol) and triethylamine (105 mL, 0.751 mmol) in dry $CH_2Cl_2$ (3 mL). The solution is stirred overnight at room temperature under $N_2$. After diluting with $CH_2Cl_2$ (20 mL), the solution is washed with saturated $NaHCO_3$ (5 mL), $H_2O$ (5 mL), and brine (5 mL). The organic layer is dried over anhydrous $MgSO_4$, filtered, and concentrated under reduced pressure to give 289 mg of a gold oil. The oil is purified by silica gel chromatography (10 g SG; 20% EtOAc/hexane) to provide 243 mg (90%) of the mesylate as an oil:

$^1$H NMR (300 MHz, $CDCl_3$) δ 7.10–7.40, 4.47, 4.17, 3.35–3.70, 3.05–3.30, 2.90–3.05, 2.97, 2.84, 2.10–2.30, 1.75–1.95, 1.30–1.70, 1.46, 0.88, 0.86.

A solution of the mesylate (795 mg, 1.70 mmol) and sodium azide (166 mg, 2.55 mmol) in DMSO (6 mL) is heated at 60° C. for 24 hours and then allowed to cool to room temperature under $N_2$. The solution is diluted with $Et_2O$ (40 mL) and washed with $H_2O$ (3×15 mL) and brine (15 mL). The organic layer is dried over anhydrous $MgSO_4$, filtered, and concentrated under reduced pressure to give 679 mg (96%) of the title compound as a clear, colorless oil:

IR (liq.) 2958, 2932, 2870, 2101, 1725, 1682, 1498, 1455, 1393, 1368, 1276, 1152, 1122, 748, 700 cm$^{-1}$;
$^1$H NMR (300 MHz, $CDCl_3$) δ 7.15–7.35, 3.10–3.80, 3.00, 2.70–2.95, 2.15–2.30, 1.30–1.90, 1.47, 0.85;

MS (EI) m/z 414 (M$^+$), 358, 268, 267, 246, 224, 212, 105, 104, 57.

Step 4.

Preparation of tert-Butyl α-(1-Aminomethyl)-3-(2-methylpropyl)-2-oxo-1-(2-phenylethyl)-3-pyrrolidineacetate A mixture of tert-butyl α-(1-azidomethyl)-3-(2-methylpropyl)-2-oxo-1-(2-phenylethyl)-3-pyrrolidineacetate (648 mg, 1.56 mmol) and 10% palladium on carbon (163 mg) in EtOH (25 mL) is hydrogenated at 30 psi in a Parr flask for 16 hours. The mixture is filtered, rinsing the residual solids with MeOH and $CH_2Cl_2$. The filtrate is concentrated and purified by silica gel chromatography (15 g SG; EtOAc, 15% MeOH/EtOAc) to provide 356 mg (57%) of the title compound as a partially crystalline solid:

IR (mull) 3004, 1718, 1672, 1498, 1394, 1311, 1296, 1263, 1223, 1156, 1149, 852, 738, 697, 620 cm$^{-1}$;
$^1$H NMR (300 MHz, $CDCl_3$) δ 7.15–7.35, 3.35–3.70, 3.05–3.30, 2.70–2.95, 2.60–2.70, 2.45–2.60, 2.20–2.40, 1.25–2.00, 1.46, 0.85 MS (FAB) m/z 389 (MH$^+$), 359, 334, 333, 316, 202, 105, 57.

Step 5.

Preparation of tert-Butyl α-[[[(4-Methoxyphenyl)sulfonyl]amino]methyl]-3-(2-methylpropyl)-2-oxo-1-(2-phenylethyl)-3-pyrrolidineacetate A cold (0° C.) solution of tert-butyl α-(1-aminomethyl)-3-(2-methylpropyl)-2-oxo-1-(2-phenylethyl)-3-pyrrolidineacetate (337 mg, 0.867 mmol) in dry $CH_2Cl_2$ (3 mL) is treated with diisopropylethylamine (240 μL, 1.30 mmol) and 4-methoxybenzenesulfonyl chloride (215 mg, 1.30 mmol). The solution was allowed to slowly warm to room temperature, stirring overnight under $N_2$. After diluting with $CH_2Cl_2$ (25 mL), the solution is washed with dilute $NaHCO_3$ (10 mL), $H_2O$ (10 mL), and brine (10 mL). The organic layer was dried over anhydrous $MgSO_4$, filtered, and concentrated under reduced pressure to give 460 mg of a yellow oil. The oil was purified by silica gel chromatography (20 g SG; 25% EtOAc/hexane) to provide 383 mg (79%) of the desired material as a white amorphous solid:

IR (liq.) 2958, 2932, 1725, 1668, 1598, 1499, 1455, 1444, 1368, 1334, 1304, 1279, 1260, 1160, 1097 cm$^{-1}$;
$^1$H NMR (300 MHz, $CDCl_3$) δ 7.79, 7.10–7.35, 6.95, 5.45–5.60, 3.81, 3.30–3.65, 2.95–3.30, 2.60–2.90, 2.00–2.20, 1.70–1.90, 1.20–1.70, 1.43, 0.80;

MS (EI) m/z 558 (M$^+$), 411, 387, 287, 246, 245, 202, 171, 107, 105, 57.

Step 6.

Preparation of α-[[[(4-Methoxyphenyl)sulfonyl]amino]methyl]-3-(2-methylpropyl)-2-oxo-1-(2-phenylethyl)-3-pyrrolidineacetic acid A cold (0° C.) solution of tert-butyl α-[[[(4-methoxyphenyl)sulfonyl]amino]methyl]-3-(2-methylpropyl)-2-oxo-1-(2-phenylethyl)-3-pyrrolidineacetate (374 mg, 0.669 mmol) in $CH_2Cl_2$ (2 mL) is treated with TFA (2 mL). The solution is maintained at 0° C. for 40 min and then allowed to warm to room temperature under $N_2$. After 1.5 hours, the solution is diluted with $CH_2Cl_2$ and stripped (5×). The residual foam is diluted with $H_2O$ (5 mL) and extracted into $CH_2Cl_2$ (3×20 mL). The extracts are combined, dried over anhydrous $MgSO_4$, filtered, and concentrated under reduced pressure to provide 301 mg (90%) of the title compound as a white, amorphous solid:

IR (mull) 3062, 3026, 1713, 1647, 1597, 1580, 1498, 1332, 1304, 1261, 1180, 1158, 1096, 834, 701 cm$^{-1}$;

$^1$H NMR (300 MHz, CDCl$_3$) δ 7.70–7.80, 7.15–7.35, 6.90–7.00, 5.45–5.55, 3.86, 3.45–3.75, 3.00–3.40, 2.89, 2.67, 1.95–2.25, 1.35–1.60, 0.84, 0.78;

MS (EI) m/z 502 (M$^+$), 411, 287, 246, 245, 244, 202, 171, 107, 105, 77.

Step 7.

Preparation of N-Benzyloxy-α-[[[(4-methoxyphenyl)sulfonyl]amino]methyl]-3-(2-methylpropyl)-2-oxo-1-(2-phenylethyl)-3-pyrrolidineacetamide A solution of α-[[[(4-methoxyphenyl)sulfonyl]amino] methyl]-3-(2-methylpropyl)-2-oxo-1-(2-phenylethyl)-3-pyrrolidineacetic acid (290 mg, 0.577 mmol) in dry CH$_2$Cl$_2$ (5 mL) is treated with CDI (112 mg, 0.692 mmol). Afar 1 h, 4-methylmorpholine (0.095 mL, 0.866 mmol) and O-benzylhydroxyamine HCl (138 mg, 0.866 mmol) are added. The solution is stirred at room temperature under N$_2$ for 65 h. The solvent had evaporated, and the residual gel is diluted with EtOAc (25 mL). The solution is washed with 1N HCl (10 mL), 1N NaOH (10 mL), and brine (10 mL). The organic layer is dried over anhydrous MgSO$_4$, filtered, and concentrated under reduced pressure to give 380 mg of an oil. The oil is purified by silica gel chromatography (30 g SG; 50% EtOAc/hexane) to provide 249 mg (71%) of the title compound as an oil:

IR (mull) 3205, 3028, 1658, 1597, 1498, 1331, 1304, 1287, 1261, 1157, 1096, 1027, 834, 749, 699 cm$^{-1}$;

$^1$H NMR (300 MHz, CDCl$_3$) δ 7.70–7.85, 7.10–7.45, 6.85–7.00, 5.70–5.80, 4.86, 3.76, 3.40–3.55, 3.00–3.25, 2.60–3.00, 2.30–2.50, 1.80–2.00, 1.30–1.60, 0.82, 0.75;

MS (FAB) m/z 608 (MH$^+$), 485, 298, 286, 244, 171, 107, 105, 91.

Step 8.

Preparation of N-Hydroxy-α-[[[(4-methoxyphenyl)sulfonyl]amino]methyl]-3-(2-methylpropyl)-2-oxo-1-(2-phenylethyl)-3-pyrrolidineacetamide A solution of N-benzyloxy-α-[[[(4-methoxyphenyl)sulfonyl]amino]methyl]-3-(2-methylpropyl)-2-oxo-1-(2-phenylethyl)-3-pyrrolidineacetamide (218 mg, 0.359 mmol) in EtOH (7 mL) is treated with palladium hydroxide on carbon (55 mg) and placed under a H$_2$ atmosphere via a balloon. After 6.5 hours, the mixture is filtered, rinsing the residual solids with MeOH and CHCl$_3$. The filtrate is concentrated to give 182 mg of a white solid. The material is crystallized from hot EtOAc with a trace of MeOH, eventually diluting with hexane, to provide 136 mg of the title compound as a solid (mp 195°–196° C.):

IR (mull) 3317, 3095, 1658, 1620, 1597, 1496, 1335, 1304, 1257, 1163, 1097, 833, 829, 805, 751 cm$^{-1}$;

$^1$H NMR (300 MHz, CDCl$_3$) δ 7.78, 7.05–7.35, 6.91, 6.20–6.35, 3.75, 3.35–3.60, 3.05–3.35, 2.60–2.90, 2.25–2.50, 1.80–2.00, 1.15–1.70, 0.83, 0.77; MS (EI) m/z 517 (M$^+$), 261, 245, 244, 202, 171, 154, 107, 105.

EXAMPLE 91

Preparation of N-Hydroxy-α-[[[(4-methoxyphenyl)sulfonyl]amino]methyl]-3-(2-methylpropyl)-2-oxo-1-(2-phenylethyl)-3-pyrrolidineacetamide (αS-diastereomer)

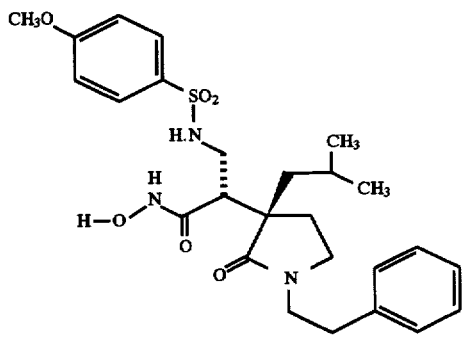

mp 60°–64° C.);

$^1$H NMR (300 MHz, CDCl$_3$) δ 7.70–7.90, 7.10–7.40, 6.85–7.05, 5.40–5.60, 3.86, 3.40–3.60, 2.95–3.30, 2.70–2.85, 2.05–2.25, 1.30–1.90, 0.65–0.90.

EXAMPLE 92

Preparation of α-[[(4-Fluorophenyl)sulfonyl]amino]-N-hydroxy-3-(2-methylpropyl)-2-oxo-1-(2-phenylethyl)-3-pyrrolidineacetamide (R-diastereomer)

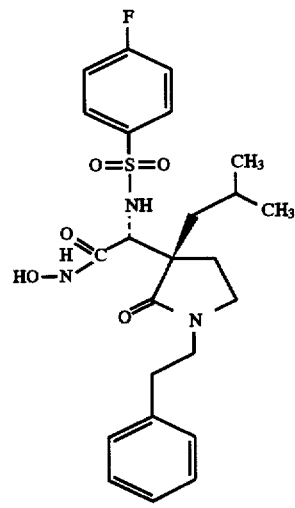

Step 1.

Preparation of tert-Butyl α-Azido-3-(2-methylpropyl)-2-oxo-1-(2-phenylethyl)-3-pyrrolidineacetate (αR-diastereomer)

Potassium bis(trimethylsilyl)amide (0.5M in toluene, 19.9 mL, 9.93 mmol) is added to a solution of tert-butyl 3-(2-methylpropyl)-2-oxo-1-(2-phenylethyl)-3-pyrrolidineacetate (EXAMPLE 1, step 3; 1.70 g, 4.73 mmol) and THF (57 mL) at –78° C. The solution is allowed to stir at –78° C. for 25 min. A solution of trisylazide (3.66 g, 11.8 mmol) in THF (34.5 mL) is added dropwise over 5 min. The solution is stirred for an additional 2 min and acetic acid (1.2 mL) is added. The solution was allowed to warm slowly and stir at room temperature overnight. Aqueous workup (EtOAc, NaHCO₃ wash, brine wash, MgSO₄) and column chromatography (7.5% EtOAc/hexane) provides 1.34 g (71%) of the title compound as a yellow oil:

¹H NMR (300 MHz, CDCl₃) δ 7.15–7.35, 4.23, 4.12, 3.65–3.80, 3.50–3.65, 3.15–3.40, 2.75–2.90, 2.35–2.50, 2.10–2.30, 1.15–1.85, 0.75–0.95;

MS (ESI) 401 (MH⁺).

Step 2.

Preparation of tert-Butyl α-Amino-3-(2-methylpropyl)-2-oxo-1-(2-phenylethyl)-3-pyrrolidineacetate (αR-diastereomer)

A mixture of tert-butyl α-azido-3-(2-methylpropyl)-2-oxo-1-(2-phenylethyl)-3-pyrrolidineacetate (159 mg, 0.397 mmol), palladium on carbon (10%, 40 mg) and EtOH (2.0 mL) is hydrogenated overnight at 30 psi. The mixture is filtered and concentrated to give 145 mg (97%) of the title compound as an oil:

¹H NMR (300 MHz, CDCl₃) δ 7.15–7.39, 3.55–3.75, 3.15–3.35, 2.84, 2.15–2.30, 1.85–1.95, 1.30–1.80, 1.46, 0.89, 0.84;

MS (ESI) 375 (MH⁺).

Following the procedures outlined in EXAMPLE 90 (steps 5–8) and making non-critical modifications, but starting with tert-butyl α-amino-3-(2-methylpropyl)-2-oxo-1-(2-phenylethyl)-3-pyrrolidineacetate (αR-diastereomer), the title compound is obtained (mp 111°–113° C.):

¹H NMR (300 MHz, CDCl₃) δ 9.05, 7.80–7.90, 7.05–7.35, 6.85, 5.25–5.50, 4.50–4.60, 3.80–3.90, 3.60–3.75, 3.05–3.60, 2.70–2.85, 2.10–2.35, 1.40–1.90, 1.55, 0.70–0.90;

MS (ESI) 492 (MH⁺).

Following the general procedures outlined in EXAMPLE 92 and making non-critical variations, the following compounds were prepared.

EXAMPLE 93

Preparation of α-[[(4-Fluorophenyl)sulfonyl]amino]-N-hydroxy-3-(2-methylpropyl)-2-oxo-1-(2-phenylethyl)-3-pyrrolidineacetamide (αS-diastereomer)

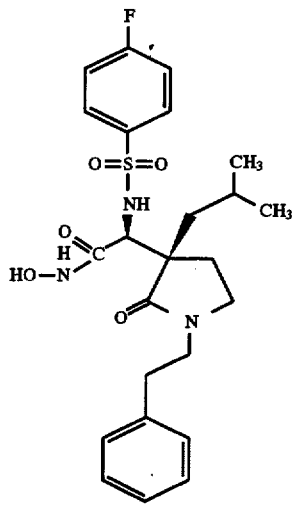

mp 99°–102° C.;

¹H NMR (300 MHz, CDCl₃) δ 7.75–7.85, 7.10–7.35, 5.06, 3.45–3.60, 3.15–3.35, 2.85, 2.35–2.50, 1.95–2.10, 1.15–1.60, 0.78, 0.74;

MS (ESI) 492 (MH⁺).

EXAMPLE 94

Preparation of α-[2-[(3,4-Difluorobenzoyl)amino]ethyl]-N-hydroxy-3-(3-hydroxypropyl)-2-oxo-1-(2-phenylethyl)-3-pyrrolidineacetamide

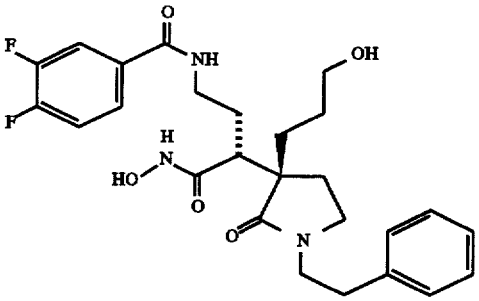

Step 1.

Preparation of tert-Butyl α-(2-Chloroethyl)-2-oxo-1-(2-phenylethyl)-3-(propen-2-yl)-3-pyrrolidineacetate A cold (−78° C.) solution of tert-butyl 2-oxo-1-(2-phenylethyl)-3-(propen-2-yl)-3-pyrrolidineacetate (prepared similarly to that described in EXAMPLE 1, step 3; 5.52 g, 16.1 mmol) in dry THF (100 mL) is treated with the dropwise addition of LDA (9.66 mL, 19.3 mmol, 2.0N). The solution is stirred for 30 min, and then treated with the dropwise addition of 1-bromo-2-chloroethane (1.61 mL, 19.3 mmol). The solution is maintained at −78° C. for 5 hours and then allowed to slowly warm to room temperature under N₂ overnight. The solution is quenched with saturated NH₄Cl (10 mL) and diluted with H₂O (25 mL). The product is extracted with EtOAc (3×100 mL), dried over anhydrous MgSO₄, filtered, and concentrated to give 6.6 g of a brown oil. The oil is purified by silica gel chromatography (275 g SG; 10% EtOAc/hexane) to provide 5.07 g (78%) of the title compound as a clear, yellow oil:

IR (liq.) 2977, 2931, 1721, 1685, 1496, 1455, 1440, 1393, 1367, 1282, 1257, 1149, 917, 748, 701 cm⁻¹;

¹H NMR (300 MHz, CDCl₃) δ 7.15–7.35, 5.45–5.65, 4.95–5.15, 3.25–3.80, 3.05–3.25, 2.81, 2.71, 1.90–2.45, 1.65–1.85, 1.43;

MS (EI) m/z 405 (M⁺), 370, 351, 349, 332, 314, 260, 259, 258, 105, 104, 57.

Step 2.

Preparation of tert-Butyl α-(2-Azidomethyl)-2-oxo-1-(2-phenylethyl)-3-(propen-2-yl)-3-pyrrolidineacetate A solution of tert-butyl α-(2-chloroethyl)-2-oxo-1-(2-phenylethyl)-3-(propen-2-yl)-3-pyrrolidineacetate (2.10 g, 5.17 mmol) in DMSO (15 mL) is treated with sodium azide (504 mg, 7.74 mmol). The mixture is heated to 60° C. (oil bath) for 17 hours. The resultant solution was cooled to room temperature, diluted with Et₂O (100 mL), washed with H₂O (3×50 mL) and brine (50 mL). The organic layer is dried over anhydrous MgSO₄, filtered, and concentrated under reduced pressure to provide a quantitative yield of the title compound as a yellow oil:

¹H NMR (300 MHz, CDCl₃) δ 7.15–7.35, 5.40–5.65, 4.95–5.15, 3.60–3.80, 3.05–3.40, 2.81, 2.60, 2.10–2.40, 1.65–2.05, 1.43.

Step 3.

Preparation of tert-Butyl α-(2-Aminoethyl)-2-oxo-1-(2-phenylethyl)-3-(propen-2-yl)-3-pyrrolidineacetate A solution of tert-butyl α-(2-azidoethyl)-2-oxo-1-(2-phenylethyl)-3-(propen-2-yl)-3-pyrrolidineacetate (2.12 g, 5.14 mmol) and triphenylphosphine (1.48 g, 5.65 mmol) in THF (15 mL) is stirred under N₂ for 7 hours. Water (1 mL) is added and the solution stirred overnight at room temperature under N₂. The solution is concentrated and purified by silica gel chromatography (75 g SG; EtOAc, 20% MeOH/EtOAc) to provide 1.94 g (97%) of the title compound as a yellow oil:

¹H NMR (300 MHz, CDCl₃) δ 7.15–7.35, 5.45–5.65, 4.95–5.15, 3.60–3.80, 3.05–3.40, 2.80, 2.50–2.80, 2.10–2.45, 1.60–1.90, 1.42.

Step 4.

Preparation of tert-Butyl α-[2-[(3,4-Difluorobenzoyl)amino]ethyl]-2-oxo-1-(2-phenylethyl)-3-(propen-2-yl)-3-pyrrolidineacetate A cold (0° C.) solution of tert-butyl α-(2-aminoethyl)-2-oxo-1-(2-phenylethyl)-3-(propen-2-yl)-3-pyrrolidineacetate (1.93 g, 4.99 mmol) in dry CH₂Cl₂ (20 mL) is treated with diisopropylethylamine (1.04 mL, 5.99 mmol) and 3,4-difluorobenzoyl chloride (691 μL, 5.49 mmol). The solution is allowed to warm to room temperature, stirring under N₂ overnight. The solution is diluted with EtOAc (100 mL) and washed with 1N HCl (25 mL), 1N NaOH (25 mL), and brine (25 mL). The organic layer is dried over anhydrous MgSO₄, filtered, and concentrated under reduced pressure to give 3.60 g of a brown oil. The oil is purified by silica gel chromatography (50 g SG; 25% EtOAc/hexane) to provide 2.10 g (80%) of the title compound as a yellow, amorphous solid:

IR (mineral oil) 3360, 1717, 1660, 1606, 1550, 1509, 1497, 1436, 1315, 1295, 1281, 1199, 1154, 831, 775 cm⁻¹;

¹H NMR (300 MHz, CDCl₃) δ 7.65–7.75, 7.50–7.60, 7.15–7.35, 6.70, 5.45–5.65, 4.90–5.10, 3.55–3.85, 3.10–3.45, 2.70–2.90, 2.62, 2.10–2.35, 1.65–1.90, 1.43;

MS (ESI) m/z 549 (MNa⁺).

Step 5.

Preparation of tert-Butyl α-[2-[(3,4-Difluorobenzoyl)amino]ethyl]-3-(3-hydroxypropyl)-2-oxo-1-(2-phenylethyl)-3-pyrrolidineacetate A cold (0° C.) solution of tert-butyl α-[2-[(3,4-difluorobenzoyl)amino]ethyl]-2-oxo-1-(2-phenylethyl)-3-(propen-2-yl)-3-pyrrolidineacetate (1.62 g, 3.07 mmol) in dry THF (10 mL) is treated with monochloroborane methylsulfide complex (640 μL, 6.14 mmol). The ice bath is removed, and after 4.5 h, 3N NaOH (7.4 mL, 22.1 mmol) is added dropwise, followed by 30% H₂O₂ (2.5 mL). The solution is stirred for 1 hour at room temperature and then for 1 hour at 50° C. After cooling to room temperature and dilution with saturated NH₄Cl (5 mL) and H₂O (15 mL), the product is extracted into EtOAc (3×50 mL). The extracts are combined, dried over anhydrous MgSO₄, filtered, and concentrated under reduced pressure to give 1.6 g of a yellow gel. The material is purified by silica gel chromatography (75 g SG; 75% EtOAc/hexane) to provide 713 mg (43%) of the title compound as a white, amorphous solid:

IR (liq.) 3335, 2934, 1721, 1666, 1606, 1554, 1511, 1455, 1368, 1316, 1296, 1283, 1250, 1204, 1153 cm⁻¹;

¹H NMR (300 MHz, CDCl₃) δ 7.65–7.75, 7.45–7.60, 7.15–7.35, 6.60–6.75, 3.75–3.95, 3.10–3.70, 2.70–2.90, 2.65, 2.20–2.40, 2.00–2.20, 1.42, 1.05–1.90;

MS (ESI) m/z 567 (MNa⁺).

Step 6.

Preparation of α-[2-[(3,4-Difluorobenzoyl)amino]ethyl]-3-(3-hydroxypropyl)-2-oxo-1-(2-phenylethyl)-3-pyrrolidineacetic acid A cold (0° C.) solution of tert-butyl α-[2-[(3,4-difluorobenzoyl)amino]ethyl]-3-(3-hydroxypropyl)-2-oxo-1-(2-phenylethyl)-3-pyrrolidineacetate (655 mg, 1.20 mmol) in CH₂Cl₂ (3 mL) is treated with TFA (2 mL) and maintained at 0° C. for 30 min. The ice bath is removed, and after 2 hours, the solution is diluted with CH₂Cl₂ and concentrated (3×). The residual oil is diluted with H₂O (10 mL) and extracted into CH₂Cl₂ (3×50 mL). The extracts are combined, dried over anhydrous MgSO₄, filtered, and concentrated under reduced pressure to provide a quantitative yield of the title compound as a white, amorphous solid:

IR (liq.) 1785, 1724, 1644, 1619, 1605, 1557, 1511, 1455, 1442, 1322, 1297, 1284, 1207, 1171, 701 cm⁻¹;

¹H NMR (300 MHz, CDCl₃) δ 7.60–7.75, 7.50–7.60, 7.15–7.40, 6.85–7.00, 4.10–4.35, 3.50–3.80, 3.20–3.45, 2.80–3.00, 2.54, 1.20–2.00;

MS (EI) m/z 488, 470, 397, 379, 260, 246, 141, 113.

Step 7.

Preparation of α-[2-[(3,4-Difluorobenzoyl)amino]ethyl]-N-benzyloxy-3-(3-hydroxypropyl)-2-oxo-1-(2-phenylethyl)-3-pyrrolidineacetamide A cold (0° C.) solution of α-[2-[(3,4-difluorobenzoyl)amino]ethyl]-3-(3-hydroxypropyl)-2-oxo-1-(2-phenylethyl)

-3-pyrrolidineacetic acid (586 mg, 1.20 mmol) in 2:1 CH$_2$Cl$_2$/DMF (7.5 mL) is treated with HOBT (195 mg, 1.44 mmol), EDC (276 mg, 1.44 mmol), and 4-methylmorpholine (158 µL, 1.44 mmol). The ice bath is removed, and after 1 hour, O-benzylhydroxylamine HCl (287 mg, 1.80 mmol) and a second portion of 4-methylmorpholine (198 µL, 1.80 mmol) are added. The solution is stirred overnight at room temperature under N$_2$. The solution is diluted with H$_2$O (25 mL) and extracted into CH$_2$Cl$_2$ (3×50 mL). The extracts are combined, dried over anhydrous MgSO$_4$, filtered, and concentrated under reduced pressure to provide an oil. The residual oil is reconstituted in EtOAc (50 mL) and washed with 1N HCl (10 mL), 1N NaOH (10 mL), H$_2$O (10 mL), and brine (10 mL). The organic layer is dried over anhydrous MgSO$_4$, filtered, and concentrated under reduced pressure to give 603 mg of a white foam. The material is purified by silica gel chromatography (25 g SG; EtOAc) to provide 433 mg (62%) of the title compound as a white, amorphous solid:

IR (liq.) 3328, 2941, 1664, 1619, 1605, 1554, 1511, 1454, 1438, 1319, 1298, 1283, 1205, 750, 700 cm$^{-1}$;

$^1$H NMR (300 MHz, CDCl$_3$) δ 7.60–7.75, 7.45–7.60, 7.10–7.45, 6.75–6.85, 4.88, 3.35– 3.70, 3.10–3.30, 2.75–2.90, 2.30–2.45, 1.10–2.15;

MS (FAB) m/z 594 (MH$^+$), 593, 592, 531, 489, 472, 471, 453, 313, 57.

Step 8.

Preparation of α-[2-[(3,4-Difluorobenzoyl)amino] ethyl]-N-hydroxy-3-(3-hydroxypropyl)-2-oxo-1-(2-phenylethyl)-3-pyrrolidineacetamide A solution of α-[2-[(3,4-difluorobenzoyl)amino]ethyl]-N-benzyloxy-3-(3-hydroxypropyl)-2-oxo-1-(2-phenylethyl)-3-pyrrolidineacetamide (215 mg, 0.368 mmol) is dissolved in EtOH (5 mL) and purged with N$_2$. Pearlman's catalyst (22 mg) is added and the atmosphere was replaced with H$_2$. After 7 hours, the mixture is filtered through celite, washing the residual solids with MeOH, EtOH, and CH$_2$Cl$_2$. The filtrate is concentrated to give 171 mg of a slightly brown foam. The material is crystallized from hot EtOAc (diluting with hexane). The product is isolated and dried in the vacuum oven (45° C.) overnight to provide 117 mg (63%) of the title compound as a cream-colored, powdery solid (mp 118° C., dec.):

IR (mineral oil) 3274, 3225, 3064, 3027, 1656, 1620, 1606, 1559, 1512, 1359, 1319, 1290, 1282, 1060, 701 cm$^{-1}$;

$^1$H NMR (300 MHz, CDCl$_3$) δ 7.45–7.80, 7.10–7.40, 3.10–3.75, 2.70–2.90, 2.40–2.60, 1.15–2.25;

MS (FAB) m/z 504 (MH$^+$), 503, 502, 488, 471, 313, 246, 141, 105.

EXAMPLE 95

Preparation of α-[2-[(3,4-Difluorobenzoyl)amino] ethyl]-N-hydroxy-3-(2-hydroxyethyl)-2-oxo-1-(2-phenylethyl)-3-pyrrolidineacetamide

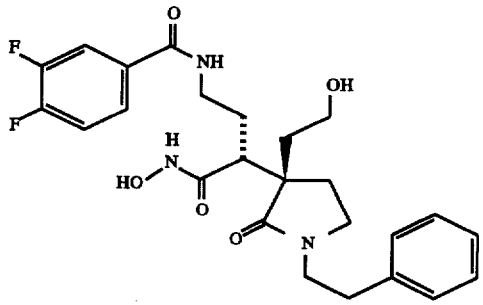

Step 1.

Preparation of α-[2-[(3,4-Difluorobenzoyl)amino] ethyl]-2-oxo-1-(2-phenylethyl)-3-(propen-2-yl)-3-pyrrolidineacetic acid A cold (0° C.) solution of tert-butyl α-[2-[(3,4-difluorobenzoyl)amino]ethyl]-2-oxo-1-(2-phenylethyl)-3-(propen-2-yl)-3-pyrrolidineacetate (EXAMPLE 94, step 4; 505 mg, 0.959 mmol) in CH$_2$Cl$_2$ (2 mL) is treated with TFA (2 mL) and maintained at 0° C. for 30 min. The ice bath is removed, and after 1 h, the solution was diluted with CH$_2$Cl$_2$ and concentrated (3×). The residual oil is diluted with H$_2$O (10 mL) and extracted into CH$_2$Cl$_2$ (3×25 mL). The extracts are combined, dried over anhydrous MgSO$_4$, filtered, and concentrated under reduced pressure to provide 430 mg (95%) of the title compound as a slightly yellow, amorphous solid:

IR (liq.) 1727, 1662, 1641, 1619, 1606, 1554, 1510, 1454, 1441, 1316, 1298, 1283, 1203, 775, 700 cm$^{-1}$;

$^1$H NMR (300 MHz, CDCl$_3$) δ 7.60–7.75, 7.50–7.60, 7.15–7.40, 6.75–6.90, 5.45–5.65, 5.10–5.20, 3.50–3.75, 3.15–3.35, 2.88, 2.52, 2.34, 1.70–2.05, 1.20–1.45;

MS (ESI) m/z 469 (M$^-$).

Step 2.

Preparation of α-[2-[(3,4-Difluorobenzoyl)amino] ethyl]-N-benzyloxy-2-oxo-1-(2-phenylethyl)-3-(propen-2-yl)-3-pyrrolidineacetamide A cold (0° C.) solution of α-[2-[(3,4-difluorobenzoyl) amino]ethyl]-2-oxo-1-(2-phenylethyl)-3-(propen-2-yl)-3-pyrrolidineacetic acid (427 mg, 0.908 mmol) in 2:1 CH$_2$Cl$_2$/DMF (6 mL) is treated with HOBT (147 mg, 1.09 mmol), EDC (209 mg, 1.09 mmol), and 4-methylmorpholine (120 µL, 1.09 mmol). The ice bath is removed, and after 1 hour, a second portion of 4-methylmorpholine (150 µL, 1.36 mmol) and O-benzylhydroxylamine HCl (217 mg, 1.36 mmol) are added. The solution is stirred overnight at room temperature under N$_2$. The solution is diluted with EtOAc (25 mL) and washed with 1N HCl (10 mL), 1N NaOH (10 mL), H$_2$O (2×10 mL), and brine (10 mL). The organic layer is dried over anhydrous MgSO$_4$, filtered, and concentrated under reduced pressure to give 530 mg of a yellow solid. The solid is purified by silica gel chromatography (30 g SG; 50% EtOAc/hexane) to provide 373 mg (71%) of the title compound as a white, amorphous solid:

IR (mineral oil) 3336, 3193, 1679, 1669, 1641, 1608, 1544, 1509, 1495, 1442, 1311, 1296, 1275, 747, 696 cm$^{-1}$;

$^1$H NMR (300 MHz, CDCl$_3$) δ 7.05–7.75, 6.65–6.85, 5.40–5.60, 4.80–5.15, 3.35–3.70, 3.05–3.30, 2.81, 1.35–2.45;

MS (ESI) m/z 574 (M$^-$).

Step 3.

Preparation of α-[2-[(3,4-Difluorebenzoyl)amino]ethyl]-N-benzyloxy-3-(2-hydroxyethyl)-2-oxo-1-(2-phenylethyl)-3-pyrrolidineacetamide α-[2-[(3,4-Difluorobenzoyl)amino]ethyl]-N-benzyloxy-2-oxo-1-(2-phenylethyl)-3-(propen-2-yl)-3-pyrrolidineacetamide (365 mg, 0.634 mmol) is dissolved in warm EtOH (10 mL) and cooled to −78° C. The solution is subjected to ozone for 3.5 min and then purged with N$_2$ for 15 min. The ozonide is quenched with NaBH$_4$ (36 mg, 0.951 mmol) and allowed to slowly warm to room temperature under N$_2$. After 5 hours, additional NaBH$_4$ (36 mg, 0.951 mmol) is added and the mixture allowed to stir overnight. The mixture is concentrated, diluted with H$_2$O (20 mL) and extracted into EtOAc (3×50 mL). The extracts are dried over anhydrous MgSO$_4$, filtered, and concentrated under reduced pressure to give 306 mg of a white foam. The foam is purified by silica gel chromatography (25 g SG; EtOAc) to provide 123 mg (34%) of the title compound as a white, amorphous solid:

IR (mineral oil) 3321, 1664, 1619, 1605, 1554, 1510, 1318, 1297, 1283, 1205, 1028, 776, 750, 699, 626 cm$^{-1}$;

$^1$H NMR (300 MHz, CDCl$_3$) δ 7.10–7.75, 6.65–6.75, 4.85, 3.10–3.70, 2.70–2.90, 2.45–2.60, 2.10–2.30, 1.50–1.95;

MS (ESI) m/z 580 (M$^+$), 578 (M$^-$).

Step 4.

Preparation of α-[2-[(3,4-Difluorobenzoyl)amino]ethyl]-N-hydroxy-3-(2-hydroxyethyl)-2-oxo-1-(2-phenylethyl)-3-pyrrolidineacetamide A solution of α-[2-[(3,4-difluorobenzoyl)amino]ethyl]-N-benzyloxy-3-(2-hydroxyethyl)-2-oxo-1-(2-phenylethyl)-3-pyrrolidineacetamide (117 mg, 0.202 mmol) is dissolved in EtOH (3 mL) and purged with N$_2$. Pearlman's catalyst (10 mg) is added and the atmosphere is replaced with H$_2$. After 6 hours, the mixture is filtered through celite, washing the residual solids with MeOH, EtOH, and CH$_2$Cl$_2$. The filtrate is concentrated and resubjected to the same procedure. The recovered material (99 mg) is purified by silica gel chromatography (8 g SG; 5, 10% MeOH/CHCl$_3$) to give 45 mg of a white, amorphous solid. The solid is triturated with Et$_2$O/hexane, filtered, and dried. This provides 39 mg (40%) of the title compound as a white, powdery solid (mp 135°–137° C.):

IR (mineral oil) 3202, 3089, 3063, 3029, 1670, 1648, 1633, 1601, 1564, 1515, 1499, 1435, 1331, 1320, 1299 cm$^{-1}$;

$^1$H NMR (300 MHz, DMSO-d$_6$) δ 8.77, 8.40–8.55, 7.80–7.90, 7.65–7.75, 7.45–7.60, 7.10–7.30, 4.30–4.40, 3.00–3.50, 2.60–2.75, 2.10–2.45, 1.50–1.90;

MS (FAB) m/z 490 (MH$^+$), 489, 474, 457, 439, 299, 246, 141, 105.

EXAMPLE 96

Preparation of [R-(R*,S*)]-α-[2-[(3-Fluorebenzoyl)amino]ethyl]-N-hydroxy-3-(3-hydroxypropyl)-2-oxo-1-(2-phenylethyl)-3-pyrrolidineacetamide

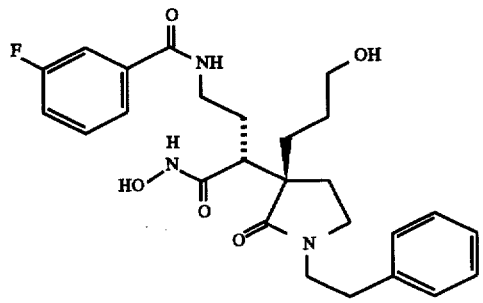

[α]$_D^{25}$=+13° (c 0.71, CHCl$_3$);

IR (mineral oil) 3233, 3085, 3064, 3026, 1662, 1586, 1547, 1497, 1484, 1319, 1299, 1271, 1225, 751, 701 cm$^{-1}$;

$^1$H NMR (300 MHz, CDCl$_3$) δ 7.45–7.60, 7.05–7.45, 3.10–3.65, 2.70–2.90, 2.45–2.60, 1.15–2.25;

MS (EI) m/z 485 (M$^+$), 248, 247, 202, 178, 156, 123, 105, 104, 95, 56.

Following the general procedures outlined in EXAMPLES 28–29 or 30–34 and making non-critical variations, the following compounds may be prepared.

EXAMPLE 97

Preparation of [S-(R*,R*)]-N$^3$-hydroxy-N$^1$-methyl-α$^1$-(1-methylethyl)-3-(2-methylpropyl)-2-oxo-1,3-pyrrolidinediacetamide

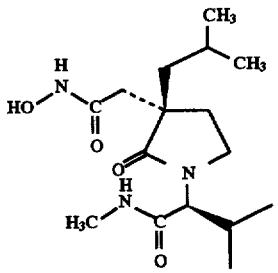

EXAMPLE 98

Preparation of [S-(R*,R*)]-N¹-cyclopropyl-N³-hydroxy-α¹-(1-methylethyl)-3-(2-methylpropyl)-2-oxo-1,3-pyrrolidinediacetamide

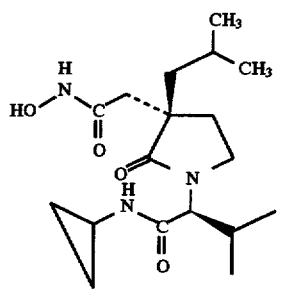

EXAMPLE 99

Preparation of [S-(R*,R*)]-N³-hydroxy-α¹-(1-methylethyl)-3-(2-methylpropyl)-2-oxo-N¹-phenyl-1,3-pyrrolidinediacetamide

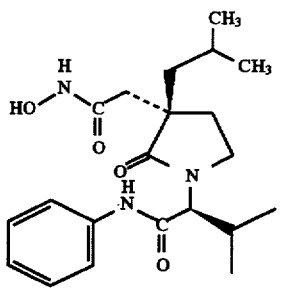

EXAMPLE 100

Preparation of [S-(R*,R*)]-N¹-(4-fluorophenyl)-N³-hydroxy-α¹-(1-methylethyl)-3-(2-methylpropyl)-2-oxo-1,3-pyrrolidinediacetamide

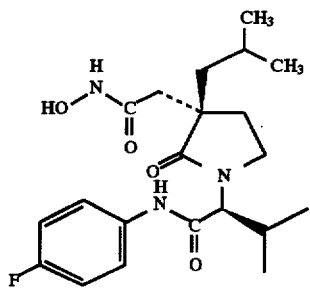

EXAMPLE 101

Preparation of [S-(R*,R*)]-N³-hydroxy-α¹-(1-methylethyl)-3-(2-methylpropyl)-2-oxo-N¹-(4-pyridinyl)-1,3-pyrrolidinediacetamide

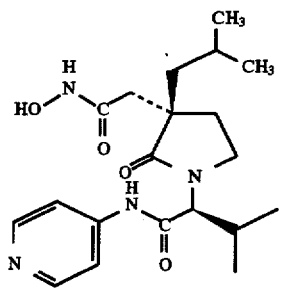

EXAMPLE 102

Preparation of [S-(R*,R*)]-α¹-tert-butyl-N¹-cyclopropyl-N³-hydroxy-3-(2-methylpropyl)-2-oxo-1,3-pyrrolidinediacetamide

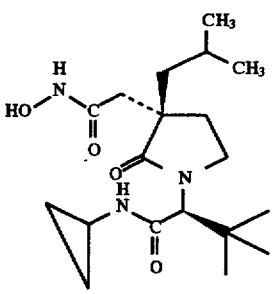

EXAMPLE 103

Preparation of [S-(R*,R*)]-α¹-tert-butyl-N³-hydroxy-3-(2-methylpropyl)-2-oxo-N¹-phenyl-1,3-pyrrolidinediacetamide

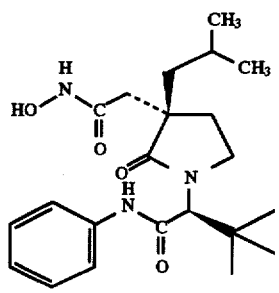

EXAMPLE 104

Preparation of [S-(R*,R*)]-α¹-tert-butyl-N¹-(4-fluorophenyl)-N³-hydroxy-3-(2-methylpropyl)-2-oxo-1,3-pyrrolidinediacetamide

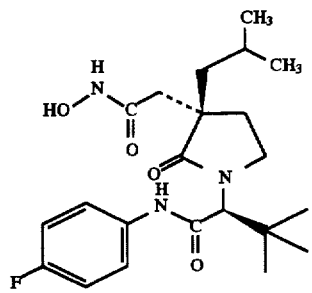

EXAMPLE 105

Preparation of [S-(R*,R*)]-α¹-tert-butyl-N³-hydroxy-3-(2-methylpropyl)-2-oxo-N¹-(4-pyridinyl)-1,3-pyrrolidinediacetamide

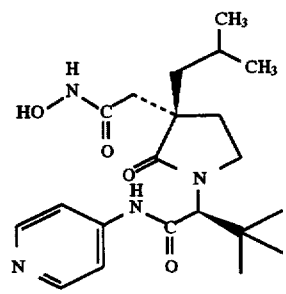

EXAMPLE 106

Preparation of [S-(R*,R*)]-α¹-cyclohexyl-N³-hydroxy-3-(2-methylpropyl)-2-oxo-N¹-phenyl-1,3-pyrrolidinediacetamide

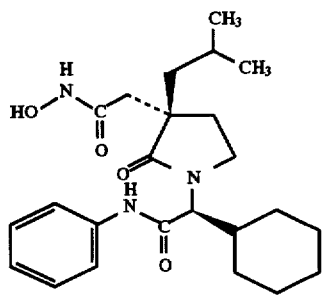

EXAMPLE 107

Preparation of [S-(R*,R*)]-α¹-cyclohexyl-N³-hydroxy-3-(2-methylpropyl)-2-oxo-N¹-(4-pyridinyl)-1,3-pyrrolidinediacetamide

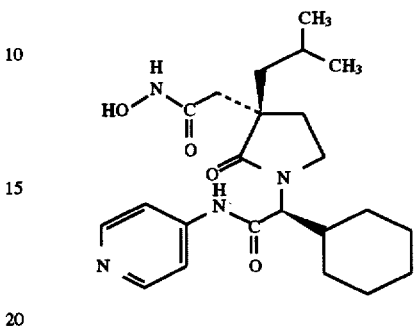

EXAMPLE 108

Preparation of [S-(R*,R*)]-3-(cyclopentylmethyl)-N³-hydroxy-N¹-methyl-α¹-(1-methylethyl)-2-oxo-1,3-pyrrolidinediacetamide

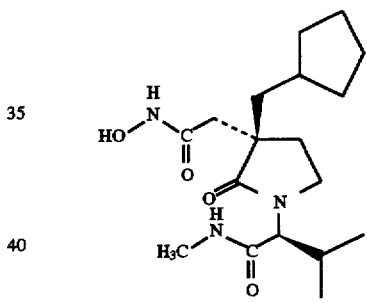

EXAMPLE 109

Preparation of [S-(R*,R*)]-3-(cyclopentylmethyl)-N¹-(cyclopropyl-N³-hydroxy-α¹-(1-methylethyl)-2-oxo-1,3-pyrrolidinediacetamide

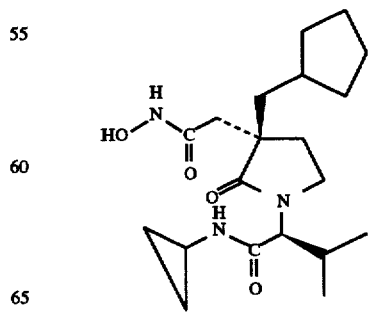

EXAMPLE 110

Preparation of [S-(R*,R*)]-3-(cyclopentylmethyl)-$N^3$-hydroxy-$\alpha^1$-(1-methylethyl)-2-oxo-$N^1$-phenyl-1,3-pyrrolidinediacetamide

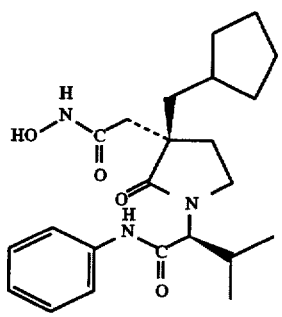

EXAMPLE 111

Preparation of [S-(R*,R*)]-3-(cyclopentylmethyl)-$N^1$-(4-fluorophenyl)-$N^3$-hydroxy-$\alpha^1$-(1-methylethyl)-2-oxo-1,3-pyrrolidinediacetamide

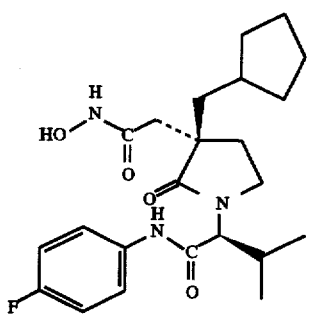

EXAMPLE 112

Preparation of [S-(R*,R*)]-3-(cyclopentylmethyl)-$N^3$-hydroxy-$\alpha^1$-(1-methylethyl)-2-oxo-$N^1$-(4-pyridinyl)-1,3-pyrrolidinediacetamide

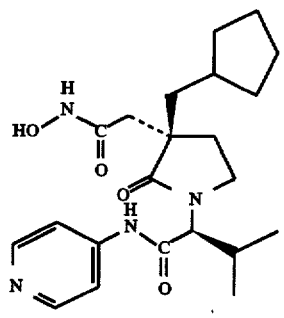

EXAMPLE 113

Preparation of [S-(R*,R*)]-$\alpha^1$-tert-butyl-3-(cyclopentylmethyl)-$N^3$-hydroxy-$N^1$-methyl-2-oxo-1,3-pyrrolidinediacetamide

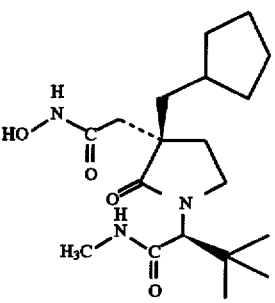

EXAMPLE 114

Preparation of [S-(R*,R*)]-$\alpha^1$-tert-butyl-3-(cyclopentylmethyl)-$N^1$-cyclopropyl-$N^3$-hydroxy-2-oxo-1,3-pyrrolidinediacetamide

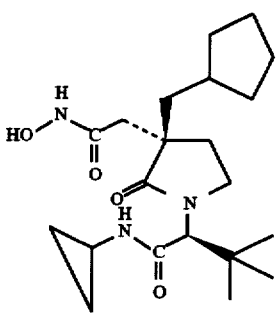

EXAMPLE 115

Preparation of [S-(R*,R*)]-$\alpha^1$-tert-butyl-3-(cyclopentylmethyl)-$N^3$-hydroxy-2-oxo-$N^1$-phenyl-1,3-pyrrolidinediacetamide

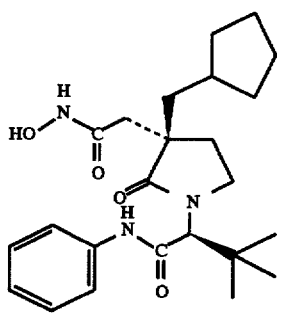

EXAMPLE 116

Preparation of [S-(R*,R*)]-α¹-tert-butyl-3-(cyclopentylmethyl)-N¹-(4-fluorophenyl)-N³-hydroxy-2-oxo-1,3-pyrrolidinediacetamide

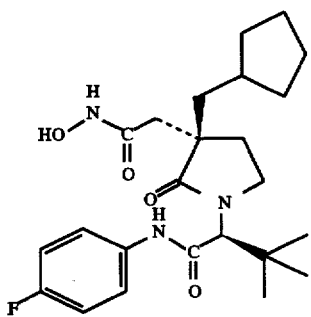

EXAMPLE 117

Preparation of [S-(R*,R*)]-α¹-tert-butyl-3-(cyclopentylmethyl)-N³-hydroxy-2-oxo-N¹-(4-pyridinyl)-1,3-pyrrolidinediacetamide

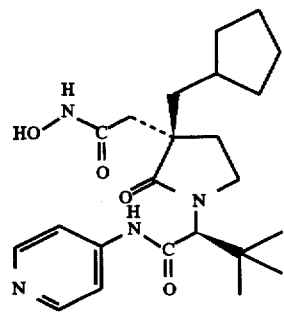

EXAMPLE 118

Preparation of [S-(R*,R*)]-α¹-cyclohexyl-3-(cyclopentylmethyl)-N³-hydroxy-N¹-methyl-2-oxo-1,3-pyrrolidinediacetamide

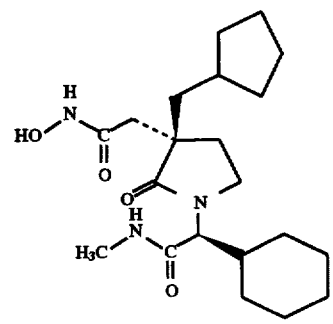

EXAMPLE 119

Preparation of [S-(R*,R*)]-α¹-cyclohexyl-3-(cyclopentylmethyl)-N¹-cyclopropyl-N³-hydroxy-2-oxo-1,3-pyrrolidinediacetamide

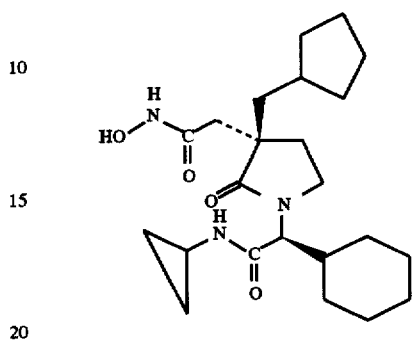

EXAMPLE 120

Preparation of [S-(R*,R*)]-α¹-cyclohexyl-3-(cyclopentylmethyl)-N³-hydroxy-2-oxo-N¹-phenyl-1,3-pyrrolidinediacetamide

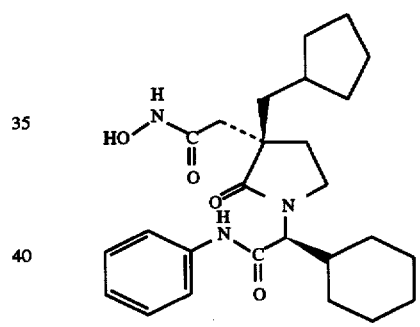

EXAMPLE 121

Preparation of [S-(R*,R*)]-α¹-cyclohexyl-3-(cyclopentylmethyl)-N¹-(4-fluorophenyl)-N³-hydroxy-2-oxo-1,3-pyrrolidinediacetamide

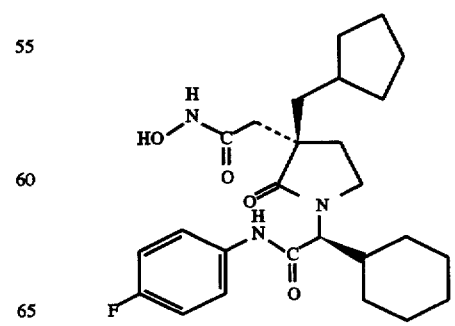

EXAMPLE 122

Preparation of [S-(R*,R*)]-α¹-cyclohexyl-3-(cyclopentylmethyl)-$N^3$-hydroxy-2-oxo-$N^1$-(4-pyridinyl)-1,3-pyrrolidinediacetamide

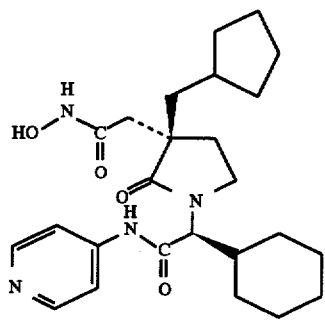

EXAMPLE 123

Preparation of [S-(R*,R*)]-$N^3$-hydroxy-$N^1$-methyl-α¹-(1-methylethyl)-2-oxo-3-(3-phenylpropyl)-1,3-pyrrolidinediacetamide

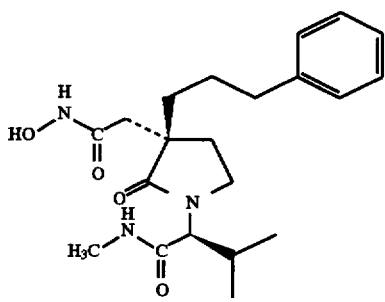

EXAMPLE 124

Preparation of [S-(R*,R*)]-$N^1$-cyclopropyl-$N^3$-hydroxy-α¹-(1-methylethyl)-2-oxo-3-(3-phenylpropyl)-1,3-pyrrolidinediacetamide

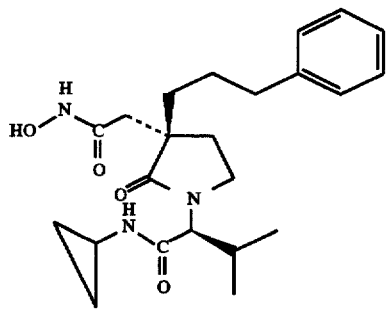

EXAMPLE 125

Preparation of [S-(R*,R*)]-$N^3$-hydroxy-α¹-(1-methylethyl)-2-oxo-$N^1$-phenyl-3-(3-phenylpropyl)-1,3-pyrrolidinediacetamide

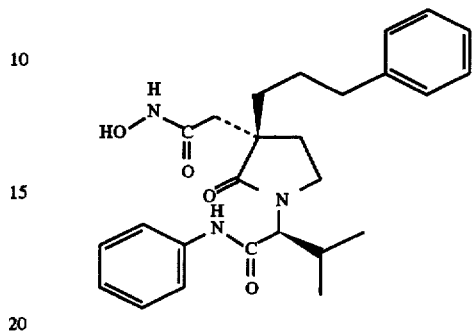

EXAMPLE 126

Preparation of [S-(R*,R*)]-$N^1$-(4-fluorophenyl)-$N^3$-hydroxy-α¹-(1-methylethyl)-2-oxo-3-(3-phenylpropyl)-1,3-pyrrolidinediacetamide

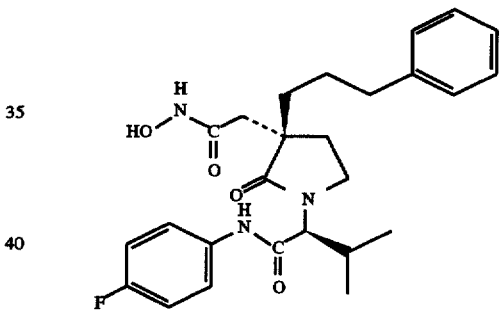

EXAMPLE 127

Preparation of [S-(R*,R*)]-$N^3$-hydroxy-α¹-(1-methylethyl)-2-oxo-3-(3-phenylpropyl)-$N^1$-(4-pyridinyl)-1,3-pyrrolidinediacetamide

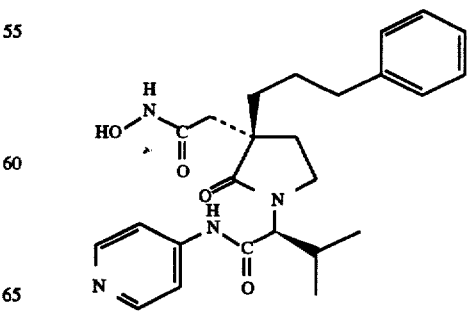

EXAMPLE 128

Preparation of [S-(R*,R*)]-α¹-tert-butyl-N³-hydroxy-N¹-methyl-2-oxo-3-(3-phenylpropyl)-1,3-pyrrolidinediacetamide

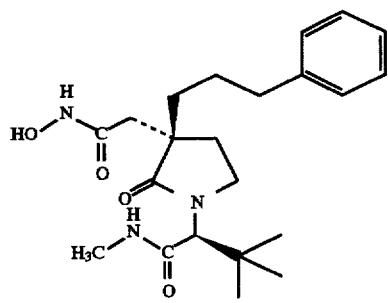

EXAMPLE 129

Preparation of [S-(R*,R*)]-α¹-tert-butyl-N¹-cyclopropyl-N³-hydroxy-2-oxo-3-(3-phenylpropyl)-1,3-pyrrolidinediacetamide

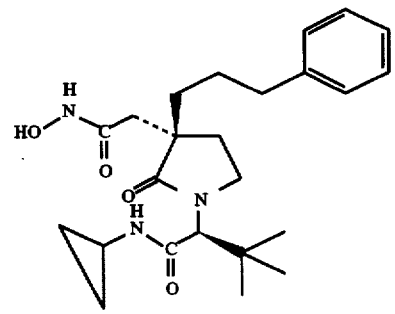

EXAMPLE 130

Preparation of [S-(R*,R*)]-α¹-tert-butyl-N³-hydroxy-2-oxo-N¹-phenyl-3-(3-phenylpropyl)-1,3-pyrrolidinediacetamide

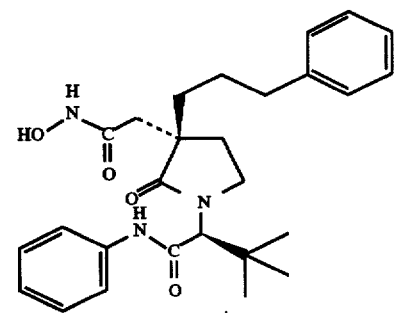

EXAMPLE 131

Preparation of [S-(R*,R*)]-α¹-tert-butyl-N¹-(4-fluorophenyl)-N³-hydroxy-2-oxo-3-(3-phenylpropyl)-1,3-pyrrolidinediacetamide

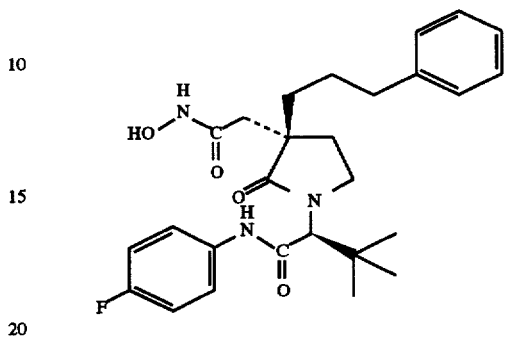

EXAMPLE 132

Preparation of [S-(R*,R*)]-α¹-tert-butyl-N³-hydroxy-2-oxo-3-(3-phenylpropyl)-N¹-(4-pyridinyl)-1,3-pyrrolidinediacetamide

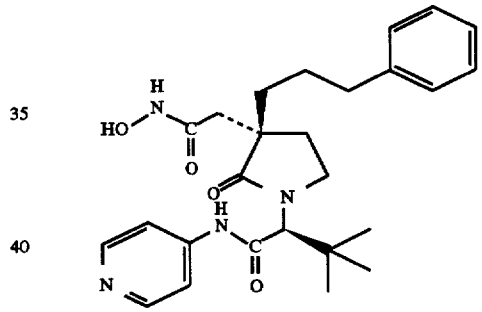

EXAMPLE 133

Preparation of [S-(R*,R*)]-α¹-cyclohexyl-N³-hydroxy-N¹-methyl-2-oxo-3-(3-phenylpropyl)-1,3-pyrrolidinediacetamide

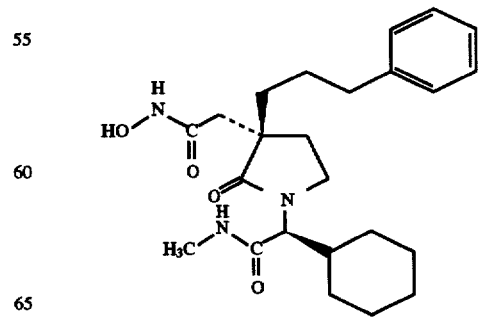

EXAMPLE 134

Preparation of [S-(R*,R*)]-α¹-cyclohexyl-N¹-cyclopropyl-N³-hydroxy-2-oxo-3-(3-phenylpropyl)-1,3-pyrrolidinediacetamide

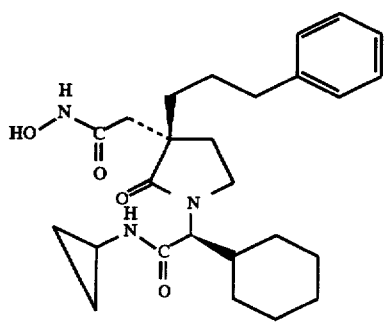

EXAMPLE 135

Preparation of [S-(R*,R*)]-α¹-cyclohexyl-N³-hydroxy-2-oxo-N¹-phenyl-3-(3-phenylpropyl)-1,3-pyrrolidinediacetamide

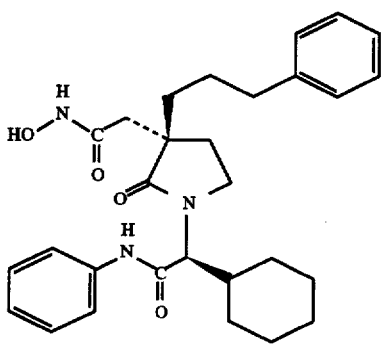

EXAMPLE 136

Preparation of [S-(R*,R*)]-α¹-cyclohexyl-N¹-(4-fluorophenyl)-N³-hydroxy-2-oxo-3-(3-phenylpropyl)-1,3-pyrrolidinediacetamide

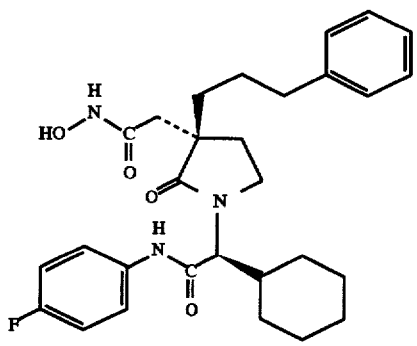

EXAMPLE 137

Preparation of [S-(R*,R*)]-α¹-cyclohexyl-N³-hydroxy-2-oxo-3-(3-phenylpropyl)-N¹-(4-pyridinyl)-1,3-pyrrolidinediacetamide

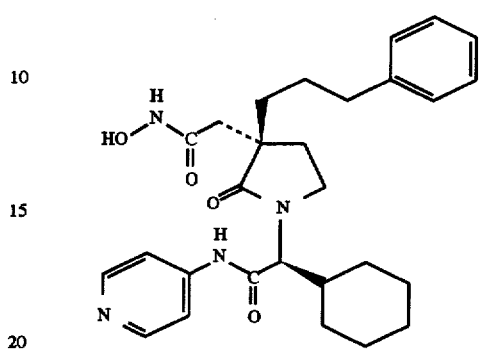

EXAMPLE 138

Preparation of [S-(R*,R*)]-3-[3-(4-fluorophenyl)propyl]-N³-hydroxy-N¹-methyl-α¹-(1-methylethyl)-2-oxo-1,3-pyrrolidinediacetamide

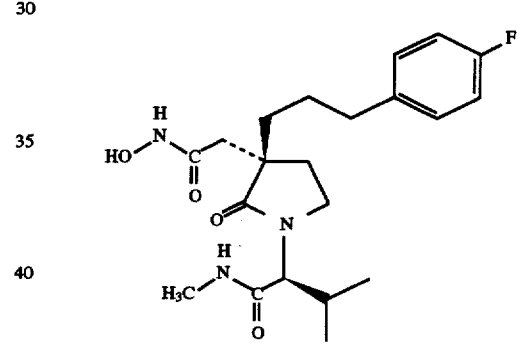

EXAMPLE 139

Preparation of [S-(R*,R*)]-N¹-cyclopropyl-3-[3-(4-fluorophenyl)propyl]-N³-hydroxy-α¹-(1-methylethyl)-2-oxo-1,3-pyrrolidinediacetamide

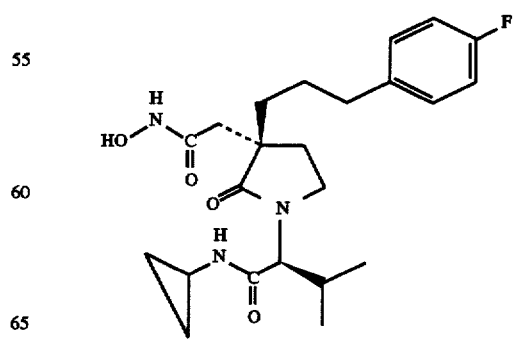

EXAMPLE 140

Preparation of [S-(R*,R*)]-3-[3-(4-fluorophenyl)propyl]-N³-hydroxy-α¹-(1-methylethyl)-2-oxo-N¹-phenyl-1,3-pyrrolidinediacetamide

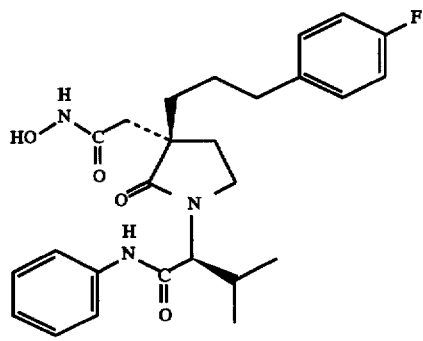

EXAMPLE 141

Preparation of [S-(R*,R*)]-N¹-(4-fluorophenyl)-3-[3-(4-fluorophenyl)propyl]-N³-hydroxy-α¹-(1-methylethyl)-2-oxo-1,3-pyrrolidinediacetamide

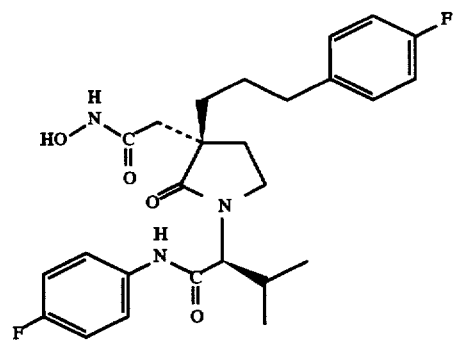

EXAMPLE 142

Preparation of [S-(R*,R*)]-3-[3-(4-fluorophenyl)propyl]-N³-hydroxy-α¹-(1-methylethyl)-2-oxo-N¹-(4-pyridinyl)-1,3-pyrrolidinediacetamide

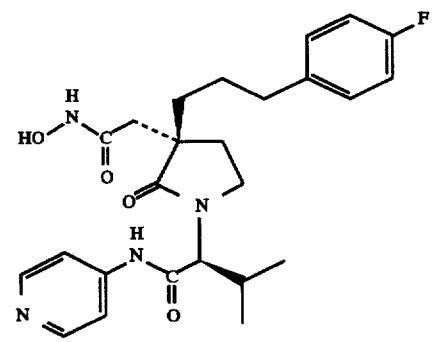

EXAMPLE 143

Preparation of [S-(R*,R*)]-α¹-tert-butyl-3-[3-(4-fluorophenyl)propyl]-N³-hydroxy-N¹-methyl-2-oxo-1,3-pyrrolidinediacetamide

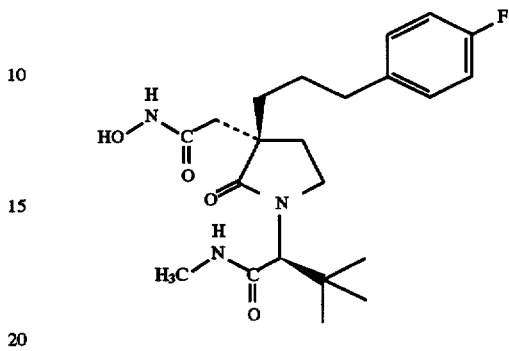

EXAMPLE 144

Preparation of [S-(R*,R*)]-α¹-tert-butyl-N¹-cyclopropyl-3-[3-(4-fluorophenyl)propyl]-N³-hydroxy-2-oxo-1,3-pyrrolidinediacetamide

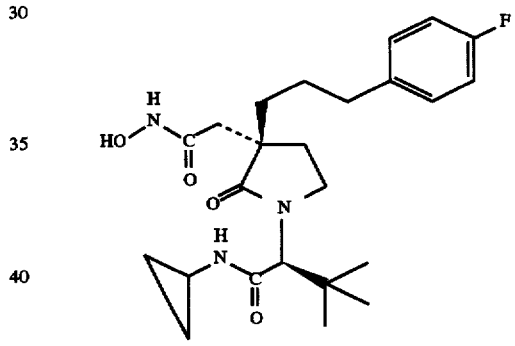

EXAMPLE 145

Preparation of [S-(R*,R*)]-α¹-tert-butyl-3-[3-(4-fluorophenyl)propyl]-N³-hydroxy-2-oxo-N¹-phenyl-1,3-pyrrolidinediacetamide

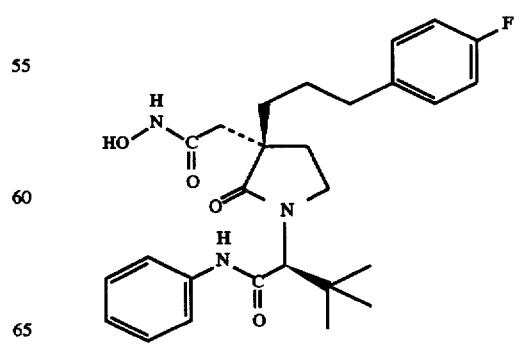

EXAMPLE 146

Preparation of [S-(R*,R*)]-α¹-tert-butyl-N¹-(4-fluorophenyl)-3-[3-(4-fluorophenyl)propyl]-N³-hydroxy-2-oxo-1,3-pyrrolidinediacetamide

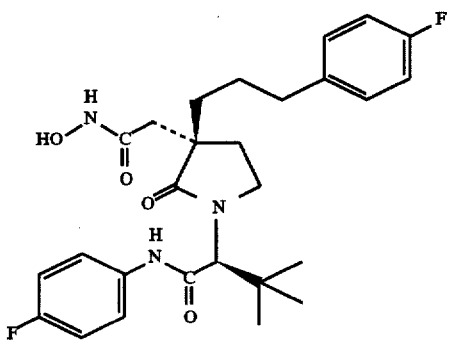

EXAMPLE 147

Preparation of [S-(R*,R*)]-α¹-tert-butyl-3-[3-(4-fluorophenyl)propyl]-N³-hydroxy-2-oxo-N¹-(4-pyridinyl)-1,3-pyrrolidinediacetamide

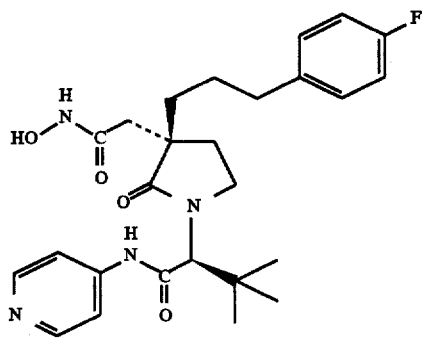

EXAMPLE 148

Preparation of [S-(R*,R*)]-α¹-cyclohexyl-3-[3-(4-fluorophenyl)propyl]-N³-hydroxy-N¹-methyl-2-oxo-1,3-pyrrolidinediacetamide

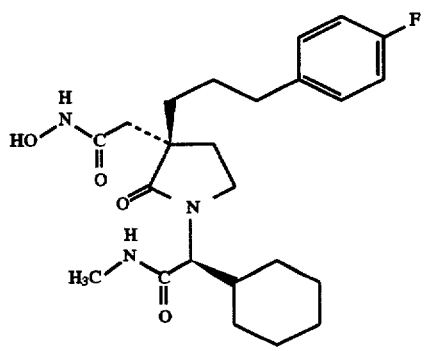

EXAMPLE 149

Preparation of [S-(R*,R*)]-α¹-cyclohexyl-N¹-cyclopropyl-3-[3-(4-fluorophenyl)propyl]-N³-hydroxy-2-oxo-1,3-pyrrolidinediacetamide

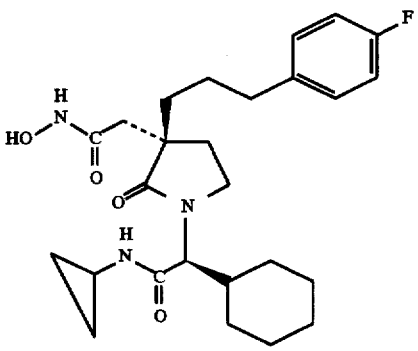

EXAMPLE 150

Preparation of [S-(R*,R*)]-α¹-cyclohexyl-3-[3-(4-fluorophenyl)propyl]-N³-hydroxy-2-oxo-N¹-phenyl-1,3-pyrrolidinediacetamide

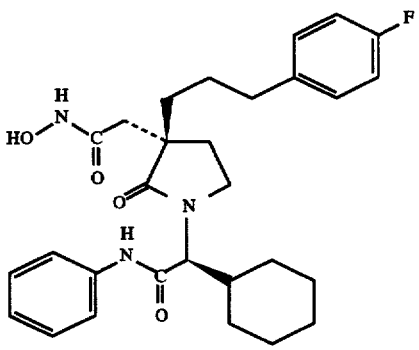

EXAMPLE 151

Preparation of [S-(R*,R*)]-α¹-cyclohexyl-N¹-(4-fluorophenyl)-3-[3-(4-fluorophenyl)propyl]-N³-hydroxy-2-oxo-1,3-pyrrolidinediacetamide

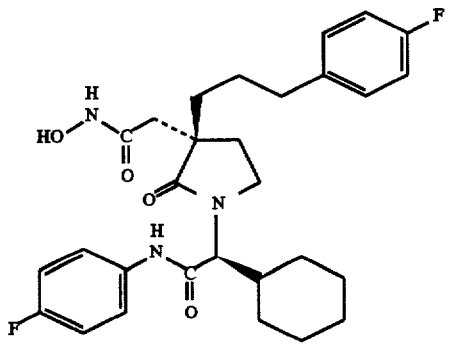

EXAMPLE 152

Preparation of [S-(R*,R*)]-α¹-cyclohexyl-3-[3-(4-fluorophenyl)propyl]-N³-hydroxy-2-oxo-N¹-(4-pyridinyl)-1,3-pyrrolidinediacetamide

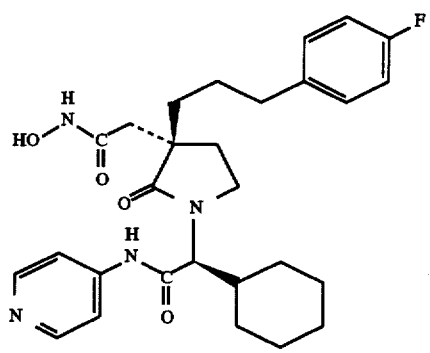

EXAMPLE 153

Preparation of [S-(R*,R*)]-3-[3-(biphen-4-yl)propyl]-N³-hydroxy-N¹-methyl-α¹-(1-methylethyl)-2-oxo-1,3-pyrrolidinediacetamide

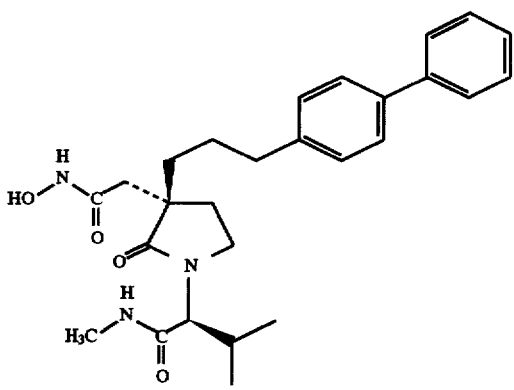

EXAMPLE 154

Preparation of [S-(R*,R*)]-3-[3-(biphen-4-yl)propyl]-N¹-cyclopropyl-N³-hydroxy-α¹-(1-methylethyl)-2-oxo-1,3-pyrrolidinediacetamide

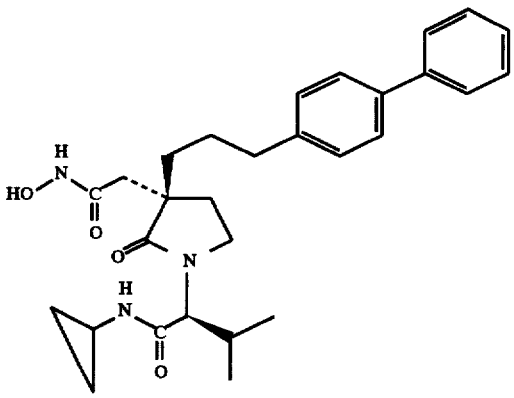

EXAMPLE 155

Preparation of [S-(R*,R*)]-3-[3-(biphen-4-yl)propyl]-N³-hydroxy-α¹-(1-methylethyl)-2-oxo-N¹-phenyl-1,3-pyrrolidinediacetamide

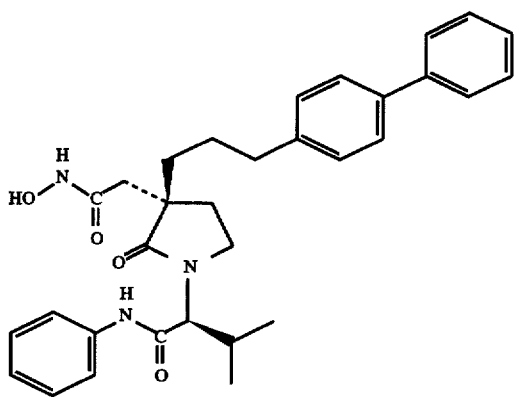

EXAMPLE 156

Preparation of [S-(R*,R*)]-3-[3-(biphen-4-yl)propyl]-N¹-(4-fluorophenyl)-N³-hydroxy-α¹-(1-methylethyl)-2-oxo-1,3-pyrrolidinediacetamide

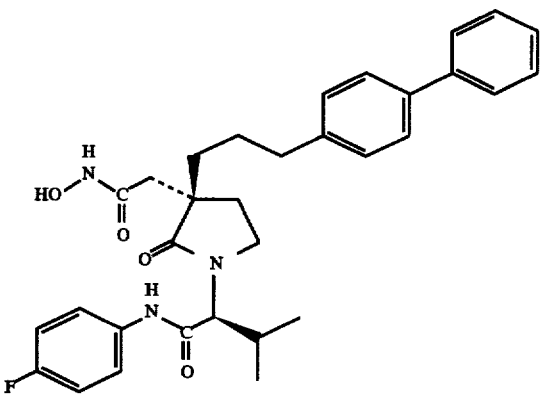

EXAMPLE 157

Preparation of [S-(R*,R*)]-3-[3-(biphen-4-yl)propyl]-N³-hydroxy-α¹-(1-methylethyl)-2-oxo-N¹-(4-pyridinyl)-1,3-pyrrolidinediacetamide

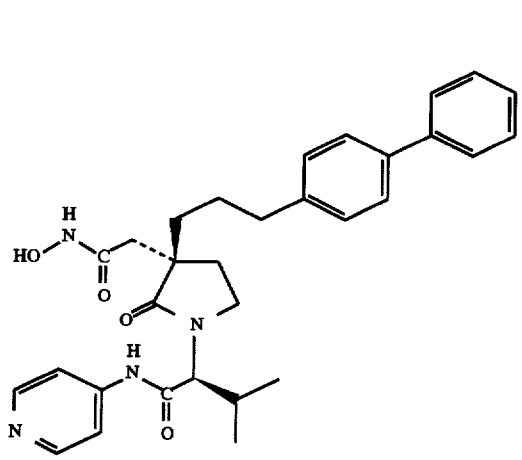

EXAMPLE 158

Preparation of [S-(R*,R*)]-3-[3-(biphen-4-yl)propyl]-α¹-tert-butyl-N³-hydroxy-N¹-methyl-2-oxo-1,3-pyrrolidinediacetamide

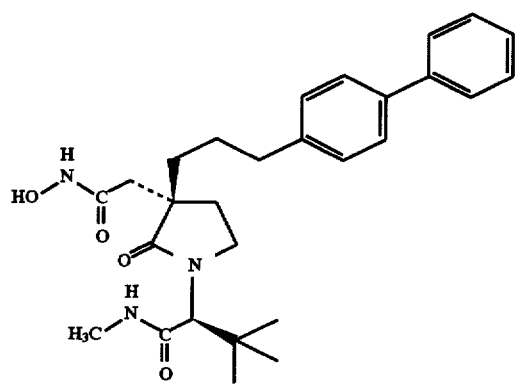

EXAMPLE 159

Preparation of [S-(R*,R*)]-3-[3-(biphen-4-yl)propyl]-α¹-tert-butyl-N¹-cyclopropyl-N³-hydroxy-2-oxo-1,3-pyrrolidinediacetamide

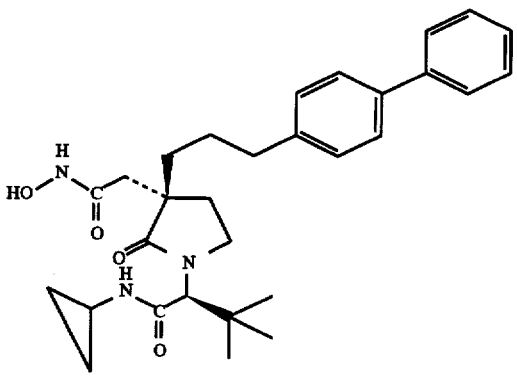

EXAMPLE 160

Preparation of [S-(R*,R*)]-3-[3-(biphen-4-yl)propyl]-α¹-tert-butyl-N³-hydroxy-2-oxo-N¹-phenyl-1,3-pyrrolidinediacetamide

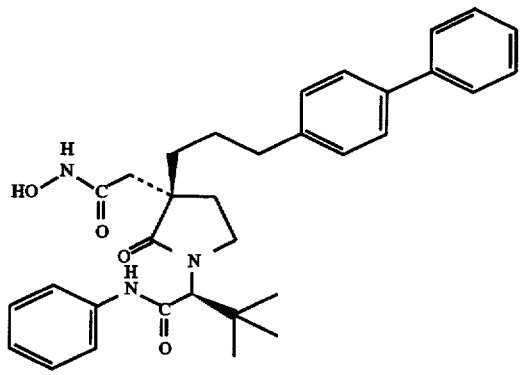

EXAMPLE 161

Preparation of [S-(R*,R*)]-3-[3-(biphen-4-yl)propyl]-α¹-tert-butyl-N¹-(4-fluorophenyl)-N³-hydroxy-2-oxo-1,3-pyrrolidinediacetamide

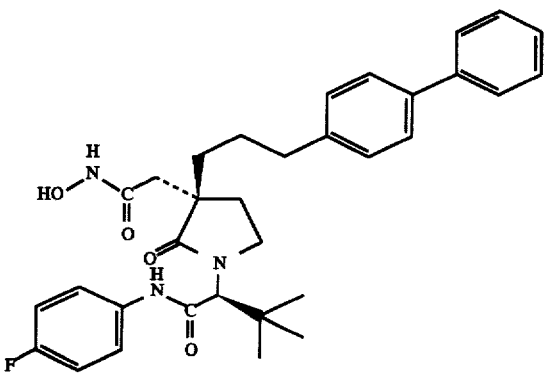

EXAMPLE 162

Preparation of [S-(R*,R*)]-3-[3-(biphen-4-yl)propyl]-α¹-tert-butyl-N³-hydroxy-2-oxo-N¹-(4-pyridinyl)-1,3-pyrrolidinediacetamide

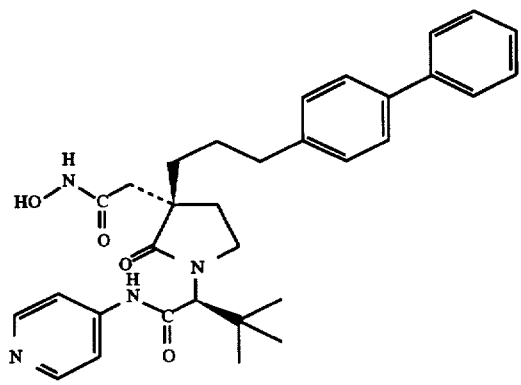

EXAMPLE 163

Preparation of [S-(R*,R*)]-3-[3-(biphen-4-yl)propyl]-α¹-cyclohexyl-N³-hydroxy-N¹-methyl-2-oxo-1,3-pyrrolidinediacetamide

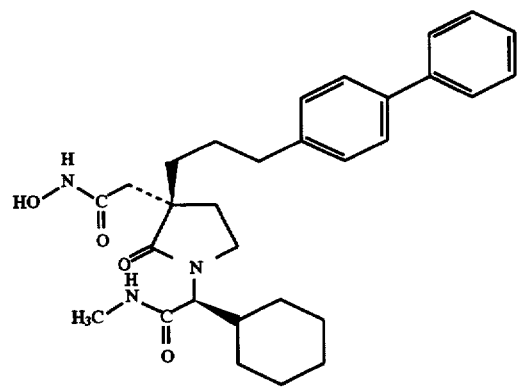

EXAMPLE 164

Preparation of [S-(R*,R*)]-3-[3-(biphen-4-yl)propyl]-α¹-cyclohexyl-N¹-cyclopropyl-N³-hydroxy-2-oxo-1,3-pyrrolidinediacetamide

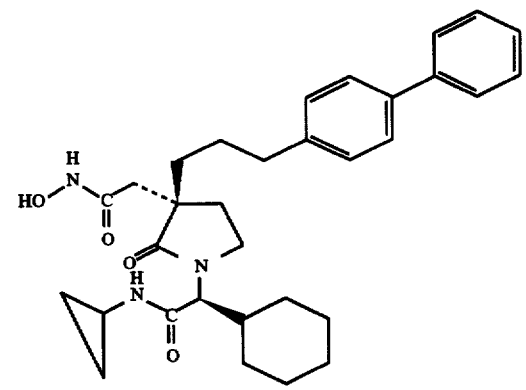

EXAMPLE 165

Preparation of [S-(R*,R*)]-3-[3-(biphen-4-yl)propyl]-α¹-cyclohexyl-N³-hydroxy-2-oxo-N¹-phenyl-1,3-pyrrolidinediacetamide

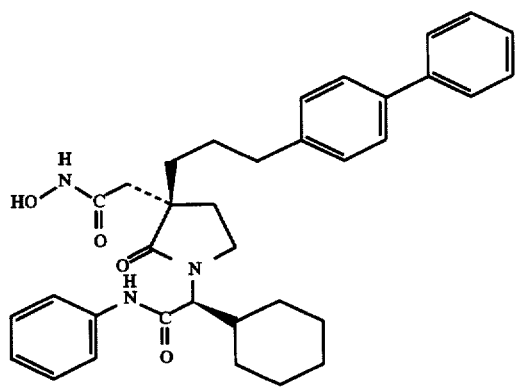

EXAMPLE 166

Preparation of [S-(R*,R*)]-3-[3-(biphen-4-yl)propyl]-α¹-cyclohexyl-N¹-(4-fluorophenyl)-N³-hydroxy-2-oxo-1,3-pyrrolidinediacetamide

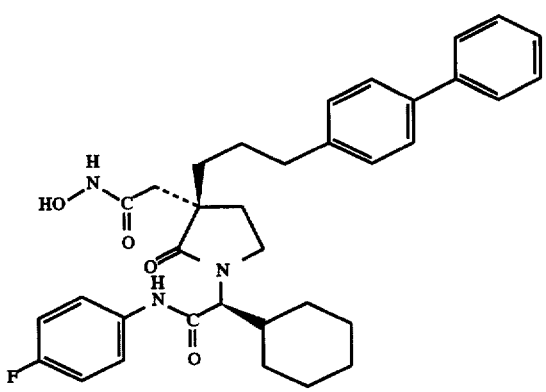

EXAMPLE 167

Preparation of [S-(R*,R*)]-3-[3-(biphen-4-yl)propyl]-α¹-cyclohexyl-N³-hydroxy-2-oxo-N¹-(4-pyridinyl)-1,3-pyrrolidinediacetamide

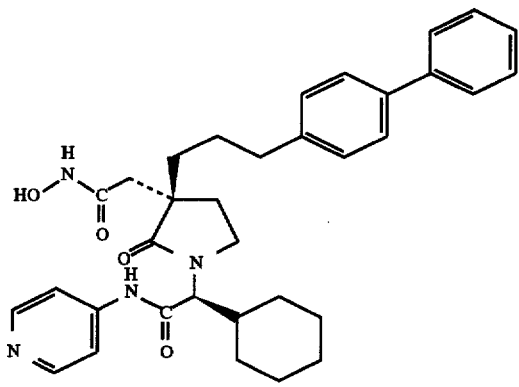

EXAMPLE 168

Preparation of [S-(R*,R*)]-3-[3-(4'-fluorobiphen-4-yl)propyl]-N³-hydroxy-N¹-methyl-α¹-(1-methylethyl)-2-oxo-1,3-pyrrolidinediacetamide

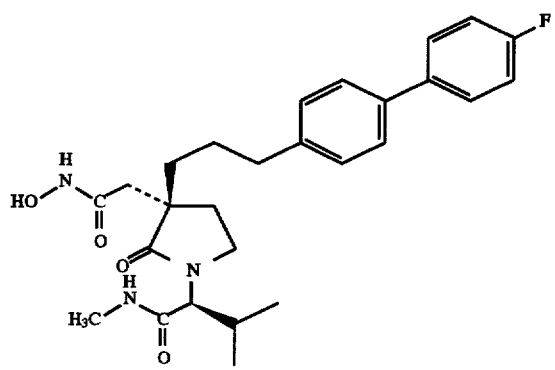

EXAMPLE 169

Preparation of [S-(R*,R*)]-3-[3-(4'-fluorobiphen-4-yl)propyl]-N¹-cyclopropyl-N³-hydroxy-α¹-(1-methylethyl)-2-oxo-1,3-pyrrolidinediacetamide

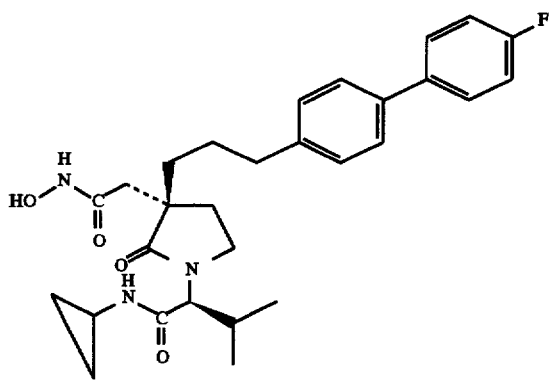

EXAMPLE 170

Preparation of [S-(R*,R*)]-3-[3-(4'-fluorobiphen-4-yl)propyl]-N³-hydroxy-α¹-(1-methylethyl)-2-oxo-N¹-phenyl-1,3-pyrrolidinediacetamide

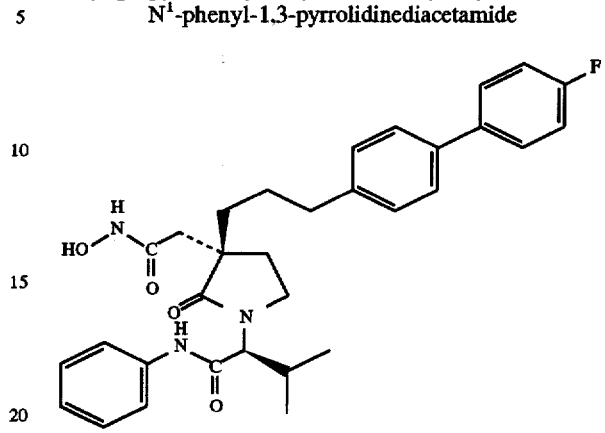

EXAMPLE 171

Preparation of [S-(R*,R*)]-3-[3-(4'-fluorobiphen-4-yl)propyl]-N¹-(4-fluorophenyl)-N³-hydroxy-α¹-(1-methylethyl)-2-oxo-1,3-pyrrolidinediacetamide

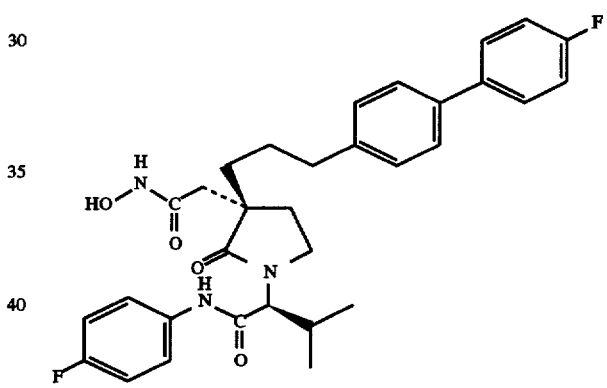

EXAMPLE 172

Preparation of [S-(R*,R*)]-3-[3-(4'-fluorobiphen-4-yl)propyl]-N³-hydroxy-α¹-(1-methylethyl)-2-oxo-N¹-(4-pyridinyl)-1,3-pyrrolidinediacetamide

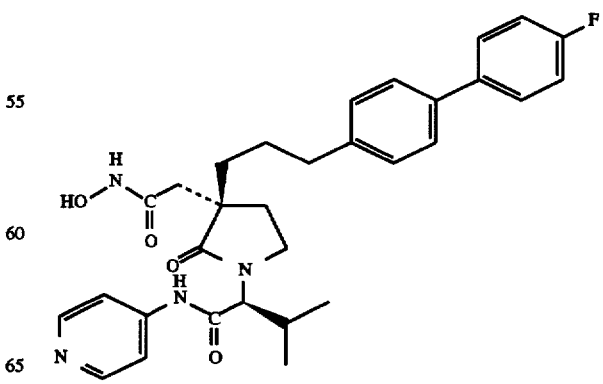

EXAMPLE 173

Preparation of [S-(R*,R*)]-α¹-tert-butyl-3-[3-(4'-fluorobiphen-4-yl)propyl]-N³-hydroxy-N¹-methyl-2-oxo-1,3-pyrrolidinediacetamide

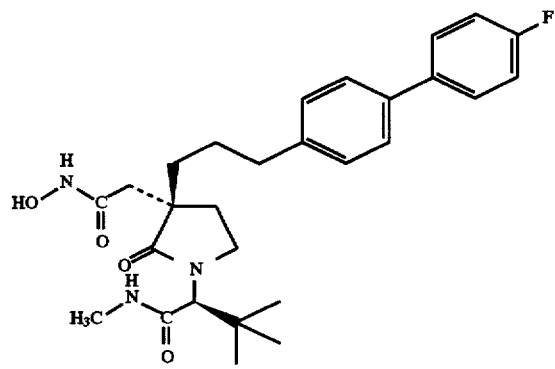

EXAMPLE 174

Preparation of [S-(R*,R*)]-α¹-tert-butyl-N¹-cyclopropyl-3-[3-(4'-fluorobiphen-4-yl)propyl]-N³-hydroxy-2-oxo-1,3-pyrrolidinediacetamide

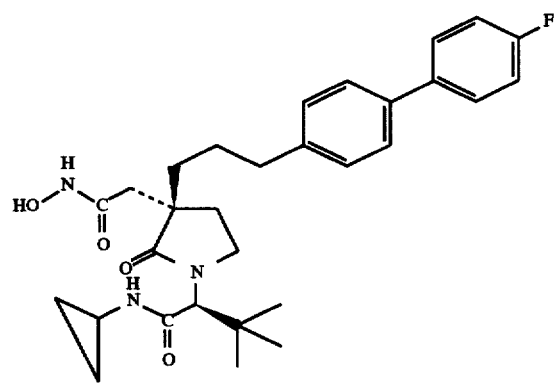

EXAMPLE 175

Preparation of [S-(R*,R*)]-α¹-tert-butyl-3-[3-(4'-fluorobiphen-4-yl)propyl]-N³-hydroxy-2-oxo-N¹-phenyl-1,3-pyrrolidinediacetamide

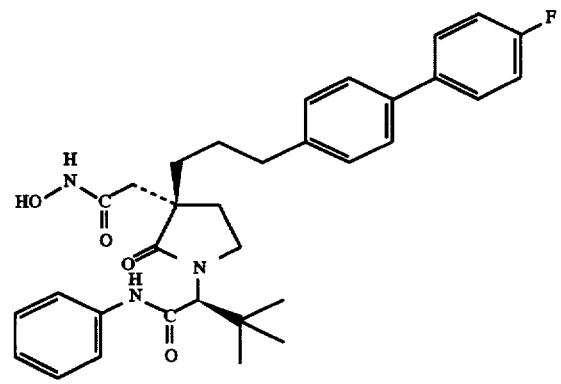

EXAMPLE 176

Preparation of [S-(R*,R*)]-α¹-tert-butyl-3-[3-(4'-fluorobiphen-4-yl)propyl]-N¹-(4-fluorophenyl)-N³-hydroxy-2-oxo-1,3-pyrrolidinediacetamide

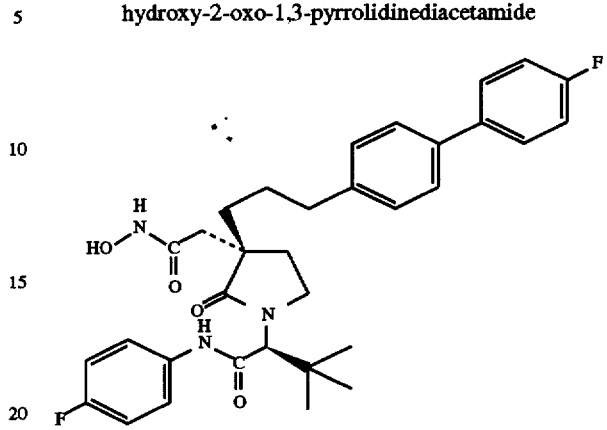

EXAMPLE 177

Preparation of [S-(R*,R*)]-α¹-tert-butyl-3-[3-(4'-fluorobiphen-4-yl)propyl]-N³-hydroxy-2-oxo-N¹-(4-pyridinyl)-1,3-pyrrolidinediacetamide

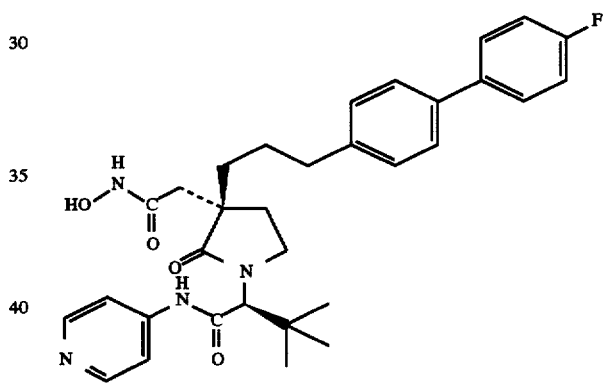

EXAMPLE 178

Preparation of [S-(R*,R*)]-α¹-cyclohexyl-3-[3-(4'-fluorobiphen-4-yl)propyl]-N³-hydroxy-N¹-methyl-2-oxo-1,3-pyrrolidinediacetamide

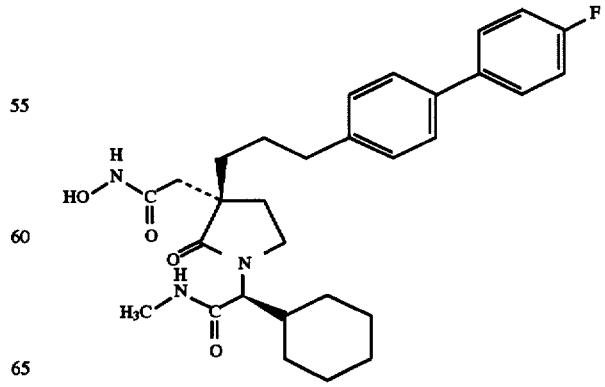

EXAMPLE 179

Preparation of [S-(R*,R*)]-α¹-cyclohexyl-N¹-cyclopropyl-3-[3-(4'-fluorobiphen-4-yl)propyl]-N³-hydroxy-2-oxo-1,3-pyrrolidinediacetamide

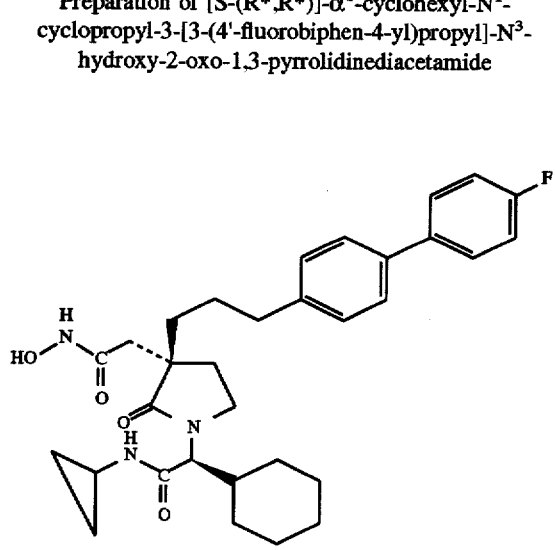

EXAMPLE 180

Preparation of [S-(R*,R*)]-α¹-cyclohexyl-3-[3-(4'-fluorobiphen-4-yl)propyl]-N³-hydroxy-2-oxo-N¹-phenyl-1,3-pyrrolidinediacetamide

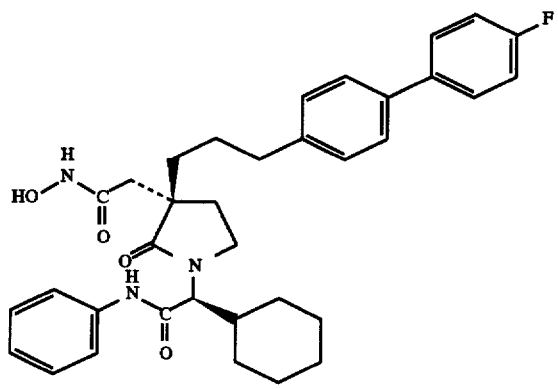

EXAMPLE 181

Preparation of [S-(R*,R*)]-α¹-cyclohexyl-3-[3-(4'-fluorobiphen-4-yl)propyl]-N¹-(4-fluorophenyl)-N³-hydroxy-2-oxo-1,3-pyrrolidinediacetamide

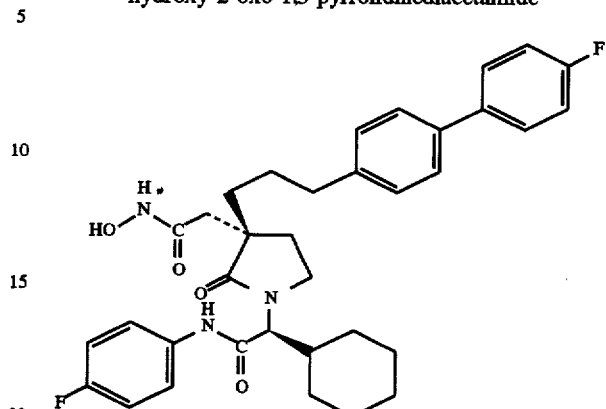

EXAMPLE 182

Preparation of [S-(R*,R*)]-α¹-cyclohexyl-3-[3-(4'-fluorobiphen-4-yl)propyl]-N³-hydroxy-2-oxo-N¹-(4-pyridinyl)-1,3-pyrrolidinediacetamide

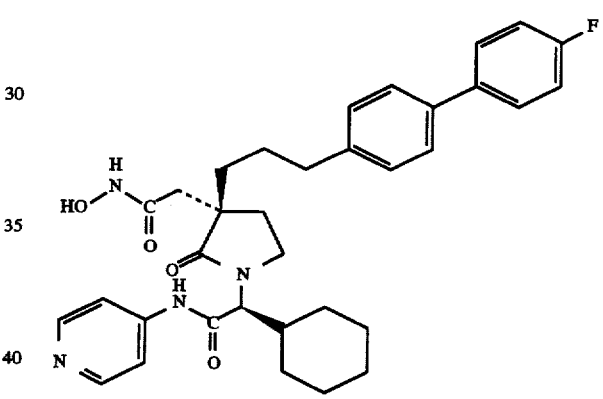

EXAMPLE 183

Preparation of [S-(R*,R*)]-3-heptyl-N³-hydroxy-N¹-methyl-α¹-(1-methylethyl)-2-oxo-1,3-pyrrolidinediacetamide

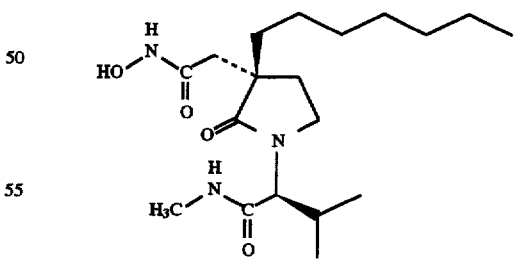

EXAMPLE 184

Preparation of [S-(R*,R*)]-N¹-cyclopropyl-3-heptyl-N³-hydroxy-α¹-(1-methylethyl)-2-oxo-1,3-pyrrolidinediacetamide

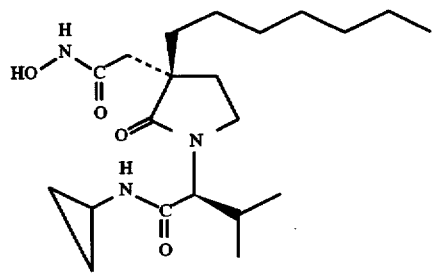

EXAMPLE 185

Preparation of [S-(R*,R*)]-3-heptyl-N³-hydroxy-α¹-(1-methylethyl)-2-oxo-N¹-phenyl-1,3-pyrrolidinediacetamide

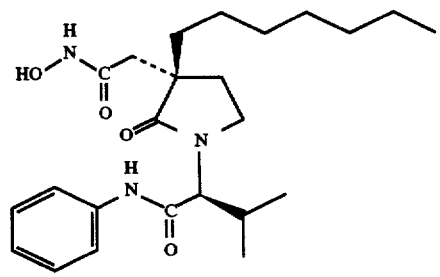

EXAMPLE 186

Preparation of [S-(R*,R*)]-3-heptyl-N¹-(4-fluorophenyl)-N³-hydroxy-α¹-(1-methylethyl)-2-oxo-1,3-pyrrolidinediacetamide

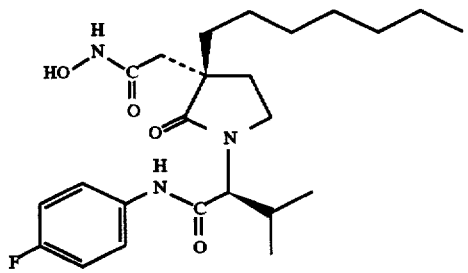

EXAMPLE 187

Preparation of [S-(R*,R*)]-3-heptyl-N³-hydroxy-α¹-(1-methylethyl)-2-oxo-N¹-(4-pyridinyl)-1,3-pyrrolidinediacetamide

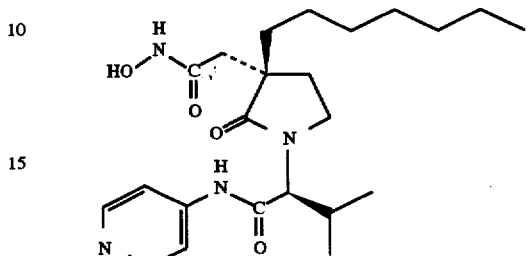

EXAMPLE 188

Preparation of [S-(R*,R*)]-α¹-tert-butyl-3-heptyl-N³-hydroxy-N¹-methyl-2-oxo-1,3-pyrrolidinediacetamide

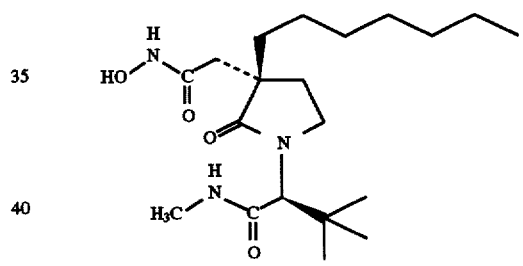

EXAMPLE 189

Preparation of [S-(R*,R*)]-α¹-tert-butyl-N¹-cyclopropyl-3-heptyl-N³-hydroxy-2-oxo-1,3-pyrrolidinediacetamide

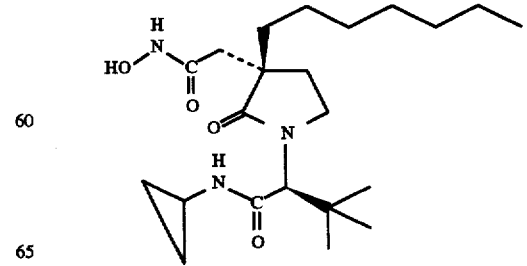

EXAMPLE 190

Preparation of [S-(R*,R*)]-α¹-tert-butyl-3-heptyl-N³-hydroxy-2-oxo-N¹-phenyl-1,3-pyrrolidinediacetamide

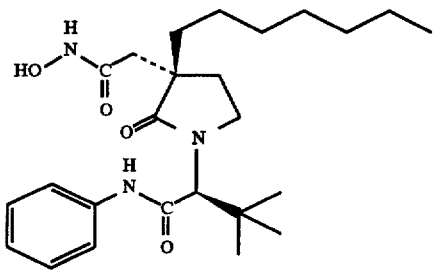

EXAMPLE 191

Preparation of [S-(R*,R*)]-α¹-tert-butyl-N¹-(4-fluorophenyl)-3-heptyl-N³-hydroxy-2-oxo-1,3-pyrrolidinediacetamide

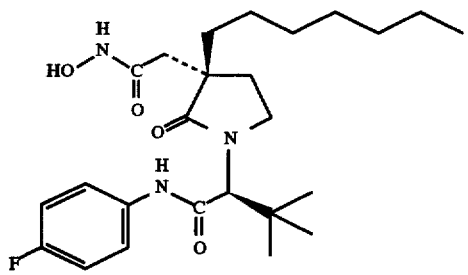

EXAMPLE 192

Preparation of [S-(R*,R*)]-α¹-tert-butyl-3-heptyl-N³-hydroxy-2-oxo-N¹-(4-pyridinyl)-1,3-pyrrolidinediacetamide

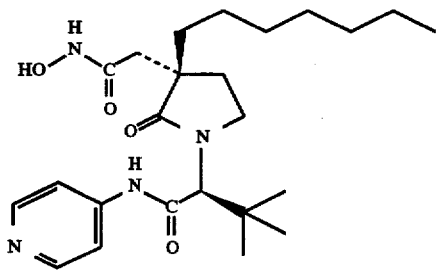

EXAMPLE 193

Preparation of [S-(R*,R*)]-α¹-cyclohexyl-3-heptyl-N³-hydroxy-N¹-methyl-2-oxo-1,3-pyrrolidinediacetamide

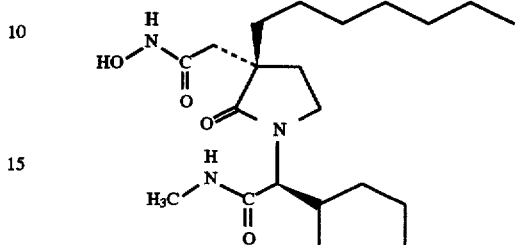

EXAMPLE 194

Preparation of [S-(R*,R*)]-α¹-cyclohexyl-N¹-cyclopropyl-3-heptyl-N³-hydroxy-2-oxo-1,3-pyrrolidinediacetamide

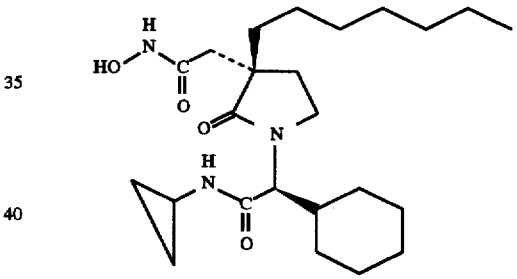

EXAMPLE 195

Preparation of [S-(R*,R*)]-α¹-cyclohexyl-3-heptyl-N³-hydroxy-2-oxo-N¹-phenyl-1,3-pyrrolidinediacetamide

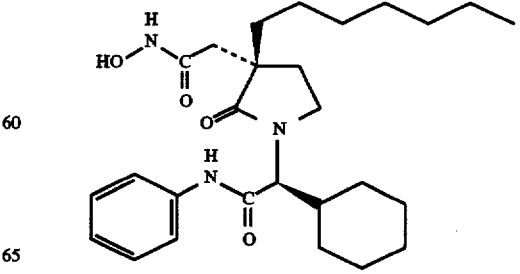

EXAMPLE 196
Preparation of [S-(R*,R*)]-α¹-cyclohexyl-3-heptyl-N¹-(4-fluorophenyl)-N³-hydroxy-2-oxo-1,3-pyrrolidinediacetamide
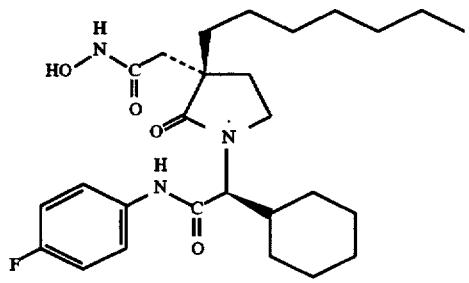
EXAMPLE 197
Preparation of [S-(R*,R*)]-α¹-cyclohexyl-3-heptyl-N³-hydroxy-2-oxo-N¹-(4-pyridinyl)-1,3-pyrrolidinediacetamide
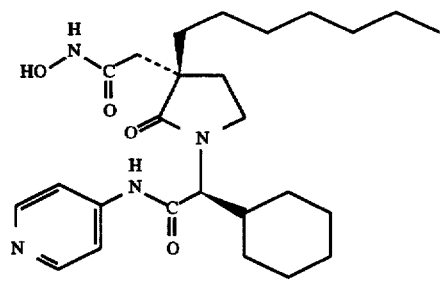
SCHEME A-1
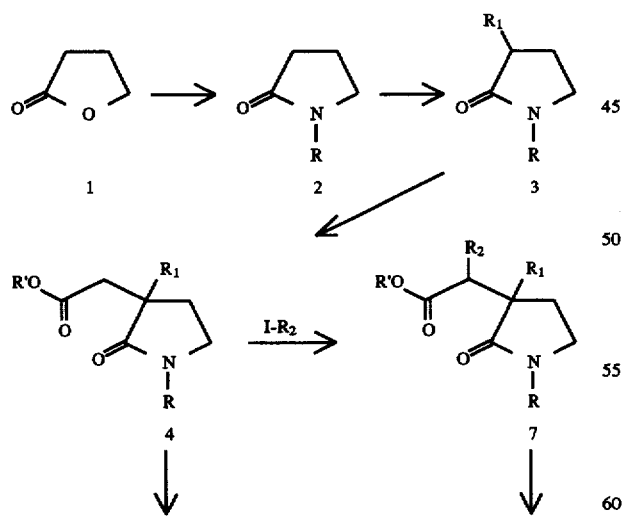
SCHEME A-1 —continued
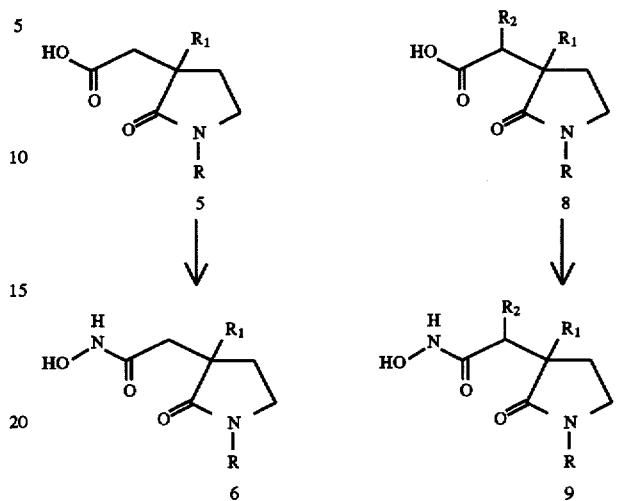
SCHEME A-2
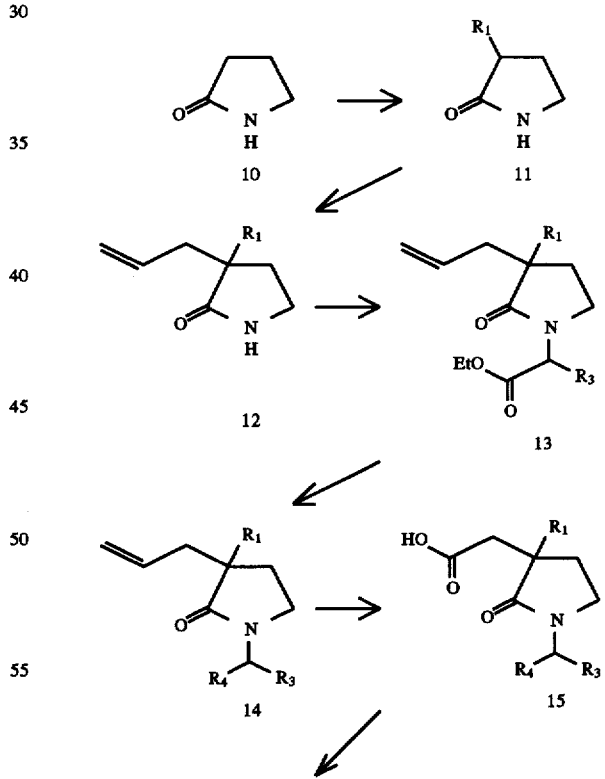

149
-continued
SCHEME A-2
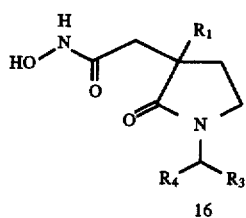
16
SCHEME A-3
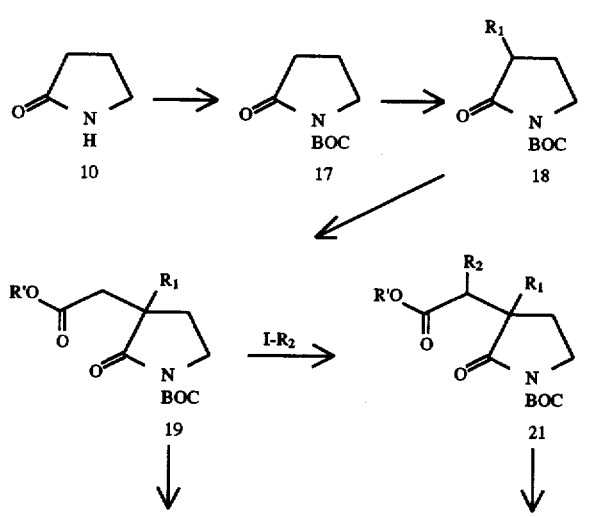
150
-continued
SCHEME A-3
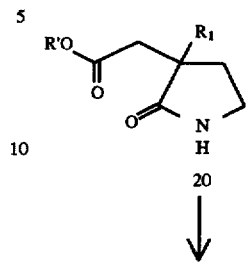
20
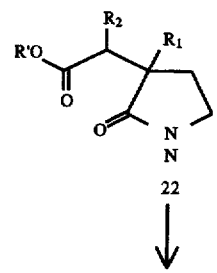
22
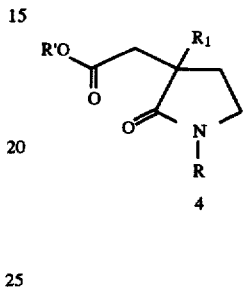
4
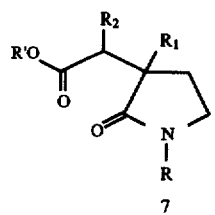
7
SCHEME A-4
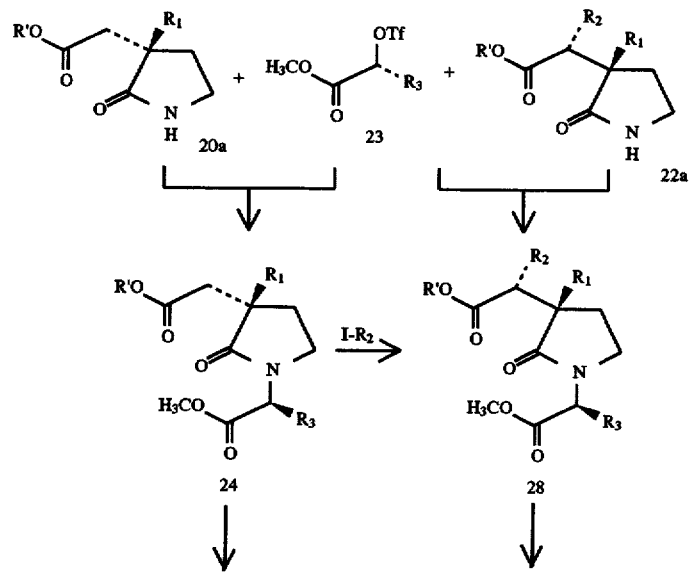

-continued
SCHEME A-4
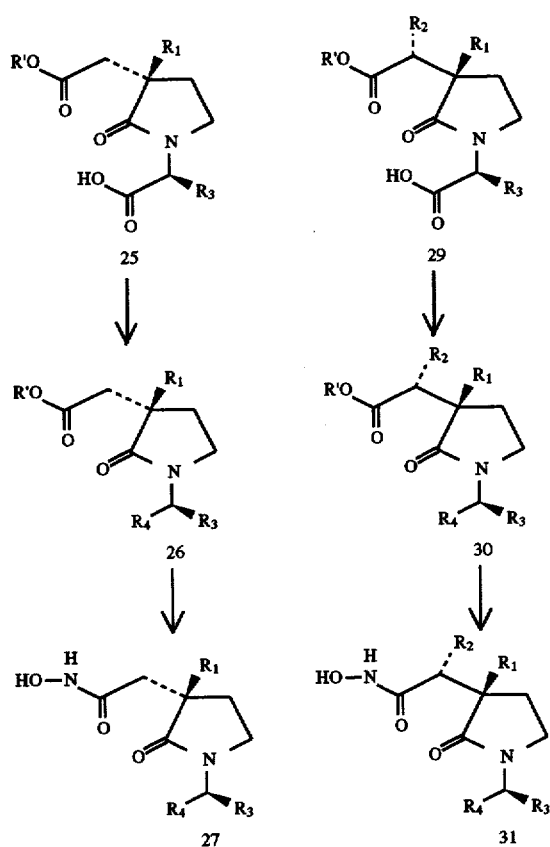
SCHEME A-5
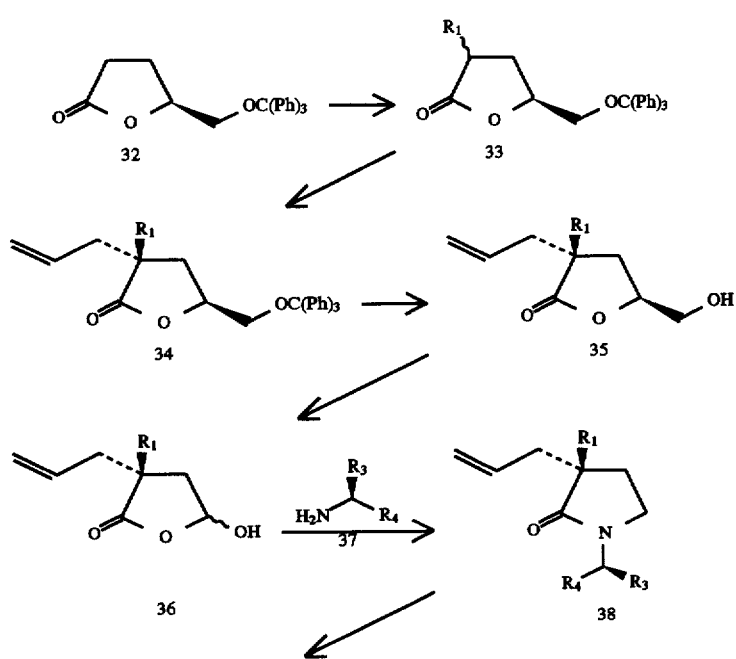

-continued
SCHEME A-5
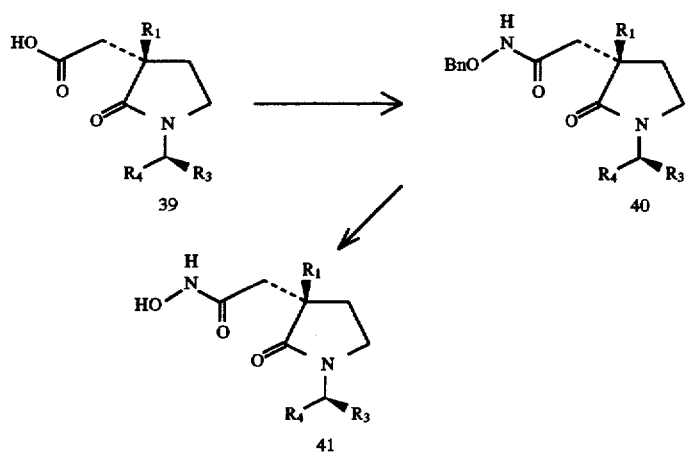
SCHEME B
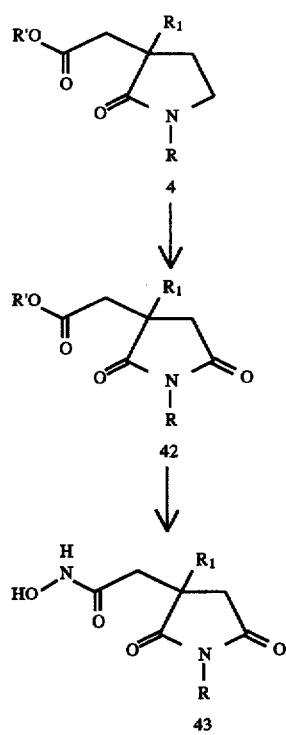
SCHEME C-1
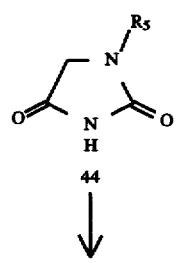
-continued
SCHEME C-1
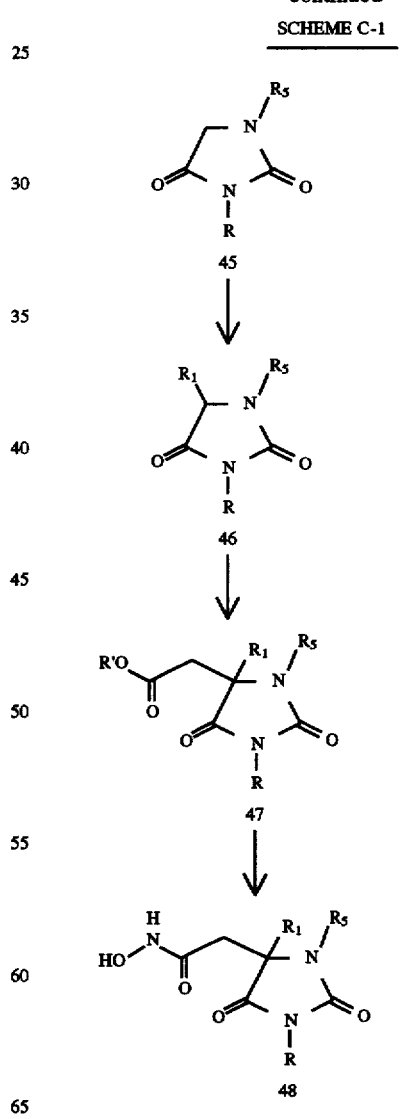

SCHEME C-2

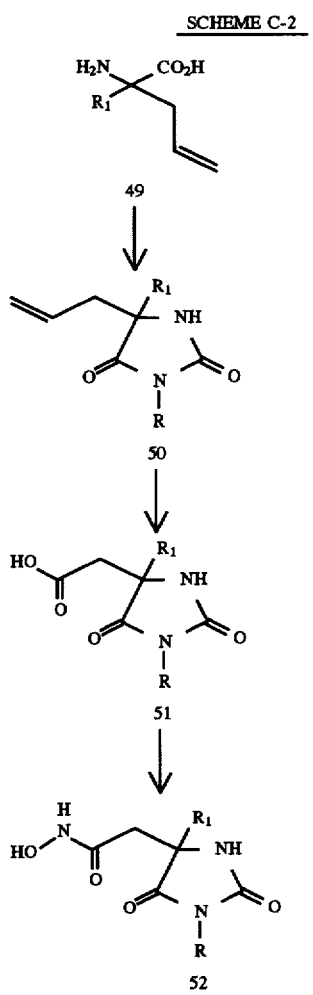

SCHEME D

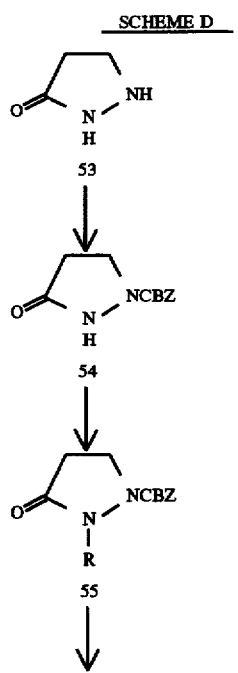

-continued
SCHEME D

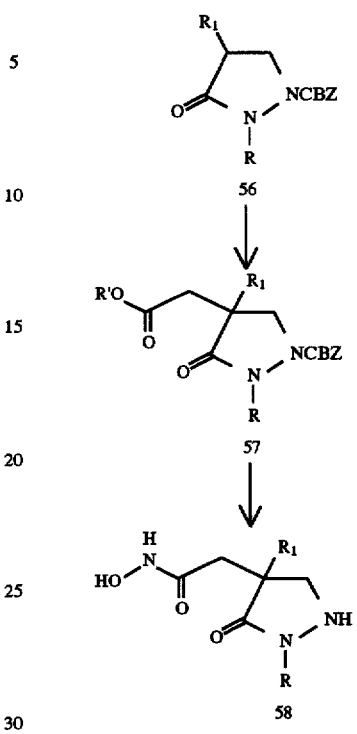

We claim:
1. A compound of formula I

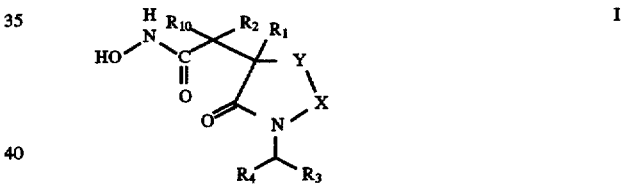

or pharmaceutical acceptable salts thereof wherein
X is
 a) —(CH$_2$)—,
 b) —NR$_5$—, or
 c) —C(=O)—;
Y is
 a) —(CH$_2$)—, or
 b) —NR$_5$—;
with the prociso that when X is —NR$_5$—, then Y is —(CH$_2$)—;
R$_1$ is
 a) H,
 b) C$_{1-20}$ alkyl,
 c) —(CH$_2$)$_i$-Aryl,
 d) —(CH$_2$)$_i$—O—R$_5$,
 e) —(CH$_2$)$_i$—Het,
 f) —(CH$_2$)$_i$—CO$_2$R$_5$,
 g) —(CH$_2$)$_i$—C(=O)NHR$_5$,
 h) —(CH$_2$)$_i$—NR$_6$R$_7$,
 i) —(CH$_2$)$_i$—SO$_2$-Aryl,
 j) —(CH$_2$)$_j$ cycloalkyl, or
 k) —(CH$_2$)$_j$-Aryl-Aryl;
R$_2$ is
 a) H,
 b) C$_{1-20}$ alkyl, c) —(CH$_2$)$_j$—R$_8$,
d) —(CH$_2$)$_j$—OR$_5$,
e) CH$_2$CR$_5$=CR$_5$R$_5$,
f) —NHR$_5$,
g) —(CH$_2$)$_j$NR$_6$R$_7$,
h) —NHSO$_2$R$_5$,
i) —(CH$_2$)$_j$—C(=O)NR$_6$R$_7$,
j) —(CH$_2$)$_j$—NR$_5$C(=O)R$_5$,
k) —(CH$_2$)$_j$—NR$_5$SO$_2$R$_5$, or
l) —(CH$_2$)$_j$—N(COR$_5$)$_2$;

R$_3$ is
a) H,
b) C$_{1-6}$ alkyl,
c) —(CH$_2$)$_j$-Aryl,
d) —(CH$_2$)$_j$—Het,
e) —(CH$_2$)$_j$—C$_{3-6}$ cycloalkyl, or
f) —C(=O)NHR$_5$;

R$_4$ is
a) H,
b) —C(=O)NHR$_5$,
c) —C(=O)NR$_6$R$_7$,
d) —C(=O)NH(CH$_2$)$_k$NR$_6$R$_7$,
e) —C(=O)NH(CH$_2$)$_j$-Aryl,
f) —C(=O)NH(CH$_2$)$_k$—O—(CH$_2$)$_k$NR$_6$R$_7$,
g) —C(=O)NH(CH$_2$)$_k$—S—(CH$_2$)$_j$NR$_6$R$_7$,
h) —C(=O)NH(CH$_2$)$_k$—NHSO$_2$-Aryl,
i) C(=O)NH(CH$_2$)$_k$—NHSO$_2$—NR$_6$R$_7$, or j) 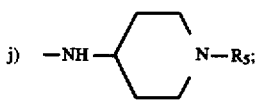

R$_5$ is
a) H,
b) C$_{1-6}$ alkyl,
c) —(CH$_2$)$_j$-Aryl,
d) —(CH$_2$)$_j$-Aryl-Aryl,
e) —(CH$_2$)$_j$-Aryl-(CH$_2$)$_j$-Aryl,
f) (CH$_2$)$_j$—Het, or
g) —(CH$_2$)$_j$-cycloalkyl R$_6$ and R$_7$ may be the same or differently
a) H,
b) C$_{1-6}$ alkyl,
c) —(CH$_2$)$_j$-Aryl,
d) Q, or
e) R$_6$ and R$_7$ taken together with the linking N-atom form azetidinyl, pyrrolidinyl, piperazinyl, piperidinyl, or morpholinyl, optionally substituted with one or more C$_{1-4}$ alkyl;

R$_8$ is
a) —S—R$_5$,
b) —SO—R$_5$,
c) —SO$_2$—R$_5$,
d) —S—(CH$_2$)$_j$—Het,
e) —NHCO$_2$R$_5$,
f) piperidinyl, g) 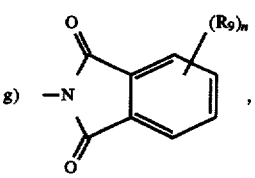

-continued h) 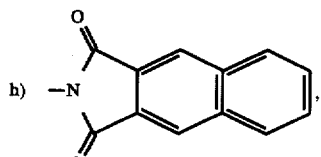

i) 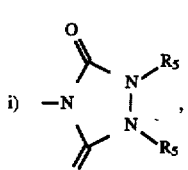

j) 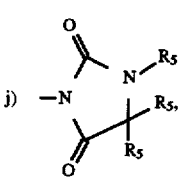

k) 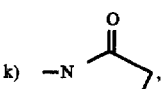

l) 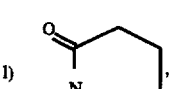

m) 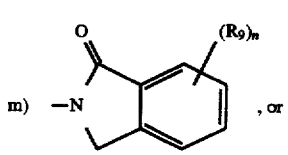, or n) 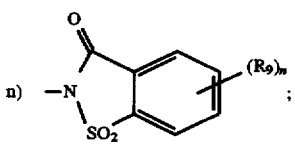;

R$_9$ is
a) halogen,
b) C$_{1-6}$ alkyl,
c) —OR$_5$,
d) —NR$_5$R$_5$,
e) —CONHR$_5$,
f) —SO$_2$NHR$_5$,
g) —NHSO$_2$R$_5$,
h) —NO$_2$,
i) —CO$_2$R$_5$, or
j) —CF$_3$;

R$_{10}$ is
a) H,
b) OH,
c) OR$_5$,
d) NHR$_5$, or
e) —(CH$_2$)$_j$—OR$_5$;

Aryl is phenyl, optionally substituted with one or more of the following:
a) halogen,
b) C$_{1-10}$ alkyl,
c) —OR$_5$, d) —NR₅R₅,
e) —CONHR₅,
f) —SO₂NHR₅,
g) —NHSO₂R₅,
h) —NO₂,
i) —CO₂R₅, or
j) —CF₃;

Het is
a 5-, or 6-membered heteroaromatic moiety having one or more atoms selected from the group consisting of N, O, and S;

Q is
a saturated 5, or 6-membered heterocyclic moiety having 1-2 atoms selected from the group consisting of N, O, and S;

i is 1, 2, 3, 4, 5 or 6;
j is 0, 1, 2, 3, or 4;
k is 2, 3, or 4;
n is 0, 1, 2, 3, or 4;

C₁₋₆ alkyl, C₁₋₁₀ alkyl, or C₁₋₂₀ alkyl in each of the above definitions, may be each and independently substituted with one to three halogen, hydroxy, or cyano; and with the proviso that when R₁ is methylbutyl R₄ is other than H.

2. A compound of formula I according to claim 1 which is an optically pure enantiomer having structure II

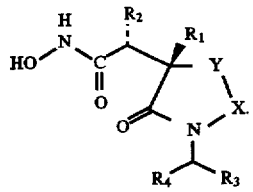

3. A compound of formula I according to claim 1 which is an optically pure enantiomer having structure III

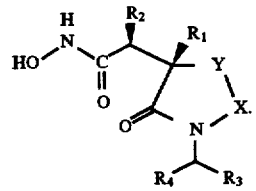

4. A compound of formula I according to claim 1 which is an optically pure enantiomer having structure IV

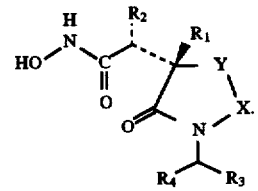

5. A compound of formula I according to claim 1 which is an optically pure enantiomer having structure V

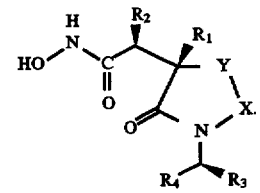

6. A compound of formula I according to claim 1 which is an optically pure enantiomer having structure VI

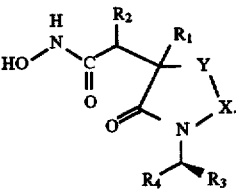

7. A compound of formula I according to claim 1 which is an optically pure enantiomer having structure VII

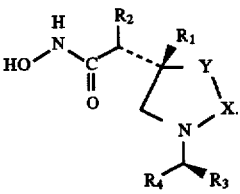

8. A compound of claim 1 wherein R₁ is 2-methylpropyl, or 3-methylbutyl.

9. A compound of claim 1 wherein R₂ is selected from the group consisting of H, methyl, 2-(1,3-dihydro-1,3-dioxo-2H-isoindol-2-yl)ethyl, 2-(1,3-dihydro-1,3-dioxo-2H-naphthoisoindol-2-yl)ethyl, 2-(4,5,6,7,-tetrafluoro-1,3-dihydro-1,3-dioxo-2H-isoindol-2-yl)ethyl, 2-(5,6,-dichloro-1,3-dihydro-1,3-dioxo-2H-isoindol-2-yl)ethyl, 2-(5-amino-1,3-dihydro-1,3-dioxo-2H-isoindol-2-yl)ethyl, 2-(4-nitro-1,3-dihydro-1,3-dioxo-2H-isoindol-2-yl)ethyl, 2-(5-nitro-1,3-dihydro-1,3-dioxo-2H-isoindol-2-yl)ethyl, 2-(4-fluoro-1,3-dihydro-1,3-dioxo-2H-isoindol-2-yl)ethyl, 2-(4,7-difluoro-1,3-dihydro-1,3-dioxo-2H-isoindol-2-yl)ethyl, 2-(5-fluoro-1,3-dihydro-1,3-dioxo-2H-isoindol-2-yl)ethyl, 2-(1,3-dihydro-1,3-dioxo-2H-isoindol-2-yl)propyl, 2-(1,3-dihydro-1,3-dioxo-2H-isoindol-2-yl)methyl, 2-(2-thienylthio)propyl, and 2-(2-thienylthio)methyl.

10. A compound of claim 1 wherein R₃ is selected from the group consisting of H, 2-methylpropyl, cyclohexylmethyl, benzyl, and phenyl.

11. A compound of claim 1 wherein R₄ is H or acetamide.

12. A compound of claim 1 wherein said compound of formula I is
1a) N-Hydroxy-3-(2-methylpropyl)-2-oxo-1-(2-phenylethyl)-3-pyrrolidineacetamide,
1b) (3S)-N-Hydroxy-3-(2-methylpropyl)-2-oxo-1-(2-phenylethyl)-3-pyrrolidineacetamide,
1c) N-Hydroxy-α-methyl-3-(2-methylpropyl)-2-oxo-1-(2-phenylethyl)-3-pyrrolidineacetamide,
1d) α-[2-(1,3-Dihydro-1,3-dioxo-2H-isoindol-2-yl)ethyl]-N-hydroxy-3-(2-methylpropyl)-2-oxo-1-(2-phenylethyl)-3-pyrrolidineacetamide,
1e) (3S)-α-[2-(1,3-Dihydro-1,3-dioxo-2H-isoindol-2-yl)ethyl]-N-hydroxy-3-(2-methylpropyl)-2-oxo-1-(2-phenylethyl)-3-pyrrolidineacetamide,
1f) α-[2-(1,3-Dihydro-1,3-dioxo-2H-naphthoisoindol-2-yl)ethyl]-N-hydroxy-3-(2-methylpropyl)-2-oxo-1-(2-phenylethyl)-3-pyrrolidineacetamide,
1g) N-Hydroxy-3-(2-methylpropyl)-2-oxo-1-(2-phenylethyl)-α-[2-(4,5,6,7-tetrafluoro-1,3-dihydro-1,3-dioxo-2H-isoindol-2-yl)ethyl]-3-pyrrolidineacetamide,
1h) α-[2-(5,6-Dichloro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide,
1i) α-[2-(5-Amino-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide,
1j) N-Hydroxy-3-(2-methylpropyl)-α-[2-(4-nitro-1,3-dihydro-1,3-dioxo-2H-isoindol-2-yl)ethyl]-2-oxo-1-(2-phenylethyl)-3-pyrrolidineacetamide, 1k) N-Hydroxy-3-(2-methylpropyl)-α-[2-(5-nitro-1,3-dihydro-1,3-dioxo-2H-isoindol-2-yl)ethyl]-2-oxo-1-(2-phenylethyl)-3-pyrrolidineacetamide, 1l) α-[2-(4-Fluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, 1m) α-[2-(4,7-Difluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, 1n) α-[2-(5-Fluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, 1o) α-[2-(1,3-Dihydro-1,3-dioxo-2H-isoindol-2-yl)propyl]-N-hydroxy-3-(2-methylpropyl)-2-oxo-1-(2-phenylethyl)-3-pyrrolidineacetamide, 1p) α-[2-(1,3-Dihydro-1,3-dioxo-2H-isoindol-2-yl)methyl]-N-hydroxy-3-(2-methylpropyl)-2-oxo-1-(2-phenylethyl)-3-pyrrolidineacetamide, 1q) N-Hydroxy-3-(2-methylpropyl)-2-oxo-1-(2-phenylethyl)-α-[2-(2-thienylthio)ethyl]-3-pyrrolidineacetamide, 1r) N-Hydroxy-3-(2-methylpropyl)-2-oxo-1-(2-phenylethyl)-α-[2-(2-thienylthio)propyl]-3-pyrrolidineacetamide, 1s) N-Hydroxy-3-(2-methylpropyl)-2-oxo-1-(2-phenylethyl)-α-[2-(2-thienylthio)methyl]-3-pyrrolidineacetamide, 1t) $N^3$-Hydroxy-$N^1$-methyl-3-(2-methylpropyl)-2-oxo-1,3-pyrrolidinediacetamide, 1u) $N^3$-Hydroxy-$N^1$-methyl-3-(2-methylpropyl)-2-oxo-$\alpha^1$-(phenylmethyl)-1,3-pyrrolidinediacetamide, 1v) N-Hydroxy-3-(2-methylpropyl)-2-oxo-1-(phenylmethyl)-3-pyrrolidineacetamide, 1w) α-[2-(1,3-Dihydro-1,3-dioxo-2H-isoindol-2-yl)ethyl]-N-hydroxy-3-(2-methylpropyl)-2-oxo-1-(phenylmethyl)-3-pyrrolidineacetamide, 1x) N-Hydroxy-3-(2-methylpropyl)-2-oxo-1-(phenylmethyl)-α-[2-(4,5,6,7-tetrafluoro-1,3-dihydro-1,3-dioxo-2H-isoindol-2-yl)ethyl]-3-pyrrolidineacetamide, 1y) 1-(3-Fluorophenyl)methyl)-α-[2-(1,3-dihydro-1,3-dioxo-2H-isoindol-2-yl)ethyl]-N-hydroxy-3-(2-methylpropyl)-2-oxo-3-pyrrolidineacetamide, 1z) $\alpha^3$-[2-(1,3-Dihydro-1,3-dioxo-2H-isoindol-2-yl)ethyl]-$N^3$-hydroxy-$N^1$-methyl-3-(2-methylpropyl)-2-oxo-1,3-pyrrolidinediacetamide, 2a) $N^3$-Hydroxy-$N^1$-methyl-3-(2-methylpropyl)-2-oxo-$\alpha^3$-[2-(4,5,6,7-tetrafluoro-1,3-dihydro-1,3-dioxo-2H-isoindol-2-yl)ethyl]-1,3-pyrrolidinediacetamide, 2d) [S-(R*,R*)]-$N^3$-Hydroxy-$N^1$-methyl-3-(2-methylpropyl)-2-oxo-$\alpha^1$-(phenylmethyl)-1,3-pyrrolidinediacetamide, 2e) [S-(R*,R*)]-$N^3$-Hydroxy-3-(2-methylpropyl)-2-oxo-$N^1$-(2-phenethyl)-$\alpha^1$-(phenylmethyl)-1,3-pyrrolidinediacetamide, 2f) [S-(R*,R*)]-$N^3$-Hydroxy-$N^1$-methyl-$\alpha^1$,3-bis(2-methylpropyl)-2-oxo-1,3-pyrrolidinediacetamide, 2g) [S-(R*,R*)]-$\alpha^1$-(Cyclohexylmethyl)-$N^3$-hydroxy-$N^1$-methyl-3-(2-methylpropyl)-2-oxo-1,3-pyrrolidinediacetamide, 2h) [S-(R*,R*)]-$N^3$-Hydroxy-$N^1$-methyl-3-(3-methylbutyl)-2-oxo-$\alpha^1$-(phenylmethyl)-1,3-pyrrolidinediacetamide, 2i) N-Hydroxy-3-(2-methylpropyl)-2,5-dioxo-1-(2-phenylethyl)-3-pyrrolidineacetamide, 2j) N-Hydroxy-3-methyl-4-(2-methylpropyl)-2,5-dioxo-1-(2-phenylethyl)-4-imidazolidineacetamide, 2k) N-Hydroxy-4-(2-methylpropyl)-2,5-dioxo-1-(2-phenylethyl)-4-imidazolidineacetamide, 2l) N-Hydroxyl-4-(2-methylpropyl)-5-oxo-1-(2-phenylethyl)-4-pyrazolidineacetamide monohydrochloride, 2m) [S-(R*,R*)]-$N^3$-Hydroxy-3-(2-methylpropyl)-2-oxo-$N^1$-phenyl-$\alpha^1$-(phenylmethyl)-1,3-pyrrolidinediacetamide, 2n) [S-(R*,R*)]-$N^3$-Hydroxy-3-(2-methylpropyl)-2-oxo-$\alpha^1$-(phenylmethyl)-$N^1$-(2-pyridinylmethyl)-1,3-pyrrolidinediacetamide, 2o) [S-(R*,R*)]-$N^3$-Hydroxy-3-(2-methylpropyl)-2-oxo-$\alpha^1$-(phenylmethyl)-$N^1$-(4-pyridinyl)-1,3-pyrrolidinediacetamide, 2p) [S-(R*,R*)]-$N^1$-(4-Fluorophenyl)-$N^3$-hydroxy-3-(2-methylpropyl)-2-oxo-$\alpha^1$-(phenylmethyl)-1,3-pyrrolidinediacetamide, 2q) [S-(R*,R*)]-$N^3$-Hydroxy-3-(2-methylpropyl)-2-oxo-$\alpha^1$-(phenylmethyl)-$N^1$-[1-(phenylmethyl)-4-piperdinyl]-1,3-pyrrolidinediacetamide, 2r) [S-(R*,R*)]-$N^3$-Hydroxy-3-(2-methylpropyl)-2-oxo-$\alpha^1$-(phenylmethyl)-$N^1$-(4-piperdinyl)-1,3-pyrrolidinediacetamide, 2s) [S-(R*,R*)]-$N^3$-Hydroxy-3-(2-methylpropyl)-2-oxo-$\alpha^1$-(phenylmethyl)-$N^1$-(4-pyridinylmethyl)-1,3-pyrrolidinediacetamide, 2t) [S-(R*,R*)]-$N^1$-(4-Fluorophenylmethyl)-$N^3$-hydroxy-3-(2-methylpropyl)-2-oxo-$\alpha^1$-(phenylmethyl)-1,3-pyrrolidinediacetamide, 2u) [S-(R*,R*)]-$N^3$-Hydroxy-$N^1$-methyl-3-(2-methylpropyl)-2-oxo-$\alpha^1$-(2-phenylethyl)-1,3-pyrrolidinediacetamide, 2v) [S-(R*,R*)]-$N^3$-Hydroxy-3-(2-methylpropyl)-2-oxo-$\alpha^1$-(2-phenylethyl)-$N^1$-(phenylmethyl)-1,3-pyrrolidinediacetamide, 2w) [S-(R*,R*)]-$N^3$-Hydroxy-$\alpha^1$,3-bis(2-methylpropyl)-2-oxo-$N^1$-2-pyridinyl-1,3-pyrrolidinediacetamide, 2x) [S-(R*,R*)]-$\alpha^1$-Cyclohexyl-$N^3$-hydroxy-$N^1$-methyl-3-(2-methylpropyl)-2-oxo-1,3-pyrrolidinediacetamide, 2y) [S-(R*,R*)]-$\alpha^1$-Cyclohexyl-$N^3$-hydroxy-3-(2-methylpropyl)-2-oxo-$N^1$-2-pyridinyl-1,3-pyrrolidinediacetamide, 3a) [S-(R*,R*)]-3-(Cyclopentylmethyl)-$N^3$-hydroxy-$N^1$-methyl-2-oxo-$\alpha^1$-(phenylmethyl)-1,3-pyrrolidinediacetamide, 3b) [3S-[1(R*),3R*(R*)]]-$\alpha^3$-[2-(Benzoylamino)ethyl]-$N^3$-hydroxy-$N^1$-methyl-3-(2-methylpropyl)-2-oxo-$\alpha^1$-(phenylmethyl)-1,3-pyrrolidinediacetamide, 3c) [S-(R*,R*)]-$N^3$-Hydroxy-3-(2-methylpropyl)-$N^1$-[2-(4-morpholinyl)ethyl]-2-oxo-$\alpha^1$-(phenylmethyl)-1,3-pyrrolidinediacetamide, 3d) [S-(R*,R*)]-N-Hydroxy-3-(2-methylpropyl)-1-[2-(4-morpholinyl)-2-oxo-1-(phenylmethyl)ethyl]-2-oxo-3-pyrrolidineacetamide, 3e) [1(1S)-[1[R*(R*)],3α,5α]]-1-[2-(3,5-Dimethyl-1-piperazinyl)-2-oxo-1-(phenylmethyl)ethyl]-N-hydroxy-3-(2-methylpropyl)-2-oxo-3-pyrrolidineacetamide, 3f) [S-(R*,R*)]-$N^3$-Hydroxy-3-(2-methylpropyl)-2-oxo-$\alpha^1$-(phenylmethyl)-$N^1$-2-pyridinyl-1,3-pyrrolidinediacetamide, 3g) [3S-[1(R*),3R*(R*)]]-$\alpha^3$-[2-(1,3-Dihydro-1,3-dioxo-2H-isoindol-2-yl)ethyl]-$N^3$-hydroxy-$N^1$-methyl-3-(2-methylpropyl)-2-oxo-$\alpha^1$-(phenylmethyl)-1,3-pyrrolidinediacetamide, 3h) [S-(R*,R*)]-$\alpha^1$-Cyclohexyl-$N^1$-cyclopropylmethyl-$N^3$-hydroxy-3-(2-methylpropyl)-2-oxo-1,3-pyrrolidinediacetamide, 3i) [S-(R*,R*)]-$\alpha^1$-Cyclohexyl-$N^1$-(4-fluorophenyl)-$N^3$-hydroxy-3-(2-methylpropyl)-2-oxo-1,3-pyrrolidinediacetamide, 3j) [S-(R*,R*)]-α¹-tert-Butyl-N³-hydroxy-N¹-methyl-3-(2-methylpropyl)-2-oxo-1,3-pyrrolidinediacetamide, 3k) N-Hydroxy-3-(2-methylpropyl)-2-oxo-1-(2-phenylethyl)-α-[2-(5-propyloxy-1,3-dihydro-1,3-dioxo-2H-isoindol-2-yl)ethyl]-3-pyrrolidineacetamide, 3l) [R-(R*,S*)]-5-Fluoro-1,3-dihydro-N-hydroxy-α-[3-(2-methylpropyl)-2-oxo-1-(2-phenylethyl)-3-pyrrolidinyl]-1,3-dioxo-2H-isoindole-2-butanamide, 3m) α-[2-(5,6-Difluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, 3n) N-Hydroxy-3-(2-methylpropyl)-2-oxo-1-(2-phenylethyl)-α-[2-(5-trifluoromethyl-1,3-dihydro-1,3-dioxo-2H-isoindol-2-yl)ethyl]-3-pyrrolidineacetamide, 3o) α-[2-(1,3,4,5,6,7-Hexahydro-1,3-dioxo-2H-isoindol-2-yl)ethyl]-N-hydroxy-3-(2-methylpropyl)-2-oxo-1-(2-phenylethyl)-3-pyrrolidineacetamide, 3p) α-[2-(1,3-Dihydro-1,3-dioxo-2H-isoindol-2-yl)ethyl]-N-hydroxy-3-(2-methylpropyl)-2-oxo-1-(3-phenylpropyl)-3-pyrrolidineacetamide, 3r) α-[2-(o-benzoic sulfimide)ethyl]-N-hydroxy-3-(2-methylpropyl)-2-oxo-1-(2-phenylethyl)-3-pyrrolidineacetamide, 3s) Ethyl Phenylmethyl[4-(hydroxyamino)-3-[3-(2-methylpropyl)-2-oxo-1-(2-phenylethyl)-3-pyrrolidinyl]-4-oxobutyl]imidodicarbonate, 3t) S-(R*,R*)]-1,3-Dihydro-N-hydroxy-α-[3-(2-methylpropyl)-2-oxo-1-(2-phenylethyl)-3-pyrrolidinyl]-1,3-dioxo-2H-isoindole-2-butanamide, 3u) 1,3-Dihydro-N-hydroxy-α-[3-(2-methylpropyl)-2-oxo-1-[2-(4-fluorophenyl)ethyl]-3-pyrrolidinyl]-1,3-dioxo-2H-isoindole-2-butanamide, 3v) α-[2-[(3,4-Difluorobenzoyl)amino]ethyl]-N-hydroxy-3-(2-methylpropyl)-2-oxo-1-(2-phenylethyl)-3-pyrrolidineacetamide, 3w) [R-(R*,S*)-α-[2-[(3-Fluorobenzoyl)amino]ethyl]-N-hydroxy-3-(2-methylpropyl)-2-oxo-1-(2-phenylethyl)-3-pyrrolidineacetamide, 3x) α-[2-[(4-Fluorobenzoyl)amino]ethyl]-N-hydroxy-3-(2-methylpropyl)-2-oxo-1-(2-phenylethyl)-3-pyrrolidineacetamide, 3y) N-Hydroxy-3-(2-methylpropyl)-α-[2-[(3-nitrobenzoyl)amino]ethyl]-2-oxo-1-(2-phenylethyl)-3-pyrrolidineacetamide, 3z) α-[2-[(3-Fluorobenzoyl)amino]ethyl]-N-hydroxy-3-(2-methylpropyl)-2-oxo-1-(2-phenylethyl)-3-pyrrolidineacetamide, 4a) α-[2-[(3-Fluorobenzoyl)amino]ethyl]-1-[2-(4-fluorophenyl)ethyl]-N-hydroxy-3-(2-methylpropyl)-2-oxo-3-pyrrolidineacetamide, 4b) α-[2-[(4-Biphenylcarbonyl)amino]ethyl]-N-hydroxy-3-(2-methylpropyl)-2-oxo-1-(2-phenylethyl)-3-pyrrolidineacetamide, 4c) N-Hydroxy-α-[2-[[(4-methylphenyl)sulfonyl]amino]ethyl]-3-(2-methylpropyl)-2-oxo-1-(2-phenylethyl)-3-pyrrolidineacetamide, 4d) α-[2-[[(4-Fluorophenyl)sulfonyl]amino]ethyl]-N-hydroxy-3-(2-methylpropyl)-2-oxo-1-(2-phenylethyl)-3-pyrrolidineacetamide, 4e) N-Hydroxy-α-[2-[[(4-methoxyphenyl)sulfonyl]amino]ethyl]-3-(2-methylpropyl)-2-oxo-1-(2-phenylethyl)-3-pyrrolidineacetamide, 4f) N-Hydroxy-3-(2-methylpropyl)-2-oxo-1-(2-phenylethyl)-α-[2-[(phenylsulfonyl)amino]ethyl]-3-pyrrolidineacetamide, 4g) [R-(R*,S*)]-α-[2-[[(4-Fluorophenyl)sulfonyl]amino]ethyl]-N-hydroxy-3-(2-methylpropyl)-2-oxo-1-(2-phenylethyl)-3-pyrrolidineacetamide, 4h) 5,6-Difluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 4i) 1,3-Dihydro-N-hydroxy-α-[3-(2-methylpropyl)-2-oxo-1-(2-phenylethyl)-3-pyrrolidinyl]-1-oxo-2H-isoindole-2-butanamide, 4j) [R-(R*,S*)]-6-Fluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 4k) [R-(R*,S*)]-5-Fluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 4l) [R-(R*,S*)]-5,6-Difluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 4m) N-Hydroxy-α-[[[(4-methoxyphenyl)sulfonyl]amino]methyl]-3-(2-methylpropyl)-2-oxo-1-(2-phenylethyl)-3-pyrrolidineacetamide (αR-diastereomer), 4n) N-Hydroxy-α-[[[(4-methoxyphenyl)sulfonyl]amino]methyl]-3-(2-methylpropyl)-2-oxo-1-(2-phenylethyl)-3-pyrrolidineacetamide (αS-diastereomer), 4o) α-[[(4-Fluorophenyl)sulfonyl]amino]-N-hydroxy-3-(2-methylpropyl)-2-oxo-1-(2-phenylethyl)-3-pyrrolidineacetamide (R-diastereomer), 4p) α-[[(4-Fluorophenyl)sulfonyl]amino]-N-hydroxy-3-(2-methylpropyl)-2-oxo-1-(2-phenylethyl)-3-pyrrolidineacetamide (αS-diastereomer), 4q) α-[2-[(3,4-Difluorobenzoyl)amino]ethyl]-N-hydroxy-3-(3-hydroxypropyl)-2-oxo-1-(2-phenylethyl)-3-pyrrolidineacetamide, 4r) α-[2-[(3,4-Difluorobenzoyl)amino]ethyl]-N-hydroxy-3-(2-hydroxyethyl)-2-oxo-1-(2-phenylethyl)-3-pyrrolidineacetamide, 4s) [R-(R*,S*)]-α-[2-[(3-Fluorobenzoyl)amino]ethyl]-N-hydroxy-3-(3-hydroxypropyl)-2-oxo-1-(2-phenylethyl)-3-pyrrolidineacetamide, 4t) S-(R*,R*)]-N³-hydroxy-N¹-methyl-α¹-(1-methylethyl)-3-(2-methylpropyl)-2-oxo-1,3-pyrrolidinediacetamide, 4u) [S-(R*,R*)]-N¹-cyclopropyl-N³-hydroxy-α¹-(1-methylethyl)-3-(2-methylpropyl)-2-oxo-1,3-pyrrolidinediacetamide, 4v) [S-(R*,R*)]-N³-hydroxy-α¹-(1-methylethyl)-3-(2-methylpropyl)-2-oxo-N¹-phenyl-1,3-pyrrolidinediacetamide, 4w) [S-(R*,R*)]-N¹-(4-fluorophenyl)-N³-hydroxy-α¹-(1-methylethyl)-3-(2-methylpropyl)-2-oxo-1,3-pyrrolidinediacetamide, 4x) [S-(R*,R*)]-N³-hydroxy-α¹-(1-methylethyl)-3-(2-methylpropyl)-2-oxo-N¹-(4-pyridinyl)-1,3-pyrrolidinediacetamide, 4y) [S-(R*,R*)]-α¹-tert-butyl-N¹-cyclopropyl-N³-hydroxy-3-(2-methylpropyl)-2-oxo-1,3-pyrrolidinediacetamide, 4z) [S-(R*,R*)]-α¹-tert-butyl-N³-hydroxy-3-(2-methylpropyl)-2-oxo-N¹-phenyl-1,3-pyrrolidinediacetamide, 5a) [S-(R*,R*)]-α¹-tert-butyl-N¹-(4-fluorophenyl)-N³-hydroxy-3-(2-methylpropyl)-2-oxo-1,3-pyrrolidinediacetamide, 5b) [S-(R*,R*)]-α¹-tert-butyl-N³-hydroxy-3-(2-methylpropyl)-2-oxo-N¹-(4-pyridinyl)-1,3-pyrrolidinediacetamide, 5c) [S-(R*,R*)]-α¹-cyclohexyl-N³-hydroxy-3-(2-methylpropyl)-2-oxo-N¹-phenyl-1,3-pyrrolidinediacetamide, 5d) [S-(R*,R*)]-α¹-cyclohexyl-N³-hydroxy-3-(2-methylpropyl)-2-oxo-N¹-(4-pyridinyl)-1,3-pyrrolidinediacetamide, 5e) [S-(R*,R*)]-3-(cyclopentylmethyl)-$N^3$-hydroxy-$N^1$-methyl-$\alpha^1$-(1-methylethyl)-2-oxo-1,3-pyrrolidinediacetamide, 5f) [S-(R*,R*)]-3-(cyclopentylmethyl)-$N^1$-cyclopropyl-$N^3$-hydroxy-$\alpha^1$-(1-methylethyl)-2-oxo-1,3-pyrrolidinediacetamide, 5g) [S-(R*,R*)]-3-(cyclopentylmethyl)-$N^3$-hydroxy-$\alpha^1$-(1-methylethyl)-2-oxo-$N^1$-phenyl-1,3-pyrrolidinediacetamide, 5h) [S-(R*,R*)]-3-(cyclopentylmethyl)-$N^1$-(4-fluorophenyl)-$N^3$-hydroxy-$\alpha^1$-(1-methylethyl)-2-oxo-1,3-pyrrolidineaceatamide, 5i) [S-(R*,R*)]-3-(cyclopentylmethyl)-$N^3$-hydroxy-$\alpha^1$-(1-methylethyl)-2-oxo-$N^1$-(4-pyridinyl)-1,3-pyrrolidinediacetamide, 5j) [S-(R*,R*)]-$\alpha^1$-tert-butyl-3-(cyclopentylmethyl)-$N^3$-hydroxy-$N^1$-methyl-2-oxo-1,3-pyrrolidinediacetamide, 5k) [S-(R*,R*)]-$\alpha^1$-tert-butyl-3-(cyclopentylmethyl)-$N^1$-cyclopropyl-$N^3$-hydroxy-2-oxo-1,3-pyrrolidinediacetamide, 5l) [S-(R*,R*)]-$\alpha^1$-tert-butyl-3-(cyclopentylmethyl)-$N^3$-hydroxy-2-oxo-$N^1$-phenyl-1,3-pyrrolidinediacetamide, 5m) [S-(R*,R*)]-$\alpha^1$-tert-butyl-3-(cyclopentylmethyl)-$N^1$-(4-fluorophenyl)-$N^3$-hydroxy-2-oxo-1,3-pyrrolidinediacetamide, 5n) [S-(R*,R*)]-$\alpha^1$-tert-butyl-3-(cyclopentylmethyl)-$N^3$-hydroxy-2-oxo-$N^1$-(4-pyridinyl)-1,3-pyrrolidinediacetamide, 5o) [S-(R*,R*)]-$\alpha^1$-cyclohexyl-3-(cyclopentylmethyl)-$N^3$-hydroxy-$N^1$-methyl-2-oxo-1,3-pyrrolidinediacetamide, 5p) [S-(R*,R*)]-$\alpha^1$-cyclohexyl-3-(cyclopentylmethyl)-$N^1$-cyclopropyl-$N^3$-hydroxy-2-oxo-1,3-pyrrolidinediacetamide, 5q) [S-(R*,R*)]-$\alpha^1$-cyclohexyl-3-(cyclopentylmethyl)-$N^3$-hydroxy-2-oxo-$N^1$-phenyl-1,3-pyrrolidinediacetamide, 5r) [S-(R*,R*)]-$\alpha^1$-cyclohexyl-3-(cyclopentylmethyl)-$N^1$-(4-fluorophenyl)-$N^3$-hydroxy-2-oxo-1,3-pyrrolidinediacetamide, 5s) [S-(R*,R*)]-$\alpha^1$-cyclohexyl-3-(cyclopentylmethyl)-$N^3$-hydroxy-2-oxo-$N^1$-(4-pyridinyl)-1,3-pyrrolidinediacetamide, 5t) [S-(R*,R*)]-$N^3$-hydroxy-$N^1$-methyl-$\alpha^1$-(1-methylethyl)-2-oxo-3-(3-phenylpropyl)-1,3-pyrrolidinediacetamide, 5u) [S-(R*,R*)]-$N^1$-cyclopropyl-$N^3$-hydroxy-$\alpha^1$-(1-methylethyl)-2-oxo-3-(3-phenylpropyl)-1,3-pyrrolidinediacetamide, 5v) [S-(R*,R*)]-$N^3$-hydroxy-$\alpha^1$-(1-methylethyl)-2-oxo-$N^1$-phenyl-3-(3-phenylpropyl)-1,3-pyrrolidinediacetamide, 5w) [S-(R*,R*)]-$N^1$-(4-fluorophenyl)-$N^3$-hydroxy-$\alpha^1$-(1-methylethyl)-2-oxo-3-(3-phenylpropyl)-1,3-pyrrolidinediacetamde, 5x) [S-(R*,R*)]-$N^3$-hydroxy-$\alpha^1$-(1-methylethyl)-2-oxo-3-(3-phenylpropyl)-$N^1$-(4-pyridinyl)-1,3-pyrrolidinediacetamide, 5y) [S-(R*,R*)]-$\alpha^1$-tert-butyl-$N^3$-hydroxy-$N^1$-methyl-2-oxo-3-(3-phenylpropyl)-1,3-pyrrolidinediacetamide, 5z) [S-(R*,R*)]-$\alpha^1$-tert-butyl-$N^1$-cyclopropyl-$N^3$-hydroxy-2-oxo-3-(3-phenylpropyl)-1,3-pyrrolidinediacetamide, 6a) [S-(R*,R*)]-$\alpha^1$-tert-butyl-$N^3$-hydroxy-2-oxo-$N^1$-phenyl-3-(3-phenylpropyl)-1,3-pyrrolidinediacetamide, 6b) [S-(R*,R*)]-$\alpha^1$-tert-butyl-$N^1$-(4-fluorophenyl)-$N^3$-hydroxy-2-oxo-3-(3-phenylpropyl)-1,3-pyrrolidinediacetamide, 6c) [S-(R*,R*)]-$\alpha^1$-tert-butyl-$N^3$-hydroxy-2-oxo-3-(3-phenylpropyl)-$N^1$-(4-pyridinyl)-1,3-pyrrolidinediacetamid, 6d) [S-(R*,R*)]-$\alpha^1$-cyclohexyl-$N^3$-hydroxy-$N^1$-methyl-2-oxo-3-(3-phenylpropyl)-1,3-pyrrolidinediacetamide, 6e) [S-(R*,R*)]-$\alpha^1$-cyclohexyl-$N^1$-cyclopropyl-$N^3$-hydroxy-2-oxo-3-(3-phenylpropyl)-1,3-pyrrolidinediacetamide, 6f) [S-(R*,R*)]-$\alpha^1$-cyclohexyl-$N^3$-hydroxy-2-oxo-$N^1$-phenyl-3-(3-phenylpropyl)-1,3-pyrrolidinediacetamide, 6g) [S-(R*,R*)]-$\alpha^1$-cyclohexyl-$N^1$-(4-fluorophenyl)-$N^3$-hydroxy-2-oxo-3-(3-phenylpropyl)-1,3-pyrrolidinediacetamide, 6h) [S-(R*,R*)]-$\alpha^1$-cyclohexyl-$N^3$-hydroxy-2-oxo-3-(3-phenylpropyl)-$N^1$-(4-pyridinyl)-1,3-pyrrolidinediacetamide, 6i) [S-(R*,R*)]-3-[3-(4-fluorophenyl)propyl]-$N^3$-hydroxy-$N^1$-methyl-$\alpha^1$-(1-methylethyl)-2-oxo-1,3-pyrrolidinediacetamide, 6j) [S-(R*,R*)]-$N^1$-cyclopropyl-3-[3-(4-fluorophenyl)propyl]-$N^3$-hydroxy-$\alpha^1$-(1-methylethyl)-2-oxo-1,3-pyrrolidinediacetamide, 6k) [S-(R*,R*)]-3-[3-(4-fluorophenyl)propyl]-$N^3$-hydroxy-$\alpha^1$-(1-methylethyl)-2-oxo-$N^1$-phenyl-1,3-pyrrolidinediacetamide, 6l) [S-(R*,R*)]-$N^1$-(4-fluorophenyl)-3-[3-(4-fluorophenyl)propyl]-$N^3$-hydroxy-$\alpha^1$-(1-methylethyl)-2-oxo-1,3-pyrrolidinediacetamide, 6m) [S-(R*,R*)]-3-[3-(4-fluorophenyl)propyl]-$N^3$-hydroxy-$\alpha^1$-(1-methylethyl)-2-oxo-$N^1$-(4-pyridinyl)-1,3-pyrrolidinediacetamide, 6n) [S-(R*,R*)]-$\alpha^1$-tert-butyl-3-[3-(4-fluorophenyl)propyl]-$N^3$-hydroxy-$N^1$-methyl-2-oxo-1,3-pyrrolidinediacetamide, 6o) [S-(R*,R*)]-$\alpha^1$-tert-butyl-$N^1$-cyclopropyl-3-[3-(4-fluorophenyl)propyl]-$N^3$-hydroxy-2-oxo-1,3-pyrrolidinediacetamide, 6p) [S-(R*,R*)]-$\alpha^1$-tert-butyl-3-[3-(4-fluorophenyl)propyl]-$N^3$-hydroxy-2-oxo-$N^1$-phenyl-1,3-pyrrolidinediacetamide, 6q) [S-(R*,R*)]-$\alpha^1$-tert-butyl-$N^1$-(4-fluorophenyl)-3-[3-(4-fluorophenyl)propyl]-$N^3$-hydroxy-2-oxo-1,3-pyrrolidinediacetamide, 6r) [S-(R*,R*)]-$\alpha^1$-tert-butyl-3-[3-(4-fluorophenyl)propyl]-$N^3$-hydroxy-2-oxo-$N^1$-(4-pyridinyl)-1,3-pyrrolidinediacetamide, 6s) [S-(R*,R*)]-$\alpha^1$-cyclohexyl-3-[3-(4-fluorophenyl)propyl]-$N^3$-hydroxy-$N^1$-methyl-2-oxo-1,3-pyrrolidinediacetamide, 6t) [S-(R*,R*)]-$\alpha^1$-cyclohexyl-$N^1$-cyclopropyl-3-[3-(4-fluorophenyl)propyl]-$N^3$-hydroxy-2-oxo-1,3-pyrrolidinediacetamide, 6u) [S-(R*,R*)]-$\alpha^1$-cyclohexyl-3-[3-(4-fluorophenyl)propyl]-$N^3$-hydroxy-2-oxo-$N^1$-phenyl-1,3-pyrrolidinediacetamide, 6v) [S-(R*,R*)]-$\alpha^1$-cyclohexyl-$N^1$-(4-fluorophenyl)-3-[3-(4-fluorophenyl)propyl]-$N^3$-hydroxy-2-oxo-1,3-pyrrolidinediacetamide, 6w) [S-(R*,R*)]-$\alpha^1$-cyclohexyl-3-[3-(4-fluorophenyl)propyl]-$N^3$-hydroxy-2-oxo-$N^1$-(4-pyridinyl)-1,3-pyrrolidinediacetamide, 6x) [S-(R*,R*)]-3-[3-(biphen-4-yl)propyl]-$N^3$-hydroxy-$N^1$-methyl-$\alpha^1$-(1-methylethyl)-2-oxo-1,3-pyrrolidinediacetamide, 6y) [S-(R*,R*)]-3-[3-(biphen-4-yl)propyl]-$N^1$-cyclopropyl-$N^3$-hydroxy-$\alpha^1$-(1-methylethyl)-2-oxo-1,3-pyrrolidinediacetamide, 6z) [S-(R*,R*)]-3-[3-(biphen-4-yl)propyl]-$N^3$-hydroxy-$\alpha^1$-(1-methylethyl)-2-oxo-$N^1$-phenyl-1,3-pyrrolidinediacetamide, 7a) [S-(R*,R*)]-3-[3-(biphen-4-yl)propyl]-$N^1$-(4-fluorophenyl)-$N^3$-hydroxy-$\alpha^1$-(1-methylethyl)-2-oxo-1,3-pyrrolidinediacetamide, 7b) [S-(R*,R*)]-3-[3-(biphen-4-yl)propyl]-$N^3$-hydroxy-$\alpha^1$-(1-methylethyl)-2-oxo-$N^1$-(4-pyridinyl)-1,3-pyrrolidinediacetamide, 7c) [S-(R*,R*)]-3-[3-(biphen-4-yl)propyl]-$\alpha^1$-tert-butyl-$N^3$-hydroxy-$N^1$-methyl-2-oxo-1,3-pyrrolidinediacetamide, 7d) [S-(R*,R*)]-3-[3-(biphen-4-yl)propyl]-$\alpha^1$-tert-butyl-$N^1$-cyclopropyl-$N^3$-hydroxy-2-oxo-1,3-pyrrolidinediacetamide, 7e) [S-(R*,R*)]-3-[3-(biphen-4-yl)propyl]-$\alpha^1$-tert-butyl-$N^3$-hydroxy-2-oxo-$N^1$-phenyl-1,3-pyrrolidinediacetamide, 7f) [S-(R*,R*)]-3-[3-(biphen-4-yl)propyl]-$\alpha^1$-tert-butyl-$N^1$-(4-fluorophenyl)-$N^3$-hydroxy-2-oxo-1,3-pyrrolidinediacetamide, 7g) [S-(R*,R*)]-3-[3-(biphen-4-yl)propyl]-$\alpha^1$-tert-butyl-$N^3$-hydroxy-2-oxo-$N^1$-(4-pyridinyl)-1,3-pyrrolidinediacetamide, 7h) [S-(R*,R*)]-3-[3-(biphen-4-yl)propyl]-$\alpha^1$-cyclohexyl-$N^3$-hydroxy-$N^1$-methyl-2-oxo-1,3-pyrrolidinediacetamide, 7i) [S-(R*,R*)]-3-[3-(biphen-4-yl)propyl]-$\alpha^1$-cyclohexyl-$N^1$-cyclopropyl-$N^3$-hydroxy-2-oxo-1,3-pyrrolidinediacetamide, 7j) [S-(R*,R*)]-3-[3-(biphen-4-yl)propyl]-$\alpha^1$-cyclohexyl-$N^3$-hydroxy-2-oxo-$N^1$-phenyl-1,3-pyrrolidinediacetamide, 7k) [S-(R*,R*)]-3-[3-(biphen-4-yl)propyl]-$\alpha^1$-cyclohexyl-$N^1$-(4-fluorophenyl)-$N^3$-hydroxy-2-oxo-1,3-pyrrolidinediacetamide, 7l) [S-(R*,R*)]-3-[3-(biphen-4-yl)propyl]-$\alpha^1$-cyclohexyl-$N^3$-hydroxy-2-oxo-$N^1$-(4-pyridinyl)-1,3-pyrrolidinediacetamide, 7m) [S-(R*,R*)]-3-[3-(4'-fluorobiphen-4-yl)propyl]-$N^3$-hydroxy-$N^1$-methyl-$\alpha^1$-(1-methylethyl)-2-oxo-1,3-pyrrolidinediacetamide, 7n) [S-(R*,R*)]-3-[3-(4'-fluorobiphen-4-yl)propyl]-$N^1$-cyclopropyl-$N^3$-hydroxy-$\alpha^1$-(1-methylethyl)-2-oxo-1,3-pyrrolidinediacetamide, 7o) [S-(R*,R*)]-3-[3-(4'-fluorobiphen-4-yl)propyl]-$N^3$-hydroxy-$\alpha^1$-(1-methylethyl)-2-oxo-$N^1$-phenyl-1,3-pyrrolidinediacetamide, 7p) [S-(R*,R*)]-3-[3-(4'-fluorobiphen-4-yl)propyl]-$N^1$-(4-fluorophenyl)-$N^3$-hydroxy-$\alpha^1$-(1-methylethyl)-2-oxo-1,3-pyrrolidinediacetamide, 7q) [S-(R*,R*)]-3-[3-(4'-fluorobiphen-4-yl)propyl]-$N^3$-hydroxy-$\alpha^1$-(1-methylethyl)-2-oxo-$N^1$-(4-pyridinyl)-1,3-pyrrolidinediacetamide, 7r) [S-(R*,R*)]-$\alpha^1$-tert-butyl-3-[3-(4'-fluorobiphen-4-yl)propyl]-$N^3$-hydroxy-$N^1$-methyl-2-oxo-1,3-pyrrolidinediacetamide, 7s) [S-(R*,R*)]-$\alpha^1$-tert-butyl-$N^1$-cyclopropyl-3-[3-(4'-fluorobiphen-4-yl)propyl]-$N^3$-hydroxy-2-oxo-1,3-pyrrolidinediacetamide, 7t) [S-(R*,R*)]-$\alpha^1$-tert-butyl-3-[3-(4'-fluorobiphen-4-yl)propyl]-$N^3$-hydroxy-2-oxo-$N^1$-phenyl-1,3-pyrrolidinediacetamide, 7u) [S-(R*,R*)]-$\alpha^1$-tert-butyl-3-[3-(4'-fluorobiphen-4-yl)propyl]-$N^1$-(4-fluorophenyl)-$N^3$-hydroxy-2-oxo-1,3-pyrrolidinediacetamide, 7v) [S-(R*,R*)]-$\alpha^1$-tert-butyl-3-[3-(4'-fluorobiphen-4-yl)propyl]-$N^3$-hydroxy-2-oxo-$N^1$-(4-pyridinyl)-1,3-pyrrolidinediacetamide, 7w) [S-(R*,R*)]-$\alpha^1$-cyclohexyl-3-[3-(4'-fluorobiphen-4-yl)propyl]-$N^3$-hydroxy-$N^1$-methyl-2-oxo-1,3-pyrrolidinediacetamide, 7x) [S-(R*,R*)]-$\alpha^1$-cyclohexyl-$N^1$-cyclopropyl-3-[3-(4'-fluorobiphen-4-yl)propyl]-$N^3$-hydroxy-2-oxo-1,3-pyrrolidinediacetamide, 7y) [S-(R*,R*)]-$\alpha^1$-cyclohexyl-3-[3-(4'-fluorobiphen-4-yl)propyl]-$N^3$-hydroxy-2-oxo-$N^1$-phenyl-1,3-pyrrolidinediacetamide, 7z) [S-(R*,R*)]-$\alpha^1$-cyclohexyl-3-[3-(4'-fluorobiphen-4-yl)propyl]-$N^1$-(4-fluorophenyl)-$N^3$-hydroxy-2-oxo-1,3-pyrrolidinediacetamide, 8a) [S-(R*,R*)]-$\alpha^1$-cyclohexyl-3-[3-(4'-fluorobiphen-4-yl)propyl]-$N^3$-hydroxy-2-oxo-$N^1$-(4-pyridinyl)-1,3-pyrrolidinediacetamide, 8b) Preparation of [S-(R*,R*)]-3-heptyl-$N^3$-hydroxy-$N^1$-methyl-$\alpha^1$-(1-methylethyl)-2-oxo-1,3-pyrrolidinediacetamide, 8c) Preparation of [S-(R*,R*)]-$N^1$-cyclopropyl-3-heptyl-$N^3$-hydroxy-$\alpha^1$-(1-methylethyl)-2-oxo-1,3-pyrrolidinediacetamide, 8d) Preparation of [S-(R*,R*)]-3-heptyl-$N^3$-hydroxy-$\alpha^1$-(1-methylethyl)-2-oxo-$N^1$-phenyl-1,3-pyrrolidinediacetamide, 8e) Preparation of [S-(R*,R*)]-3-heptyl-$N^1$-(4-fluorophenyl)-$N^3$-hydroxy-$\alpha^1$-(1-methylethyl)-2-oxo-1,3-pyrrolidinediacetamide, 8f) Preparation of [S-(R*,R*)]-3-heptyl-$N^3$-hydroxy-$\alpha^1$-(1-methylethyl)-2-oxo-$N^1$-(4-pyridinyl)-1,3-pyrrolidinediacetamide, 8g) Preparation of [S-(R*,R*)]-$\alpha^1$-tert-butyl-3-heptyl-$N^3$-hydroxy-$N^1$-methyl-2-oxo-1,3-pyrrolidinediacetamide, 8h) Preparation of [S-(R*,R*)]-$\alpha^1$-tert-butyl-$N^1$-cyclopropyl-3-heptyl-$N^3$-hydroxy-2-oxo-1,3-pyrrolidinediacetamide, 8i) Preparation of [S-(R*,R*)]-$\alpha^1$-tert-butyl-3-heptyl-$N^3$-hydroxy-2-oxo-$N^1$-phenyl-1,3-pyrrolidinediacetamide, 8j) Preparation of [S-(R*,R*)]-$\alpha^1$-tert-butyl-$N^1$-(4-fluorophenyl)-3-heptyl-$N^3$-hydroxy-2-oxo-1,3-pyrrolidinediacetamide, 8k) Preparation of [S-(R*,R*)]-$\alpha^1$-tert-butyl-3-heptyl-$N^3$-hydroxy-2-oxo-$N^1$-(4-pyridinyl)-1,3-pyrrolidinediacetamide, 8l) Preparation of [S-(R*,R*)]-$\alpha^1$-cyclohexyl-3-heptyl-$N^3$-hydroxy-$N^1$-methyl-2-oxo-1,3-pyrrolidinediacetamide, 8m) Preparation of [S-(R*,R*)]-$\alpha^1$-cyclohexyl-$N^1$-cyclopropyl-3-heptyl-$N^3$-hydroxy-2-oxo-1,3-pyrrolidinediacetamide, 8n) Preparation of [S-(R*,R*)]-$\alpha^1$-cyclohexyl-3-heptyl-$N^3$-hydroxy-2-oxo-$N^1$-phenyl-1,3-pyrrolidinediacetamide, 8o) Preparation of [S-(R*,R*)]-$\alpha^1$-cyclohexyl-3-heptyl-$N^1$-(4-fluorophenyl)-$N^3$-hydroxy-2-oxo-1,3-pyrrolidinediacetamide, or 8p) Preparation of [S-(R*,R*)]-$\alpha^1$-cyclohexyl-3-heptyl-$N^3$-hydroxy-2-oxo-$N^1$-(4-pyridinyl)-1,3-pyrrolidinediacetamide.

13. A compound of claim 12 which is 1a) (3S)-$\alpha$-[2-(1,3-Dihydro-1,3-dioxo-2H-isoindol-2-yl)ethyl]-N-hydroxy-3-(2-methylpropyl)-2-oxo-1-(2-phenylethyl)-3-pyrrolidineacetamide, 1b) [S,S-(R*,R*)]-$\alpha^3$-[2-(1,3-Dihydro-1,3-dioxo-2H-isoindol-2-yl)ethyl]-$N^3$-hydroxy-$N^1$-methyl-3-(2-methylpropyl)-2-oxo-$\alpha^1$-(phenylmethyl)-1,3-pyrrolidinediacetamide, 1c) [S-(R*,R*)]-$N^3$-Hydroxy-3-(2-methylpropyl)-2-oxo-$N^1$-(2-phenethyl)-$\alpha^1$-(phenylmethyl)-1,3-pyrrolidinediacetamide, 1d) [S-(R*,R*)]-$\alpha^1$-(Cyclohexylmethyl)-$N^3$-hydroxy-$N^1$-methyl-3-(2-methylpropyl)-2-oxo-1,3-pyrrolidinediacetamide, 1e) [S-(R*,R*)]-$N^3$-Hydroxy-$N^1$-methyl-3-(2-methylpropyl)-2-oxo-$\alpha^1$-(phenylmethyl)-1,3-pyrrolidinediacetamide, 1f) [S-(R*,R*)]-N³-Hydroxy-3-(2-methylpropyl)-2-oxo-N¹-phenyl-α¹-(phenylmethyl)-1,3-pyrrolidinediacetamide, 1g) [S-(R*,R*)]-N³-Hydroxy-3-(2-methylpropyl)-2-oxo-α¹-(phenylmethyl)-N¹-(2-pyridinylmethyl)-1,3-pyrrolidinediacetamide, 1h) [S-(R*,R*)]-N³-Hydroxy-3-(2-methylpropyl)-2-oxo-α¹-(phenylmethyl)-N¹-(4-pyridinyl)-1,3-pyrrolidinediacetamide, 1i) [S-(R*,R*)]-N¹-(4-Fluorophenyl)-N³-hydroxy-3-(2-methylpropyl)-2-oxo-α¹-(phenylmethyl)-1,3-pyrrolidinediacetamide, 1j) [S-(R*,R*)]-N³-Hydroxy-3-(2-methylpropyl)-2-oxo-α¹-(phenylmethyl)-N¹-[1-(phenylmethyl)-4-piperdinyl]-1,3-pyrrolidinediacetamide, 1k) [S-(R*,R*)]-N³-Hydroxy-3-(2-methylpropyl)-2-oxo-α¹-(phenylmethyl)-N¹-(4-piperdinyl)-1,3-pyrrolidinediacetamide, 1l) [S-(R*,R*)]-N³-Hydroxy-3-(2-methylpropyl)-2-oxo-α¹-(phenylmethyl)-N¹-(4-pyridinylmethyl)-1,3-pyrrolidinediacetamide, 1m) [S-(R*,R*)]-N¹-(4-Fluorophenylmethyl)-N³-hydroxy-3-(2-methylpropyl)-2-oxo-α¹-(phenylmethyl)-1,3-pyrrolidinediacetamide, 1n) [S-(R*,R*)]-N³-Hydroxy-N¹-methyl-3-(2-methylpropyl)-2-oxo-α¹-(2-phenylethyl)-1,3-pyrrolidinediacetamide, 1o) [S-(R*,R*)]-N³-Hydroxy-3-(2-methylpropyl)-2-oxo-α¹-(2-phenylethyl)-N¹-(phenylmethyl)-1,3-pyrrolidinediacetamide, 1p) [S-(R*,R*)]-N³-Hydroxy-α¹,3-bis(2-methylpropyl)-2-oxo-N¹-2-pyridinyl-1,3-pyrrolidinediacetamide, 1q) [S-(R*,R*)]-α¹-Cyclohexyl-N³-hydroxy-N¹-methyl-3-(2-methylpropyl)-2-oxo-1,3-pyrrolidinediacetamide, 1r) [S-(R*,R*)]-α¹-Cyclohexyl-N³-hydroxy-3-(2-methylpropyl)-2-oxo-N¹-2-pyridinyl-1,3-pyrrolidinediacetamide, 1s) [S-(R*,R*)]-3-(Cyclopentylmethyl)-N³-hydroxy-N¹-methyl-2-oxo-α¹-(phenylmethyl)-1,3-pyrrolidinediacetamide, 1t) [S-(R*,R*)]-3-(Cyclopentylmethyl)-N³-hydroxy-N¹-methyl-2-oxo-α¹-(phenylmethyl)-1,3-pyrrolidinediacetamide, 1u) [3S-[1(R*),3R*(R*)]]-α³-[2-(Benzoylamino)ethyl]-N³-hydroxy-N¹-methyl-3-(2-methylpropyl)-2-oxo-α¹-(phenylmethyl)-1,3-pyrrolidinediacetamide, 1v) [S-(R*,R*)]-N³-Hydroxy-3-(2-methylpropyl)-N¹-[2-(4-morpholinyl)ethyl]-2-oxo-α¹-(phenylmethyl)-1,3-pyrrolidinediacetamide, 1w) [S-(R*,R*)]-N-Hydroxy-3-(2-methylpropyl)-1-[2-(4-morpholinyl)-2-oxo-1-(phenylmethyl)ethyl]-2-oxo-3-pyrrolidineacetamide, 1x) [1(1S)-[1[R*(R*)],3α,5α]]-1-[2-(3,5-Dimethyl-1-piperazinyl)-2-oxo-1-(phenylmethyl)ethyl]-N-hydroxy-3-(2-methylpropyl)-2-oxo-3-pyrrolidineacetamide, 1y) [S-(R*,R*)]-N³-Hydroxy-3-(2-methylpropyl)-2-oxo-α¹-(phenylmethyl)-N¹-2-pyridinyl-1,3-pyrrolidinediacetamide, 1z) [3S-[1(R*),3R*(R*)]]-α³-[2-(1,3-Dihydro-1,3-dioxo-2H-isoindol-2-yl)ethyl]-N³-hydroxy-N¹-methyl-3-(2-methylpropyl)-2-oxo-α¹-(phenylmethyl)-1,3-pyrrolidinediacetamide, 2a) [S-(R*,R*)]-α¹-Cyclohexyl-N¹-cyclopropylmethyl-N³-hydroxy-3-(2-methylpropyl)-2-oxo-1,3-pyrrolidinediacetamide, 2b) [S-(R*,R*)]-α¹-Cyclohexyl-N¹-(4-fluorophenyl)-N³-hydroxy-3-(2-methylpropyl)-2-oxo-1,3-pyrrolidinediacetamide, 2c) [S-(R*,R*)]-α¹-tert-Butyl-N³-hydroxy-N¹-methyl-3-(2-methylpropyl)-2-oxo-1,3-pyrrolidinediacetamide, 2d) N-Hydroxy-3-(2-methylpropyl)-2-oxo-1-(2-phenylethyl)-α-[2-(5-propyloxy-1,3-dihydro-1,3-dioxo-2H-isoindol-2-yl)ethyl]-3-pyrrolidineacetamide, 2e) [R-(R*,S*)]-5-Fluoro-1,3-dihydro-N-hydroxy-α-[3-(2-methylpropyl)-2-oxo-1-(2-phenylethyl)-3-pyrrolidinyl]-1,3-dioxo-2H-isoindole-2-butanamide, 2f) α-[2-(5,6-Difluoro-1,3-dihydro-1,3-dioxo-2H-isoindol-2-yl)ethyl]-N-hydroxy-3-(2-methylpropyl)-2-oxo-1-(2-phenylethyl)-3-pyrrolidineacetamide, 2g) N-Hydroxy-3-(2-methylpropyl)-2-oxo-1-(2-phenylethyl)-α-[2-(5-trifluoromethyl-1,3-dihydro-1,3-dioxo-2H-isoindol-2-yl)ethyl]-3-pyrrolidineacetamide, 2h) α-[2-(1,3,4,5,6,7-Hexahydro-1,3-dioxo-2H-isoindol-2-yl)ethyl]-N-hydroxy-3-(2-methylpropyl)-2-oxo-1-(2-phenylethyl)-3-pyrrolidineacetamide, 2i) α-[2-(1,3-Dihydro-1,3-dioxo-2H-isoindol-2-yl)ethyl]-N-hydroxy-3-(2-methylpropyl)-2-oxo-1-(3-phenylpropyl)-3-pyrrolidineacetamide, 2j) 1-[2-(4-Fluorophenyl)ethyl]-α-[2-(1,3-dihydro-1,3-dioxo-2H-isoindol-2-yl)ethyl]-N-hydroxy-3-(2-methylpropyl)-2-oxo-3-pyrrolidineacetamide, 2k) α-[2-(o-benzoic sulfimide)ethyl]-N-hydroxy-3-(2-methylpropyl)-2-oxo-1-(2-phenylethyl)-3-pyrrolidineacetamide, 2l) Ethyl Phenylmethyl[4-(hydroxyamino)-3-[3-(2-methylpropyl)-2-oxo-1-(2-phenylethyl)-3-pyrrolidinyl]-4-oxobutyl]imidodicarbonate, 2m) S-(R*,R*)]-1,3-Dihydro-N-hydroxy-α-[3-(2-methylpropyl)-2-oxo-1-(2-phenylethyl)-3-pyrrolidinyl]-1,3-dioxo-2H-isoindole-2-butanamide, 2n) 1,3-Dihydro-N-hydroxy-α-[3-(2-methylpropyl)-2-oxo-1-[2-(4-fluorophenyl)ethyl]-3-pyrrolidinyl]-1,3-dioxo-2H-isoindole-2-butanamide, 2o) α-[2-[(3,4-Difluorobenzoyl)amino]ethyl]-N-hydroxy-3-(2-methylpropyl)-2-oxo-1-(2-phenylethyl)-3-pyrrolidineacetamide, 2p) [R-(R*,S*)-α-[2-[(3-Fluorobenzoyl)amino]ethyl]-N-hydroxy-3-(2-methylpropyl)-2-oxo-1-(2-phenylethyl)-3-pyrrolidineacetamide, 2q) α-[2-[(4-Fluorobenzoyl)amino]ethyl]-N-hydroxy-3-(2-methylpropyl)-2-oxo-1-(2-phenylethyl)-3-pyrrolidineacetamide, 2r) N-Hydroxy-3-(2-methylpropyl)-α-[2-[(3-nitrobenzoyl)amino]ethyl]-2-oxo-1-(2-phenylethyl)-3-pyrrolidineacetamide, 2s) α-[2-[(3-Fluorobenzoyl)amino]ethyl]-N-hydroxy-3-(2-methylpropyl)-2-oxo-1-(2-phenylethyl)-3-pyrrolidineacetamide, 2t) α-[2-[(3-Fluorobenzoyl)amino]ethyl]-1-[2-(4-fluorophenyl)ethyl]-N-hydroxy-3-(2-methylpropyl)-2-oxo-3-pyrrolidineacetamide, 2u) α-[2-[(4-Biphenylcarbonyl)amino]ethyl]-N-hydroxy-3-(2-methylpropyl)-2-oxo-1-(2-phenylethyl)-3-pyrrolidineacetamide, 2v) N-Hydroxy-α-[2-[[(4-methylphenyl)sulfonyl]amino]ethyl]-3-(2-methylpropyl)-2-oxo-1-(2-phenylethyl)-3-pyrrolidineacetamide, 2w) α-[2-[[(4-Fluorophenyl)sulfonyl]amino]ethyl]-N-hydroxy-3-(2-methylpropyl)-2-oxo-1-(2-phenylethyl)-3-pyrrolidineacetamide, 2x) N-Hydroxy-α-[2-[[(4-methoxyphenyl)sulfonyl]amino]ethyl]-3-(2-methylpropyl)-2-oxo-1-(2-phenylethyl)-3-pyrrolidineacetamide, 2y) N-Hydroxy-3-(2-methylpropyl)-2-oxo-1-(2-phenylethyl)-α-[2-(phenylsulfonyl)amino]ethyl]-3-pyrrolidineacetamide, 2z) [R-(R*,S*)]-α-[2-[[(4-Fluorophenyl)sulfonyl]amino] ethyl]-N-hydroxy-3-(2-methylpropyl)-2-oxo-1-(2-phenylethyl)-3-pyrrolidineacetamide, 3a) 5,6-Difluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 3b) 1,3-Dihydro-N-hydroxy-α-[3-(2-methylpropyl)-2-oxo-1-(2-phenylethyl)-3-pyrrolidinyl]-1-oxo-2H-isoindole-2-butanamide, 3c) [R-(R*,S*)]-6-Fluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 3d) [R-(R*,S*)]-5-Fluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 3e) [R-(R*,S*)]-5,6-Difluoro-1,3-dihydro-N-hydroxy-α-[3-(2-methylpropyl)-2-oxo-1-(2-phenylethyl)-3-pyrrolidinyl]-1-oxo-2H-isoindole-2-butanamide, 3f) N-Hydroxy-α-[[[(4-methoxyphenyl)sulfonyl]amino]-methyl]-3-(2-methylpropyl)-2-oxo-1-(2-phenylethyl)-3-pyrrolidineacetamide (αR-diastereomer), 3g) N-Hydroxy-α-[[[(4-methoxyphenyl)sulfonyl]amino]-methyl]-3-(2-methylpropyl)-2-oxo-1-(2-phenylethyl)-3-pyrrolidineacetamide (αS-diastereomer), 3h) α-[[(4-Fluorophenyl)sulfonyl]amino]-N-hydroxy-3-(2-methylpropyl)-2-oxo-1-(2-phenylethyl)-3-pyrrolidineacetamide (R-diastereomer), 3i) α-[[(4-Fluorophenyl)sulfonyl]amino]-N-hydroxy-3-(2-methylpropyl)-2-oxo-1-(2-phenylethyl)-3-pyrrolidineacetamide (αS-diastereomer), 3j) α-[2-[(3,4-Difluorobenzoyl)amino]ethyl]-N-hydroxy-3-(3-hydroxypropyl)-2-oxo-1-(2-phenylethyl)-3-pyrrolidineacetamide, 3k) α-[2-[(3,4-Difluorobenzoyl)amino]ethyl]-N-hydroxy-3-(2-hydroxyethyl)-2-oxo-1-(2-phenylethyl)-3-pyrrolidineacetamide, or 3l) [R-(R*,S*)]-α-[2-[(3-Fluorobenzoyl)amino]ethyl]-N-hydroxy-3-(3-hydroxypropyl)-2-oxo-1-(2-phenylethyl)-3-pyrrolidineacetamide.

14. A method of inhibiting excess matrix metalloproteinase which comprises administering to a patient in need thereof an effective amount of a compound of claim 1.

15. A method of claim 14 wherein matrix metalloproteinases comprises collagenases, stromelysins, or gelatinases.

16. A method of treating a human, suffering from or susceptible to a diseases involving connective tissue degradation which comprises administering to a patient in need thereof an effective amount of a compound of claim 1.

17. A method of 16 wherein the diseases related to connective tissue degradation is osteoarthrits; rheumatoid arthritis, septic arthritis, osteopenias such as osteoporosis, tumor metastasis (invasion and growth), periodontitis, gingivitis, corneal ulceration, dermal ulceration, or gastric ulceration.

18. A pharmaceutical composition which comprises an amount of the compound of claim 1 effective to inhibit excess matrix metalloproteinase and a pharmaceutically acceptable carrier.

19. The method of claim 14 wherein the effective inhibitory amount of the compound of claim 1 is administered orally, parenterally, or topically in a pharmaceutical composition.

20. The method of claim 16 wherein the effective amount of the compound of claim 1 is administered orally, parenterally, or topically in a pharmaceutical composition.

21. The method of claim 14 or 16 wherein said compound is administered in an amount of from about 0.1 to about 100 mg/kg of body weight/day.

* * * * *